United States Patent
Stokes et al.

(10) Patent No.: US 10,696,652 B2
(45) Date of Patent: Jun. 30, 2020

(54) INDOLYL-PYRIDONE DERIVATIVES HAVING CHECKPOINT KINASE 1 INHIBITORY ACTIVITY

(71) Applicant: Vernalis (R&D) Ltd., Great Abington, Cambridge (GB)

(72) Inventors: Stephen Stokes, Great Abington (GB); Nicolas Foloppe, Great Abington (GB); Andrea Fiumana, Great Abington (GB); Martin Drysdale, Great Abington (GB); Simon Bedford, Great Abington (GB); Paul Webb, Great Abington (GB)

(73) Assignee: Vernalis (R&D) Ltd., Great Abington (GB)

( * ) Notice: Subject to any disclaimer, the term of this patent is extended or adjusted under 35 U.S.C. 154(b) by 0 days.

(21) Appl. No.: 15/962,306

(22) Filed: Apr. 25, 2018

(65) Prior Publication Data

US 2018/0244652 A1    Aug. 30, 2018

Related U.S. Application Data

(60) Division of application No. 15/427,457, filed on Feb. 8, 2017, now abandoned, which is a continuation of application No. 14/536,764, filed on Nov. 10, 2014, now Pat. No. 9,604,975, which is a division of application No. 12/812,791, filed as application No. PCT/GB2009/000149 on Jan. 20, 2009, now Pat. No. 8,916,591.

(30) Foreign Application Priority Data

Jan. 22, 2008 (GB) .................................. 0801090.2
Oct. 11, 2008 (GB) .................................. 0818695.9

(51) Int. Cl.
| | | |
|---|---|---|
| C07D 401/14 | (2006.01) | |
| C07D 413/14 | (2006.01) | |
| A61K 31/4439 | (2006.01) | |
| A61K 31/4545 | (2006.01) | |
| A61K 31/496 | (2006.01) | |
| A61K 31/5377 | (2006.01) | |

(52) U.S. Cl.
CPC ........ C07D 401/14 (2013.01); A61K 31/4439 (2013.01); A61K 31/4545 (2013.01); A61K 31/496 (2013.01); A61K 31/5377 (2013.01); C07D 413/14 (2013.01)

(58) Field of Classification Search
CPC ........................... C07D 401/14; C07D 413/14
See application file for complete search history.

(56) References Cited

U.S. PATENT DOCUMENTS 8,916,591 B2    12/2014    Stokes et al.
2012/0071512 A1    3/2012    Hu et al.

FOREIGN PATENT DOCUMENTS

| WO | 2002079192 A1 | 10/2002 |
| WO | 2003035065 A1 | 5/2003 |
| WO | 2005000804 A2 | 1/2005 |
| WO | 2006134318 A1 | 12/2006 |
| WO | 2008025526 A1 | 3/2008 |

OTHER PUBLICATIONS

International Search Report for PCT/GB2009/000149 (WO 2009/093012), dated Mar. 6, 2009.
Hayashi et al., Protein kinase C theta (PKCq): A key player in T cell life and death, Pharmacological Research 55 (2007), pp. 537-544.
LeRoith et al., The insulin-like growth factor system and cancer, Cancer Letters, 195, pp. 127-137 (2003).
Simone, Oncology: Introduction, Cecil Textbook of Medicine, ed Bennett et al. W.B. Saunders CO. 20th ed, vol. 1, 1996, pp. 1004-1010.
Sura, Systems for Identifying Drugs Are Often Faulty, Cancer Models, Science, vol. 278, No. 5340, pp. 1041-1042, Nov. 1997.
Johnson et al., Relationships between drug activity in NCI preclinical in vitro and in vivo models and early clinical trials, British Journal of Cancer (2001) 64(10): 1424-1431. Lodish et al., "Endocrine side, etc.," Endocrine-Related Cancer (2010) 17, R233-R244.
Ouaissi et al., "Rationale for Possible, etc., "Journal of Biomedicine and Biotechnology, 2011, Article: ID 315939, 1-8.
Golub et al, Science, vol. 286, Oct. 15, 1999, pp. 531-537.
Oct. 30, 2017—U.S. Non-final Office Action—U.S. Appl. No. 15/427,457.

*Primary Examiner* — Samira J Jean-Louis
(74) *Attorney, Agent, or Firm* — Banner & Witcoff, Ltd.

(57) ABSTRACT

A method of treating a mammal suffering from a cancer responsive to inhibition of protein kinase activity, by administering to the mammal an amount of a compound of formula (I), or a pharmaceutically acceptable salt thereof, effective to inhibit protein kinase activity, wherein the compound of formula (I) is:

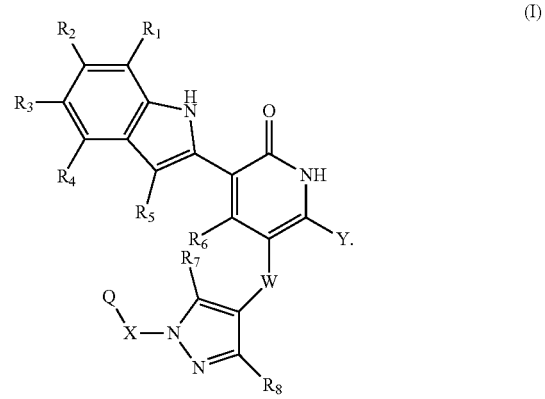

(I)

16 Claims, 1 Drawing Sheet

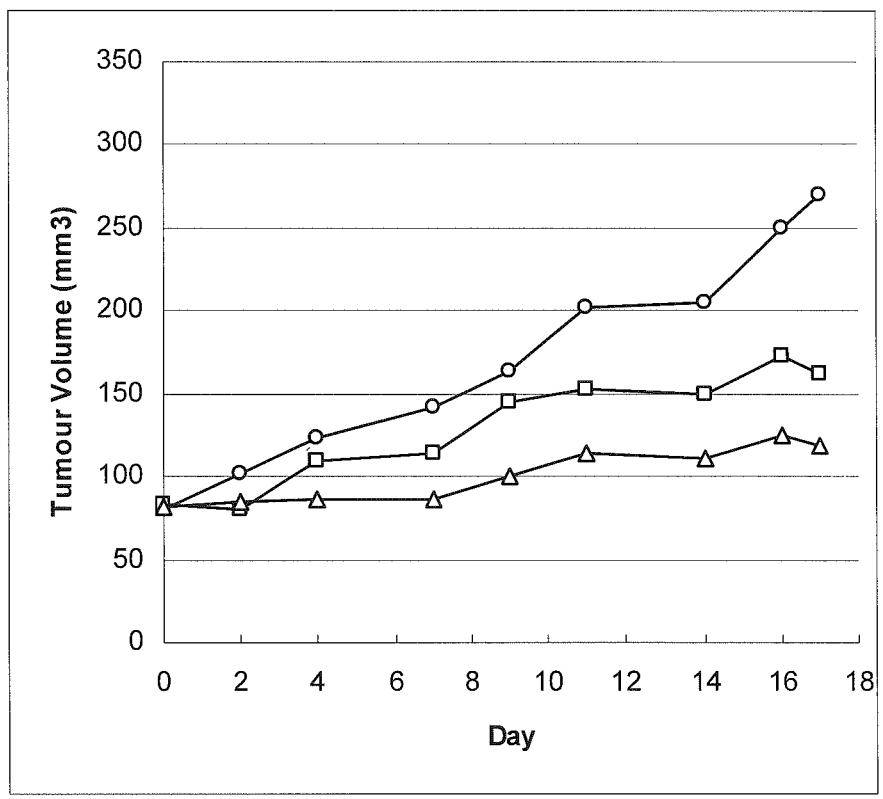

INDOLYL-PYRIDONE DERIVATIVES HAVING CHECKPOINT KINASE 1 INHIBITORY ACTIVITY

CROSS REFERENCE TO RELATED APPLICATIONS

This application is a divisional application of U.S. application Ser. No. 15/427,457 filed Feb. 8, 2017, which is a continuation application of U.S. application Ser. No. 14/536,764 filed Nov. 10, 2014, now U.S. Pat. No. 9,604,975, which is a divisional application of U.S. application Ser. No. 12/812,791 filed Sep. 23, 2010, now U.S. Pat. No. 8,916,591, which is a National Stage application of co-pending PCT application PCT/GB2009/000149 filed Jan. 20, 2009, which claims the benefit of Great Britain application number 0801090.2 filed Jan. 22, 2008 and Great Britain application number 0818695.9 filed Oct. 11, 2008. These applications are incorporated herein by reference in their entireties.

FIELD OF THE INVENTION

This invention relates to indolyl-pyridone derivatives having checkpoint kinase 1 (CHK1) inhibitory activity, to the use of such compounds in medicine, particularly in relation to the treatment of cancer, via the inhibition of aberrant cell proliferation, and to pharmaceutical compositions containing such compounds.

BACKGROUND OF THE INVENTION

Many standard cancer chemotherapeutic agents act primarily through their ability to induce DNA damage causing tumor growth inhibition. However, these agents cause cell cycle arrest by induction of checkpoints at either S-phase or G2-M boundary. The G2 arrest allows the cell time to repair the damaged DNA before entering mitosis. CHK1 and an unrelated serine/threonine kinase, CHK2, play a central role in arresting the cell cycle at the G2-M boundary (O'Connell et al EMBO J (1997) vol 16 p 545-554). CHK1/2 induce this checkpoint by phosphorylating serine 216 of the CDC25 phosphatase, inhibiting the removal of two inactivating phosphates on cyclin dependent kinases (CDKs) (Zheng et al Nature (1998) vol 395 p 507-510). Another overlapping pathway mediated by p53 also elicits cycle arrest in response to DNA-damage. However, p53 is mutationally inactivated in many cancers, resulting in a partial deficiency in their ability to initiate a DNA-repair response. If CHK1 activity is also inhibited in p53-negative cancers, all ability to arrest and repair DNA in response to DNA-damage is removed resulting in mitotic catastrophe and enhancing the effect of the DNA damaging agents (Konarias et al Oncogene (2001) vol 20 p 7453-7463, Bunch and Eastman Clin. Can. Res. (1996) vol 2 p 791-797, Tenzer and Pruschy Curr. Med Chem (2003) vol 3 p 35-46). In contrast, normal cells would be relatively unaffected due to retention of a competent p53-mediated cell-cycle arrest pathway. The inhibition of DNA damage checkpoints is therefore expected to sensitize aberrantly proliferating cells to DNA damaging agents. Such sensitization is in turn expected to increase the therapeutic index of such chemotherapeutic agents or ionizing radiation. (Clary, D. O. Inhibition of Chk kinases in a leukemia model abrogates DNA damage checkpoints and promotes mitotic catastrophe. Proc Am Assoc Cancer Res (AACR) 2007, 48: Abst 5385) Therefore it is expected that efficacious inhibitors of CHK1 will lead to a corresponding Improvement in the efficacy of current DNA-damage inducing chemotherapeutic regimens (Sausville et al, J. Clinical Oncology (2001) vol 19 p 2319-2333). A number of putative CHK1 inhibitors are currently in phase I clinical trials including XL-844 (a dual CHK1/CHK2 inhibitor for the treatment of lymphoma and solid tumours), PF 00477736 (Phase I Study of PF-00477736 with gemcitabine in patients with advanced solid malignancies) & AZD7762 (Phase I open label multi center dose escalation study to assess safety tolerability and pharmacokinetics of AZD7762 administered as a single intravenous agent and in combo with weekly standard dose gemcitabine in patients with advanced solid malignancies). Thus, there remains an unmet medical need for low molecular weight CHK1 inhibitors with pharmacokinetic and pharmacodynamic properties making them suitable for use as pharmaceutical agents. The object of the present invention is to provide such pharmaceutical agents and treatments.

It has now been found that certain indolyl-pyridone derivatives show efficacy as CHK1 inhibitors.

BRIEF DESCRIPTION OF THE INVENTION

The present invention relates to a class of substituted indolyl-pyridone compounds useful as CHK1 inhibitors, for example, for the treatment of cancer. A core indolyl-pyridone template, with substitution on the pyridone portion by a substituted-pyrazolyl amido-linked group are principle characterizing features of the compounds with which the invention is concerned.

BRIEF DESCRIPTION OF THE DRAWING

FIG. 1 shows the In vivo potentiation results of the compound of Example 20 in combination with gemcitabine.

DETAILED DESCRIPTION OF THE INVENTION

According to the present invention, there is provided a compound of formula (I) or a pharmaceutically acceptable salt thereof:

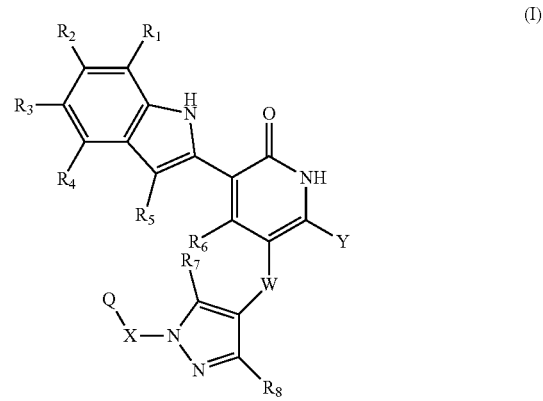

wherein
$R_1$, $R_2$, $R_5$ and $R_6$ are independently selected from hydrogen, hydroxy, methyl, trifluoromethyl, hydroxymethyl, methoxy, trifluoromethoxy, methylamino and dimethylamino;

$R_3$ and $R_4$, are independently selected from hydrogen, hydroxy, $C_1$-$C_3$ alkyl, fluoro-($C_1$-$C_3$)-alkyl, hydroxy-($C_1$-$C_3$)-alkyl, $C_1$-$C_3$ alkoxy, fluoro-($C_1$-$C_3$)-alkoxy, hydroxy- $(C_1-C_3)$-alkoxy, $-N(R_{11})-R_{12}$, -Alk-N$(R_{11})-R_{12}$, $-O$-Alk-N$(R_{11})-R_{12}$, $-C(=O)OH$, carboxy-$(C_1-C_3)$-alkyl, or $-C(=O)-NH-R_{13}$;

Alk is a straight or branched chain divalent $C_1-C_6$ alkylene radical;

$R_7$ and $R_8$ are independently selected from hydrogen, hydroxy, or $C_1-C_3$ alkoxy;

X is a straight chain divalent $C_1-C_3$ alkylene radical, optionally substituted on one or more carbons by $R_9$ and/or $R_{10}$;

$R_9$ and $R_{10}$ are independently selected from methyl, hydroxy, or fluoro;

$R_{11}$ is hydrogen, $C_1-C_3$ alkyl, or fluoro-$(C_1-C_3)$-alkyl, and $R_{12}$ is $C_1-C_3$ alkyl or hydroxy-$(C_1-C_6)$-alkyl, either of which may be optionally substituted on the alkyl portion by phenyl, $C_1-C_3$ alkoxy-$(C_1-C_3)$-alkyl, halo-$(C_1-C_4)$-alkyl, $C_3-C_6$ cycloalkyl, methylsulfonyl-$(C_1-C_3)$-alkyl or $-N(R_{18})-R_{19}$;

$R_{13}$ is hydrogen, $C_1-C_3$ alkyl, fluoro-$(C_1-C_3)$-alkyl, or a radical of formula -Alk-N$(R_{14})-R_{15}$;

$R_{14}$ and $R_{15}$ are independently selected from hydrogen, $C_1-C_3$ alkyl, or fluoro-$(C_1-C_3)$-alkyl;

or $R_{11}$ and $R_{12}$, or $R_{14}$ and $R_{15}$, together with the nitrogen atom to which they are respectively attached, form an optionally substituted, 4- to 6-membered, monocyclic heterocyclic ring having no more than three additional heteroatoms independently selected from oxygen, sulphur and nitrogen;

W is selected from $-C(=O)-N(-R_{16})-$ or $-N(-R_{17})-C(=O)-$;

$R_{16}$ or $R_{17}$ is selected from hydrogen, $C_1-C_3$ alkyl, or fluoro-$(C_1-C_3)$-alkyl;

$R_{18}$ and $R_{19}$ are selected from hydrogen, $C_1-C_3$ alkyl, or fluoro-$(C_1-C_3)$-alkyl, or $R_{18}$ and $R_{19}$ together with the nitrogen atom to which they are respectively attached, form an optionally substituted, 4- to 6-membered, monocyclic heterocyclic ring having no more than three additional heteroatoms independently selected from oxygen, sulphur and nitrogen;

Y is hydrogen, $C_1-C_3$ alkyl, $C_1-C_3$ alkoxy, or halo; and

Q is selected from optionally substituted phenyl, optionally substituted cyclohexyl, or an optionally substituted 6-membered monocyclic heteroaryl ring.

The active compounds of formula (I) are inhibitors of CHK1, and are useful for the treatment, prevention and suppression of a proliferative disease such as cancer in combination with radiotherapy or chemotherapy.

According to a further embodiment of the present invention there is provided the use of a compound of formula (I), or a pharmaceutically acceptable salt thereof, in the manufacture of a medicament for enhancing a therapeutic effect of radiation or chemotherapy in the treatment of cancer.

According to a further embodiment of the present invention there is provided a method of treatment of cancer comprising administration to a subject in need of such treatment an effective dose of the compound of formula (I), or a pharmaceutically acceptable salt thereof.

According to a further embodiment of the present invention there is provided a pharmaceutical composition comprising a compound of formula (I), or a pharmaceutically acceptable salt thereof, and a pharmaceutically acceptable carrier.

Terminology

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences, such as $-CH_2-$, $-CH_2CH_2-$, $-CH_2CH_2CH_2-$, $-CH_2CH(CH_3)CH_2-$ and $-CH_2C(CH_3)_2CH_2-$. For the avoidance of doubt, it is to be understood that a divalent branched chain $(C_a-C_b)$alkylene radical includes those wherein one of the carbons of the hydrocarbon chain is a ring carbon of a cycloalkyl ring (ie is a spiro centre), such as those of formulae (II):

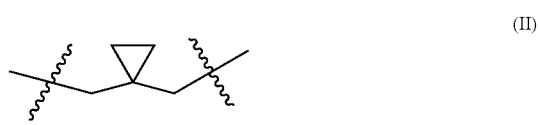 [SMILES: *CC1(C*)CC1]

(II)

As used herein, the term "fluoro-$(C_a-C_b)$-alkyl" wherein a and b are integers refers to a straight or branched chain alkyl radical having from a to b carbon atoms substituted by one or more fluoro atoms. The term includes, for example, fluoromethyl, difluoromethyl and trifluoromethyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "carbocyclic" refers to a mono- or bi-cyclic radical whose ring atoms are all carbon, and includes monocyclic aryl, cycloalkyl, and cycloalkenyl radicals, provided that no single ring present has more than 8 ring members. A "carbocyclic" group includes a mono-bridged or multiply-bridged cyclic alkyl group.

As used herein the term "aryl" refers to a mono-, bi- or tri-cyclic carbocyclic aromatic radical. Illustrative of such radicals are phenyl, biphenyl and napthyl.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, to groups consisting of a monocyclic non-aromatic radical containing one or more such heteroatoms which is covalently linked to another such radical or to a monocyclic carbocyclic radical, and to a mono-, bi- or tri-cyclic non-aromatic radical containing one or more heteroatoms selected from S, N and O which is mono-bridged or multiply-bridged. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl group, or R$^A$ and R$^B$ when attached to the same nitrogen may form a cyclic amino ring such as a morpholinyl, piperidinyl or piperazinyl ring. An "optional substituent" or "substituent" may be one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides, alkaline earth metal hydroxides e.g. calcium, barium and magnesium hydroxides, with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see Handbook of Pharmaceutical Salts: Properties, Selection, and Use by Stahl and Wermuth (Wiley-VCH, Weinheim, Germany, 2002).

Compounds of the invention are expected to be isolatable as hydrates and solvates. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. Any reference herein to a compound of formula(I) is to be understood as including such hydrates and solvates.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Also included within the scope of the invention are metabolites of compounds of formula (I), that is, compounds formed in vivo upon administration of the drug. Some examples of metabolites include (i) where the compound of formula (I) contains a methyl group, an hydroxymethyl derivative thereof (—CH$_3$→—CH$_2$OH):

(ii) where the compound of formula (I) contains an alkoxy group, an hydroxy derivative thereof (—OR→—OH), (iii) where the compound of formula (I) contains a tertiary amino group, a secondary amino derivative thereof (—NR$^1$R$^2$→—NHR$^1$ or —NHR$^2$), (iv) where the compound of formula (I) contains a secondary amino group, a primary derivative thereof (—NHR$^1$→—NH$_2$), (v) where the compound of formula (I) contains a phenyl moiety, a phenol derivative thereof (-Ph→-PhOH), and (vi) where the compound of formula (I) contains an amide group, a carboxylic acid derivative thereof (—CONH$_2$→COOH).

Variable substituents present in compounds (I) will now be further described. It is to be understood in the further description that any disclosed substituent or substituent class may be present in any combination with any of the other disclosed substituent classes. Specific examples of the variable substituents include those present in the compounds of the Examples herein.

The Groups R$_1$, R$_2$, R$_5$ and R$_6$

R$_1$, R$_2$, R$_5$ and R$_6$ are independently selected from hydrogen, or small substituents such as hydroxy, methyl, trifluoromethyl, hydroxymethyl, methoxy, trifluoromethoxy, methylamino and dimethylamino. Currently it is preferred that R$_1$, R$_2$, R$_5$ and R$_6$ are each hydrogen.

The Groups R$_3$ and R$_4$

R$_3$ and R$_4$ are hydrogen, hydroxy, C$_1$-C$_3$ alkyl, fluoro-(C$_1$-C$_3$)-alkyl, hydroxy-(C$_1$-C$_3$)-alkyl, C$_1$-C$_3$ alkoxy, fluoro-(C$_1$-C$_3$)-alkoxy, hydroxy-(C$_1$-C$_3$)-alkoxy, —N(R$_{11}$)—R$_{12}$, -Alk-N(R$_{11}$)—R$_{12}$, —O-Alk-N(R$_{11}$)—R$_{12}$, —C(=O)OH, carboxy-(C$_1$-C$_3$)-alkyl, or —C(=O)—NH—R$_{13}$.

In some embodiments of the invention, one of R$_3$ and R$_4$ is hydrogen and the other is selected from —N(R$_{11}$)—R$_{12}$, -Alk-N(R$_{11}$)—R$_{12}$, and —O-Alk-N(R$_{11}$)—R$_{12}$, especially the latter two. Currently it is preferred that R$_4$ be hydrogen. R$_{11}$ and R$_{12}$ together with the nitrogen atom to which they are attached, may form an optionally substituted, 4- to 6-membered, monocyclic heterocyclic ring having no more than three additional heteroatoms independently selected from oxygen, sulphur and nitrogen. Preferred structures include those wherein R$_{11}$ and R$_{12}$ together with the nitrogen atom to which they are attached form an azetidine, pyrrolidine, piperidine, morpholine, or piperazine ring, optionally substituted by C$_1$-C$_3$ alkyl, hydroxy-(C$_1$-C$_3$)-alkyl, fluoro, or hydroxy. Particularly preferred are those compounds wherein R$_{11}$ and R$_{12}$ together with the nitrogen atom to which they are attached form 1-hydroxy-azetidin-3-yl, pyrrolidin-1-yl, piperidin-1-yl, morpholin-4-yl, piperazin-1-yl, 1-methyl-piperidin-4-yl, 1-fluoro-piperidin-4-yl, 1-hydroxy-piperidin-4-yl, 1-(hydroxymethyl)-piperidin-4-yl, or 1-methyl-piperazin-4-yl. In this subclass Alk may be, for example C$_1$-C$_6$ alkylene, preferably methylene, or ethylene. In this subclass Alk may be, for example —CH$_2$—, —CH$_2$CH$_2$—, —CH$_2$CH$_2$CH$_2$— or —CH$_2$CH(CH$_3$)CH$_2$— or a divalent branched chain alkylene radical —CH$_2$C(CH$_3$)$_2$ CH$_2$— or of formula (II):

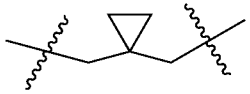

(II)

In other embodiments of the invention, one of R$_3$ and R$_4$ is hydrogen and the other is selected from —N(R$_{11}$)—R$_{12}$, -Alk-N(R$_{11}$)—R$_{12}$, and —O-Alk-N(R$_{11}$)—R$_{12}$, especially the latter two, wherein R$_{11}$ and R$_{12}$ are independently selected from C$_1$-C$_3$ alkyl, for example methyl and ethyl, or R$_{11}$ is C$_1$-C$_3$ alkyl, for example methyl or ethyl and R$_{12}$ is —N(R$_{18}$)—R$_{19}$ wherein R$_{18}$ and R$_{19}$ are independently selected from C$_1$-C$_3$ alkyl, for example methyl and ethyl. In this subclass also Alk may be, for example —CH$_2$—, —CH$_2$CH$_2$—, —CH$_2$CH$_2$CH$_2$— or —CH$_2$CH(CH$_3$)CH$_2$— or preferably a divalent branched chain alkylene radical —CH$_2$C(CH$_3$)$_2$CH$_2$— or of formula (II):

(II)

In other embodiments of the invention, one of R$_3$ and R$_4$ is hydrogen and the other is selected from —N(R$_{11}$)—R$_{12}$, -Alk-N(R$_{11}$)—R$_{12}$, or —O-Alk-N(R$_{11}$)—R$_{12}$, wherein R$_{11}$ is hydrogen or C$_1$-C$_3$ alkyl, particularly methyl or ethyl, and R$_{12}$ is hydroxy-(C$_1$-C$_6$)-alkyl, such as 2-hydroxy-ethyl. In this subclass also Alk may be, for example —CH$_2$—, —CH$_2$CH$_2$—, —CH$_2$CH$_2$CH$_2$— or —CH$_2$CH(CH$_3$)CH$_2$— or preferably a divalent branched chain alkylene radical —CH$_2$C(CH$_3$)$_2$CH$_2$— or of formula (II):

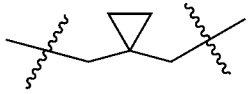

(II)

The Group Y

Y is hydrogen, C$_1$-C$_3$ alkyl, C$_1$-C$_3$ alkoxy, or halo. Presently, it is preferred that Y is hydrogen, methyl, methoxy, or halo. Particularly preferred are those compounds wherein Y is hydrogen or methyl.

The Group W

W is selected from —C(=O)—N(—R$_{16}$)— or —N(—R$_{17}$)—C(=O)—. R$_{16}$ and R$_{17}$ are selected from hydrogen C$_1$-C$_3$ alkyl such as methyl and fluoro-(C$_1$-C$_3$)-alkyl such as trifluoromethyl. Preferred structures include those wherein W is —C(=O)—NH— (ie where the nitrogen is linked to the pyrazole ring, or —NH—C(=O)— (ie where the carbonyl group is linked to the pyrazole ring), particularly the latter.

The Radicals R$_7$ and R$_8$

R$_7$ and R$_8$ are independently selected from hydrogen, hydroxy, or C$_1$-C$_3$ alkoxy. Preferred structures include those wherein R$_7$ and R$_8$ are independently selected from hydrogen, hydroxy, or methoxy. Particularly preferred cases are wherein one or both of R$_7$ and R$_8$ is/are hydrogen.

The Divalent Radical X

X is a straight chain divalent C$_1$-C$_3$ alkylene radical, optionally substituted on one or more carbons by R$_9$ and/or R$_{10}$. R$_9$ and R$_{10}$ are independently selected from methyl, hydroxy, or fluoro. Currently, it is preferred that both R$_9$ and R$_{10}$ when present are methyl. For example, X may be —CH$_2$—, —CH(CH$_3$)— or

—C(CH$_3$)$_2$—.

The Group Q

Q is selected from optionally substituted phenyl, optionally substituted cyclohexyl, or an optionally substituted 6-membered monocyclic heteroaryl ring.

In a subclass of compounds with which the invention is concerned, Q is unsubstituted or substituted phenyl. Unsubstituted phenyl is currently preferred, but when substituents are present the phenyl ring may be substituted by no more than two substituents independently selected from C$_1$-C$_3$ alkyl, halo-(C$_1$-C$_3$)alkyl, C$_1$-C$_3$ alkoxy, halo, or cyano. Preferred substituents are methyl, trifluoromethyl, methoxy, fluoro, chloro, or cyano. Preferred structures include those wherein Q is 2-methyl-phenyl, 3-methyl-phenyl, 4-methyl-phenyl, 3-trifluoromethyl-phenyl, 4-trifluoromethyl-phenyl, 4-methoxy-phenyl, 2-fluoro-phenyl, 3-fluoro-phenyl, 4-fluoro-phenyl, 3-chloro-phenyl, 4-chloro-phenyl, 3-cyano-phenyl, 4-cyano-phenyl, 3,4-difluoro-phenyl, 3,5-difluoro-phenyl, or 3-fluoro-4-methyl-phenyl.

In another subclass of compounds with which the invention is concerned, Q is optionally substituted cyclohexyl.

In yet a further subclass of compounds with which the invention is concerned, Q is an optionally substituted 6-membered monocyclic heteroaryl ring, preferably pyridyl, particularly pyrid-3-yl or pyrid-4-yl.

Currently, it is preferred that Q is phenyl, 3-methyl-phenyl, 4-methyl-phenyl, 3-trifluoromethyl-phenyl, 3-fluoro-phenyl, 4-fluoro-phenyl, 3-chloro-phenyl, 4-chloro-phenyl, 3,4-difluoro-phenyl, or 3,5-difluoro-phenyl, particularly phenyl, 4-methyl-phenyl, or 4-chloro-phenyl.

In a currently preferred subclass of compounds of formula (I) of the invention, R$_1$, R$_2$, R$_4$, R$_5$, R$_6$, R$_7$ and R$_8$ are each hydrogen; Y is hydrogen or methyl; W is —NH—C(=O)— wherein the carbonyl group is linked to the pyrazole ring; R$_3$ is —N(R$_{11}$)—R$_{12}$, -Alk-N(R$_{11}$)—R$_{12}$, or —O-Alk-N(R$_{11}$)—R$_{12}$; R$_{11}$ and R$_{12}$ together with the nitrogen atom to which they are attached form an optionally substituted, 5- to 6-membered, monocyclic heterocyclic ring having no more than three additional heteroatoms independently selected from oxygen, sulphur and nitrogen. or R$_{11}$ and R$_{12}$ are independently selected from methyl and ethyl; Alk is —CH$_2$—, —CH$_2$CH$_2$—, —CH$_2$CH$_2$CH$_2$— or —CH$_2$C(CH$_3$)$_2$CH$_2$—; X is —CH$_2$—, —CH(CH$_3$)— or —C(CH$_3$)$_2$—; and Q is phenyl, optionally substituted by one or two substituents selected from C$_1$-C$_3$ alkyl, fluoro-(C$_1$-C$_3$) alkyl, C$_1$-C$_3$ alkoxy, fluoro-(C$_1$-C$_3$) alkoxy, halo, and cyano. In this preferred subclass, R$_{11}$ and R$_{12}$ together with the nitrogen atom to which they are attached may form a piperidine, morpholine, or piperazine ring, optionally substituted by C$_1$-C$_3$ alkyl or fluoro. Furthermore, in this preferred subclass Q may be unsubstituted phenyl.

Specific compounds of the invention include those of the Examples herein, and their pharmaceutically acceptable salts.

Utility

The present invention may be employed in respect of a human or animal subject, more preferably a mammal, more preferably a human subject.

As used herein, the term "treatment" as used herein includes prophylactic treatment.

Compounds of the invention may be used alone in the treatment of cancers and autoimmune disorders such as organ transplant rejection, lupus, multiple sclerosis, rheumatoid arthritis and osteoarthritis. However, as explained above in the background to the present invention, the main utility of inhibitors of CHK1 is considered to be their ability to improve the efficacy of current DNA-damage inducing radiotherapy or chemotherapeutic regimens for cancer treatment. The compound of formula (I) is therefore preferably used in combination for the treatment of cancer with radiation therapy or one or more cytotoxic or cytostatic drugs, or drugs which induce cytotoxicity or cytostasis. The compound of the invention and the other component may be in the same pharmaceutical formulation or in separate formulations for administration simultaneously or sequentially.

Non-limiting examples of chemotherapeutic agents, radiotheraputic agents and other active and ancillary agents are set forth below.

(i) Alkylating agents.
(ii) Nitrogen mustards such as chlorambucil
cyclophosphamide
ifosfamide
mechlorethamine
melphalan (iii) Nitrosoureas such as carmustine (BCNU)
lomustine (CCNU)
semustine (methyl-CCNU)

(iv) Ethylenimine/Methyl-melamine such as hexamethylmelamine (HMM/altetamine)
thriethylenemelamine (TEM)
trethylene thiophosphoramide (thiotepa)

(v) Alkyl sulphonates such as busulphan.
(vi) Triazines such as dacarbazine (DTIC).
(vii) Antimetabolites such as the Folic acid analogues such as Methoxtrexate
pemetrexed (multi-targeted antifolate)
Trimetrexate (viii) Pyrimidine analogues such as 2,2'-difluorodeoxy-cytidine
5-azacytidine
5-fluorouracil
cytosine arabinoside (araC/cytarabine)
Fluorodeoxyuridine
Gemcitabine (ix) Purine analogues such as 2-chlorodeoxyadenosine (cladribine/2-CdA)
2'-deoxycoformycin (pentostatin)
6-Mercaptopurine
6-thioguanine
Azathioprine
erthyrohydroxynonyl-adenine (EHNA)
fludarabine phosphate (x) Type I Topoisomerase Inhibitors such as camptothecin
irinotecan
topotecan (xi) Biological response modifiers such as G-CSF and GM-CSF.
(xii) Differentiation agents such as retinoic acid derivatives.
(xiii) Hormones and antagonists.
(xiv) Adrenocorticosteroids/antagonists such as ainoglutethimide
dexamethasone
prednisone and equivalents (xv) Progestins such as hydroxyprogesterone caproate
medroxyprogesterone acetate
megestrol acetate (xvi) Estrogens such as diethylstilbestrol
ethynyl estradiol/equivalents (xvii) Antiestrogens such as tamoxifen.
(xviii) Andogens such as testosterone propionate
fluoxymesterone/equivalents (xix) Anti-androgens such as Flutimide
gonadotropin-releasing hormone analogues
Leuprolide (xx) Nonsteroidal antiandrogens.
(xxi) Natural products.
(xxii) Antimitotic drugs.
(xxiii) Taxanes such as docetaxel (Taxotere)
estramustine/estramustine phosphate
Paclitaxel
vinblastine (VLB)
vinca alkaloids
Vincristine
Vinorelbine (xxiv) Epipodophylotoxins such as etoposide or teniposide.
(xxv) Antibiotics such as actimomycin D
aphidicolin
Bleomycin
Dactinomycin
daunomycin (rubidomycin)
doxorubicin (adriamycin)
mitomycin C
Mitroxantroneidarubicin
splicamycin (mithramycin)

(xxvi) Enzymes such as L-asparaginase and L-arginase.
(xxvii) Radiosensitizers such as 5-bromodeozyuridine
5-idoddeoxyuridine
Bromodeoxycytidine
Desmethylmisonidazole
EO9
Etanidazole
Metronidazole
Misonidazole
Nicotinamide
Nimorazole
Pimonidazole
RB 6145
RSU 1069
SR4233

(xxviii) Platinum coordination complexes such as

Anthracenedione
Carboplatin
Cisplatin
Mitoxantrone
oxaliplatin (xxix) Substituted ureas such as hydroxyurea.
(xxx) Methyhydrazine derivatives such as N-methylhyrazine (MIH) and procarbazine.
(xxxi) Adrenocortical suppressant mitocane (o,p'-DDD) ainoglutethimide.
(xxxii) Cytokines such as interferon ($\alpha$, $\beta$, $\gamma$) and interleukin-2.
(xxxiii) Photosensitisers such as bacteriochlorophyll-a
benzoporphyrin derivatives
hematoporphyrin derivatives
napthalocyanines
Npe6
pheboride-a
photofrin
phthalocyanines
tin etioporphyrin (SnET2)
zinc phthalocyanines (xxxiv) Radiation such as gamma radiation
infrared radiation
microwave radiation
ultraviolet light
visible light
X-ray It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone, fillers for example lactose, sugar, maize-starch, calcium phosphate, sorbitol or glycine, tabletting lubricant, for example magnesium stearate, talc, polyethylene glycol or silica, disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats, emulsifying agents, for example lecithin, sorbitan monooleate, or acacia, non-aqueous vehicles (which may include edible oils), for example almond oil, fractionated coconut oil, oily esters such as glycerine, propylene glycol, or ethyl alcohol, preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

There are multiple synthetic strategies for the synthesis of the compounds (I) with which the present invention is concerned, but all rely on known chemistry, known to the synthetic organic chemist. Thus, compounds according to formula (I) can be synthesized according to procedures described in the standard literature and are well-known to the one skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem.

Res.", "Chem. Rev", or primary literature sources identified by standard literature searches online or from secondary sources such as "Chemical Abstracts" or "Beilstein". Such literature methods include those of the preparative Examples herein, and methods analogous thereto.

Examples of methods known in the art of organic chemistry in general, by which the compounds of the present invention may be prepared, are included in the following reaction schemes and procedures.

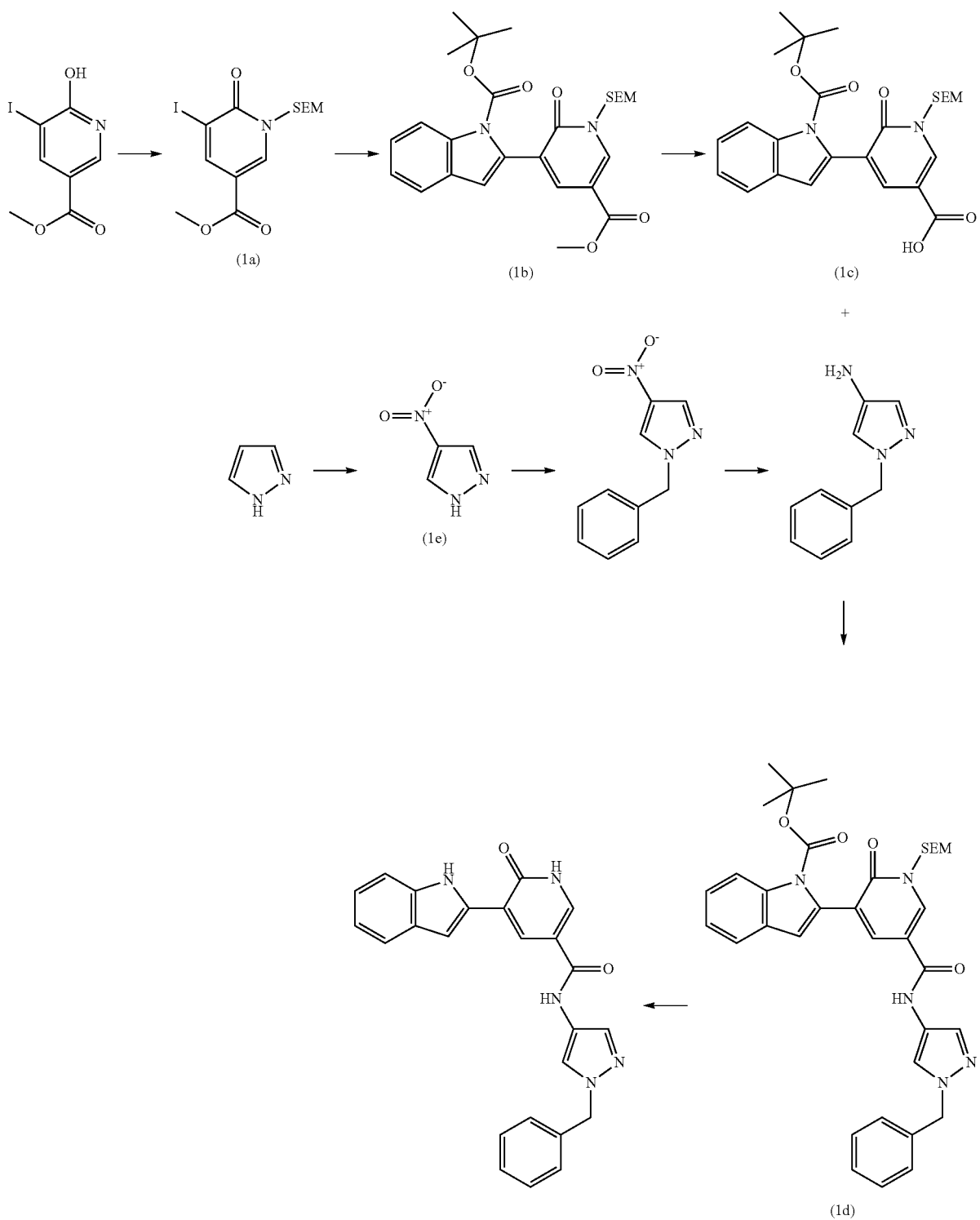

Scheme 2
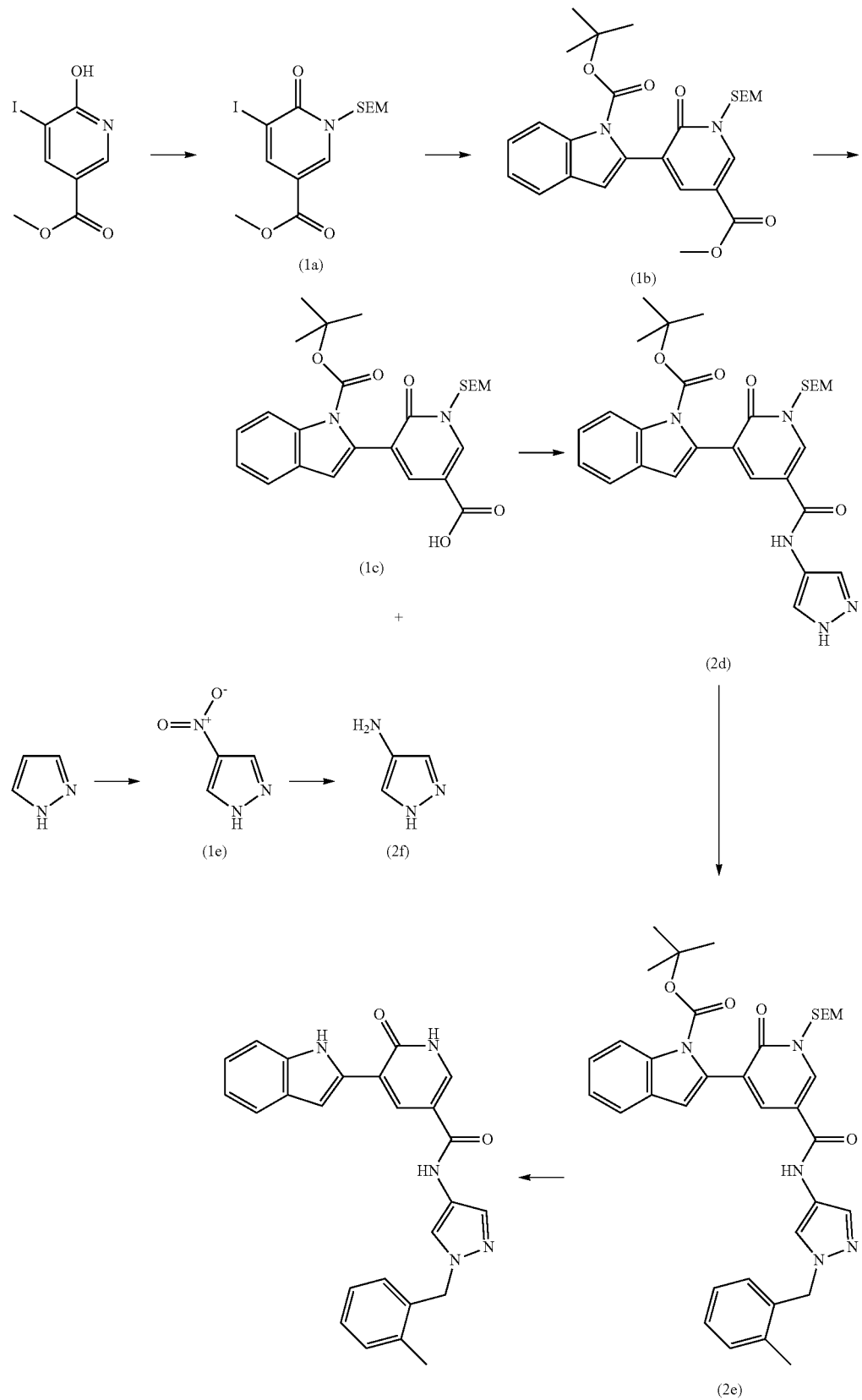

Scheme 3
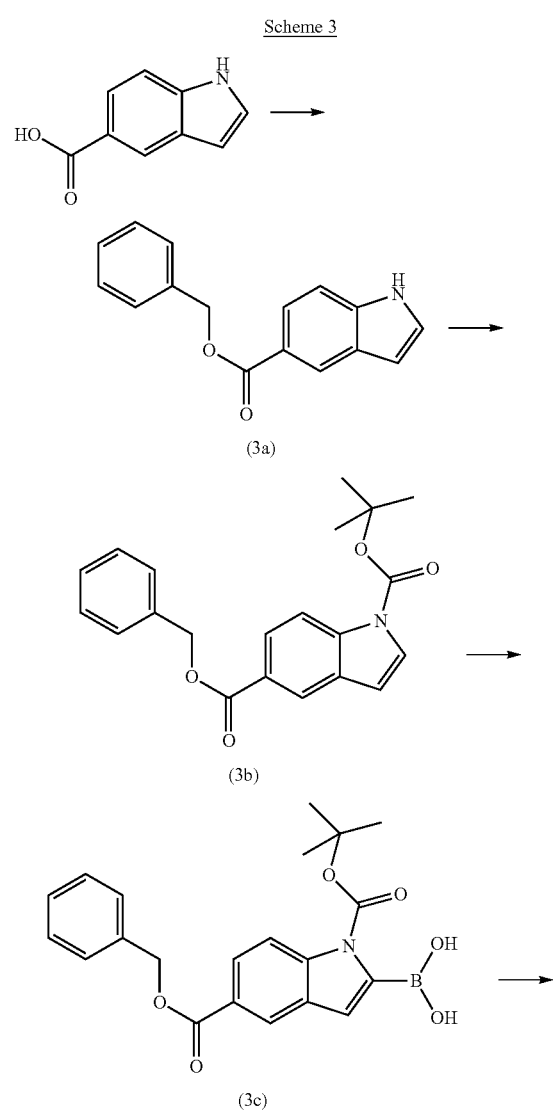
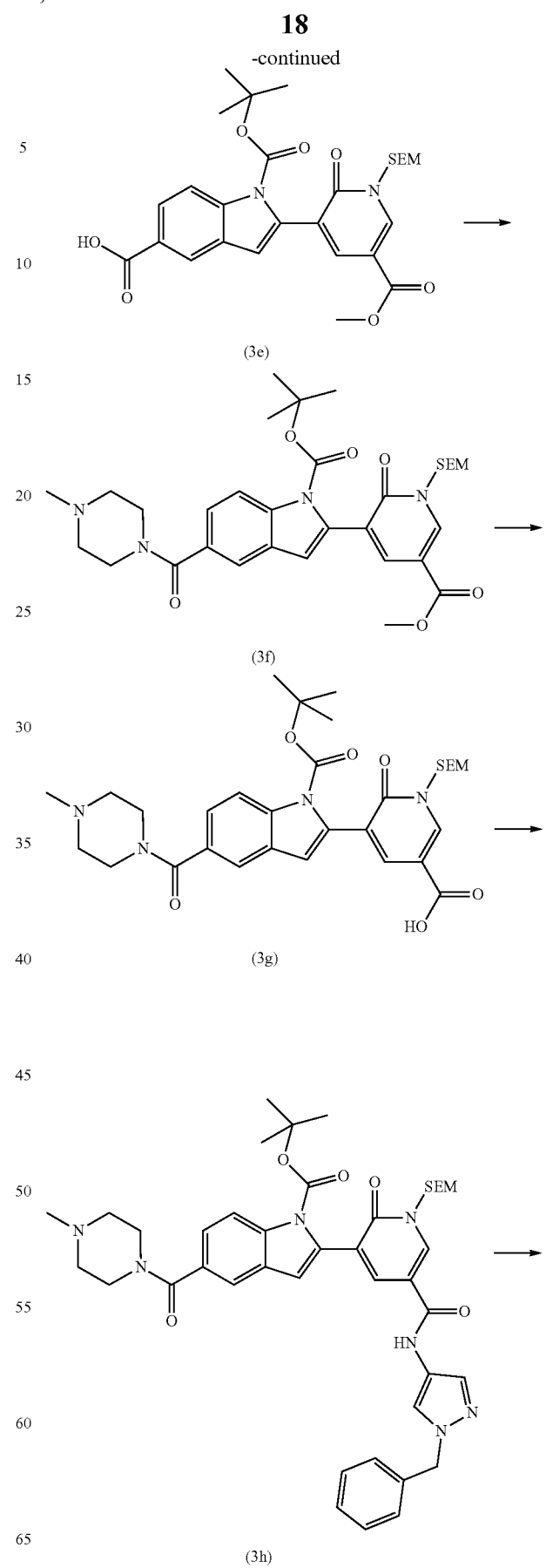

19
-continued
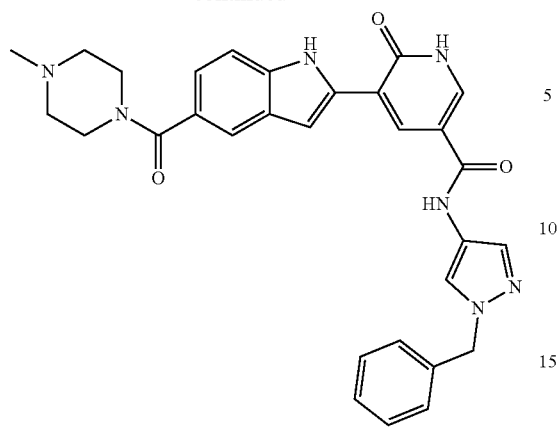
Scheme 4
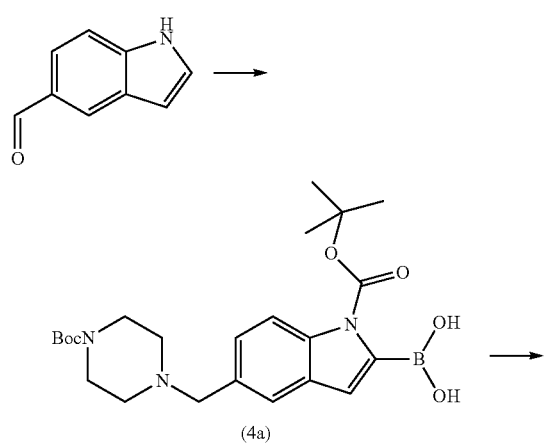
20
-continued
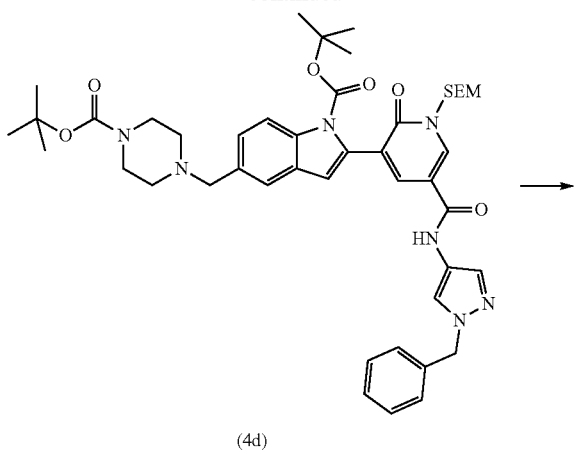
(4d)
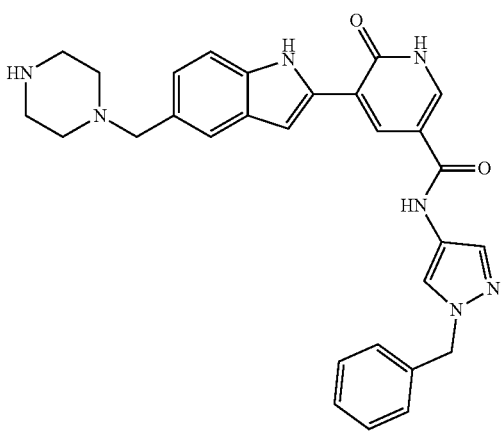 [SMILES: O=C(Nc1cnn(Cc2ccccc2)c1)c1c[nH]c(=O)c(-c2cc3cc(CN4CCNCC4)ccc3[nH]2)c1]
Scheme 5
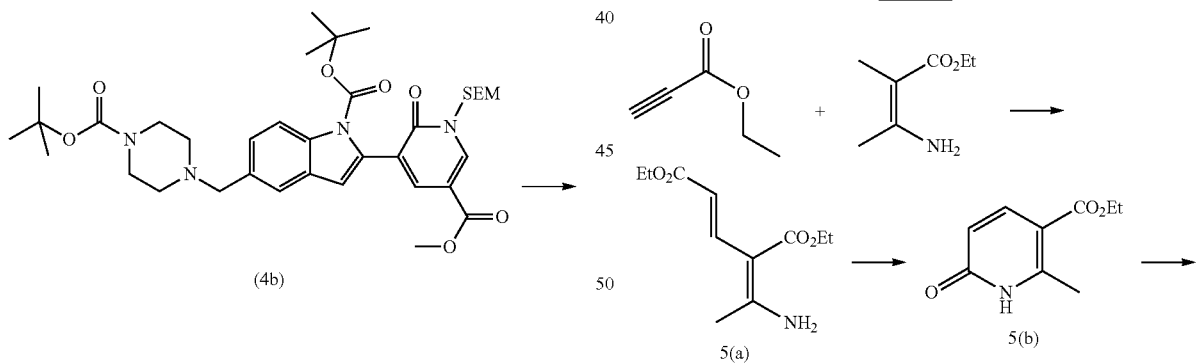
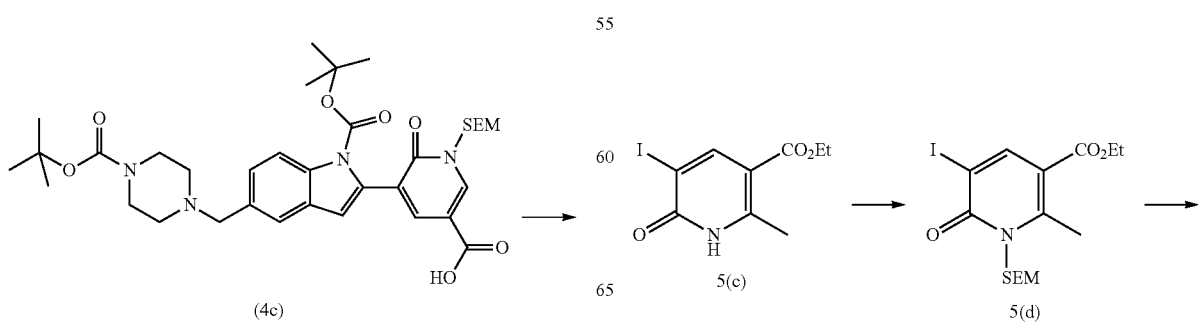

-continued
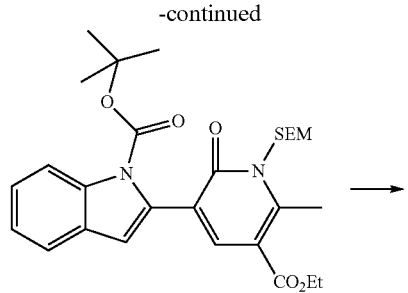
5(e)
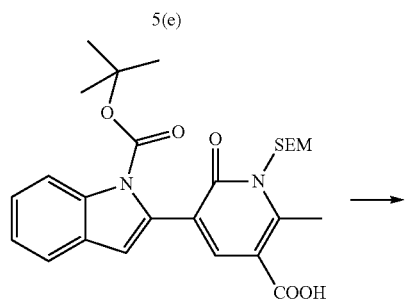
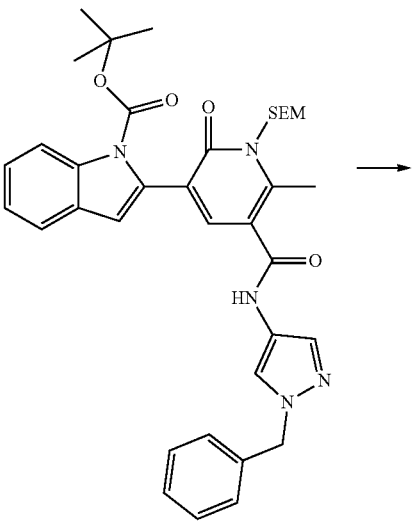
5(g)
Scheme 6
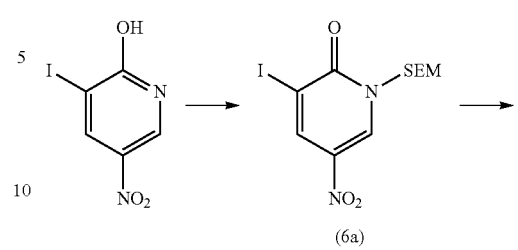
(6a)
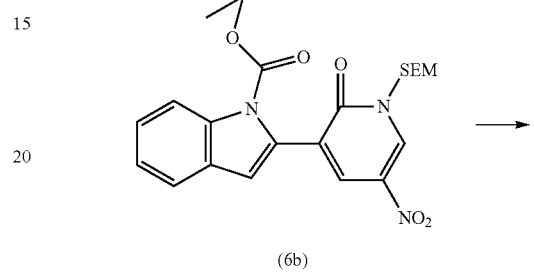
(6b)
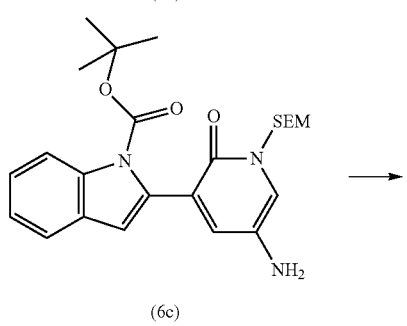
(6c)
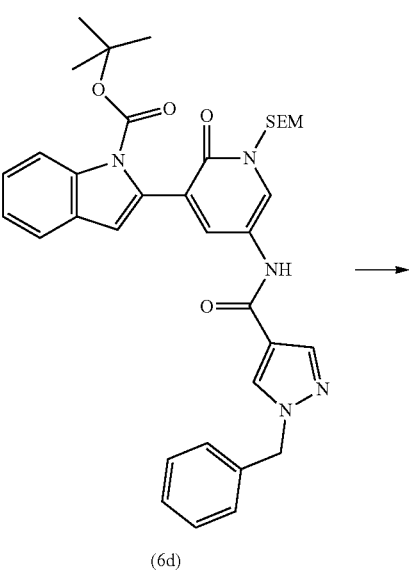
(6d)

23
-continued
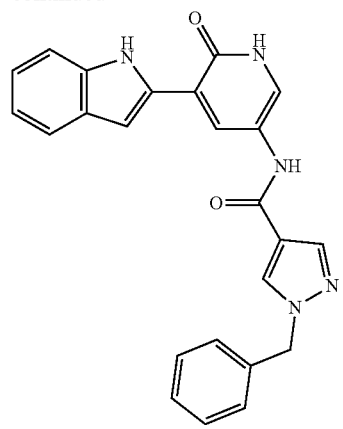 [SMILES: Cc1[nH]c(=O)c(-c2cc3ccccc3[nH]2)cc1C(=O)Nc1cnn(Cc2ccccc2)c1]
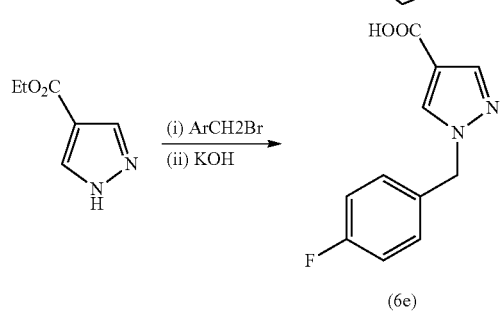
(6e)
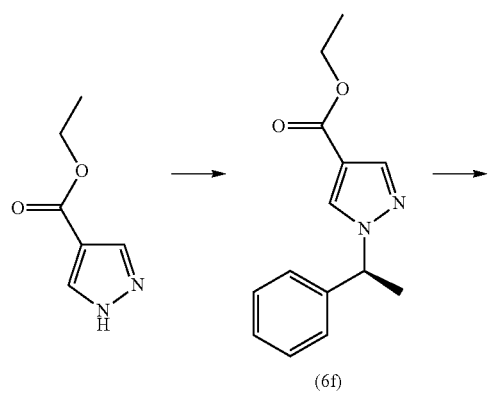
(6f)
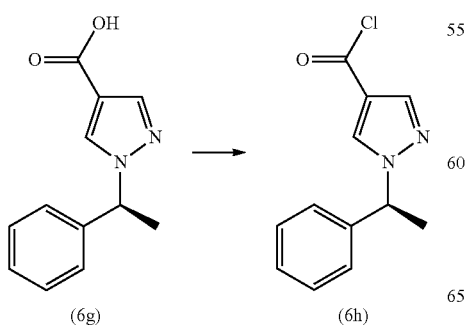
(6g)　(6h)
24
-continued
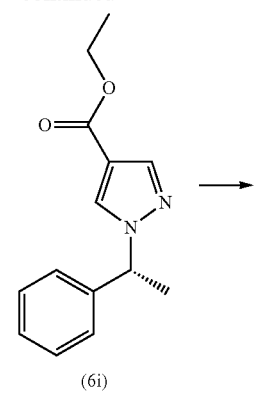
(6i)
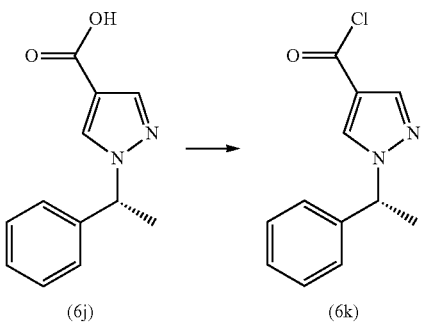
(6j)　(6k)
Scheme 7
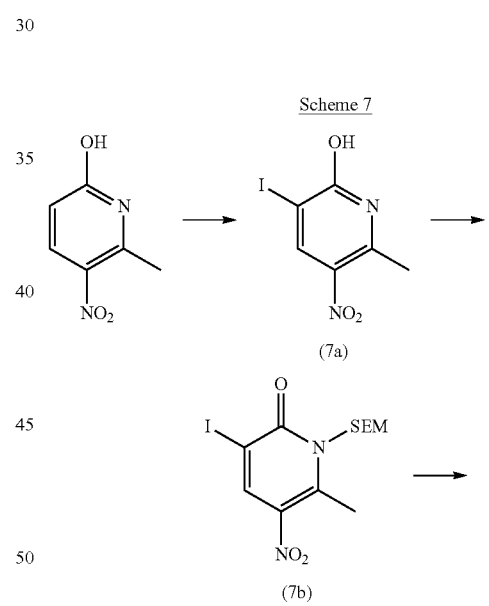
(7a)
(7b)
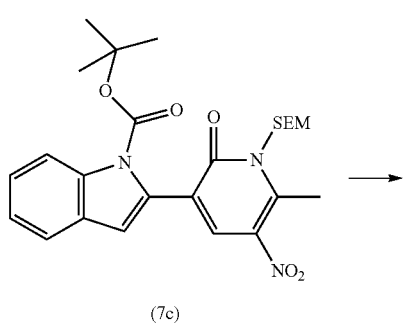
(7c)

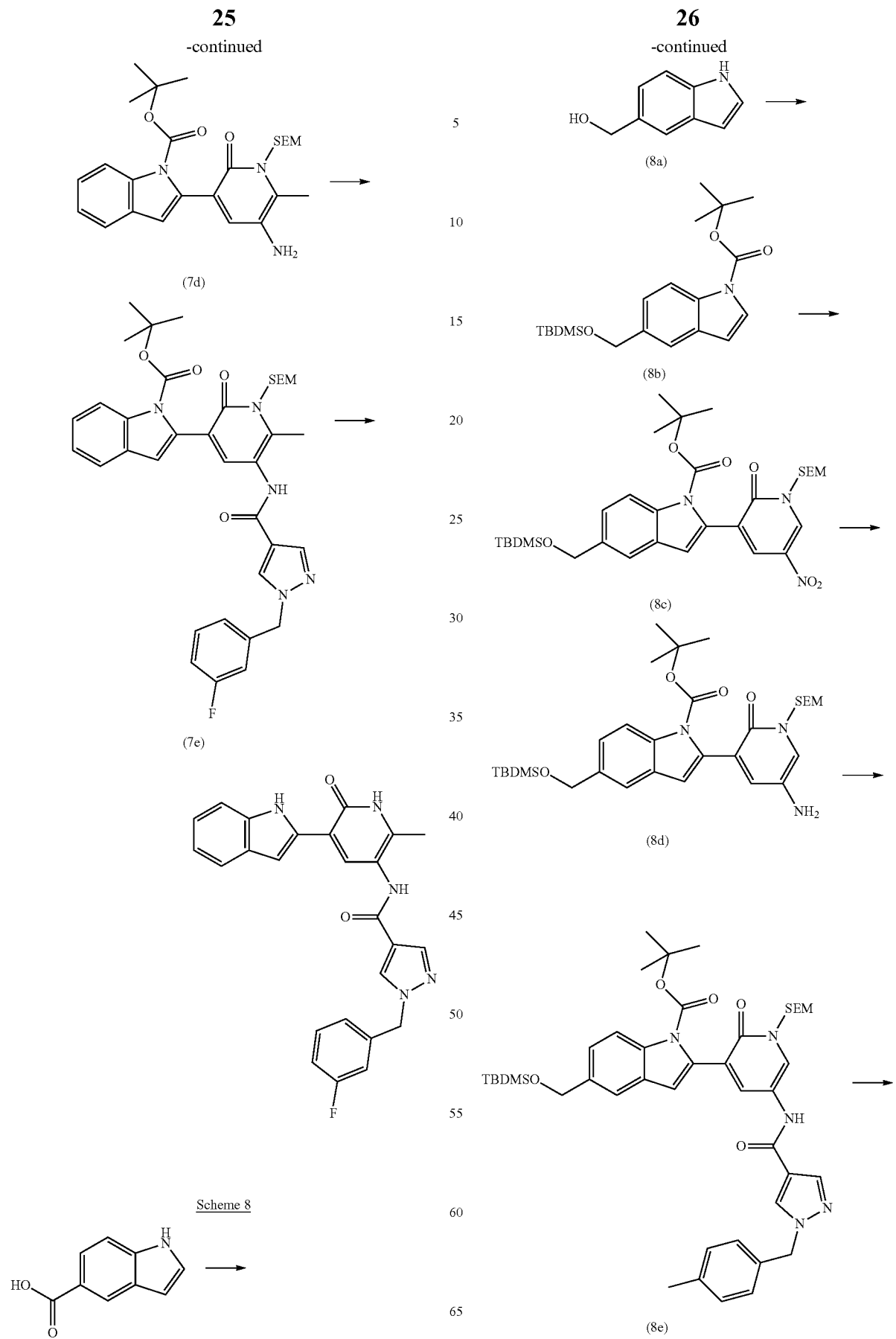

27 28
-continued
Scheme 9
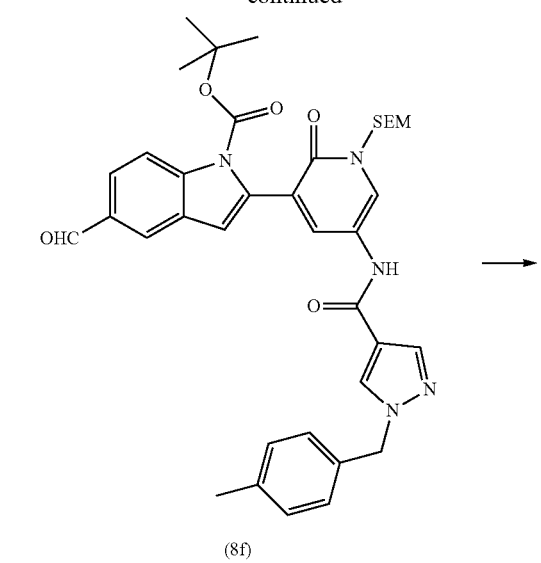
(8f)
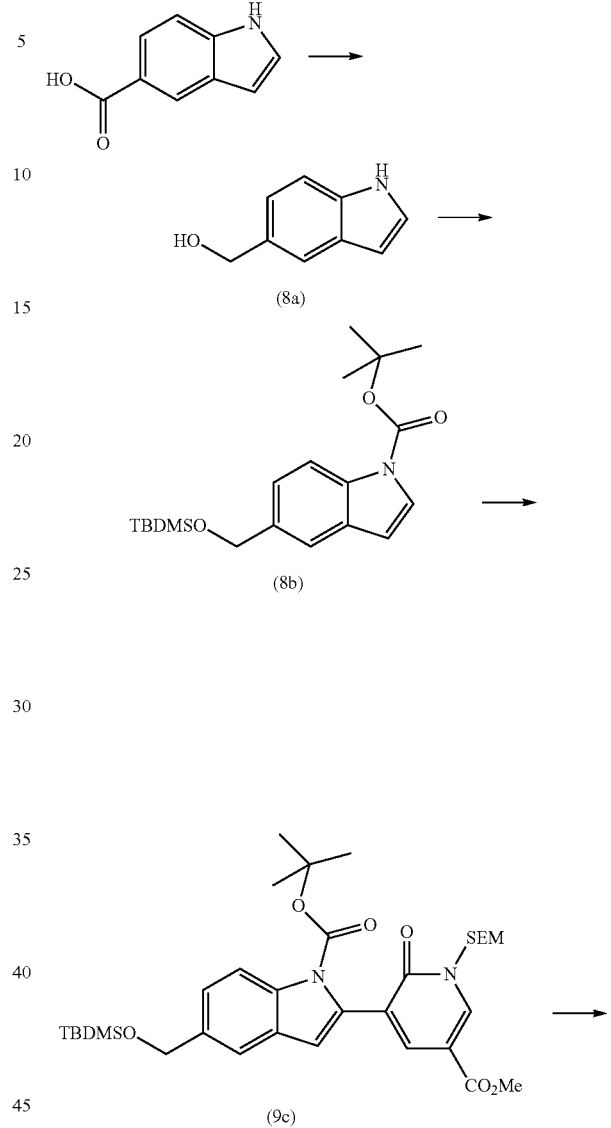
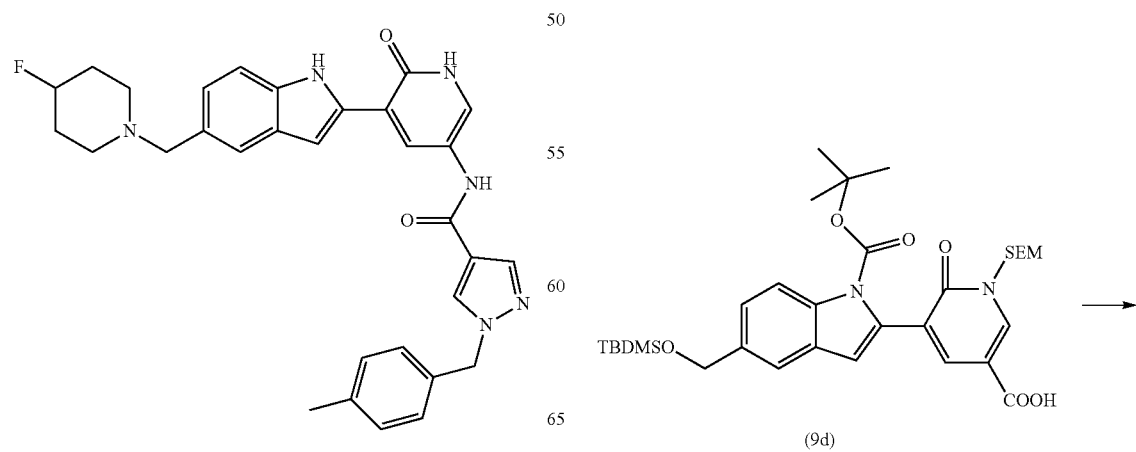

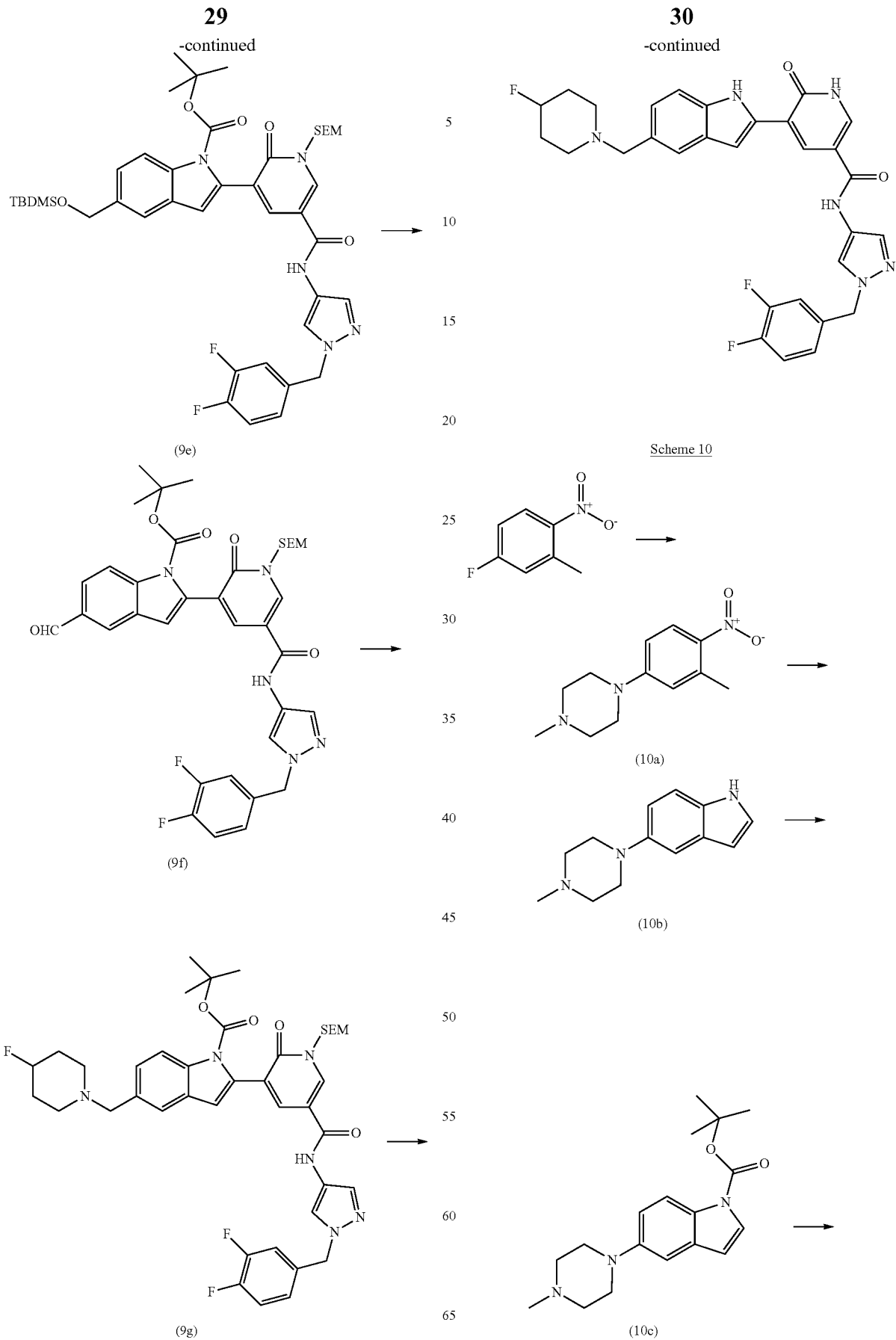

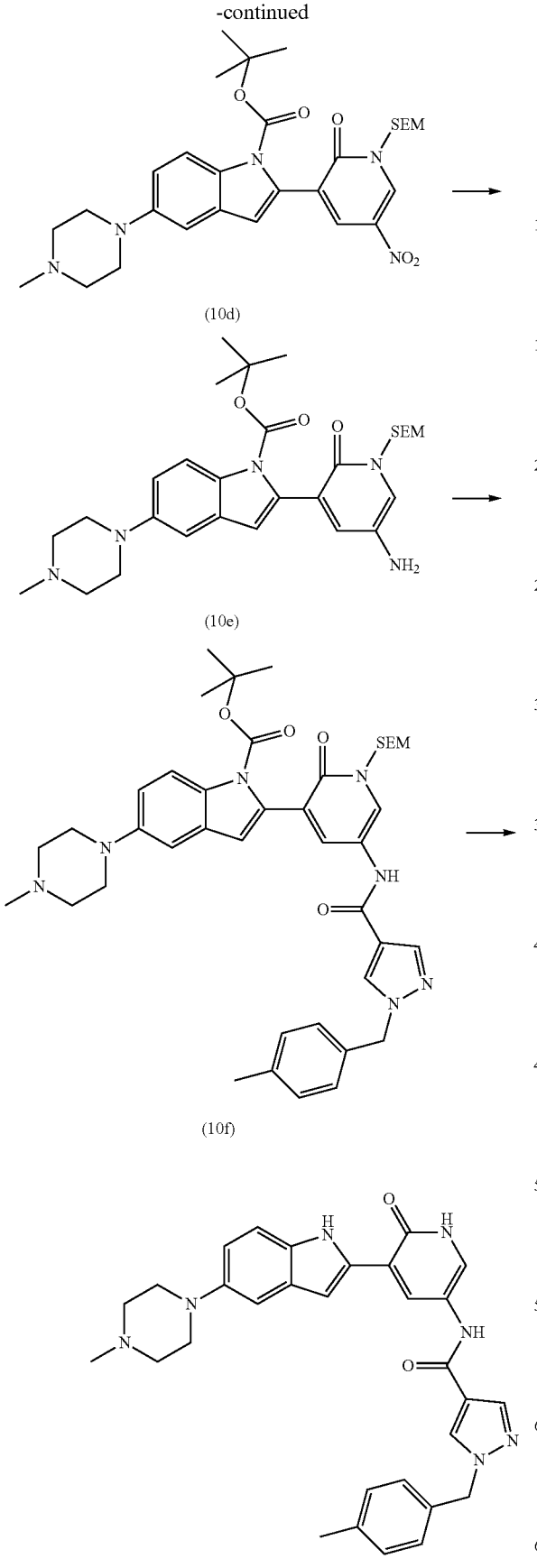

33
-continued

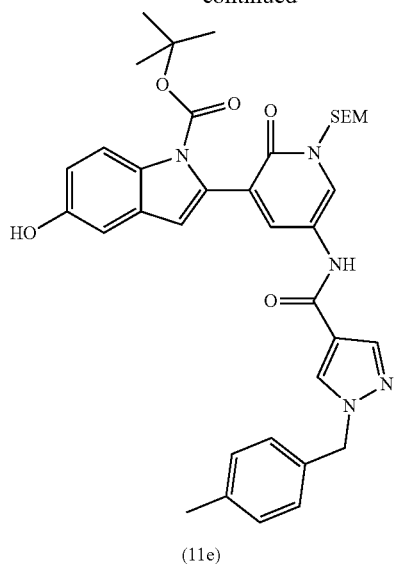

(11e)

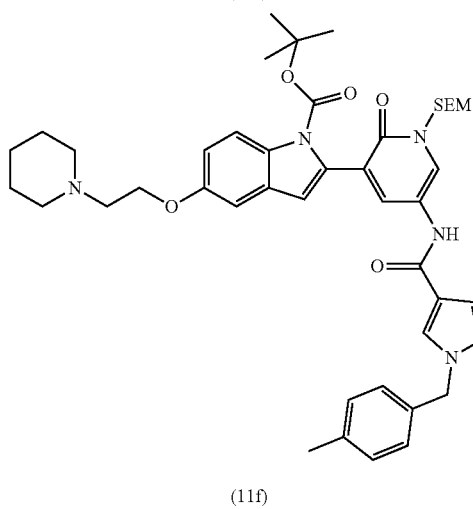

(11f)

EXAMPLES

The following examples illustrate the preparation of specific compounds of the invention and are not intended to be limiting of the full scope of the invention.

34

Example 1

5-(1H-Indol-2-yl)-6-oxo-1,6-dihydro-pyridine-3-carboxylic acid (1-benzyl-1H-pyrazol-4-yl)-amide

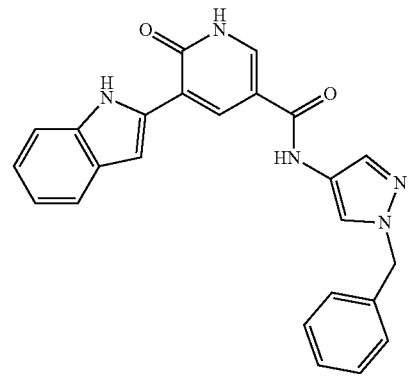 [SMILES: O=C(Nc1cnn(Cc2ccccc2)c1)c1c[nH]c(=O)c(-c2cc3ccccc3[nH]2)c1]

The title compound was prepared according to the route outlined in Scheme 1.

Step 1: Preparation of 5-Iodo-6-(2-trimethylsilanyl-ethoxy)-nicotinic acid methyl ester (1a)

6-Hydroxy-5-iodo-nicotinic acid methyl ester (2.0 g, 7.17 mmol) was stirred in anhydrous 1,2-dimethoxyethane (60 mL) at ambient temperature, with potassium fluoride (4.17 g, 71.7 mmol). 2-(Trimethylsilyl)ethoxymethyl chloride (1.20 g, 1.27 mL, 7.17 mmol) was added drop wise and the reaction stirred at ambient temperature for 3 hours. The reaction mixture was filtered through celite, and the filter cake washed with methanol (2×25 mL). The filtrate and the washings were combined and concentrated in vacuo. The residue was partitioned between water and dichloromethane, and the organic layer was separated. The aqueous was extracted with a further portion of dichloromethane and the combined dichloromethane layers were dried ($Na_2SO_4$) and concentrated in vacuo. The resultant crude product was purified by flash chromatography on $SiO_2$ eluting first with 20% ethyl acetate/hexane and then 66% ethyl acetate/hexane to firstly afford the undesired oxygen substituted compound and then the desired title compound as an off-white solid, 2.28 g, 78%.

Step 2: Preparation of 2-[5-Methoxycarbonyl-2-oxo-1-(2-trimethylsilanyl-ethoxymethyl)-1,2-dihydro-pyridin-3-yl]-indole-1-carboxylic acid tert-butyl ester (1b)

Intermediate (1a), 5-iodo-6-(2-trimethylsilanyl-ethoxy)-nicotinic acid methyl ester (1.14 g, 2.79 mmol), 1-(tert-butoxycarbonyl) indole-2-boronic acid (1.09 g, 4.18 mmol), bis(triphenylphosphine) palladium(II) dichloride (0.1 g, 0.143 mmol), potassium acetate (0.82 g, 8.37 mmol) and anhydrous N,N-dimethylformamide (15 mL) were combined in a 20 mL microwave vial. The contents of the vial were degassed and then were heated at 60° C. for 20 minutes under microwave irradiation. The reaction mixture was concentrated in vacuo. The residue was partitioned between water and dichloromethane, and the organic layer was separated. The aqueous was extracted with a further portion of dichloromethane and the combined dichloromethane layers were dried (Na$_2$SO$_4$) and concentrated in vacuo. The resultant crude product was purified by flash chromatography on SiO$_2$ eluting with 20% ethyl acetate/hexane to afford the desired title compound as an oil 1.39 g, 100%.

Step 3: Preparation of 2-[5-Carboxy-2-oxo-1-(2-trimethylsilanyl-ethoxymethyl)-1,2-dihydro-pyridin-3-yl]-indole-1-carboxylic acid tert-butyl ester (1c)

Intermediate (1b), 2-[5-methoxycarbonyl-2-oxo-1-(2-trimethylsilanyl-ethoxymethyl)-1,2-dihydro-pyridin-3-yl]-indole-1-carboxylic acid tert-butyl ester (2.88 g, 5.78 mmol) was stirred in a mixture of tetrahydrofuran (40 mL) and water (20 mL). Lithium hydroxide (0.469 g, 11.2 mmol) was added and the reaction stirred at reflux for 2 hours. After cooling the reaction mixture was concentrated in vacuo, and the residue was taken up in water and the pH adjusted to 5 with the careful addition of an aqueous 2M hydrochloric acid solution. This aqueous solution was extracted with dichloromethane (×3), and the combined extracts were washed with brine, dried (Na$_2$SO$_4$) and concentrated in vacuo to afford the desired title compound as a yellow solid 2.30 g, 85%.

Step 4: Preparation of 2-[5-(1-Benzyl-1H-pyrazol-4-ylcarbamoyl)-2-oxo-1-(2-trimethylsilanyl-ethoxymethyl)-1,2-dihydro-pyridin-3-yl]-indole-1-carboxylic acid tert-butyl ester (1d)

Intermediate (1c), 2-[5-carboxy-2-oxo-1-(2-trimethylsilanyl-ethoxymethyl)-1,2-dihydro-pyridin-3-yl]-indole-1-carboxylic acid tert-butyl ester (300 mg, 0.62 mmol), N-(3-dimethylaminopropyl)-N'-ethylcarbodiimide hydrochloride (357 mg, 1.86 mmol), 1-hydroxybenzotriazole hydrate (251 mg, 1.86 mmol), N,N-diisopropylethylamine (320 mg, 0.431 mL, 2.48 mmol), 1-benzyl-1H-pyrazol-4-ylamine (322 mg, 1.86 mmol) and tetrahydrofuran (12 mL) were combined in a 20 mL microwave vial. The contents of the vial were heated at 90° C. for 30 minutes under microwave irradiation. The reaction mixture was concentrated in vacuo. The residue was partitioned between water and dichloromethane, and the organic layer was separated. The aqueous was extracted with a further portion of dichloromethane and the combined dichloromethane layers were dried (Na$_2$SO$_4$) and concentrated in vacuo. The resultant crude product was purified by flash chromatography on SiO$_2$ eluting with 20% ethyl acetate/hexane and then 2% methanol/dichloromethane to afford the desired title compound as a solid, 315 mg, 80%.

Step 5: Preparation of Title compound: 5-(1H-Indol-2-yl)-6-oxo-1,6-dihydro-pyridine-3-carboxylic acid (1-benzyl-1H-pyrazol-4-yl)-amide Intermediate (1d), 2-[5-(1-benzyl-1H-pyrazol-4-ylcarbamoyl)-2-oxo-1-(2-trimethylsilanyl-ethoxymethyl)-1,2-dihydro-pyridin-3-yl]-indole-1-carboxylic acid tert-butyl ester (315 mg, 0.492 mmol) was stirred in tetrahydrofuran (15 mL) and 1,2-diaminoethane (89 mg, 98 ul, 1.48 mmol) was added followed by tetrabutylammonium fluoride solution 1.0M in tetrahydrofuran (2.46 mL, 2.46 mmol). The reaction mixture was heated at reflux for 18 hours, and cooled to ambient temperature. The reaction mixture was concentrated in vacuo. The residue was partitioned between water and dichloromethane, and the organic layer was separated. The aqueous was extracted with a further portion of dichloromethane and the combined dichloromethane layers were washed with water (×3) dried (Na$_2$SO$_4$) and concentrated in vacuo. The resultant crude product was purified by flash chromatography on SiO$_2$ eluting with dichloromethane—8% methanol/dichloromethane (gradient) to afford a solid. This solid was triturated with diethyl ether to afford the desired title compound as a yellow solid, 41 mg, 20%.

LC/MS: RT=2.33 Min (270 nm), m/z=410, 411 [M+H]. Total run time 3.75 min (short pos).

$^1$H NMR (d$_6$ DMSO): δ 5.33 (s, 2H), 6.97-7.01 (m, 1H), 7.07-7.11 (m, 1H), 7.24-7.38 (m, 6H), 7.49 (d, 1H), 7.55 (d, 1H), 7.61 (s, 1H), 8.10 (s, 1H), 8.11 (d, 1H), 8.56 (d, 1H), 10.30 (s, 1H), 11.50 (s, 1H), 12.30 (s, 1H).

Example 2

5-(1H-Indol-2-yl)-6-oxo-1,6-dihydro-pyridine-3-carboxylic acid [1-(4-methoxy-benzyl)-1H-pyrazol-4-yl]-amide

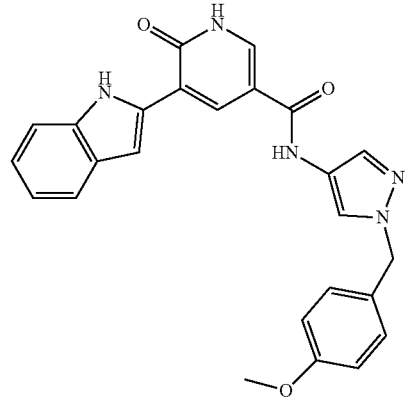 [SMILES: COc1ccc(Cn2cc(NC(=O)c3c[nH]c(=O)c(-c4cc5ccccc5[nH]4)c3)cn2)cc1]

The title compound was prepared according to the route outlined in Scheme 1.

Step1: Preparation of 4-Nitro-1H-pyrazole (1e)

Pyrazole (16 g, 235 mmol) was added in portions to sulfuric acid, 98%, (100 mL) keeping the temperature below 40° C. To this solution was added nitric acid, 70%, (16 mL) maintaining the temperature below 55° C. After addition the reaction was heated at 55° C. for 3 hours, and then cooled to 0° C., before carefully adding to ice/water (400 mL) with stirring. This mixture was neutralized by the careful addition of aqueous 50% sodium hydroxide solution using external cooling and efficient stirring. The resultant solution was extracted with ethyl acetate (3×300 mL), and the combined extracts were washed with brine (2×250 mL) dried (Na$_2$SO$_4$) and concentrated in vacuo to yield a white solid, which was used without further purification, 24.74 g, 93%.

Step 2: Preparation of 1-(4-Methoxy-benzyl)-4-nitro-1H-pyrazole

4-Nitro-1H-pyrazole (565 mg, 5 mmol) was stirred in acetonitrile (15 mL) with potassium carbonate (829 mg, 6 mmol) for 5 minutes and then 4-methoxybenzyl chloride (861 mg, 0.746 mL, 5.5 mmol) was added. The reaction was stirred at ambient temperature for 18 hours, and then partitioned between ethyl acetate and an aqueous 2M hydrochloric acid solution. The organic layer was separated and the aqueous was extracted with a further portion of ethyl acetate. The combined ethyl acetate layers were dried (Na$_2$SO$_4$) and concentrated in vacuo. The resultant crude product was purified by flash chromatography on SiO$_2$ eluting with 20% ethyl acetate/hexane and then 50% ethyl acetate/dichloromethane to afford the desired title compound as an oil, 1.08 g, 93%.

Step 3: Preparation of 1-(4-Methoxy-benzyl)-1H-pyrazol-4-ylamine 1-(4-Methoxy-benzyl)-4-nitro-1H-pyrazole (240 mg, 1.03 mmol) was stirred in ethanol (10 mL) and the flask was evacuated and then flushed with nitrogen. Platinum, sulfided, 5 wt. % on carbon, reduced, dry (10 mg, catalytic amount) was added and after two vacuum/H$_2$ cycles to replace the nitrogen inside with hydrogen, the mixture was shaken for 18 hours under ordinary hydrogen pressure (1 atm). The reaction mixture was filtered and the filtrate was concentrated in vacuo to yield a red oil, which was used without further purification, 168 mg, 81%.

Step 4: Preparation of 2-[5-[1-(4-Methoxy-benzyl)-1H-pyrazol-4-ylcarbamoyl]-2-oxo-1-(2-trimethylsilanyl-ethoxymethyl)-1,2-dihydro-pyridin-3-yl]-indole-1-carboxylic acid tert-butyl ester The title compound was prepared according to the experimental used in Example 1, Step 4 using intermediate (1c) and 1-(4-methoxy-benzyl)-1H-pyrazol-4-ylamine.

After the usual aqueous work up, the resultant crude product was purified by flash chromatography on SiO$_2$ eluting with hexane—50% ethyl acetate/hexane. This afforded the title compound as a pink solid, 180 mg, 50%.

Step 5: Preparation of Title Compound: 5-(1H-Indol-2-yl)-6-oxo-1,6-dihydro-pyridine-3-carboxylic acid [1-(4-methoxy-benzyl)-1H-pyrazol-4-yl]-amide The title compound was prepared according to the experimental used in Example 1, Step 5 with 2-[5-[1-(4-methoxy-benzyl)-1H-pyrazol-4-ylcarbamoyl]-2-oxo-1-(2-trimethylsilanyl-ethoxymethyl)-1,2-dihydro-pyridin-3-yl]-indole-1-carboxylic acid tert-butyl ester.

After the usual aqueous work up the resultant crude product was purified by flash chromatography on SiO$_2$ eluting with 50% ethyl acetate/dichloromethane and then 5% methanol/dichloromethane to afford a solid which was further purified via preparative HPLC at pH 9, to furnish the title compound as a yellow solid, 40 mg, 36%.

LC/MS: RT=2.29 Min (270 nm), m/z=440 [M+H]. Total run time 3.75 min (short pos).

$^1$H NMR (d$_6$ DMSO): δ 3.75 (s, 3H), 5.25 (s, 2H), 6.91-6.95 (m, 2H), 6.98-7.03 (m, 1H), 7.09-7.13 (m, 1H), 7.23-7.28 (m, 3H), 7.51 (d, 1H), 7.56 (d, 1H), 7.6 (d, 1H), 8.06 (s, 1H), 8.12 (d, 1H), 8.57 (d, 1H), 10.3 (s, 1H), 11.51 (br s, 1H), 12.5 (br s, 1H).

Example 3

5-(1H-Indol-2-yl)-6-oxo-1,6-dihydro-pyridine-3-carboxylic acid [1'-(2-methyl-benzyl)-1H-pyrazol-4-yl]-amide

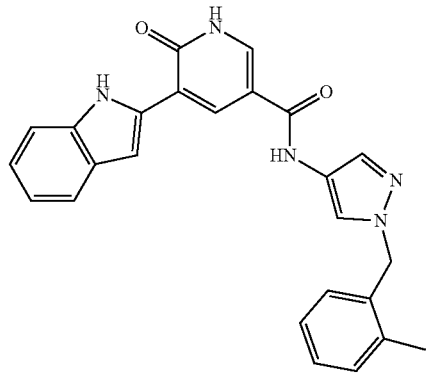 [SMILES: Cc1ccccc1Cn1cc(NC(=O)c2c[nH]c(=O)c(-c3cc4ccccc4[nH]3)c2)cn1]

The title compound was prepared according to the route outlined in Scheme 2.

Step 1: Preparation of 1H-Pyrazol-4-ylamine (2f)

Intermediate (1e), 4-nitro-1H-pyrazole (2.8 g, 24.8 mmol), was stirred in ethanol (200 mL) and the flask was evacuated and then flushed with nitrogen. Palladium, 10 wt. % on activated carbon (300 mg, catalytic amount) was added and after two vacuum/H$_2$ cycles to replace the nitrogen inside with hydrogen, the mixture was shaken for 18 hours under ordinary hydrogen pressure (1 atm). Palladium, 10 wt. % on activated carbon (300 mg) was added and after two vacuum/H$_2$ cycles to replace the nitrogen inside with hydrogen, the mixture was shaken for a further 4 hours. The reaction mixture was filtered through celite and the filter cake was washed through with ethanol (2×50 mL). The combined washings and the filtrate were concentrated in vacuo. The residue obtained was triturated with ethyl acetate to yield a light pink solid, 1.48 g, 72%. The filtrate subsequently obtained was concentrated in vacuo to yield another batch of sufficiently pure material, 0.54 g, 26%, as a dark pink solid.

Step 2: Preparation of 2-[2-Oxo-5-(1H-pyrazol-4-ylcarbamoyl)-1-(2-trimethylsilanyl-ethoxymethyl)-1,2-dihydro-pyridin-3-yl]-indole-1-carboxylic acid tert-butyl ester (2d)

To a solution of intermediate (1c), 2-[5-carboxy-2-oxo-1-(2-trimethylsilanyl-ethoxymethyl)-1,2-dihydro-pyridin-3-yl]-indole-1-carboxylic acid tert-butyl ester, (3 g, 6.2 mmol) in tetrahydrofuran (100 mL) was added intermediate (2f), 1H-pyrazol-4-ylamine (0.62 g, 7.46 mmol), 1-hydroxybenzotriazole hydrate (1.09 g, 8.07 mmol), N,N-diisopropylethylamine (2.4 g, 3.24 mL, 18.6 mmol) and N-(3-dimethylaminopropyl)-N'-ethylcarbodiimide hydrochloride (1.55 g, 8.07 mmol). The reaction mixture was heated at 40° C. for 2 hours. The reaction mixture was cooled and partitioned between ethyl acetate and aqueous saturated sodium hydrogen bicarbonate solution. The ethyl acetate layer was separated and washed with brine, dried (Na$_2$SO$_4$) and concentrated in vacuo. The resultant crude product was purified by flash chromatography on SiO$_2$ eluting with hexane—66% ethyl acetate/hexane (gradient) to afford the desired title compound as a yellow solid, 1.36 g, 40%.

Step 3: 2-[5-[1-(2-Methyl-benzyl)-1H-pyrazol-4-ylcarbamoyl]-2-oxo-1-(2-trimethylsilanyl-ethoxymethyl)-1,2-dihydro-pyridin-3-yl]-indole-1-carboxylic acid tert-butyl ester (2e)

Intermediate (2d), 2-[2-oxo-5-(1H-pyrazol-4-ylcarbamoyl)-1-(2-trimethylsilanyl-ethoxymethyl)-1,2-dihydro-pyridin-3-yl]-indole-1-carboxylic acid tert-butyl ester (50 mg, 0.091 mmol), Cs$_2$CO$_3$ (45 mg, 0.136 mmol) and 2-methyl-benzyl bromide (21 mg, 15 ul, 0.11 mmol) were stirred in N,N-dimethylformamide (5 mL) at ambient temperature for 48 hours. The inorganics were separated via filtration and the filtrate was concentrated in vacuo. The resultant crude product was purified by flash chromatography on SiO$_2$ eluting with hexane—50% ethyl acetate/hexane (gradient) to afford the desired title compound as a solid, 55 mg, 93%.

Step 4: Preparation of Title Compound: 5-(1H-Indol-2-yl)-6-oxo-1,6-dihydro-pyridine-3-carboxylic acid [1-(2-methyl-benzyl)-1H-pyrazol-4-yl]-amide The title compound was prepared according to the experimental used in Example 1, Step 5 with intermediate (2e), 2-[5-[1-(2-methyl-benzyl)-1H-pyrazol-4-ylcarbamoyl]-2-oxo-1-(2-trimethylsilanyl-ethoxymethyl)-1,2-dihydro-pyridin-3-yl]-indole-1-carboxylic acid tert-butyl ester. After the usual aqueous work up, the resultant crude product was purified by trituration with acetonitrile. This afforded the title compound as a yellow solid, 30 mg, 84%.

LC/MS: RT=2.41 Min (270 nm), m/z=424 [M+H]. Total run time 3.75 min (short pos).

$^1$H NMR (d$_6$ DMSO): δ 2.29 (s, 3H), 5.33 (s, 2H), 6.98 (br t, 2H), 7.08 (br t, 1H), 7.17 (m, 4H), 7.29 (s, 1H), 7.47 (d, 1H), 7.54 (d, 1H), 7.69 (br s, 1H), 8.00 (s, 1H), 8.12 (br s, 1H), 8.74 (br m, 1H), 10.50 (br s, 1H), 11.57 (br s, 1H)

Example 4

5-(1H-Indol-2-yl)-6-oxo-1,6-dihydro-pyridine-3-carboxylic acid[1-(3-methyl-benzyl)-1H-pyrazol-4-yl]-amide

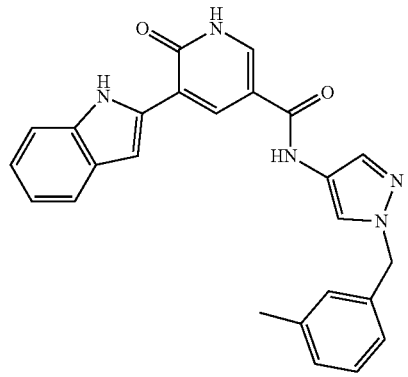 [SMILES: Cc1cccc(Cn2cc(NC(=O)c3c[nH]c(=O)c(-c4cc5ccccc5[nH]4)c3)cn2)c1]

The title compound was prepared by the route outlined in Scheme 2, following the same procedures as for Example 3.

LC/MS: RT=2.41 Min (270 nm), m/z=424 [M+H]. Total run time 3.75 min (short pos).

$^1$H NMR (d$_4$ MeOD): δ 2.30 (s, 3H), 5.28 (s, 2H), 7.05 (m, 5H), 7.15 (s, 1H), 7.22 (t, 1H), 7.42 (d, 1H), 7.54 (t, 1H), 7.68 (s, 1H), 8.07 (m, 2H), 8.61 (d, 1H), NHs not seen.

Example 5

5-(1H-Indol-2-yl)-6-oxo-1,6-dihydro-pyridine-3-carboxylic acid[1-(4-methyl-benzyl)-1H-pyrazol-4-yl]-amide

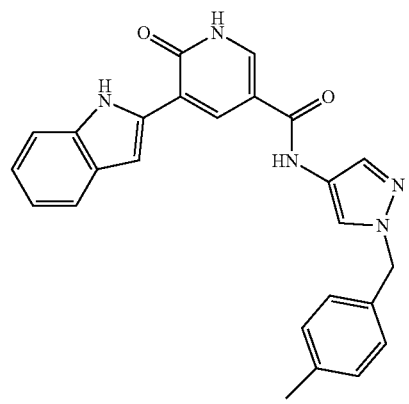 [SMILES: Cc1ccc(Cn2cc(NC(=O)c3c[nH]c(=O)c(-c4cc5ccccc5[nH]4)c3)cn2)cc1]

The title compound was prepared by the route outlined in Scheme 2, following the same procedures as for Example 3.

LC/MS: RT=2.31 Min (270 nm), m/z=424 [M+H]. Total run time 3.75 min (short pos).

$^1$H NMR (d$_6$ DMSO): δ 3.31 (s, 3H), 5.26 (s, 2H), 6.98 (td, 1H), 7.09 (td, 1H), 7.15 (br s, 4H), 7.24 (d, 1H), 7.48 (dd, 1H), 7.54 (d, 1H), 7.58 (d, 1H), 8.05 (s, 1H), 8.01 (br s, 1H), 8.55 (d, 1H) 10.27 (s, 1H), 11.49 (br s, 1H), 12.46 (br s, 1H)

Example 6

5-(1H-Indol-2-yl)-6-oxo-1,6-dihydro-pyridine-3-carboxylic acid [1-(3-cyano-benzyl)-1H-pyrazol-4-yl]-amide

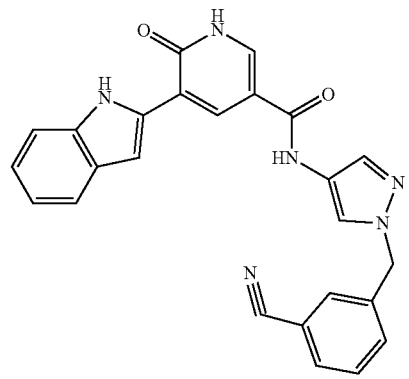 [SMILES: N#Cc1cccc(Cn2cc(NC(=O)c3c[nH]c(=O)c(-c4cc5ccccc5[nH]4)c3)cn2)c1]

The title compound was prepared by the route outlined in Scheme 2, following the same procedures as for Example 3.

LC/MS: RT=2.12 Min (270 nm), m/z=435 [M+H]. Total run time 3.75 min (short pos).

$^1$H NMR (d$_6$ DMSO): δ 5.41 (s, 2H), 6.98 (t, 1H), 7.08 (t, 1H), 7.24 (s, 1H), 7.49 (d, 1H), 7.55 (m, 3H), 7.63 (s, 1H), 7.69 (s, 1H), 7.78 (dt, 1H), 8.11 (d, 1H), 8.19 (s, 1H), 8.55 (d, 1H), 10.35 (s, 1H), 11.52 (s, 1H), 12.42 (br s, 1H)

Example 7

5-(1H-Indol-2-yl)-6-oxo-1,6-dihydro-pyridine-3-carboxylic acid [1-(4-cyano-benzyl)-1H-pyrazol-4-yl]-amide

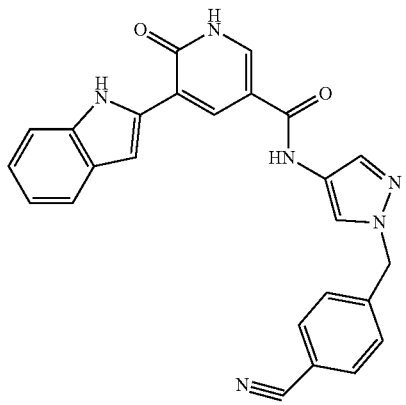 [SMILES: N#Cc1ccc(Cn2cc(NC(=O)c3c[nH]c(=O)c(-c4cc5ccccc5[nH]4)c3)cn2)cc1]

The title compound was prepared by the route outlined in Scheme 2, following the same procedures as for Example 3.

LC/MS: RT=2.15 Min (270 nm), m/z=435 [M+H]. Total run time 3.75 min (short pos).

$^1$H NMR (d$_6$ DMSO): δ 5.41 (s, 2H), 6.99 (t, 1H), 7.09 (t, 1H), 7.25 (s, 1H), 7.36 (d, 2H), 7.49 (d, 1H), 7.54 (d, 1H), 7.64 (s, 1H), 7.83 (d, 2H), 8.12 (br m, 1H), 8.19 (s, 1H), 8.55 (d, 1H), 10.33 (s, 1H), 11.50 (s, 1H), 12.47 (br s, 1H)

Example 8

5-(1H-Indol-2-yl)-6-oxo-1,6-dihydro-pyridine-3-carboxylic acid [1-(2-fluoro-benzyl)-1H-pyrazol-4-yl]-amide

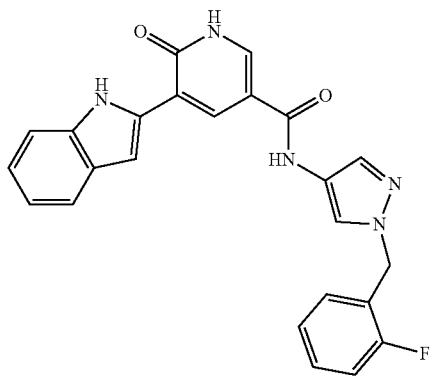 [SMILES: O=C(Nc1cnn(Cc2ccccc2F)c1)c1c[nH]c(=O)c(-c2cc3ccccc3[nH]2)c1]

The title compound was prepared by the route outlined in Scheme 2, following the same procedures as for Example 3.

LC/MS: RT=2.24 Min (270 nm), m/z=428 [M+H]. Total run time 3.75 min (short pos).

$^1$H NMR (d$_6$ DMSO): δ 5.39 (s, 2H), 6.98 (td, 1H), 7.11 (td, 1H), 7.21 (m, 4H), 7.37 (m, 1H), 7.48 (d, 1H), 7.54 (d, 1H), 7.61 (d, 1H), 8.11 (m, 2H), 8.55 (d, 1H), 10.30 (s, 1H), 11.49 (br s, 1H), 12.47 (br s, 1H)

Example 9

5-(1H-Indol-2-yl)-6-oxo-1,6-dihydro-pyridine-3-carboxylic acid [1-(3-fluoro-benzyl)-1H-pyrazol-4-yl]-amide

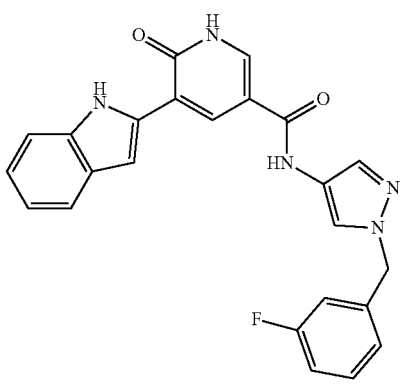 [SMILES: O=C(Nc1cnn(Cc2cccc(F)c2)c1)c1c[nH]c(=O)c(-c2cc3ccccc3[nH]2)c1]

The title compound was prepared by the route outlined in Scheme 2, following the same procedures as for Example 3.

LC/MS: RT=2.24 Min (270 nm), m/z=428 [M+H]. Total run time 3.75 min (short pos).

$^1$H NMR (d$_6$ DMSO): δ 5.35 (s, 2H), 6.98 (t, 1H), 7.04 (m, 5H), 7.24 (br s, 1H), 7.40 (qd, 1H), 7.48 (d, 1H), 7.54 (d, 1H), 7.62 (s, 1H), 8.11 (d, 1H), 8.14 (s, 1H), 8.55 (d, 1H), 10.30 (br s, 1H), 11.53 (brs, 1H)

Example 10

5-(1H-Indol-2-yl)-6-oxo-1,6-dihydro-pyridine-3-carboxylic acid [1-(4-fluoro-benzyl)-1H-pyrazol-4-yl]-amide

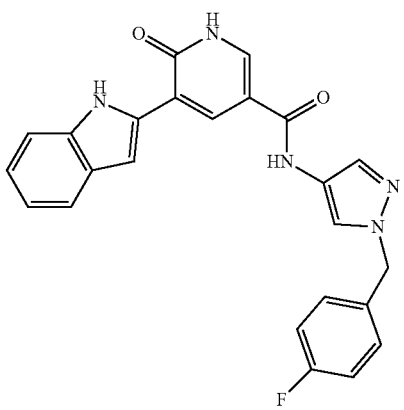 [SMILES: O=C(Nc1cnn(Cc2ccc(F)cc2)c1)c1c[nH]c(=O)c(-c2cc3ccccc3[nH]2)c1]

The title compound was prepared by simple modifications of the protocol described for Example 3, but still using the route outlined in Scheme 2.

The principal modification was for Step 3, and this is described below.

2-[2-Oxo-5-(1H-pyrazol-4-ylcarbamoyl)-1-(2-trimethyl-silanyl-ethoxymethyl)-1,2-dihydro-pyridin-3-yl]-indole-1-carboxylic acid tert-butyl ester, (2d), (100 mg, 0.182 mmol) was stirred in acetone (5 mL) with potassium carbonate (126 mg, 0.91 mmol) and 4-fluorobenzyl bromide (41 mg, 27 ul, 0.218 mmol) was added. The reaction mixture was heated at 50° C. for 8 hours, and then cooled to ambient temperature. The inorganics were separated via filtration, and the filter cake was washed through with ethyl acetate (2×5 mL). The combined washings and the filtrate were concentrated in vacuo, and the residue obtained was purified by flash chromatography on $SiO_2$ eluting with 20% ethyl acetate/hexane to afford the desired compound as an oil, 87 mg, 72%.

The title compound was isolated as a yellow solid.

LC/MS: RT=2.29 Min (270 nm), m/z=428 [M+H]. Total run time 3.75 min (short pos).

$^1$H NMR ($d_6$ DMSO): δ 5.35 (s, 2H), 6.98-7.03 (m, 1H), 7.09-7.14 (m, 1H), 7.18-7.24 (m, 2H), 7.27 (d, 1H), 7.31-7.36 (m, 2H), 7.51 (d, 1H), 7.57 (d, 1H), 7.63 (d, 1H), 8.12-8.15 (m, 2H), 8.58 (d, 1H), 10.34 (s, 1H), 11.54 (brs, 1H), 12.1 (brs, 1H).

Example 11

5-(1H-Indol-2-yl)-6-oxo-1,6-dihydro-pyridine-3-carboxylic acid [1-(3,4-difluoro-benzyl)-1H-pyrazol-4-yl]-amide

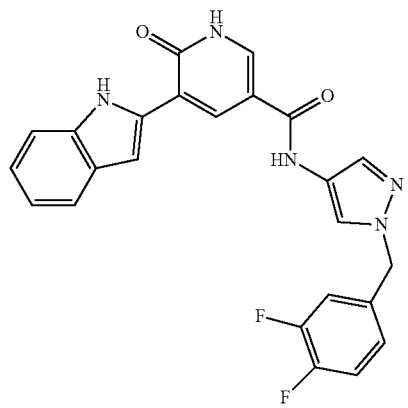 [SMILES: O=C(Nc1cnn(Cc2ccc(F)c(F)c2)c1)c1c[nH]c(=O)c(-c2cc3ccccc3[nH]2)c1]

The title compound was prepared by the route outlined in Scheme 2, following the same procedures as for Example 10.

LC/MS: RT=1.21 Min (270 nm), m/z=446 [M+H]. Total run time 1.9 min (super short pos).

$^1$H NMR ($d_6$ DMSO): δ 5.35 (s, 2H), 7.00 (t, 1H), 7.10 (t, 1H), 7.30 (br s, 1H), 7.35 (m, 1H), 7.45 (q, 1H), 7.55 (d, 1H), 7.60 (d, 1H), 7.70 (s, 1H) 8.15 (d, 1H), 8.20 (s, 1H), 8.60 (d, 1H), 10.35 (s, 1H), NH (×3) not seen.

Example 12

5-(1H-Indol-2-yl)-6-oxo-1,6-dihydro-pyridine-3-carboxylic acid [1-(4-chloro-benzyl)-1H-pyrazol-4-yl]-amide

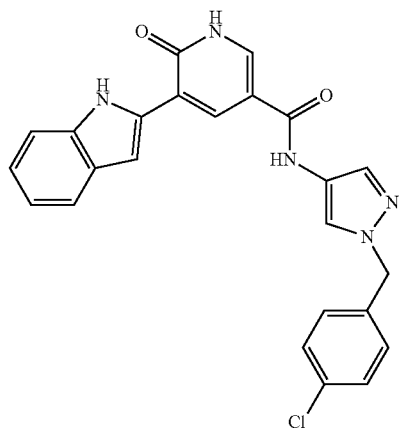 [SMILES: O=C(Nc1cnn(Cc2ccc(Cl)cc2)c1)c1c[nH]c(=O)c(-c2cc3ccccc3[nH]2)c1]

The title compound was prepared by the route outlined in Scheme 2, following the same procedures as for Example 10.

LC/MS: RT=1.24 Min (270 nm), m/z=444 [M+H]. Total run time 1.9 min (super short pos).

$^1$H NMR ($d_6$ DMSO): δ 5.40 (d, 2H), 7.05 (t, 1H), 7.15 (t, 1H), 7.35 (d, 2H), 7.50 (d, 2H), 7.55 (d, 1H), 7.65 (d, 1H), 7.70 (s, 1H) 8.20 (d, 1H), 8.25 (s, 1H), 8.65 (d, 1H), 10.45 (s, 1H), NH (×3) not seen.

Example 13

5-(1H-Indol-2-yl)-6-oxo-1,6-dihydro-pyridine-3-carboxylic acid [1-(3,5-difluoro-benzyl)-1H-pyrazol-4-yl]-amide

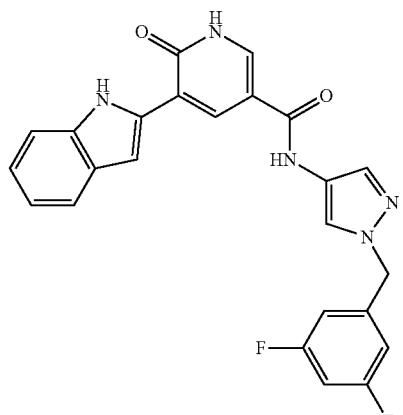

The title compound was prepared by the route outlined in Scheme 2, following the same procedures as for Example 10.

LC/MS: RT=1.22 Min (270 nm), m/z=446 [M+H]. Total run time 1.9 min (super short pos).

$^1$H NMR ($d_6$ DMSO): δ 5.40 (s, 2H), 7.00 (m, 2H), 7.05 (t, 1H), 7.15 (t, 1H), 7.25 (m, 1H), 7.30 (d, 1H), 7.55 (d, 1H), 7.60 (d, 1H), 7.70 (s, 1H) 8.15 (d, 1H), 8.25 (s, 1H), 8.60 (d, 1H), 10.40 (s, 1H), NH (×2) not seen.

Example 14

5-(1H-Indol-2-yl)-6-oxo-1,6-dihydro-pyridine-3-carboxylic acid [1-(3-fluoro-4-methyl-benzyl)-1H-pyrazol-4-yl]-amide

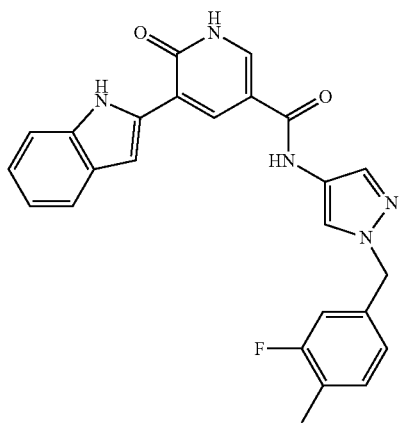 [SMILES: Cc1ccc(Cn2cc(NC(=O)c3c[nH]c(=O)c(-c4cc5ccccc5[nH]4)c3)cn2)cc1F]

The title compound was prepared by the route outlined in Scheme 2, following the same procedures as for Example 10.

LC/MS: RT=1.25 Min (270 nm), m/z=442 [M+H]. Total run time 1.9 min (super short pos).

$^1$H NMR (d$_6$ DMSO): δ □ 2.25 (s, 3H), 5.30 (s, 2H), 7.00 (m, 3H), 7.10 (t, 1H), 7.30 (m, 2H), 7.50 (d, 1H), 7.60 (d, 1H), 7.70 (s, 1H) 8.15 (m, 2H), 8.55 (d, 1H), 10.35 (s, 1H), NHs not seen.

Example 15

5-[5-(4-Methyl-piperazine-1-carbonyl)-1H-indol-2-yl]-6-oxo-1,6-dihydro-pyridine-3-carboxylic acid (1-benzyl-1H-pyrazol-4-yl)-amide

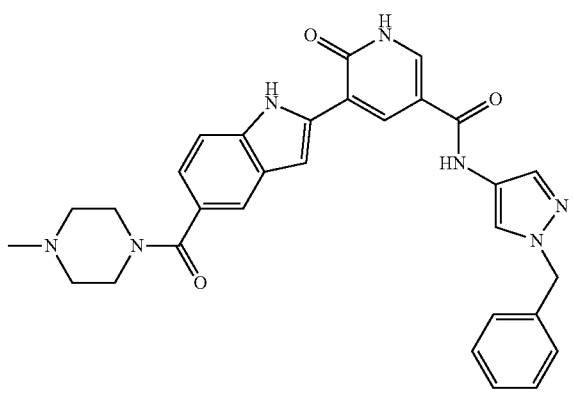 [SMILES: CN1CCN(C(=O)c2ccc3[nH]c(-c4cc(C(=O)Nc5cnn(Cc6ccccc6)c5)c[nH]c4=O)cc3c2)CC1]

The title compound was prepared by the route outlined in Scheme 3.

Step 1: Preparation of 1H-Indole-5-carboxylic acid benzyl ester (3a)

To a solution of indole-5-carboxylic acid (2.63 g, 16.34 mmol) in N,N-dimethylformamide (50 mL) was added sodium bicarbonate (8.24 g, 98.04 mmol) and benzyl bromide (11.66 mL, 98.04 mmol). The reaction was stirred for 48 hours at ambient temperature under nitrogen. The reaction was then partitioned between ethyl acetate and water. The organic layer was separated and the aqueous extracted with a further portion of ethyl acetate. The combined organic layers were dried (MgSO$_4$) and evaporated in vacuo. The resultant crude product was purified by flash chromatography on SiO$_2$, eluting with 20% ethyl acetate/hexane followed by 50% ethyl acetate/hexane to afford the title compound as an oil, 4.82 g, quantitative.

Step 2: Preparation of Indole-1,5-dicarboxylic acid 5-benzyl ester 1-tert-butyl ester (3b)

To a solution of intermediate (3a), 1H-indole-5-carboxylic acid benzyl ester, (4.8 g, 16.34 mmol) in acetonitrile (100 mL) was added di-tert-butyl dicarbonate (3.92 g, 17.97 mmol) and 4-dimethylaminopyridine (0.2 g, 1.63 mmol). The reaction was stirred at ambient temperature under nitrogen for 12 hours. The reaction was concentrated in vacuo and the resultant crude product was purified by flash chromatography on SiO$_2$, eluting with 20% ethyl acetate/hexane to afford the title compound as an off white solid, 5.04 g, 88%.

Step 3: Preparation of Indole-2-boronic acid-1,5-dicarboxylic acid 5-benzyl ester 1-tert-butyl ester (3c)

To a solution of intermediate (3b), indole-1,5-dicarboxylic acid 5-benzyl ester 1-tert-butyl ester, (5.04 g, 14.36 mmol) in tetrahydrofuran (50 mL) at 0° C. was added triisopropyl borate (5 mL, 21.54 mmol). Freshly prepared lithium diisopropylamide solution (18.67 mmol) in tetrahydrofuran (10 mL) was then added drop wise at 0° C. and the reaction was stirred at 0° C. for 2 hours under nitrogen. The pH of the reaction mixture was adjusted to pH 7 by the careful addition of an aqueous 2M hydrochloric acid solution and stirred at ambient temperature for a further 30 minutes. The organics were separated, dried (Na$_2$SO$_4$) and concentrated in vacuo. This afforded the title compound, which was used without further purification, 5.05 g, quantitative.

Step 4: Preparation of 2-[5-Methoxycarbonyl-2-oxo-1-(2-trimethylsilanyl-ethoxymethyl)-1,2-dihydro-pyridin-3-yl]-indole-1,5-dicarboxylic acid 5-benzyl ester 1-tert-butyl ester (3d)

To a solution of intermediate (1a), 5-iodo-6-oxo-1-(2-trimethylsilanyl-ethoxymethyl)-1,6-dihydro-pyridine-3-carboxylic acid ester, (2.94 g, 7.18 mmol) in N,N-dimethylformamide (16 mL) was added intermediate (3c), indole-2-boronic acid-1,5-dicarboxylic acid 5-benzyl ester 1-tert-butyl ester, (5.05 g, 14.36 mmol) and potassium acetate (2.11 g, 21.54 mmol). The reaction mixture was degassed for 10 minutes after which bis(triphenylphosphine)palladium (II) dichloride (0.25 g, 0.359 mmol) was added and the reaction mixture degassed for a further 10 minutes. The reaction mixture was then heated to 60° C. in the microwave for 20 mins. The reaction mixture was concentrated in vacuo, and the residue partitioned between dichloromethane and water. The organic layer was separated and the aqueous extracted with a further portion of dichloromethane. The combined organics were dried (MgSO$_4$) and evaporated in vacuo. The resultant crude product was purified by flash chromatography on SiO$_2$, eluting with 20% ethyl acetate/hexane to afford the title compound as a yellow oil, 2.07 g, 46%.

Step 5: Preparation of 2-[5-Methoxycarbonyl-2-oxo-1-(2-trimethylsilanyl-ethoxymethyl)-1,2-dihydro-pyridin-3-yl]-indole-1,5-dicarboxylic acid 1-tert-butyl ester (3e)

To a degassed solution of intermediate (3d), 2-[5-methoxycarbonyl-2-oxo-1-(2-trimethylsilanyl-ethoxymethyl)-1,2-dihydro-pyridin-3-yl]-indole-1,5-dicarboxylic acid 5-benzyl ester 1-tert-butyl ester, (2.07 g, 3.27 mmol) in methanol (30 mL) was added palladium, 10 wt. % on activated carbon (50 mg) and the reaction further degassed. The reaction was heated to 30° C. for 72 hours under a hydrogen atmosphere. The reaction mixture was then filtered through a celite pad and the pad rinsed with hot methanol (20 mL). The combined filtrate and washings were concentrated in vacuo and poured onto 4×10 g PE-AX columns. The columns were then flushed with methanol and eluted with 20% acetic acid/methanol. The combined organics were concentrated in vacuo. To the residue was added ether and this was concentrated in vacuo. This process was repeated twice more and furnished the desired title compound as a brown solid, 627 mg, 35%.

Step 6: Preparation of 2-[5-Methoxycarbonyl-2-oxo-1-(2-trimethylsilanyl-ethoxymethyl)-1,2-dihydro-pyridin-3-yl]-5-(4-methyl-piperazine-1-carbonyl)-indole-1-carboxylic acid tert-butyl ester (3f)

The title compound was prepared according to the experimental used in Example 3, Step 2 with intermediate (3e), 2-[5-methoxycarbonyl-2-oxo-1-(2-trimethylsilanyl-ethoxymethyl)-1,2-dihydro-pyridin-3-yl]-indole-1,5-dicarboxylic acid 1-tert-butyl ester. After the usual aqueous work up, the crude product was purified by flash chromatography on SiO$_2$, eluting with 6% methanol/dichloromethane to afford the title compound as a yellow gum, 219 mg, 95%.

Step 7: Preparation of 2-[5-Carboxy-2-oxo-1-(2-trimethylsilanyl-ethoxymethyl)-1,2-dihydro-pyridin-3-yl]-5-(4-methyl-piperazine-1-carbonyl)-indole-1-carboxylic acid tert-butyl ester (3g)

The title compound was prepared according to the experimental used in Example 1, Step 3 with intermediate (3f), 2-[5-methoxycarbonyl-2-oxo-1-(2-trimethylsilanyl-ethoxymethyl)-1,2-dihydro-pyridin-3-yl]-5-(4-methyl-piperazine-1-carbonyl)-indole-1-carboxylic acid tert-butyl ester. After the usual work up, the desired title compound was isolated as a yellow solid, 142 mg, 66%.

Step 8: Preparation of 2-[5-(1-Benzyl-1H-pyrazol-4-ylcarbamoyl)-2-oxo-1-(2-trimethylsilanyl-ethoxymethyl)-1,2-dihydro-pyridin-3-yl]-5-(4-methylpiperazine-1-carbonyl)-indole-1-carboxylic acid tert-butyl ester (3h)

The title compound was prepared according to the experimental used in Example 1, Step 4 with intermediate (3g), 2-[5-carboxy-2-oxo-1-(2-trimethylsilanyl-ethoxymethyl)-1,2-dihydro-pyridin-3-yl]-5-(4-methyl-piperazine-1-carbonyl)-indole-1-carboxylic acid tert-butyl ester. After the usual work up, the crude product was purified by flash chromatography on SiO$_2$, eluting with 5% methanol/dichloromethane to afford the title compound as a brown foam, 178 mg, quantitative.

Step 9: Preparation of title compound 5-[5-(4-Methyl-piperazine-1-carbonyl)-1H-indol-2-yl]-6-oxo-1,6-dihydro-pyridine-3-carboxylic acid (1-benzyl-1H-pyrazol-4-yl)-amide The title compound was prepared according to the experimental used in Example 1, Step 5 with intermediate (3h), 2-[5-(1-benzyl-1H-pyrazol-4-ylcarbamoyl)-2-oxo-1-(2-trimethylsilanyl-ethoxymethyl)-1,2-dihydro-pyridin-3-yl]-5-(4-methylpiperazine-1-carbonyl)-indole-1-carboxylic acid tert-butyl ester. After the usual work up the crude product was taken up in methanol (1 mL) and loaded onto a 5 g SCX column. The column was flushed with methanol and then eluted with ammonia solution 7N in methanol. The eluent was concentrated in vacuo and the residue further purified by preparative HPLC at pH 4 to afford the title compound as a brown solid, 13 mg, 10%.

LC/MS RT=1.52 Min (270 nm), m/z=536 [M+H]. Total run time 3.75 min (short pos).

$^1$H NMR (d$_6$ DMSO): δ 2.21 (s, 3H), 2.33 (br m, 4H), 3.53-3.56 (br m, 4H) 0.33 (s, 2H), 7.13 (dd, 1H), 7.31 (m, 6H), 7.53 (d, 1H), 7.61 (s, 2H), 8.10 (s, 1H), 8.14 (d, 1H), 8.58 (d, 1H), 10.31 (s, 1H), 11.72 (s, 1H), 12.5 (s, 1H).

Example 16

6-Oxo-5-(5-piperazin-1-ylmethyl-1H-indol-2-yl)-1,6-dihydro-pyridine-3-carboxylic acid (1-benzyl-1H-pyrazol-4-yl)-amide

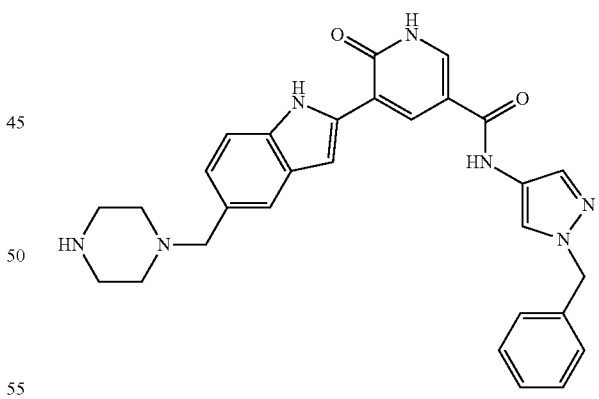

The title compound was prepared by the route outlined in Scheme 4.

Step1: Preparation of Indole-2-boronic acid-5-(4-tert-butoxycarbonyl-piperazin-1-ylmethyl)-indole-1-carboxylic acid tert-butyl ester (4a)

To a stirred solution of indole-5-carboxaldehyde (2 g, 13.8 mmol) in toluene (10 mL) was added 4-dimethylaminopyridine (1 mol %, 10 mg) and di-tert-butyl dicarbonate (3.14 g, 14.5 mmol) and the mixture stirred at ambient temperature for 30 minutes. After this time, tert-butyl piperazine-1-carboxylate (2.56 g, 13.8 mmol) was added followed by sodium triacetoxyborohydride (4.44 g, 20.7 mmol) in portions. After stirring for 90 minutes, a 2.5% v/v solution of acetic acid in water (10 mL) was added, stirred briefly and the organic layer separated. This layer was washed with water (50 mL) and concentrated to near dryness. Methanol (50 mL) was added and the reaction concentrated to dryness. The residue was triturated with toluene and the liquors concentrated to dryness to yield the protected indole. This residue was dissolved in anhydrous tetrahydrofuran (6 mL).

This solution was added via syringe into a nitrogen-purged flask and cooled to 5° C. Triisopropyl borate (4.77 mL, 20.7 mmol) was added, followed by slow addition of lithium diisopropylamide solution 2M in tetrahydrofuran (8.95 mL, 17.9 mmol), ensuring the temperature remained between 0 and 5° C. The mixture was stirred at 5° C. for one hour then quenched by the addition of an aqueous 2M hydrochloric acid solution (2 mL). The pH was adjusted to 7 with aqueous ammonia solution, the ice bath removed and the resultant biphasic mixture stirred at ambient temperature for 30 minutes. The organic layer was separated, dried (MgSO$_4$) and concentrated in vacuo to afford the title compound, 6.34 g, quantitative.

Step 2: Preparation of 5-(4-tert-Butoxycarbonyl-piperazin-1-ylmethyl)-2-[5-methoxycarbonyl-2-oxo-1-(2-trimethylsilanyl-ethoxymethyl)-1,2-dihydro-pyridin-3-yl]-indole-1-carboxylic acid tert-butyl ester (4b)

Intermediate (4a), indole-2-boronic acid-5-(4-tert-butoxycarbonyl-piperazin-1-ylmethyl)-indole-1-carboxylic acid tert-butyl ester (6.34 g, 13.8 mmol), potassium acetate (2.59 g, 26.4 mmol) and intermediate (1a), 5-iodo-6-(2-trimethylsilanyl-ethoxy)-nicotinic acid methyl ester (3.51 g, 8.6 mmol) were dissolved in N,N-dimethylformamide (70 mL). The reaction was degassed three times using alternating cycles of vacuum and dry nitrogen and then bis(triphenylphosphine)palladium(II) dichloride (0.45 g, 0.64 mmol) was added. The mixture was again degassed then heated under a nitrogen atmosphere at 60° C. for one hour. The mixture was cooled, concentrated to dryness and the residue was partitioned between water and ethyl acetate. The organic layer was separated and the aqueous was extracted with a further portion of ethyl acetate. The combined ethyl acetate layers were dried (Na$_2$SO$_4$) and concentrated in vacuo. The resultant crude product was purified by flash chromatography on SiO$_2$ eluting with hexane—20% ethyl acetate/hexane (gradient) to afford the desired title compound as a copper coloured solid, 2.4 g, 40%.

Step 3: Preparation of 5-(4-tert-Butoxycarbonyl-piperazin-1-ylmethyl)-2-[5-carboxy-2-oxo-1-(2-trimethylsilanyl-ethoxymethyl)-1,2-dihydro-pyridin-3-yl]-indole-1-carboxylic acid tert-butyl ester (4c)

The title compound was prepared according to the experimental used in Example 1, Step 3 with intermediate (4b), 5-(4-tert-butoxycarbonyl-piperazin-1-ylmethyl)-2-[5-meth-oxycarbonyl-2-oxo-1-(2-trimethylsilanyl-ethoxymethyl)-1,2-dihydro-pyridin-3-yl]-indole-1-carboxylic acid tert-butyl ester. After the usual work up, the title compound was isolated as a brown foam, 2.35 g, quantitative.

Step 4: Preparation of 2-[5-(1-Benzyl-1H-pyrazol-4-ylcarbamoyl)-2-oxo-1-(2-trimethylsilanyl-ethoxymethyl)-1,2-dihydro-pyridin-3-yl]-5-(4-tert-butoxycarbonyl-piperazin-1-ylmethyl)-indole-1-carboxylic acid tert-butyl ester (4d)

Intermediate (4c), 5-(4-tert-butoxycarbonyl-piperazin-1-ylmethyl)-2-[5-carboxy-2-oxo-1-(2-trimethylsilanyl-ethoxymethyl)-1,2-dihydro-pyridin-3-yl]-indole-1-carboxylic acid tert-butyl ester, (1 g, 1.46 mmol), benzyl-1H-pyrazole-4-yl amine (0.75 g, 4.39 mmol), 1-hydroxybenzotriazole hydrate (0.59 g, 4.39 mmol) and tetrahydrofuran (15 mL) were placed in a microwave vial. To this solution was added N,N-diisopropylethylamine (0.58 g, 0.78 mL, 4.49 mmol) and N-(3-dimethylaminopropyl)-N'-ethylcarbodiimide hydrochloride (0.84 g, 4.39 mmol), the vial capped and heated in the microwave at 90° C. for 30 minutes. After cooling, the mixture was concentrated in vacuo and the residue partitioned between water and dichloromethane. The organic layer was separated and the aqueous was extracted with a further portion of dichloromethane. The combined dichloromethane layers were dried (Na$_2$SO$_4$) and concentrated in vacuo. The resultant crude product was purified by flash chromatography on SiO$_2$ eluting with dichloromethane—15% methanol/dichloromethane (gradient) to afford the desired title compound as a yellow foam, 1.0 g, 82%.

Step 5: Preparation of Title Compound 6-Oxo-5-(5-piperazin-1-ylmethyl-1H-indol-2-yl)-1,6-dihydro-pyridine-3-carboxylic acid (1-benzyl-1H-pyrazol-4-yl)-amide To a solution of intermediate (4d), 2-[5-(1-benzyl-1H-pyrazol-4-ylcarbamoyl)-2-oxo-1-(2-trimethylsilanyl-ethoxymethyl)-1,2-dihydro-pyridin-3-yl]-5-(4-tert-butoxycarbonyl-piperazin-1-ylmethyl)-indole-1-carboxylic acid tert-butyl ester, 120 mg, 0.14 mmol) in methanol (4 mL) was added hydrochloric acid, 37% (0.75 mL). The mixture was heated at 90° C. for 3 hours. The reaction was allowed to attain ambient temperature and the pH adjusted to 7 by the careful addition of ammonia solution 7N in methanol. The mixture was concentrated in vacuo and the resultant crude residue was purified via preparative HPLC at pH 9, to furnish the title compound as a yellow solid, 1.83 mg, 3%.

LC/MS: RT=1.59 Min (270 nm), m/z=508 [M+H]$^+$. Total run time 3.75 min (short pos).

$^1$H NMR (d$_4$ MeOD): δ 2.71 (br t, 4H), 3.18 (t, 4H), 3.70 (s, 2H), 5.32 (s, 2H), 7.13 (m, 2H), 7.29 (m, 5H), 7.41 (d, 1H), 7.50 (br s, 1H), 7.68 (s, 1H), 8.07 (s, 2H), 8.45 (s, 1H), 8.57 (d, 1H), NHs not seen.

Example 17

5-(1H-Indol-2-yl)-2-methyl-6-oxo-1,6-dihydro-pyridine-3-carboxylic acid (1-benzyl-1H-pyrazol-4-yl)-amide

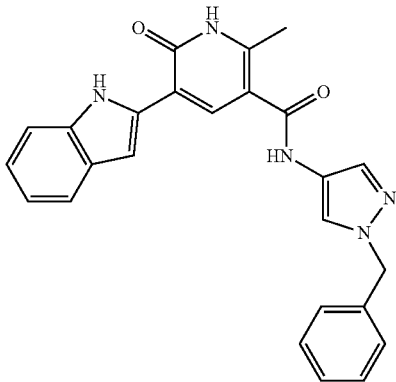 [SMILES: Cc1[nH]c(=O)c(-c2cc3ccccc3[nH]2)cc1C(=O)Nc1cnn(Cc2ccccc2)c1]

The title compound was prepared by the route outlined in Scheme 5.

Step 1: Preparation of (E)-4-[1-Amino-eth-(Z)-ylidene]-pent-2-enedioic acid diethyl ester (5a)

Ethyl propiolate (39.2 g, 41 mL, 400 mmol) was added to ethyl 3-aminocrotonate (51.75 g, 400 mmol) and the mixture heated at 90° C. for 90 minutes to give a dark red oil. The mixture was allowed to cool, to give the product as a dark orange solid, 87.0 g (96%).

Step 2: Preparation of 2-Methyl-6-oxo-1,6-dihydro-pyridine-3-carboxylic acid ethyl ester (5b)

A solution of intermediate (5a), (E)-4-[1-amino-eth-(Z)-ylidene]-pent-2-enedioic acid diethyl ester (51 g, 225 mmol) in N,N-dimethylformamide (250 mL) was heated at 175° C. for 24 hours to give a dark brown solution. The resulting solution was allowed to cool and a pale brown precipitate slowly formed. The precipitate was removed by filtration and the solids washed with dichloromethane (75 mL) and hexane (100 mL) to give a pale yellow powder. The solids were dried in vacuo (60° C.) to give the title compound as a pale yellow powder, 14.45 g (36%)

Step 3: Preparation of 5-Iodo-2-methyl-6-oxo-1,6-dihydro-pyridine-3-carboxylic acid ethyl ester (5c)

N-Iodosuccinimide (40 g, 180 mmol) was added to a suspension of intermediate (5b), 2-methyl-6-oxo-1,6-dihydro-pyridine-3-carboxylic acid ethyl ester (18.1 g, 100 mmol) in acetonitrile (400 mL), under a nitrogen atmosphere. The resulting suspension was heated at 95° C. for 5 hours to give an initial orange solution. An off-white precipitate slowly formed. The resulting suspension was allowed to cool and was poured into water (1200 mL) to give an off-white precipitate. The separated by filtration and the solids washed with water (500 mL) to give an off-white powder. The solids were dried in vacuo (60° C.) to give the product as an off-white powder, 28.3 g (92%)

Step 4: Preparation of 5-Iodo-2-methyl-6-oxo-1-(2-trimethylsilanyl-ethoxymethyl)-1,6-dihydro-pyridine-3-carboxylic acid ethyl ester (5d)

The title compound was prepared according to the experimental used in Example 1, Step 1 using intermediate (5c), 5-iodo-2-methyl-6-oxo-1,6-dihydro-pyridine-3-carboxylic acid ethyl ester. After the usual work up, the resultant crude product was purified by flash chromatography on $SiO_2$ eluting with 20% ethyl acetate/hexane, to give the product as a yellow/green oil, 30.5 g (76%)

Step 5: Preparation of 2-Methyl-5-(1-methyl-1H-indol-2-yl)-6-oxo-1-(2-trimethylsilanyl-ethoxymethyl)-1,6-dihydro-pyridine-3-carboxylic acid ethyl ester. (5e)

A microwave vial (20 mL) was charged with intermediate (5d), 5-iodo-methyl-6-oxo-1-(2-trimethylsilanyl-ethoxymethyl)-1,6-dihydro-pyridine-3-carboxylic acid ethyl ester (0.87 g, 1.99 mmol), potassium carbonate (0.825 g, 5.97 mmol), 1-(tert-butoxycarbonyl) indole-2-boronic acid (0.624 g, 2.39 mmol), [1,1'-Bis(diphenylphosphino)ferrocene)]dichloropalladium(II), complex with dichloromethane (0.082 g, 5 mol %), tetrahydrofuran (14 mL) and water (2.3 mL). The contents of the vial were degassed and then heated at 60° C. for 1 hour under microwave irradiation. After cooling, the reaction mixture was partitioned between brine (50 mL) and ethyl acetate (50 mL). The organic layer was separated, dried ($Na_2SO_4$) and concentrated in vacuo. The resultant crude product was purified by flash chromatography on $SiO_2$ with hexane—15% ethyl acetate/hexane (gradient) to afford the title compound as a yellow foam, 1.02 g, 97%.

Step 6: Preparation of 2-Methyl-5-(1-methyl-1H-indol-2-yl)-6-oxo-1-(2-trimethylsilanyl-ethoxymethyl)-1,6-dihydro-pyridine-3-carboxylic acid (5f)

The title compound was prepared according to the experimental used in Example 1, Step 3 using intermediate (5e), 2-methyl-5-(1-methyl-1H-indol-2-yl)-6-oxo-1-(2-trimethylsilanyl-ethoxymethyl)-1,6-dihydro-pyridine-3-carboxylic acid ethyl ester. After the usual work up, the title compound was isolated as a yellow solid, 419 mg, 92%.

Step 7: Preparation of 2-Methyl-5-(1-methyl-1H-indol-2-yl)-6-oxo-1-(2-trimethylsilanyl-ethoxymethyl)-1,6-dihydro-pyridine-3-carboxylic acid (1-benzyl-1H-pyrazol-4-yl)-amide (5g)

The title compound was prepared according to the experimental used in Example 16, Step 4 with intermediate (5f), 2-methyl-5-(1-methyl-1H-indol-2-yl)-6-oxo-1-(2-trimethylsilanyl-ethoxymethyl)-1,6-dihydro-pyridine-3-carboxylic acid. After the usual work up, the crude product was purified by flash chromatography on $SiO_2$ eluting with hexane—33% ethyl acetate/hexane (gradient) to afford the desired title compound as a yellow solid, 110 mg, 84%.

Step 8: Preparation of the Title Compound: 5-(1H-Indol-2-yl)-2-methyl-6-oxo-1,6-dihydro-pyridine-3-carboxylic acid (1-benzyl-1H-pyrazol-4-yl)-amide The title compound was prepared according to the experimental used in Example 1, Step 5 with intermediate (5g), 2-methyl-5-(1-methyl-1H-indol-2-yl)-6-oxo-1-(2-trimethylsilanyl-ethoxymethyl)-1,6-dihydro-pyridine-3-carboxylic acid (1-benzyl-1H-pyrazol-4-yl)-amide. Purification of the crude product was accomplished using trituration with acetonitrile. The title compound was isolated as a yellow solid, 14 mg, 20%.

LC/MS: RT=2.29 Min (270 nm), m/z=424 [M+H]. Total run time 3.75 min (short pos).

$^1$H NMR (d$_6$ DMSO): δ 2.46 (s, 3H), 5.32 (s, 2H), 6.97 (t, 1H), 7.07 (t, 1H), 7.22-7.38 (m, 6H), 7.47 (d, 1H), 7.52 (d, 1H), 7.57 (s, 1H), 8.10 (s, 1H), 8.26 (s, 1H), 10.31 (s, 1H), 11.39 (s, 1H), 12.28 (br s, 1H).

Example 18

5-(1H-Indol-2-yl)-2-methyl-6-oxo-1,6-dihydro-pyridine-3-carboxylic acid [1-(3-fluoro-benzyl)-1H-pyrazol-4-yl]-amide

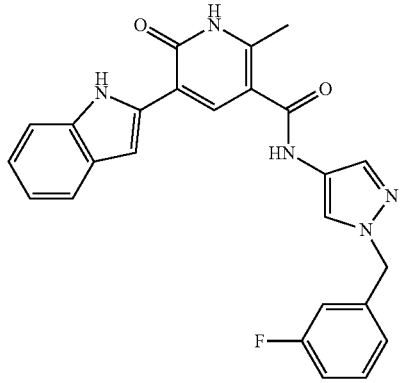 [SMILES: Cc1[nH]c(=O)c(-c2cc3ccccc3[nH]2)cc1C(=O)Nc1cnn(Cc2cccc(F)c2)c1]

The title compound was prepared by the route outlined in Scheme 5, following the same procedures as for Example 17.

LC/MS: RT=2.28 Min (270 nm), m/z=442 [M+H]. Total run time 3.75 min (short pos).

$^1$H NMR (d$_6$ DMSO): δ 2.47 (s, 3H), 5.35 (s, 2H), 6.97-7.16 (m, 5H), 7.21 (s, 1H), 7.40 (m, 1H), 7.47 (d, 1H), 7.52 (d, 1H), 7.59 (s, 1H), 8.16 (s, 1H), 8.27 (s, 1H), 10.33 (s, 1H), 11.39 (s, 1H), 12.28 (br s, 1H).

Example 19

5-(1H-Indol-2-yl)-2-methyl-6-oxo-1,6-dihydro-pyridine-3-carboxylic acid [1-(3,4-difluoro-benzyl)-1H-pyrazol-4-yl]-amide

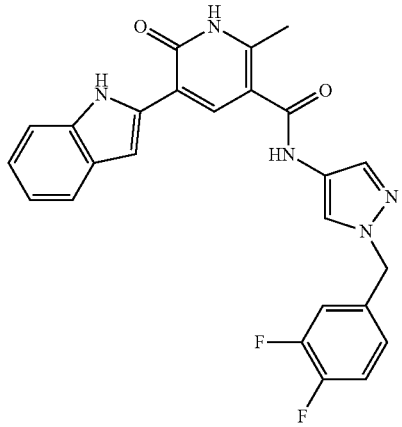 [SMILES: Cc1[nH]c(=O)c(-c2cc3ccccc3[nH]2)cc1C(=O)Nc1cnn(Cc2ccc(F)c(F)c2)c1]

The title compound was prepared by the route outlined in Scheme 5, following the same procedures as for Example 17.

LC/MS: RT=2.32 Min (270 nm), m/z=460 [M+H]. Total run time 3.75 min (short pos).

$^1$H NMR (d$_6$ DMSO): δ 2.47 (s, 3H), 5.32 (s, 2H), 6.98-7.59 (m, 9H), 8.17 (s, 1H), 8.26 (s, 1H), 10.33 (s, 1H), 11.39 (s, 1H), 12.28 (br s, 1H).

Example 20

1-Benzyl-1H-pyrazole-4-carboxylic acid [5-(1H-indol-2-yl)-6-oxo-1,6-dihydro-pyridin-3-yl]-amide

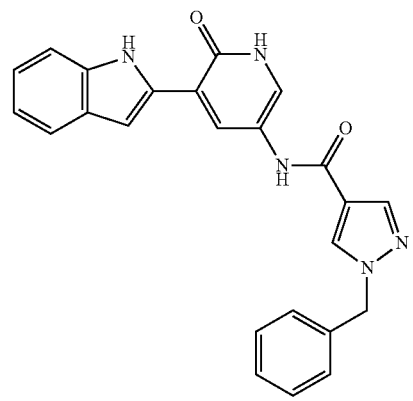 [SMILES: O=C(Nc1c[nH]c(=O)c(-c2cc3ccccc3[nH]2)c1)c1cnn(Cc2ccccc2)c1]

The title compound was prepared by the route outlined in Scheme 6.

Step 1: Preparation of 3-Iodo-5-nitro-1-(2-trimethylsilanyl-ethoxymethyl)-1H-pyridin-2-one (6a)

The title compound was prepared according to the experimental used in Example 1, Step 1 using 2-hydroxy-3-iodo-5-nitro pyridine. After the usual work up, the resultant crude product was purified by flash chromatography on SiO$_2$ eluting first with hexane and then 20% ethyl acetate/hexane to firstly afford the undesired oxygen substituted compound and then the desired title compound as a yellow oil, 4.36 g, 59%.

Step 2: Preparation of 2-[5-Nitro-2-oxo-1-(2-trimethylsilanyl-ethoxymethyl)-1,2-dihydro-pyridin-3-yl]-indole-1-carboxylic acid tert-butyl ester (6b)

The title compound was prepared according to the experimental used in Example 17, Step 5 using intermediate (6a), 3-iodo-5-nitro-1-(2-trimethylsilanyl-ethoxymethyl)-1H-pyridin-2-one. After the usual work up, the crude product was purified by flash chromatography on SiO$_2$ eluting with hexane—20% ethyl acetate/hexane (gradient) to afford the desired title compound as an oil 0.523 g, 64%.

Step 3: Preparation of 2-[5-Amino-2-oxo-1-(2-trimethylsilanyl-ethoxymethyl)-1,2-dihydro-pyridin-3-yl]-indole-1-carboxylic acid tert-butyl ester (6c)

A round bottom flask was charged with intermediate (6b), 2-[5-nitro-2-oxo-1-(2-trimethylsilanyl-ethoxymethyl)-1,2-dihydro-pyridin-3-yl]-indole-1-carboxylic acid tert-butyl ester (0.485 g, 1 mmol), tetrahydrofuran (5 mL) and palladium acetate (11 mg, 5 mol %). The flask was sealed and purged with nitrogen. While purging the flask with nitrogen, a solution of potassium fluoride (116 mg, 2 mmol) in water (2 mL), which had been thoroughly degassed, was added via syringe. The nitrogen inlet was removed and replaced with a balloon of nitrogen. Poly(methylhydrosiloxane) (0.44 mL) was added drop wise and the reaction was stirred at ambient temperature for 18 hours. The reaction mixture was diluted with dichloromethane (20 mL) and aqueous saturated sodium bicarbonate solution (20 mL). The organic layer was separated, filtered through a bed of celite and concentrated in vacuo. The resultant crude product was purified by flash chromatography on SiO$_2$ eluting with hexane—50% ethyl acetate/hexane (gradient) to afford the desired title compound as a brown solid 0.308 g, 67%.

Step 4: Preparation of 2-[5-[(1-Benzyl-1H-pyrazole-4-carbonyl)-amino]-2-oxo-1-(2-trimethylsilanyl-ethoxymethyl)-1,2-dihydro-pyridin-3-yl]-indole-1-carboxylic acid tert-butyl ester (6d)

To a solution of (6c), 2-[5-amino-2-oxo-1-(2-trimethylsilanyl-ethoxymethyl)-1,2-dihydro-pyridin-3-yl]-indole-1-carboxylic acid tert-butyl ester (0.3 g, 0.659 mmol) in acetonitrile (10 mL) was added 1-benzyl-1H-pyrazole-4-carboxylic acid (0.111 g, 0.549 mmol) and triethylamine (0.133 g, 0.184 mL, 1.32 mmol). O-benzotriazole-N,N,N',N'-tetramethyluroniumhexafluorophosphate (0.312 g, 0.823 mmol) was added last and the reaction mixture was stirred at ambient temperature for 18 hours. The reaction mixture was concentrated in vacuo and the residue was partitioned between ethyl acetate (25 mL) and aqueous saturated sodium hydrogen carbonate solution (20 mL). The organic layer was separated and the aqueous was extracted with a further portion of ethyl acetate (25 mL). The combined ethyl acetate layers were washed with brine, dried (Na$_2$SO$_4$) and concentrated in vacuo. The resultant crude product was purified by flash chromatography on SiO$_2$ eluting with hexane—35% ethyl acetate/hexane—50% ethyl acetate/hexane (gradient) to afford the desired title compound as a light brown solid, 0.246 g, 70%.

Step 5: Preparation of the Title Compound: 1-Benzyl-1H-pyrazole-4-carboxylic acid [5-(1H-indol-2-yl)-6-oxo-1,6-dihydro-pyridin-3-yl]-amide The title compound was prepared according to the experimental used in Example 1, Step 5 with intermediate (6d), 2-[5-[(1-benzyl-1H-pyrazole-4-carbonyl)-amino]-2-oxo-1-(2-trimethylsilanyl-ethoxymethyl)-1,2-dihydro-pyridin-3-yl]-indole-1-carboxylic acid tert-butyl ester.

The resultant crude product was purified by trituration with acetonitrile, to afford the title compound as a yellow solid, 64 mg, 42%.

LC/MS: RT=2.16 Min (270 nm), m/z=410 [M+H]. Total run time 3.75 min (short pos).

$^1$H NMR (d$_6$ DMSO): δ 5.41 (s, 2H), 6.99 (t, 1H), 7.06-7.10 (m, 2H), 7.29-7.41 (m, 5H), 7.52 (t, 2H), 7.81 (d, 1H), 8.03 (s, 1H), 8.18 (d, 1H), 8.40 (s, 1H), 9.77 (s, 1H), 11.54 (s, 1H), 11.98 (br s, 1H).

Example 21

1-(4-Fluoro-benzyl)-1H-pyrazole-4-carboxylic acid [5-(1H-indol-2-yl)-6-oxo-1,6-dihydro-pyridin-3-yl]-amide

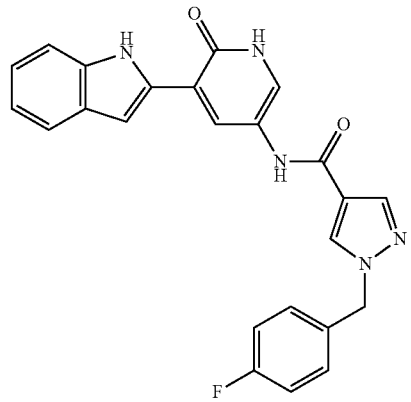 [SMILES: O=C(Nc1c[nH]c(=O)c(-c2cc3ccccc3[nH]2)c1)c1cnn(Cc2ccc(F)cc2)c1]

The title compound was prepared by the route outlined in Scheme 6, following the same procedures as for Example 20, but using intermediate (6e) in Step 4.

Preparation of 1-(4-Fluoro-benzyl)-1H-pyrazole-4-carboxylic acid (6e).

1H-Pyrazole-4-carboxylic acid ethyl ester (1 g, 7.14 mmol) was stirred in acetone (15 mL) with potassium carbonate (4.93 g, 35.7 mmol) and 4-fluorobenzyl bromide (1.62 g, 0.746 mL, 8.56 mmol) was added. The reaction was heated at 50° C. for 4 hours. The reaction was cooled and the inorganics were separated via filtration. The filter cake was washed through with ethyl acetate (2×10 mL) and the combined washings and filtrate were concentrated in vacuo.

The residue was refluxed in methanol (10 mL) containing potassium hydroxide (0.8 g, 14.28 mmol), for 18 hours. The reaction was cooled and concentrated in vacuo. The residue was dissolved in H$_2$O and washed with dichloromethane. The aqueous layer was separated and carefully acidified using an aqueous 6N hydrochloric acid solution. The resulting precipitate was filtered, washed with copious amounts of water and dried in vacuo to afford the title compound, 1.05 g, 67%.

The title compound, Example 21, was purified by trituration with acetonitrile, and isolated as a green solid, 80 mg, 51%.

LC/MS: RT=1.14 Min (270 nm), m/z=428 [M+H]. Total run time 1.9 min (super short pos).

$^1$H NMR (d$_6$ DMSO): δ 5.44 (s, 2H), 6.96-7.01 (m, 1H), 7.05-7.20 (m, 5H), 7.40-7.47 (m, 1H), 7.49-7.55 (m, 2H), 7.80-7.84 (m, 1H), 8.06 (s, 1H), 8.18 (d, 1H), 8.44 (s, 1H), 9.80 (s, 1H), 11.56 (br s, 1H), 12.01 (br s, 1H).

Example 22

1-(3-Fluoro-benzyl)-1H-pyrazole-4-carboxylic acid [5-(1H-indol-2-yl)-6-oxo-1,6-dihydro-pyridin-3-yl]-amide

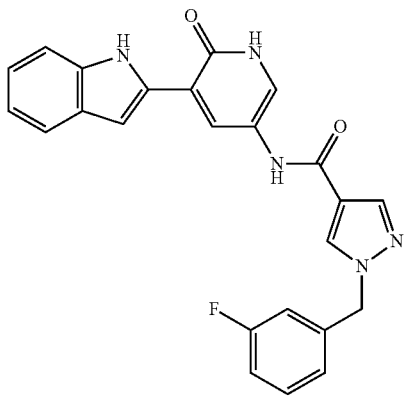 [SMILES: O=C(Nc1c[nH]c(=O)c(-c2cc3ccccc3[nH]2)c1)c1cnn(Cc2cccc(F)c2)c1]

The title compound was prepared by the route outlined in Scheme 6, following the same experimental procedures as for Examples 20 and 21.

LC/MS: RT=1.14 Min (270 nm), m/z=428 [M+H]. Total run time 1.9 min (super short pos).

$^1$H NMR (d$_6$ DMSO): δ 5.44 (s, 2H), 6.96-7.01 (m, 1H), 7.05-7.22 (m, 5H), 7.40-7.47 (m, 1H), 7.50-7.55 (m, 2H), 7.82 (m, 1H), 8.06 (s, 1H), 8.19 (d, 1H), 8.45 (s, 1H), 9.81 (s, 1H), 11.56 (br s, 1H), 12.02 (br s, 1H).

Example 23

1-(3-Trifluoromethyl-benzyl)-1H-pyrazole-4-carboxylic acid [5-(1H-indol-2-yl)-6-oxo-1,6-dihydro-pyridin-3-yl]-amide

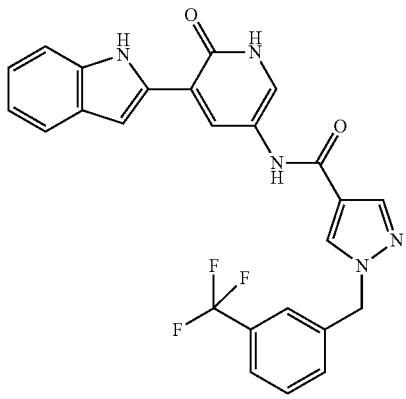 [SMILES: O=C(Nc1c[nH]c(=O)c(-c2cc3ccccc3[nH]2)c1)c1cnn(Cc2cccc(C(F)(F)F)c2)c1]

The title compound was prepared by the route outlined in Scheme 6, following the same experimental procedures as for Examples 20 and 21.

LC/MS: RT=1.21 Min (270 nm), m/z=478 [M+H]. Total run time 1.9 min (super short pos).

$^1$H NMR (d$_6$ DMSO): δ 5.53 (s, 2H), 6.96-7.01 (m, 1H), 7.05-7.10 (m, 2H), 7.49-7.72 (m, 6H), 7.80-7.84 (m, 1H), 8.07 (s, 1H), 8.18 (d, 1H), 8.48 (s, 1H), 9.80 (s, 1H), 11.56 (br s, 1H), 12.02 (br s, 1H).

Example 24

1-(3,4-Difluoro-benzyl)-1H-pyrazole-4-carboxylic acid [5-(1H-indol-2-yl)-6-oxo-1,6-dihydro-pyridin-3-yl]-amide

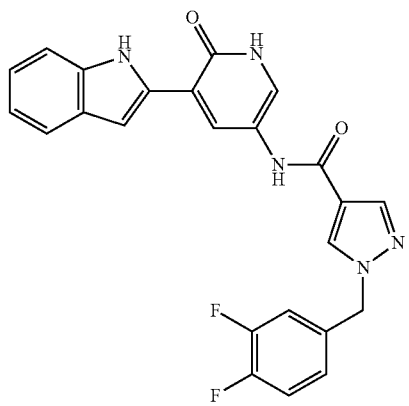 [SMILES: O=C(Nc1c[nH]c(=O)c(-c2cc3ccccc3[nH]2)c1)c1cnn(Cc2ccc(F)c(F)c2)c1]

The title compound was prepared by the route outlined in Scheme 6, following the same experimental procedures as for Examples 20 and 21.

LC/MS: RT=1.16 Min (270 nm), m/z=446 [M+H]. Total run time 1.9 min (super short pos).

$^1$H NMR (d$_6$ DMSO): δ 5.41 (s, 2H), 6.96-7.01 (m, 1H), 7.05-7.10 (m, 2H), 7.12-7.18 (m, 1H), 7.37-7.55 (m, 4H), 7.81 (d, 1H), 8.05 (s, 1H), 8.19 (d, 1H), 8.44 (s, 1H), 9.80 (s, 1H), 11.56 (br s, 1H), 12.01 (br s, 1H).

Example 25

1-(4-Trifluoromethyl-benzyl)-1H-pyrazole-4-carboxylic acid [5-(1H-indol-2-yl)-6-oxo-1,6-dihydro-pyridin-3-yl]-amide

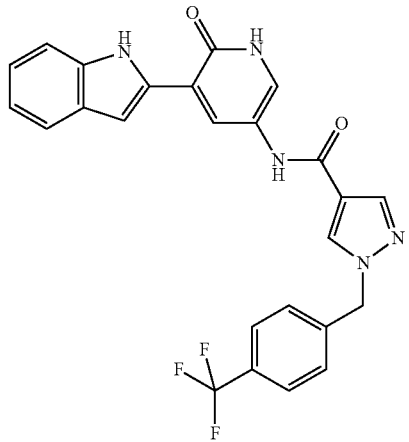 [SMILES: O=C(Nc1c[nH]c(=O)c(-c2cc3ccccc3[nH]2)c1)c1cnn(Cc2ccc(C(F)(F)F)cc2)c1]

The title compound was prepared by the route outlined in Scheme 6, following the same experimental procedures as for Examples 20 and 21.

LC/MS: RT=1.21 Min (270 nm), m/z=478 [M+H]. Total run time 1.9 min (super short pos).

$^1$H NMR (d$_6$ DMSO): δ 5.54 (s, 2H), 6.95-7.01 (m, 1H), 7.05-7.10 (m, 2H), 7.44-7.56 (m, 4H), 7.76 (d, 2H), 8.08 (s,

1H), 8.19 (d, 1H), 8.48 (s, 1H), 9.82 (s, 1H), 11.56 (br s, 1H), 11.91 (br s, 1H), NH not seen.

Example 26

1-(3-Methyl-benzyl)-1H-pyrazole-4-carboxylic acid [5-(1H-indol-2-yl)-6-oxo-1,6-dihydro-pyridin-3-yl]-amide

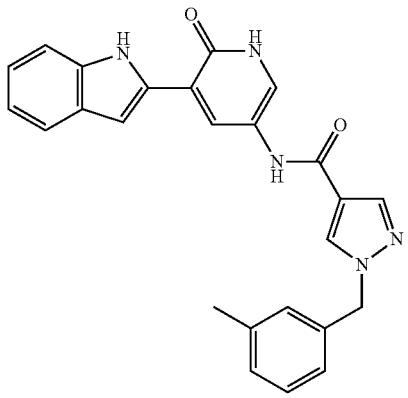 [SMILES: Cc1cccc(Cn2cc(C(=O)Nc3c[nH]c(=O)c(-c4cc5ccccc5[nH]4)c3)cn2)c1]

The title compound was prepared by the route outlined in Scheme 6, following the same experimental procedures as for Examples 20 and 21.

LC/MS: RT=2.29 Min (270 nm), m/z=424 [M+H]. Total run time 3.75 min (short pos).

$^1$H NMR (d$_6$ DMSO): δ 2.30 (s, 3H), 5.36 (s, 2H), 6.95-7.01 (m, 1H), 7.04-7.17 (m, 5H), 7.24-7.29 (m, 1H), 7.48-7.56 (m, 2H), 7.81 (s, 1H), 8.04 (s, 1H), 8.18 (d, 1H), 8.39 (s, 1H), 9.78 (s, 1H), 11.55 (br s, 1H), 12.01 (br s, 1H).

Example 27

1-(3-Chloro-benzyl)-1H-pyrazole-4-carboxylic acid [5-(1H-indol-2-yl)-6-oxo-1,6-dihydro-pyridin-3-yl]-amide

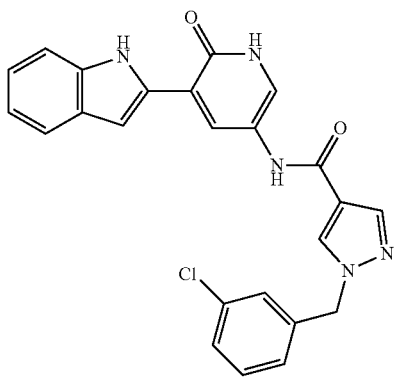 [SMILES: O=C(Nc1c[nH]c(=O)c(-c2cc3ccccc3[nH]2)c1)c1cnn(Cc2cccc(Cl)c2)c1]

The title compound was prepared by the route outlined in Scheme 6, following the same experimental procedures as for Examples 20 and 21.

LC/MS: RT=2.31 Min (270 nm), m/z=444, 446 [M+H]. Total run time 3.75 min (short pos).

$^1$H NMR (d$_6$ DMSO): δ 5.43 (s, 2H), 6.95-7.11 (m, 3H), 7.22-7.28 (m, 1H), 7.34-7.57 (m, 5H), 7.81 (d, 1H), 8.06 (s, 1H), 8.19 (d, 1H), 8.45 (s, 1H), 9.81 (s, 1H), 11.56 (br s, 1H), 12.02 (br s, 1H).

Example 28

1-(4-Chloro-benzyl)-1H-pyrazole-4-carboxylic acid [5-(1H-indol-2-yl)-6-oxo-1,6-dihydro-pyridin-3-yl]-amide

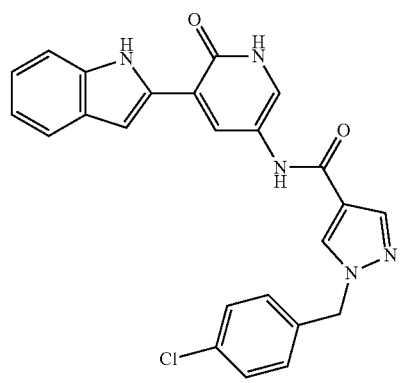

The title compound was prepared by the route outlined in Scheme 6, following the same experimental procedures as for Examples 20 and 21.

LC/MS: RT=2.31 Min (270 nm), m/z=444, 446 [M+H]. Total run time 3.75 min (short pos).

$^1$H NMR (d$_6$ DMSO): δ 5.41 (s, 2H), 6.96-7.11 (m, 3H), 7.29-7.34 (m, 2H), 7.43-7.56 (m, 4H), 7.81 (d, 1H), 8.05 (s, 1H), 8.18 (d, 1H), 8.42 (s, 1H), 9.80 (s, 1H), 11.56 (br s, 1H), 12.02 (br s, 1H).

Example 29

1-(4-Methyl-benzyl)-1H-pyrazole-4-carboxylic acid [5-(1H-indol-2-yl)-6-oxo-1,6-dihydro-pyridin-3-yl]-amide

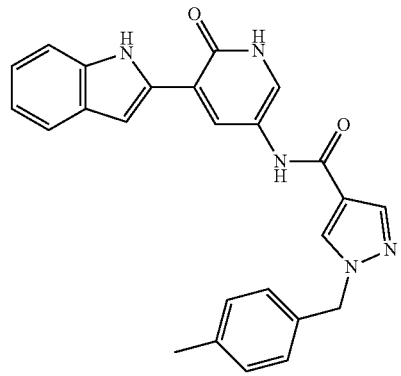 [SMILES: Cc1ccc(Cn2cc(C(=O)Nc3c[nH]c(=O)c(-c4cc5ccccc5[nH]4)c3)cn2)cc1]

The title compound was prepared by the route outlined in Scheme 6, following the same experimental procedures as for Examples 20 and 21.

LC/MS: RT=2.28 Min (270 nm), m/z=424 [M+H]. Total run time 3.75 min (short pos).

¹H NMR (d₆ DMSO): δ 2.29 (s, 3H), 5.35 (s, 2H), 6.94-7.11 (m, 3H), 7.19 (m, 4H), 7.48-7.56 (m, 2H), 7.81 (d, 1H), 8.02 (s, 1H), 8.18 (d, 1H), 8.37 (s, 1H), 9.77 (s, 1H), 11.56 (br s, 1H), 12.01 (br s, 1H).

Example 30

1-(3-Fluoro-benzyl)-1H-pyrazole-4-carboxylic acid [5-(1H-indol-2-yl)-2-methyl-6-oxo-1,6-dihydro-pyridin-3-yl]-amide

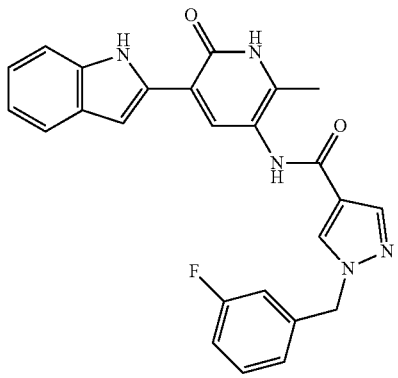 [SMILES: Cc1[nH]c(=O)c(-c2cc3ccccc3[nH]2)cc1NC(=O)c1cnn(Cc2cccc(F)c2)c1]

The title compound was prepared by the route outlined in Scheme 7.

Step 1: Preparation of 3-Iodo-6-methyl-5-nitro-1H-pyridin-2-one (7a)

The title compound was prepared according to the experimental used in Example 17, Step 3 using 2-hydroxy-6-methyl-5-nitropyridine. The usual work up afforded the title compound as a pale yellow solid, 4.95 g, 81%.

Step 2: Preparation of 3-Iodo-6-methyl-5-nitro-1-(2-trimethylsilanyl-ethoxymethyl)-1H-pyridin-2-one (7b)

The title compound was prepared according to the experimental used in Example 1, Step 1, using intermediate (7a), 3-iodo-6-methyl-5-nitro-1H-pyridin-2-one. After the usual work up, the crude product was purified by flash chromatography on SiO₂ eluting first with hexane and then 10% ethyl acetate/hexane to firstly afford the undesired oxygen substituted compound and then the desired title compound as a yellow oil, 3.6 g, 42%.

Step 3: Preparation of 2-[6-Methyl-5-nitro-2-oxo-1-(2-trimethylsilanyl-ethoxymethyl)-1,2-dihydro-pyridin-3-yl]-indole-1-carboxylic acid tert-butyl ester (7c)

The title compound was prepared according to the experimental used in Example 17, Step 5, with intermediate 7(b), 3-iodo-6-methyl-5-nitro-1-(2-trimethylsilanyl-ethoxymethyl)-1H-pyridin-2-one. After the usual work up, the crude product was purified by flash chromatography on SiO₂ with hexane—10% ethyl acetate/hexane (gradient) to afford the title compound as a cream coloured solid, 3.46 g, 72%.

Step 4: Preparation of 2-[5-Amino-6-methyl-2-oxo-1-(2-trimethylsilanyl-ethoxymethyl)-1,2-dihydro-pyridin-3-yl]-indole-1-carboxylic acid tert-butyl ester (7d)

The title compound was prepared according to the experimental used in Example 20, Step 3 with intermediate (7c), 2-[6-methyl-5-nitro-2-oxo-1-(2-trimethylsilanyl-ethoxymethyl)-1,2-dihydro-pyridin-3-yl]-indole-1-carboxylic acid tert-butyl ester. After the usual work up, the crude product was purified by flash chromatography on SiO₂ with hexane—65% ethyl acetate/hexane (gradient) to afford the title compound as a yellow foam, 2.27 g, 83%.

Step 5: Preparation of 2-[5-{[1-(3-Fluoro-benzyl)-1H-pyrazole-4-carbonyl]-amino}-6-methyl-2-oxo-1-(2-trimethylsilanyl-ethoxymethyl)-1,2-dihydro-pyridin-3-yl]-indole-1-carboxylic acid tert-butyl ester (7e)

The title compound was prepared according to the experimental used in Example 20, Step 4 with intermediate (7d), 2-[5-amino-6-methyl-2-oxo-1-(2-trimethylsilanyl-ethoxymethyl)-1,2-dihydrpyridin-3-yl]-indole-1-carboxylic acid tert-butyl ester, and 1-(3-Fluoro-benzyl)-1H-pyrazole-4-carboxylic acid, which was synthesized according to the protocol described for intermediate (6e) in Example 21. The resultant crude product was purified by flash chromatography on SiO₂ with hexane—50% ethyl acetate/hexane (gradient) to afford the title compound as a yellow oil, 80 mg, 70%.

Step 6: Preparation of the Title Compound: 1-(3-Fluoro-benzyl)-1H-pyrazole-4-carboxylic acid [5-(1H-indol-2-yl)-2-methyl-6-oxo-1,6-dihydro-pyridin-3-yl]-amide The title compound was prepared according to the experimental from Example 1, Step 5, with intermediate (7e), 2-[5-{[1-(3-fluoro-benzyl)-1H-pyrazole-4-carbonyl]-amino}-6-methyl-2-oxo-1-(2-trimethylsilanyl-ethoxymethyl)-1,2-dihydro-pyridin-3-yl]-indole-1-carboxylic acid tert-butyl ester. The title compound was purified by trituration with acetonitrile, and isolated as a pale green solid, 8 mg, 15%.

LC/MS: RT=1.93 Min (270 nm), m/z=442 [M+H]. Total run time 3.75 min (short pos).

¹H NMR (d₆ DMSO): δ 2.18 (s, 3H), 5.45 (s, 2H) 6.95-7.01 (m, 1H), 7.04-7.1 (m, 1H), 7.12-7.22 (m, 4H), 7.42-7.56 (m, 3H), 7.99 (s, 1H), 8.07 (s, 1H), 8.46 (s, 1H), 9.57 (s, 1H), 11.45 (br s, 1H), 12.18 (br s, 1H).

Example 31

1-Benzyl-1H-pyrazole-4-carboxylic acid [5-(1H-indol-2-yl)-2-methyl-6-oxo-1,6-dihydro-pyridin-3-yl]-amide

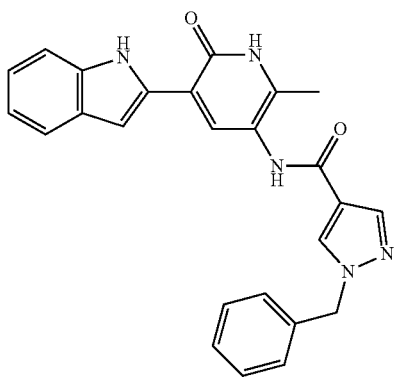 [SMILES: Cc1[nH]c(=O)c(-c2cc3ccccc3[nH]2)cc1NC(=O)c1cnn(Cc2ccccc2)c1]

The title compound was prepared by the route outlined in Scheme 7, following the same procedures as for Example 30.

LC/MS: RT=2.15 Min (270 nm), m/z=424 [M+H]. Total run time 3.75 min (short pos).

$^1$H NMR (d$_6$ DMSO): δ 2.16 (s, 3H), 5.40 (s, 2H), 6.96 (t, 1H), 7.05 (t, 1H), 7.16 (s, 1H), 7.29-7.40 (m, 5H), 7.44 (d, 1H), 7.49 (d, 1H), 7.96 (s, 1H), 8.03 (s, 1H), 8.40 (s, 1H), 9.50 (s, 1H), 11.42 (s, 1H), 12.14 (br s, 1H).

Example 32

1-(4-Fluoro-benzyl)-1H-pyrazole-4-carboxylic acid [5-(1H-indol-2-yl)-2-methyl-6-oxo-1,6-dihydro-pyridin-3-yl]-amide

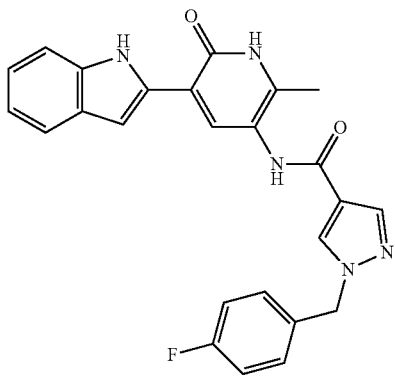 [SMILES: Cc1[nH]c(=O)c(-c2cc3ccccc3[nH]2)cc1NC(=O)c1cnn(Cc2ccc(F)cc2)c1]

The title compound was prepared by the route outlined in Scheme 7, following the same procedures as for Example 30.

LC/MS: RT=2.18 Min (270 nm), m/z=442 [M+H]. Total run time 3.75 min (short pos).

$^1$H NMR (d$_6$ DMSO): δ 2.16 (s, 3H), 5.40 (s, 2H), 6.96 (t, 1H), 7.05 (t, 1H), 7.16 (s, 1H), 7.19-7.39 (m, 4H), 7.44 (d, 1H), 7.49 (d, 1H), 7.95 (s, 1H), 8.03 (s, 1H), 8.40 (s, 1H), 9.50 (s, 1H), 11.42 (s, 1H), 12.14 (br s, 1H).

Example 33

1-(3,4-Difluoro-benzyl)-1H-pyrazole-4-carboxylic acid [5-(1H-indol-2-yl)-2-methyl-6-oxo-1,6-dihydro-pyridin-3-yl]-amide

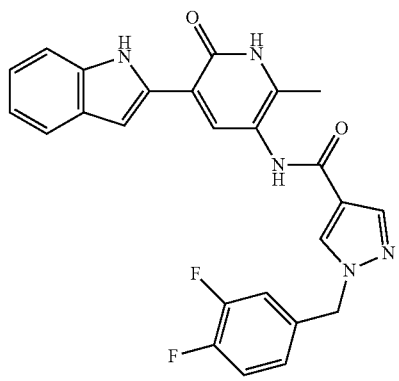 [SMILES: Cc1[nH]c(=O)c(-c2cc3ccccc3[nH]2)cc1NC(=O)c1cnn(Cc2ccc(F)c(F)c2)c1]

The title compound was prepared by the route outlined in Scheme 7, following the same procedures as for Example 30.

LC/MS: RT=2.21 Min (270 nm), m/z=460 [M+H]. Total run time 3.75 min (short pos).

$^1$H NMR (d$_6$ DMSO): δ 2.16 (s, 3H), 5.40 (s, 2H), 6.96 (t, 1H), 7.05 (t, 1H), 7.16 (m, 2H), 7.38-7.50 (m, 4H), 7.96 (s, 1H), 8.05 (s, 1H), 8.42 (s, 1H), 9.52 (s, 1H), 11.43 (s, 1H), 12.15 (br s, 1H).

Example 34

5-(1H-Indol-2-yl)-6-oxo-1,6-dihydro-pyridine-3-carboxylic acid (1-cyclohexylmethyl-1H-pyrazol-4-yl)-amide

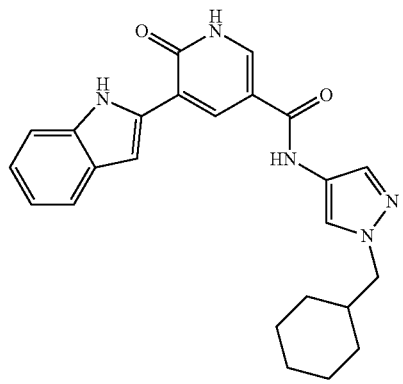 [SMILES: O=C(Nc1cnn(CC2CCCCC2)c1)c1c[nH]c(=O)c(-c2cc3ccccc3[nH]2)c1]

The title compound was prepared according to the general route outlined in Scheme 1.

LC/MS: RT=2.20 Min (270 nm), m/z=416 [M+H]. Total run time 3.75 min (short pos).

$^1$H NMR (d$_6$ DMSO): δ 0.92-1.02 (m, 2H), 1.15-1.26 (m, 3H) 1.53 (d, 2H), 1.6-1.72 (m, 3H), 1.75-1.85 (m, 1H), 3.95 (d, 2H), 6.99-7.03 (m, 1H), 7.09-7.13 (m, 1H), 7.28 (d, 1H), 7.51 (d, 1H), 7.56-7.59 (m, 2H), 7.99 (s, 1H), 8.13 (br s, 1H), 8.59 (d, 1H), 10.28 (br s, 1H), 11.52 (br s, 1H), 12.49 (br s, 1H).

Example 35

5-(1H-Indol-2-yl)-6-oxo-1,6-dihydro-pyridine-3-carboxylic acid (1-pyridin-3-ylmethyl-1H-pyrazol-4-yl)-amide

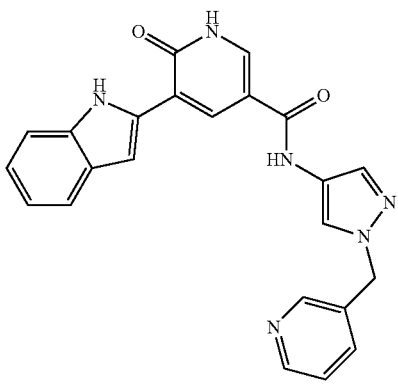 [SMILES: O=C(Nc1cnn(Cc2cccnc2)c1)c1c[nH]c(=O)c(-c2cc3ccccc3[nH]2)c1]

The title compound was prepared according to the general route outlined in Scheme 1.

LC/MS: RT=1.83 Min (270 nm), m/z=409 [M−H]. Total run time 3.75 min (short pos/neg).

$^1$H NMR (d$_6$ DMSO): δ 5.38 (s, 2H), 6.98 (td, 1H), 7.10 (td, 1H), 7.24 (d, 1H), 7.38 (ddd, 1H), 7.48 (dd, 1H), 7.54 (d, 1H), 7.62 (d, 1H), 7.65 (dt, 1H), 8.11 (d, 1H), 8.17 (s, 1H), 8.51 (m, 2H), 8.56 (d, 1H), 10.31 (s, 1H), 11.52 (br s, 1H), 12.50 (br s, 1H).

Example 36

5-(1H-Indol-2-yl)-6-oxo-1,6-dihydro-pyridine-3-carboxylic acid (1-pyridin-4-ylmethyl-1H-pyrazol-4-yl)-amide

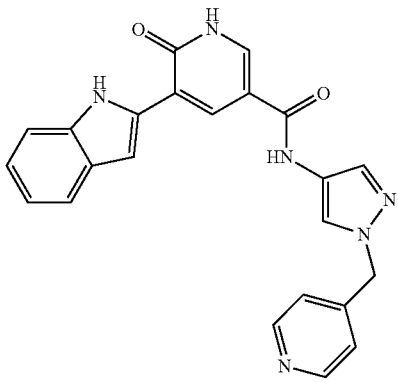 [SMILES: O=C(Nc1cnn(Cc2ccncc2)c1)c1c[nH]c(=O)c(-c2cc3ccccc3[nH]2)c1]

The title compound was prepared according to the general route outlined in Scheme 1.

LC/MS: RT=1.78 Min (270 nm), m/z=411 [M+H]. Total run time 3.75 min (short pos/neg).

$^1$H NMR (d$_6$ DMSO): δ 5.41 (s, 2H), 6.98 (td, 1H), 7.09 (t, 1H), 7.12 (d, 2H), 7.25 (d, 1H), 7.48 (d, 1H), 7.54 (d, 1H), 7.66 (s, 1H), 8.13 (d, 1H), 8.19 (s, 1H), 8.53 (m, 2H), 8.55 (d, 1H), 10.34 (s, 1H), 11.53 (br s, 1H), 12.45 (br s, 1H)

Example 37

1-(4-Methyl-benzyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

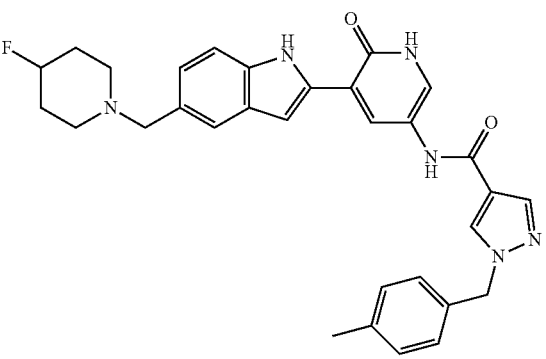 [SMILES: Cc1ccc(Cn2cc(C(=O)Nc3c[nH]c(=O)c(-c4cc5cc(CN6CCC(F)CC6)ccc5[nH]4)c3)cn2)cc1]

The title compound was prepared according to the route outlined in Scheme 8.

Step 1: Preparation of (1H-Indol-5-yl)-methanol (8a)

To a mechanically stirred solution of indole-5-carboxylic acid (26.3 g, 163 mmol) in tetrahydrofuran (600 mL), was added a solution of lithium aluminium hydride 1.0M in tetrahydrofuran (200 mL, 200 mmol) drop wise at ambient temperature. A solution of lithium aluminium hydride 2.0M in tetrahydrofuran (22 mL, 44 mmol) was added drop wise at ambient temperature, and then the reaction mixture was carefully heated up to reflux and held there for 1 hour. The reaction mixture was cooled to ambient temperature and then water (13 mL) was added drop wise, followed by an aqueous 10% sodium hydroxide solution (13 mL), and water (20 mL). The suspension was stirred at ambient temperature for 30 minutes, filtered through a bed of celite and the filter cake washed with ethyl acetate (2×200 mL). The filtrate and the washings were combined and the organics were separated, dried (Na$_2$SO$_4$) and concentrated in vacuo, to give a dark red oil. The resultant crude product was suspended in hexane (200 mL), and ethyl acetate (10 mL) was added. This mixture was stirred at ambient temperature for 18 hours, and the solids were separated via filtration and washed with hexane to afford the title compound as a light brown solid, 22.25 g, 93%.

Step 2: Preparation of 5-(tert-Butyl-dimethyl-silanyloxymethyl)-indole-1-carboxylic acid tert-butyl ester (8b)

To a mechanically stirred solution of (1H-Indol-5-yl)-methanol, (8a), (22.2 g, 151 mmol) in dichloromethane (300 mL) at ambient temperature was added N,N-diisopropylethylamine (39.0 g, 52.6 mL, 302 mmol) followed by a solution of tert-butyldimethylsilyl chloride (25 g, 166 mmol) in dichloromethane (400 mL). 4-Dimethylaminopyridine (1.84 g, 15.1 mmol) was added and the reaction was stirred at ambient temperature for 2 hours. The reaction mixture was concentrated in vacuo and the residue was taken up in ethyl acetate (400 mL), washed with an aqueous 0.5N hydrochloric acid solution (600 mL), brine, dried (Na$_2$SO$_4$) and concentrated in vacuo to yield a red oil.

This red oil was dissolved in dichloromethane (350 mL) and to this was added di-tert-butyl dicarbonate (36.2 g, 166 mmol) drop wise at ambient temperature as a solution in dichloromethane (50 mL). 4-Dimethylaminopyridine (1.84 g, 15.1 mmol) was added and the reaction stirred at ambient temperature for 2 hours. The reaction mixture was concentrated in vacuo and the residue was taken up in ethyl acetate (300 mL), washed with an aqueous 0.5N hydrochloric acid solution (200 mL), brine, dried (Na$_2$SO$_4$) and concentrated in vacuo to yield a light brown oil. The resultant crude product was purified by flash chromatography on SiO$_2$ eluting first with hexane and then 10% ethyl acetate/hexane to afford the desired title compound as a white solid, 52.22 g, 96%.

Step 3: Preparation of 5-(tert-Butyl-dimethyl-silanyloxymethyl)-2-[3-nitro-6-oxo-5-(2-trimethylsilanyl-ethoxymethyl)-cyclohexa-,3-dienyl]-indole-1-carboxylic acid tert-butyl ester (8c)

To a solution of diisopropylamine (2.1 g, 2.89 mL, 20.8 mmol) in anhydrous tetrahydrofuran (10 mL) was added butyllithium solution 2.5M in hexanes (7.71 mL, 19.3 mmol) drop wise at −78° C. After addition the reaction mixture was allowed to attain 0° C., where it was stirred for 30 minutes to form the lithiumdiisopropyl amide solution.

5-(tert-Butyl-dimethyl-silanyloxymethyl)-indole-1-carboxylic acid tert-butyl ester (8b) (5.89 g, 16.3 mmol) was stirred in tetrahydrofuran (80 mL) and triisopropyl borate (4.18 g, 5.13 mL, 22.2 mmol) was added, and the reaction mixture was cooled to −5° C. To this was added the previously described lithiumdiisopropyl amide solution drop wise keeping the temperature between −5° C. and 0° C. After addition the reaction was stirred at −5° C. for 30 mins and then allowed to attain ambient temperature. The reaction mixture was concentrated in vacuo to yield crude indole-2-boronic acid-5-(tert-Butyl-dimethyl-silanyloxymethyl)-indole-1-carboxylic acid tert-butyl ester, which was dissolved in tetrahydrofuran (100 mL). Water (20 mL), potassium carbonate (6.17 g, 44.6 mmol), 3-iodo-5-nitro-1-(2-trimethylsilanyl-ethoxymethyl)-1H-pyridin-2-one, intermediate (6a) (5.87 g, 14.8 mmol) in tetrahydrofuran (20 mL) and [1,1'-Bis(diphenylphosphino)ferrocene)]dichloropalladium (II), complex with dichloromethane (0.605 g, 5 mol %) were added. The red suspension was degassed for 10 minutes and then heated at 60° C. for 2 hours. The reaction mixture was cooled and was partitioned between ethyl acetate (200 mL) and aqueous saturated sodium bicarbonate solution (200 mL). The organic layer was separated and the aqueous was extracted with a further portion of ethyl acetate. The combined ethyl acetate layers were washed with brine, dried (Na$_2$SO$_4$), filtered through a plug of celite and concentrated in vacuo. The resultant crude product was purified by flash chromatography on SiO$_2$ eluting with hexane—15% ethyl acetate/hexane (gradient) to afford the desired title compound as a yellow solid, 8.44 g, 90%.

Step 4: Preparation of 2-[5-Amino-2-oxo-1-(2-trimethylsilanyl-ethoxymethyl)-1,2-dihydro-pyridin-3-yl]-5-(tert-butyl-dimethyl-silanyloxymethyl)-indole-1-carboxylic acid tert-butyl ester (8d)

The title compound was prepared by the route outlined in Scheme 8 and using the experimental from Example 20, Step 3, with intermediate (8c) 5-(tert-butyl-dimethyl-silanyloxymethyl)-2-[3-nitro-6-oxo-5-(2-trimethylsilanyl-ethoxymethyl)-cyclohexa-,3-dienyl]-indole-1-carboxylic acid tert-butyl ester (11.58 g, 18.4 mmol).

The resultant crude product was purified by flash chromatography on SiO$_2$ with hexane—50% ethyl acetate/hexane (gradient) to afford the title compound as a dark yellow foam, 10.21 g, 93%.

Step 5: Preparation of 5-(tert-Butyl-dimethyl-silanyloxymethyl)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (8e)

The title compound was prepared by the route outlined in Scheme 8 and using the experimental from Example 20, step 4, with intermediate (8d), 2-[5-amino-2-oxo-1-(2-trimethylsilanyl-ethoxymethyl)-1,2-dihydro-pyridin-3-yl]-5-(tert-butyl-dimethyl-silanyloxymethyl)-indole-1-carboxylic acid tert-butyl ester (1.0 g, 1.67 mmol) and 1-(4-methyl-benzyl)-1H-pyrazole-4-carboxylic acid (0.43 g, 1.99 mmol) which had been synthesized according to the protocol described for intermediate (6e) in example 21.

The resultant crude product was purified by flash chromatography on SiO$_2$ with hexane—50% ethyl acetate/hexane (gradient) to afford the title compound as a pink oil, 0.721 g, 54%.

Step 6: Preparation of 5-Formyl-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (8f)

Intermediate 8(e), 5-(tert-butyl-dimethyl-silanyloxymethyl)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (0.72 g, 0.9 mmol) was stirred in tetrahydrofuran (20 mL) and cooled to 0° C. Tetrabutylammonium fluoride solution 1.0M in tetrahydrofuran (0.9 mL, 0.9 mmol) was added drop wise at 0° C., and then the reaction was allowed to attain ambient temperature, where it was stirred for a further 2 hours. The reaction mixture was diluted with ethyl acetate (30 mL), washed with water (30 mL), aqueous 0.5N hydrochloric acid solution (30 mL), brine, dried (Na$_2$SO$_4$) and concentrated in vacuo to yield a green foam. This green foam was dissolved in anhydrous dichloromethane (20 mL) and manganese dioxide (1.17 g, 13.5 mmol) was added. The reaction was refluxed for 1 hour and, after cooling, the mixture was filtered through a bed of celite. The filter cake was washed through with tetrahydrofuran (20 mL) and the filtrate was concentrated in vacuo. The resultant crude product was purified by flash chromatography on SiO$_2$ with hexane—50% ethyl acetate/hexane (gradient) to afford the title compound as a tan solid, 0.454 g, 74%.

Step 7: Preparation of 5-(4-Fluoro-piperidin-1-ylmethyl)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (8g)

To a solution of intermediate (8f), 5-Formyl-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester, (150 mg, 0.22 mmol) in dichloromethane (10 mL) was added 4-fluoropiperidine hydrochloride (61 mg, 0.44 mmol), sodium triacetoxyborohydride (140 mg, 0.66 mmol) and acetic acid (1 drop). The reaction mixture was stirred at ambient temperature for 3 hours and then diluted with ethyl acetate. The mixture was washed with saturated aqueous sodium bicarbonate solution, brine, dried ($Na_2SO_4$) and concentrated in vacuo. The resultant crude product was purified by flash chromatography on $SiO_2$ with hexane—ethyl acetate (gradient) and then ion exchange using an SCX-2 column to afford the title compound as a yellow solid, 96 mg, 57%.

Step 8: Preparation of the Title Compound: 1-(4-Methyl-benzyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide A 2-5 mL microwave vial was charged with intermediate (8g), 5-(4-fluoro-piperidin-1-ylmethyl)-2-[5-{[1-(4-methyl-benzyl)-1H-pyrazole-4carbonyl]amino}-2-oxo-1-(2-trimethylsilanyl-ethoxymethyl)-1,2-dihydro-pyridin-3-yl]-indolecarboxylic acid tert-butyl ester (96 mg, 0.125 mmol), tetrahydrofuran (3 mL), 1,2-diaminoethane (38 mg, 42 ul, 0.63 mmol) and finally tetrabutylammonium fluoride solution 1.0M in tetrahydrofuran (0.63 mL, 0.63 mmol). The vial was heated under microwave irradiation at 120° C. for 20 mins. After cooling, the reaction mixture was diluted with ethyl acetate (20 mL) and washed with water (4×20 mL) and brine (4×20 mL). The organics were dried ($Na_2SO_4$) and concentrated in vacuo. The resultant yellow solid was purified via trituration using acetonitrile, to afford the title compound as a yellow solid, 42 mg, 63%.

LC/MS: RT=1.51 Min (270 nm), m/z=539 [M+H]. Total run time 3.75 min (short pos).

$^1$H NMR (d$_6$ DMSO): δ 1.66-1.88 (m, 4H), 2.26-2.32 (m, 5H), 2.55 (m, 2H), 3.50 (s, 2H), 4.59-4.75 (m, 1H), 5.34 (s, 2H), 7.00-7.05 (m, 2H), 7.19 (m, 4H), 7.41 (s, 1H), 7.44 (d, 1H), 7.81 (d, 1H), 8.01 (s, 1H), 8.16 (d, 1H), 8.36 (s, 1H), 9.76 (s, 1H), 11.50 (s, 1H), 11.96 (br s, 1H).

Example 38

1-(4-Methyl-benzyl)-1H-pyrazole-4-carboxylic acid [6-oxo-5-(5-piperidin-1-ylmethyl-1H-indol-2-yl)-1,6-dihydro-pyridin-3-yl]-amide

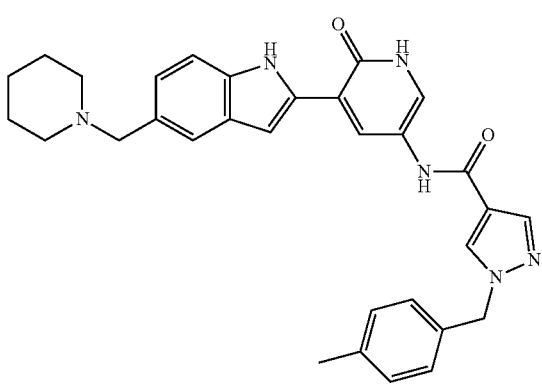 [SMILES: Cc1ccc(Cn2cc(C(=O)Nc3c[nH]c(=O)c(-c4cc5cc(CN6CCCCC6)ccc5[nH]4)c3)cn2)cc1]

The title compound was prepared by the route outlined in Scheme 8, following the same experimental procedures as for Example 37. It was purified by trituration with acetonitrile, and isolated as a yellow solid, 70 mg, 66%.

LC/MS: RT=1.51 Min (270 nm), m/z=521 [M+H]. Total run time 3.75 min (short pos).

$^1$H NMR (d$_6$ DMSO): δ 1.37-1.48 (m, 6H), 2.29-2.33 (m, 7H), 3.45 (s, 2H), 5.34 (s, 2H), 7.00-7.04 (m, 2H), 7.19 (m, 4H), 7.40-7.44 (d, 2H), 7.81 (d, 1H), 8.01 (s, 1H), 8.16 (d, 1H), 8.36 (s, 1H), 9.76 (s, 1H), 11.49 (s, 1H), 11.96 (br s, 1H).

Example 39

1-(4-Methyl-benzyl)-1H-pyrazole-4-carboxylic acid {5-[5-(4-hydroxymethyl-piperidin-1-ylmethyl)-1H-indol-2-yl]-6-oxo-1,6-dihydro-pyridin-3-yl}-amide

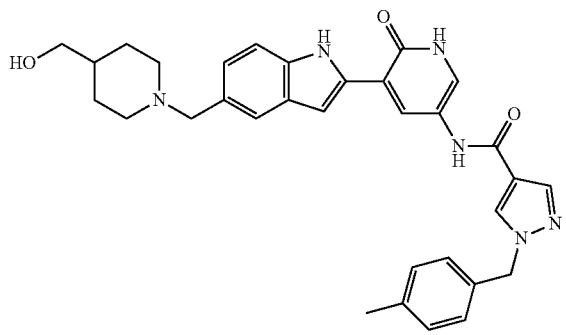 [SMILES: Cc1ccc(Cn2cc(C(=O)Nc3c[nH]c(=O)c(-c4cc5cc(CN6CCC(CO)CC6)ccc5[nH]4)c3)cn2)cc1]

The title compound was prepared by the route outlined in Scheme 8, following the same experimental procedures as for Example 37.

The crude product was purified by flash chromatography on $SiO_2$ with dichloromethane—40% methanol/dichloromethane (gradient) and then trituration with diethyl ether to afford the title compound as a yellow solid, 9 mg, 13%.

LC/MS: RT=1.44 Min (270 nm), m/z=551 [M+H]. Total run time 3.75 min (short pos).

$^1$H NMR (d$_6$ DMSO): δ 1.06-1.15 (m. 2H), 1.32 (m, 1H), 1.59 (m, 2H), 1.86 (m, 2H), 2.29 (s, 3H), 2.81 (m, 2H), 3.22 (m, 2H), 3.46 (s, 2H), 4.36 (t, 1H), 5.34 (s, 2H), 6.99-7.03 (m, 2H), 7.19 (m, 4H), 7.39-7.43 (d, 2H), 7.81 (d, 1H), 8.01 (s, 1H), 8.15 (d, 1H), 8.36 (s, 1H), 9.76 (s, 1H), 11.50 (s, 1H), NH not seen.

Example 40

1-(4-Methyl-benzyl)-1H-pyrazole-4-carboxylic acid [5-(5-morpholin-4-ylmethyl-1H-indol-2-yl)-6-oxo-1,6-dihydro-pyridin-3-yl]-amide

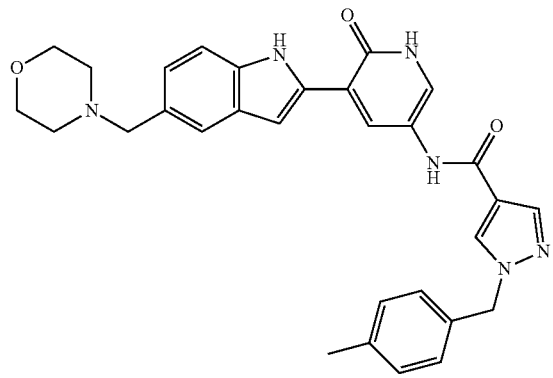 [SMILES: Cc1ccc(Cn2cc(C(=O)Nc3c[nH]c(=O)c(-c4cc5cc(CN6CCOCC6)ccc5[nH]4)c3)cn2)cc1]

The title compound was prepared by the route outlined in Scheme 8, following the same experimental procedures as for Example 37.

The title compound was purified by trituration with acetonitrile, and isolated as a yellow solid, 39 mg, 51%.

LC/MS: RT=1.41 Min (270 nm), m/z=523 [M+H]. Total run time 3.75 min (short pos).

$^1$H NMR (d$_6$ DMSO): δ 2.29 (s, 3H), 2.36 (m, 4H), 3.49 (s, 2H), 3.56 (m, 4H), 5.34 (s, 2H), 7.00-7.05 (m, 2H), 7.19 (m, 4H), 7.43-7.46 (d, 2H), 7.82 (d, 1H), 8.01 (s, 1H), 8.16 (d, 1H), 8.36 (s, 1H), 9.76 (s, 1H), 11.51 (s, 1H), 11.97 (br s, 1H).

Example 41

1-(4-Methyl-benzyl)-1H-pyrazole-4-carboxylic acid [6-oxo-5-(5-pyrrolidin-1-ylmethyl-1H-indol-2-yl)-1,6-dihydro-pyridin-3-yl]-amide

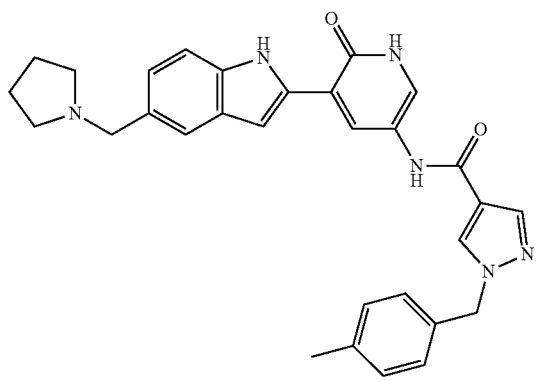 [SMILES: Cc1ccc(Cn2cc(C(=O)Nc3c[nH]c(=O)c(-c4cc5cc(CN6CCCC6)ccc5[nH]4)c3)cn2)cc1]

The title compound was prepared by the route outlined in Scheme 8, following the same experimental procedures as for Example 37.

The title compound was purified by trituration with acetonitrile, and isolated as a yellow solid, 35 mg, 56%.

LC/MS: RT=1.47 Min (270 nm), m/z=507 [M+H]. Total run time 3.75 min (short pos).

$^1$H NMR (d$_6$ DMSO): δ 1.68 (m, 4H), 2.29 (s, 3H), 2.43 (m, 4H), 3.61 (s, 2H), 5.34 (s, 2H), 7.00-7.05 (m, 2H), 7.19 (m, 4H), 7.42-7.44 (d, 2H), 7.82 (d, 1H), 8.01 (s, 1H), 8.16 (d, 1H), 8.36 (s, 1H), 9.75 (s, 1H), 11.49 (s, 1H), 11.96 (br s, 1H).

Example 42

1-(4-Methyl-benzyl)-1H-pyrazole-4-carboxylic acid {5-[5-(3-hydroxy-azetidin-1-ylmethyl)-1H-indol-2-yl]-6-oxo-1,6-dihydro-pyridin-3-yl}-amide

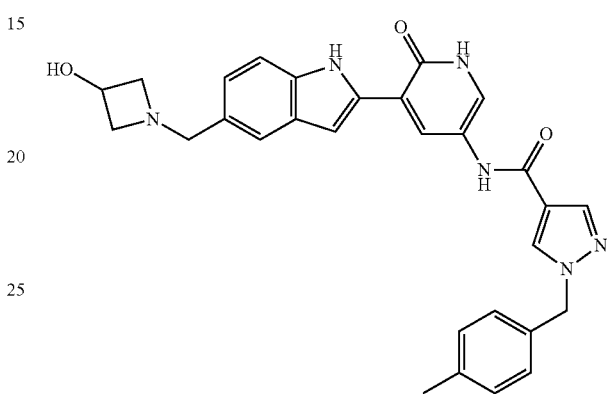

The title compound was prepared by the route outlined in Scheme 8, following the same experimental procedures as for Example 37.

The title compound was purified by trituration with acetonitrile, and isolated as a yellow solid, 18 mg, 40%.

LC/MS: RT=1.42 Min (270 nm), m/z=509 [M+H]. Total run time 3.75 min (short pos).

$^1$H NMR (d$_6$ DMSO): δ 2.29 (s, 3H), 2.74 (m, 2H), 3.44 (m, 2H), 3.57 (s, 2H), 4.16 (m, 1H), 5.23 (d, 1H), 5.34 (s, 2H), 6.97-7.02 (m, 2H), 7.19 (m, 4H), 7.38-7.42 (d, 2H), 7.81 (d, 1H), 8.01 (s, 1H), 8.15 (d, 1H), 8.36 (s, 1H), 9.75 (s, 1H), 11.49 (s, 1H), 11.90 (br s, 1H).

Example 43

1-(4-Methyl-benzyl)-1H-pyrazole-4-carboxylic acid [5-(5-{[(2-hydroxy-ethyl)-methyl-amino]-methyl}-indol-2-yl)-6-oxo-1,6-dihydro-pyridin-3-yl]-amide

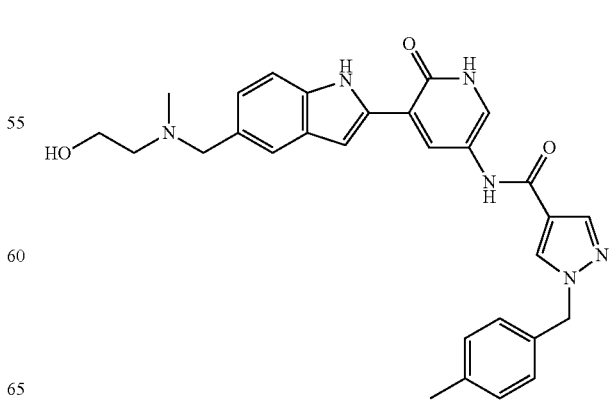

The title compound was prepared by the route outlined in Scheme 8, following the same experimental procedures as for Example 37.

The title compound was purified by trituration with acetonitrile, and isolated as a yellow solid, 37 mg, 50%.

LC/MS: RT=1.42 Min (270 nm), m/z=511 [M+H]. Total run time 3.75 min (short pos).

$^1$H NMR (d$_6$ DMSO): δ 2.15 (s, 3H), 2.29 (s, 3H), 2.43 (t, 2H), 3.48-3.55 (m, 4H), 4.32 (t, 1H), 5.35 (s, 2H), 7.00-7.05 (m, 2H), 7.19 (m, 4H), 7.42-7.44 (d, 2H), 7.82 (d, 1H), 8.01 (s, 1H), 8.15 (d, 1H), 8.36 (s, 1H), 9.75 (s, 1H), 11.49 (s, 1H), 11.96 (br s, 1H).

Example 44

1-(4-Chloro-benzyl)-1H-pyrazole-4-carboxylic acid [6-oxo-5-(5-piperidin-1-ylmethyl-1H-indol-2-yl)-1,6-dihydro-pyridin-3-yl]-amide

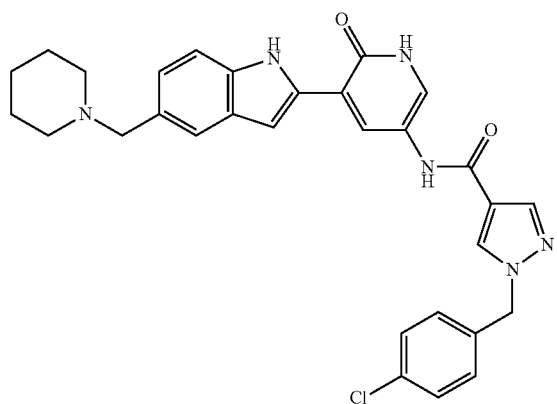 [SMILES: O=C(Nc1c[nH]c(=O)c(-c2cc3cc(CN4CCCCC4)ccc3[nH]2)c1)c1cnn(Cc2ccc(Cl)cc2)c1]

The title compound was prepared by the route outlined in Scheme 8, following the same experimental procedures as for Example 37.

The title compound was purified by flash chromatography on SiO$_2$ with dichloromethane—12% methanol/dichloromethane—12% methanol/2% ammonia solution 7N in methanol/dichloromethane (gradient) and isolated as a yellow solid, 2.1 mg, 12%.

LC/MS: RT=0.93 Min (270 nm), m/z=541 [M+H]. Total run time 1.9 min (super short pos).

$^1$H NMR (d$_6$ DMSO): □ δ 1.24-1.26 (m, 2H), 1.34-1.39 (m, 2H), 1.48-1.49 (m, 4H), 2.32-2.36 (m, 2H), 3.45-3.51 (m, 2H), 5.41 (s, 2H), 7.01 (d, 1H), 7.04 (dd, 1H), 7.31 (d, 2H), 7.41-7.42 (m, 4H), 7.82 (d, 1H), 8.04 (s, 1H), 8.17 (d, 1H), 8.42 (s, 1H), 9.79 (1H, s), 11.51 (1H, s), NH not seen.

Example 45

1-(4-Chloro-benzyl)-1H-pyrazole-4-carboxylic acid [5-(5-{[ethyl-(2-hydroxy-ethyl)-amino]-methyl}-1H-indol-2-yl)-6-oxo-1,6-dihydro-pyridin-3-yl]-amide

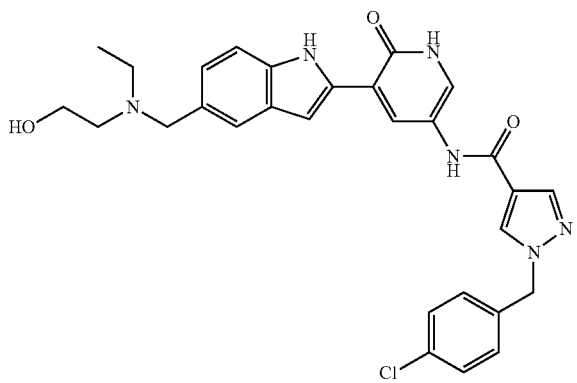 [SMILES: CCN(CCO)Cc1ccc2[nH]c(-c3cc(NC(=O)c4cnn(Cc5ccc(Cl)cc5)c4)c[nH]c3=O)cc2c1]

The title compound was prepared by the route outlined in Scheme 8, following the same experimental procedures as for Example 37.

The resultant crude product was purified by trituration with acetonitrile to afford the title compound as brown solid, 8 mg, 20%

LC/MS: RT=0.91 Min (270 nm), m/z=545 [M+H]. Total run time 1.9 min (super short pos).

$^1$H NMR (d$_6$ DMSO): □ δ 1.27 (t, 3H), 3.11-3.18 (m, 4H), 3.66-3.75 (m, 2H), 4.38 (d, 2H), 5.39 (s, 2H), 7.11 (s, 1H), 7.22 (dd, 1H), 7.30 (d, 2H), 7.41 (d, 2H), 7.58 (d, 1H), 7.72 (s, 1H), 7.83 (d, 1H), 8.03 (s, 1H), 8.26 (d, 1H), 8.40 (s, 1H), 9.18 (s, 1H), 9.80 (s, 1H), 11.76 (s, 1H), NH not seen.

Example 46

1-(4-Chloro-benzyl)-1H-pyrazole-4-carboxylic acid (5-{5-[(2-hydroxy-ethylamino)-methyl]-1H-indol-2-yl}-6-oxo-1,6-dihydro-pyridin-3-yl)-amide

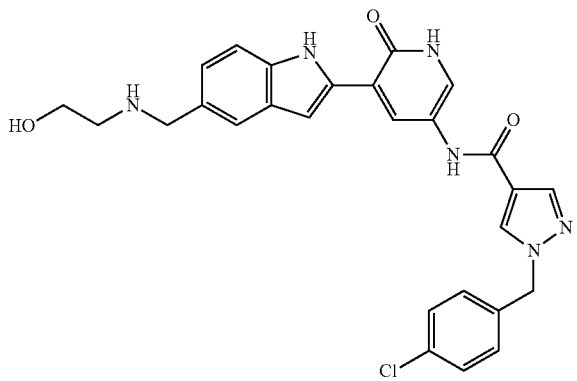 [SMILES: O=C(Nc1c[nH]c(=O)c(-c2cc3cc(CNCCO)ccc3[nH]2)c1)c1cnn(Cc2ccc(Cl)cc2)c1]

The title compound was prepared by the route outlined in Scheme 8, following the same experimental procedures as for Example 37.

The resultant crude product was taken up in methanol (1 mL) and loaded onto a 5 g SCX column. The column was flushed with methanol and then eluted with ammonia solution 7N in methanol. The eluent was concentrated in vacuo and the residue further purified by preparative HPLC at pH 4 to afford the title compound as a yellow solid, 3 mg, 8%.

LC/MS: RT=0.90 Min (270 nm), m/z=456 [Fragment]. Total run time 1.9 min (super short pos).

$^1$H NMR (d$_6$ DMSO): □ δ 2.90-2.93 (m, 2H), 3.63 (m, 2H), 4.15 (s, 2H), 5.10 (s, 1H), 5.41 (s, 2H), 7.09 (d, 1H), 7.20 (dd, 1H), 7.31 (d, 2H), 7.50 (d, 2H), 7.55 (d, 1H), 7.66 (s, 1H), 7.80 (d, 1H), 8.05 (s, 1H), 8.25 (d, 1H), 8.43 (s, 1H), 9.82 (s, 1H), 11.68 (s, 1H), NHs not seen.

Example 47

1-(4-Chloro-benzyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

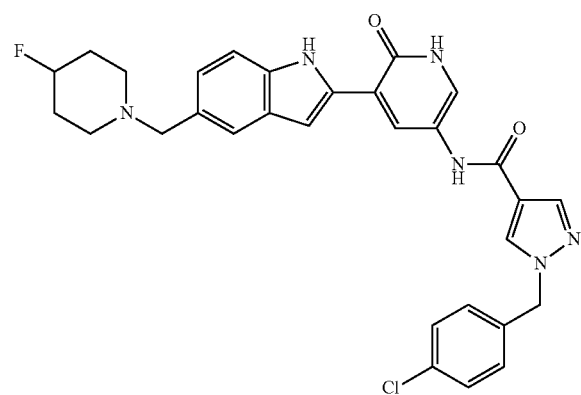 [SMILES: O=C(Nc1c[nH]c(=O)c(-c2cc3cc(CN4CCC(F)CC4)ccc3[nH]2)c1)c1cnn(Cc2ccc(Cl)cc2)c1]

The title compound was prepared by the route outlined in Scheme 8, following the same experimental procedures as for Example 37.

The title compound was purified by flash chromatography on SiO$_2$ with dichloromethane—10% methanol/dichloromethane—10% methanol/1% ammonia solution 7N in methanol/dichloromethane (gradient) and isolated as a yellow solid, 30 mg, 65%.

LC/MS: RT=1.73 Min (270 nm), m/z=560, 561 [M+H]. Total run time 3.75 min (short pos).

$^1$H NMR (d$_6$ DMSO): □ δ 1.23 (m, 2H), 1.69 (m, 2H), 1.79-1.86 (m, 2H), 2.29-2.33 (m, 2H), 3.51 (s, 2H), 4.61-4.73 (m, 1H), 5.41 (s, 2H), 7.01 (d, 1H), 7.04 (dd, 1H), 7.31 (d, 2H), 7.42-7.46 (m, 4H), 7.82 (d, 1H), 8.04 (s, 1H), 8.17 (d, 1H), 8.41 (s, 1H), 9.78 (s, 1H), 11.51 (s, 1H), 11.98 (s, 1H).

Example 48

1-(4-Chloro-benzyl)-1H-pyrazole-4-carboxylic acid {5-[5-(4-hydroxy-piperidin-1-ylmethyl)-1H-indol-2-yl]-6-oxo-1,6-dihydro-pyridin-3-yl}-amide

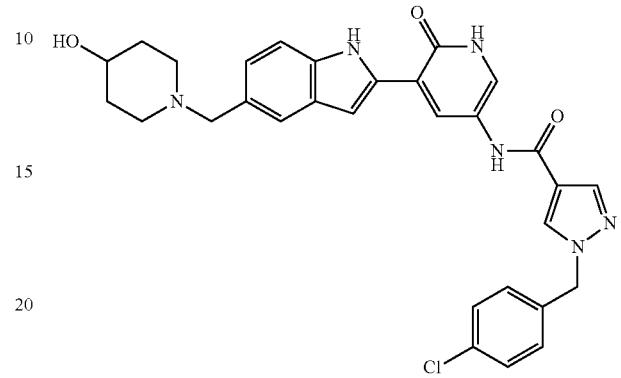

The title compound was prepared by the route outlined in Scheme 8, following the same experimental procedures as for Example 37.

It was purified by flash chromatography on SiO$_2$ with dichloromethane—10% methanol/dichloromethane—10% methanol/1% ammonia solution 7N in methanol/dichloromethane (gradient) and then by trituration with acetonitrile. The desired compound was isolated as a yellow solid, 8 mg, 10%.

LC/MS: RT=0.91 Min (270 nm), m/z=557 [M+H]. Total run time 1.9 min (super short pos).

$^1$H NMR (d$_6$ DMSO): □ δ 1.36-1.39 (m, 2H), 1.68-1.71 (m, 2H), 2.01 (m, 2H), 2.67 (m, 2H), 3.46 (m, 2H), 4.51 (s, 1H), 5.41 (s, 2H), 7.01-7.03 (m, 2H), 7.31 (d, 2H), 7.44 (m, 4H), 7.82 (d, 1H), 8.04 (s, 1H), 8.17 (d, 1H), 8.42 (s, 1H), 9.78 (s, 1H), 11.50 (s, 1H), 11.98 (s, 1H), OH not seen.

Example 49

1-Benzyl-1H-pyrazole-4-carboxylic acid {5-[5-(4-fluoro-piperidin-1-ylmethyl)-1H-indol-2-yl]-6-oxo-1,6-dihydro-pyridin-3-yl}-amide

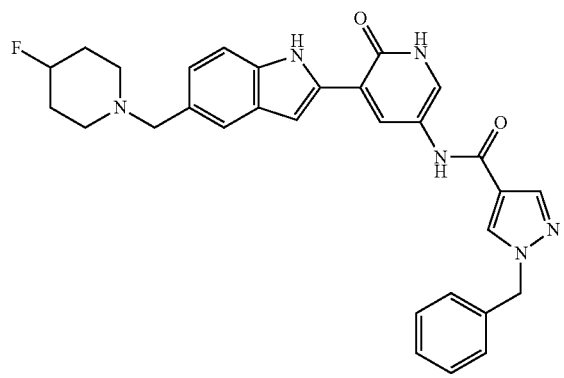 [SMILES: O=C(Nc1c[nH]c(=O)c(-c2cc3cc(CN4CCC(F)CC4)ccc3[nH]2)c1)c1cnn(Cc2ccccc2)c1]

The title compound was prepared by the route outlined in Scheme 8, following the same experimental procedures as for Example 37.

Purification by trituration with acetonitrile afforded the title compound as a yellow solid, 51 mg, 85%

LC/MS: RT=0.91 Min (270 nm), m/z=525 [M+H]. Total run time 1.9 min (super short pos/neg).

$^1$H NMR (d$_6$ DMSO): δ 1.68 (m, 2H), 1.78 (m, 2H), 2.26 (m, 2H), 2.60 (m, 2H), 3.50 (s, 2H), 4.66 (dm, 1H), 5.40 (s, 2H), 6.99 (d, 1H), 7.02 (dd, 1H), 7.40 (m, 7H), 7.85 (d, 1H), 8.07 (s, 1H), 8.25 (d, 1H), 8.46 (s, 1H), 9.92 (s, 1H), 11.51 (br s, 1H), 11.96 (br s, 1H)

Example 50

1-Benzyl-1H-pyrazole-4-carboxylic acid [6-oxo-5-(5-pyrrolidin-1-ylmethyl-1H-indol-2-yl)-1,6-dihydro-pyridin-3-yl]-amide

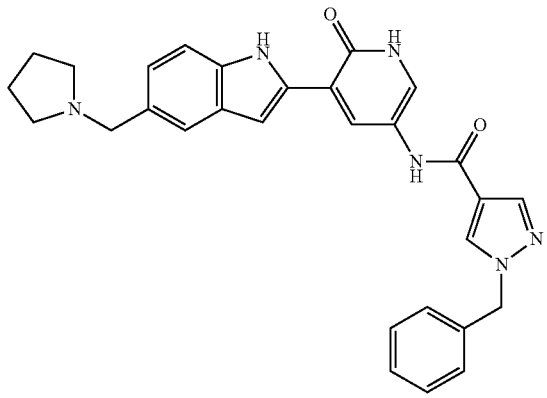 [SMILES: O=C(Nc1c[nH]c(=O)c(-c2cc3cc(CN4CCCC4)ccc3[nH]2)c1)c1cnn(Cc2ccccc2)c1]

The title compound was prepared by the route outlined in Scheme 8, following the same experimental procedures as for Example 37.

Purification by trituration with acetonitrile afforded the title compound as a yellow solid, 38 mg, 46%

LC/MS: RT=0.90 Min (270 nm), m/z=493 [M+H]. Total run time 1.9 min (super short pos/neg).

$^1$H NMR (d$_6$ DMSO): δ 1.68 (br s, 4H), 2.43 (br s, 4H), 3.61 (br s, 2H), 5.40 (s, 2H), 6.99 (d, 1H), 7.04 (dd, 1H), 7.38 (m, 7H), 7.84 (d, 1H), 8.06 (s, 1H), 8.22 (br s, 1H), 8.44 (s, 1H), 9.87 (s, 1H), 11.49 (s, 1H), 11.96 (br s, 1H)

Example 51

1-Benzyl-1H-pyrazole-4-carboxylic acid [5-(5-morpholin-4-ylmethyl-1H-indol-2-yl)-6-oxo-1,6-dihydro-pyridin-3-yl]-amide

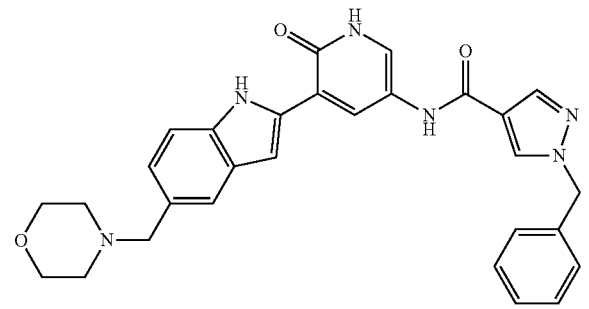 [SMILES: O=C(Nc1c[nH]c(=O)c(-c2cc3cc(CN4CCOCC4)ccc3[nH]2)c1)c1cnn(Cc2ccccc2)c1]

The title compound was prepared by the route outlined in Scheme 8, following the same experimental procedures as for Example 37, with a slight modification to the protocol in Step 5.

Step 5: Preparation of 5-(tert-Butyl-dimethyl-silanyloxymethyl)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (8e)

Intermediate (8d), 2-[5-amino-2-oxo-1-(2-trimethylsilanyl-ethoxymethyl)-1,2-dihydro-pyridin-3-yl]-5-(tert-butyl-dimethyl-silanyloxymethyl)-indole-1-carboxylic acid tert-butyl ester, (600 mg, 1 mmol) was stirred in dichloromethane (50 mL) at RT with triethylamine (202 mg, 0.278 mL, 2 mmol). The reaction mixture was cooled to 5° C. and then a solution of 1-Benzyl-1H-pyrazole-4-carbonyl chloride (265 mg, 1.2 mmol), which had been prepared according to the protocol below, in dichloromethane (10 ml), was added drop wise. After addition the reaction was stirred at RT for 18 hrs and then the reaction mixture was washed with saturated sodium hydrogen carbonate solution (2×50 mL), brine (50 ml), dried (Na$_2$SO$_4$) and concentrated in vacuo. The resultant crude product was purified by flash chromatography on SiO$_2$ eluting with hexane—50% ethyl acetate/hexane (gradient) to afford the desired compound as a pale green foam, 750 mg, 96%.

Preparation of 1-Benzyl)-1H-pyrazole-4-carbonyl chloride used in Step 5, above.

1-Benzyl-1H-pyrazole-4-carboxylic acid (1.6 g, 7.92 mmol) was stirred as a suspension in toluene (20 mL) at RT and thionyl chloride (1.88 g, 1.15 mL, 15.8 mmol) was added. The reaction mixture was slowly heated to reflux and heating continued for 4 hrs. After cooling the reaction was concentrated in vacuo. Toluene was added to the residue and concentrated in vacuo. This was repeated a further three times with toluene and twice with isohexane. The crude oil obtained was used without further purification, 1.65 g, 95%.

The title compound was purified by trituration with acetonitrile afforded the title compound as a yellow solid, 25 mg, 36%

LC/MS: RT=1.64 Min (270 nm), m/z=509 [M+H]. Total run time 3.75 min (short pos).

$^1$H NMR (d$_6$ DMSO): δ 2.29-2.39 (m, 4H), 3.50 (s, 2H), 3.52-3.60 (m, 4H), 5.41 (s, 2H), 7.00-7.02 (m, 2H), 7.28-7.46 (m, 7H), 7.82 (s, 1H), 8.04 (s, 1H), 8.16-8.19 (d, 1H), 8.40 (s, 1H), 9.77 (s, 1H), 11.51 (s, 1H), 11.96 (br s, 1H).

Example 52

1-Benzyl-1H-pyrazole-4-carboxylic acid [6-oxo-5-(5-piperidin-1-ylmethyl-1H-indol-2-yl)-1,6-dihydro-pyridin-3-yl]-amide

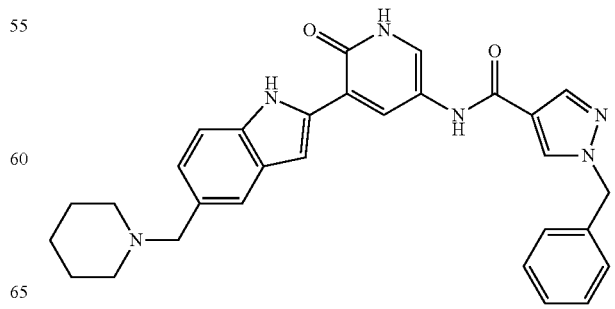

The title compound was prepared by the route outlined in Scheme 8, following the same experimental procedures as for Example 51.

The title compound was purified by trituration with acetonitrile, and isolated as a yellow solid, 0.467 g, 42%.

LC/MS: RT=1.44 Min (270 nm), m/z=507 [M+H]. Total run time 3.75 min (short pos).

¹H NMR (d₆ DMSO): δ 1.37 (m, 2H), 1.47 (m, 4H), 2.32 (m, 4H), 3.45 (s, 2H), 5.41 (s, 2H), 7.00-7.03 (m, 2H), 7.28-7.44 (m, 7H), 7.82 (d, 1H), 8.03 (s, 1H), 8.16 (d, 1H), 8.41 (s, 1H), 9.79 (s, 1H), 11.50 (s, 1H), 11.99 (br s, 1H).

Example 53

1-(4-Chloro-benzyl)-1H-pyrazole-4-carboxylic acid {5-[5-(4-methyl-piperazin-1-ylmethyl)-1H-indol-2-yl]-6-oxo-1,6-dihydro-pyridin-3-yl}-amide

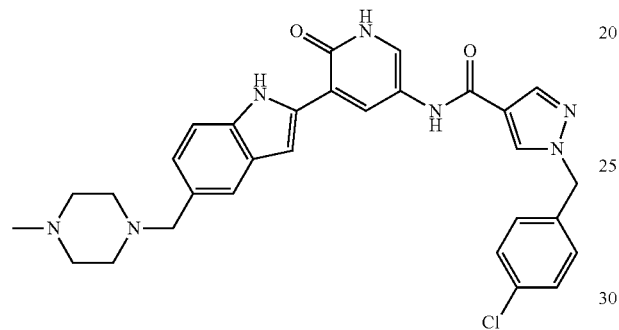

The title compound was prepared by the route outlined in Scheme 8, following the same experimental procedures as for Example 51.

The title compound was purified by preparative HPLC at pH 9 and isolated as a yellow solid, 3 mg, 4%.

LC/MS: RT=1.64 Min (270 nm), m/z=556 [M+H]. Total run time 3.75 min (short pos).

¹H NMR (d₆ DMSO): δ 2.14 (s, 3H), 2.20-2.40 (m, 8H), 3.48 (s, 2H), 5.41 (s, 2H), 7.0-7.48 (m, 8H), 7.81 (d, 1H), 8.04 (s, 1H), 8.16 (d, 1H), 8.42 (s, 1H), 9.78 (s, 1H), 11.50 (s, 1H), 11.92 (br s, 1H).

Example 54

1-(4-Methyl-benzyl)-1H-pyrazole-4-carboxylic acid (5-{5-[(2-hydroxy-ethylamino)-methyl]-1H-indol-2-yl}-6-oxo-1,6-dihydro-pyridin-3-yl)-amide

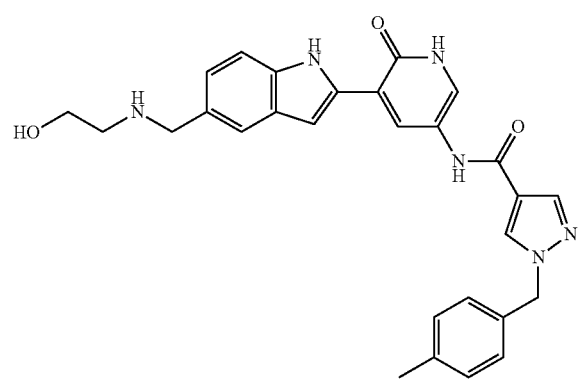 [SMILES: Cc1ccc(Cn2cc(C(=O)Nc3c[nH]c(=O)c(-c4cc5cc(CNCCO)ccc5[nH]4)c3)cn2)cc1]

The title compound was prepared by the route outlined in Scheme 8, following the same experimental procedures as for Example 51.

The title compound was purified by trituration with acetonitrile, and isolated as a yellow solid, 5 mg, 9%.

LC/MS: RT=1.41 Min (270 nm), m/z=497 [M+H]. Total run time 3.75 min (short pos).

¹H NMR (d₆ DMSO): δ 2.29 (s, 3H), 2.60 (q, 2H), 3.47 (q, 2H), 3.75 (s, 2H), 4.45 (t, 1H), 5.34 (s, 2H), 7.00 (s, 1H), 7.05 (d, 1H), 7.19 (m, 4H), 7.41-7.45 (m, 2H), 7.82 (d, 1H), 8.01 (s, 1H), 8.16 (d, 1H), 8.36 (s, 1H), 9.75 (s, 1H), 11.48 (s, 1H).

Example 55

1-(4-Chloro-benzyl)-1H-pyrazole-4-carboxylic acid [6-oxo-5-(5-pyrrolidin-1-ylmethyl-1H-indol-2-yl)-1,6-dihydro-pyridin-3-yl]-amide

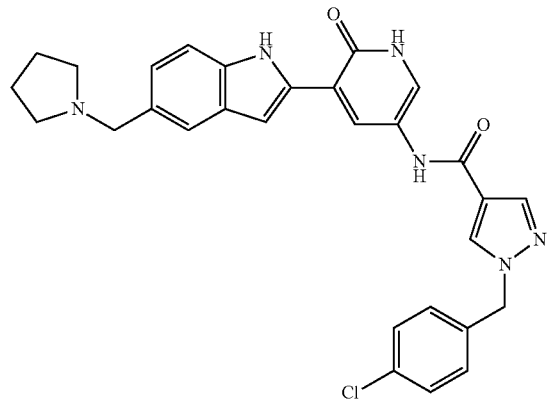 [SMILES: O=C(Nc1c[nH]c(=O)c(-c2cc3cc(CN4CCCC4)ccc3[nH]2)c1)c1cnn(Cc2ccc(Cl)cc2)c1]

The title compound was prepared by the route outlined in Scheme 8, following the same experimental procedures as for Example 51.

The title compound was purified by trituration with acetonitrile, and isolated as a yellow solid, 33 mg, 49%.

LC/MS: RT=0.96 Min (270 nm), m/z=527 [M+H]. Total run time 1.9 min (super short pos).

¹H NMR (d₆ DMSO): δ 1.62 (m, 4H), 2.40-2.48 (m, 4H), 3.60 (s, 2H), 5.41 (s, 2H), 6.96-7.46 (m, 8H), 7.80-7.84 (d, 1H), 8.04 (s, 1H), 8.17 (d, 1H), 8.42 (s, 1H), 9.78 (s, 1H), 11.50 (s, 1H), 11.90-12.00 (br s, 1H).

Example 56

1-Benzyl-1H-pyrazole-4-carboxylic acid [5-(5-{[ethyl-(2-hydroxy-ethyl)-amino]-methyl}-1H-indol-2-yl)-6-oxo-1,6-dihydro-pyridin-3-yl]-amide

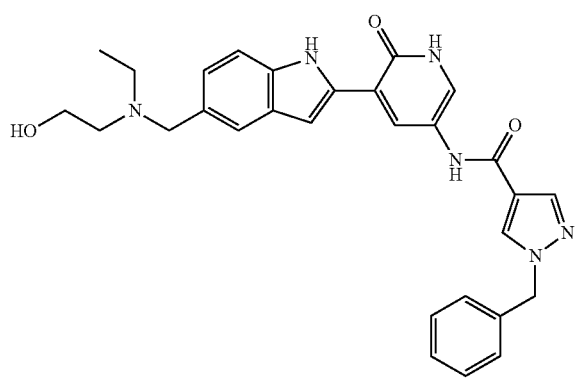 [SMILES: CCN(CCO)Cc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51.

The title compound was purified by trituration with acetonitrile, and isolated as a yellow solid, 13 mg, 17%.

LC/MS: RT=0.88 Min (270 nm), m/z=511 [M+H]. Total run time 1.9 min (super short pos).

$^1$H NMR (d$_6$ DMSO): δ 0.97-1.01 (t, 3H), 3.41-3.47 (q, 2H), 3.60 (s, 2H), 4.24-4.27 (t, 1H), 5.41 (s, 2H), 6.99-7.44 (m, 9H), 7.81-7.82 (d, 1H), 8.03 (s, 1H), 8.16-8.17 (d, 1H), 8.41 (s, 1H), 9.78 (s, 1H), 11.51 (s, 1H), 11.90-11.98 (br s, 1H).

Example 57

1-Benzyl-1H-pyrazole-4-carboxylic acid {5-[5-(3-fluoro-piperidin-1-ylmethyl)-1H-indol-2-yl]-6-oxo-1,6-dihydro-pyridin-3-yl}-amide

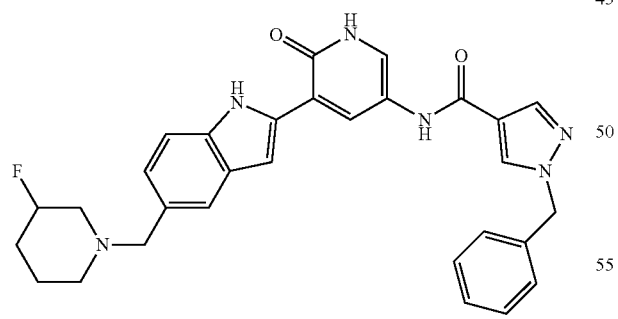

The title compound was prepared by the route outlined in Scheme 8, following the same experimental procedures as for Example 51.

The title compound was purified by trituration with acetonitrile, and isolated as a yellow solid, 25 mg, 33%.

LC/MS: RT=0.91 Min (270 nm), m/z=525 [M+H]. Total run time 1.9 min (super short pos).

$^1$H NMR (d$_6$ DMSO): δ 1.40-1.60 (m, 2H), 1.64-1.73 (m, 1H), 1.76-1.80 (m, 1H), 2.17-2.25 (m, 1H), 2.26-2.36 (m, 1H), 2.40-2.47 (m, 1H), 2.64-2.76 (m, 1H), 3.49-3.59 (d, 2H), 4.51-4.69 (m, 1H), 5.41 (s, 2H), 7.01-7.46 (m, 9H), 7.81-7.82 (d, 1H), 8.03 (s, 1H), 8.16-8.17 (d, 1H), 8.40 (s, 1H), 9.77 (s, 1H), 11.53 (s, 1H), 11.85-11.95 (br s, 1H).

Example 58

1-Benzyl-1H-pyrazole-4-carboxylic acid {5-[5-(4-methyl-piperazin-1-ylmethyl)-1H-indol-2-yl]-6-oxo-1,6-dihydro-pyridin-3-yl}-amide

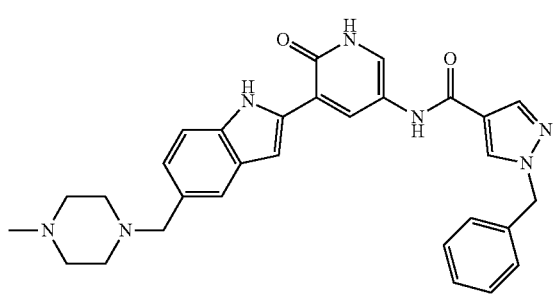 [SMILES: CN1CCN(Cc2ccc3[nH]c(-c4cc(NC(=O)c5cnn(Cc6ccccc6)c5)c[nH]c4=O)cc3c2)CC1]

The title compound was prepared by the route outlined in Scheme 8, following the same experimental procedures as for Example 51.

The title compound was purified by trituration with acetonitrile, and isolated as a yellow solid, 34 mg, 47%.

LC/MS: RT=1.55 Min (270 nm), m/z=522 [M+H]. Total run time 3.75 min (short pos).

$^1$H NMR (d$_6$ DMSO): δ 2.14 (s, 3H), 2.24-2.41 (m, 8H), 3.48 (s, 2H), 5.41 (s, 2H), 7.00-7.44 (m, 9H), 7.81-7.82 (d, 1H), 8.03 (s, 1H), 8.16-8.18 (d, 1H), 8.41 (s, 1H), 9.78 (s, 1H), 11.52 (s, 1H), 11.94-11.96 (br s, 1H).

Example 59

1-(4-Methyl-benzyl)-1H-pyrazole-4-carboxylic acid {5-[5-(4-methyl-piperazin-1-ylmethyl)-1H-indol-2-yl]-6-oxo-1,6-dihydro-pyridin-3-yl}-amide

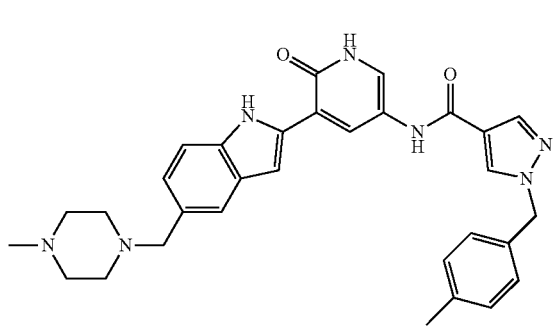 [SMILES: Cc1ccc(Cn2cc(C(=O)Nc3c[nH]c(=O)c(-c4cc5cc(CN6CCN(C)CC6)ccc5[nH]4)c3)cn2)cc1]

The title compound was prepared by the route outlined in Scheme 8, following the same experimental procedures as for Example 51.

The title compound was purified by trituration with acetonitrile, and isolated as a yellow solid, 63 mg, 62%.

LC/MS: RT=1.39 Min (270 nm), m/z=536 [M+H]. Total run time 3.75 min (short pos).

$^1$H NMR (d$_6$ DMSO): δ 2.14 (s, 3H), 2.26-2.44 (m, 11H), 3.48 (s, 2H), 5.34 (s, 2H), 7.00-7.03 (m, 2H), 7.19 (m, 4H), 7.41-7.44 (m, 2H), 7.82 (d, 1H), 8.01 (s, 1H), 8.16 (d, 1H), 8.36 (s, 1H), 9.76 (s, 1H), 11.50 (s, 1H), 11.97 (br s, 1H).

Example 60

1-Benzyl-1H-pyrazole-4-carboxylic acid {5-[5-(4-hydroxy-piperidin-1-ylmethyl)-1H-indol-2-yl]-6-oxo-1,6-dihydro-pyridin-3-yl}-amide

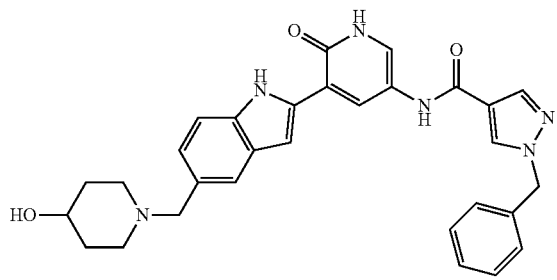 [SMILES: O=C(Nc1c[nH]c(=O)c(-c2cc3cc(CN4CCC(O)CC4)ccc3[nH]2)c1)c1cnn(Cc2ccccc2)c1]

The title compound was prepared by the route outlined in Scheme 8, following the same experimental procedures as for Example 51.

The title compound was purified by trituration with acetonitrile, and isolated as a yellow solid, 18 mg, 35%.

LC/MS: RT=1.59 Min (270 nm), m/z=523 [M+H]. Total run time 3.75 min (short pos).

$^1$H NMR (d$_6$ DMSO): δ 1.30-1.43 (m, 2H), 1.64-1.73 (m, 2H), 1.97-2.03 (t, 2H), 2.63-2.72 (m, 2H), 3.40-3.44 (m, 1H), 3.46 (s, 2H), 4.49-4.50 (d, 1H), 5.41 (s, 2H), 6.99-7.43 (m, 9H), 7.82-7.84 (d, 1H), 8.03 (s, 1H), 8.16-8.17 (d, 1H), 8.41 (s, 1H), 9.78 (s, 1H), 11.58 (s, 1H), 11.90 (br s, 1H).

Example 61

1-Benzyl-1H-pyrazole-4-carboxylic acid (5-{5-[(2-hydroxy-ethylamino)-methyl]-1H-indol-2-yl}-6-oxo-1,6-dihydro-pyridin-3-yl)-amide

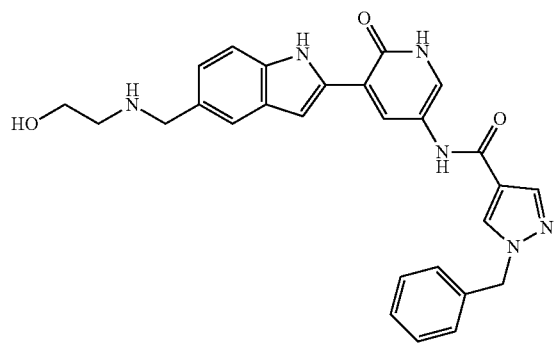 [SMILES: O=C(Nc1c[nH]c(=O)c(-c2cc3cc(CNCCO)ccc3[nH]2)c1)c1cnn(Cc2ccccc2)c1]

The title compound was prepared by the route outlined in Scheme 8, following the same experimental procedures as for Example 51.

The title compound was purified by trituration with acetonitrile, and isolated as a yellow solid, 8 mg, 15%.

LC/MS: RT=1.58 Min (270 nm), m/z=422 [Fragment]. Total run time 3.75 min (short pos).

$^1$H NMR (d$_6$ DMSO): δ 2.57-2.61 (t, 2H), 3.45-3.49 (m, 2H), 3.74 (s, 2H), 4.39-4.46 (m, 1H), 5.41 (s, 2H), 6.99-7.45 (m, 9H), 7.82-7.83 (d, 1H), 8.03 (s, 1H), 8.17-8.18 (d, 1H), 8.41 (s, 1H), 9.78 (s, 1H), 11.51 (s, 1H).

Example 62

1-(4-Methyl-benzyl)-1H-pyrazole-4-carboxylic acid (5-{5-[4-(2-hydroxy-ethyl)-piperazin-1-ylmethyl]-1H-indol-2-yl}-6-oxo-1,6-dihydro-pyridin-3-yl)-amide

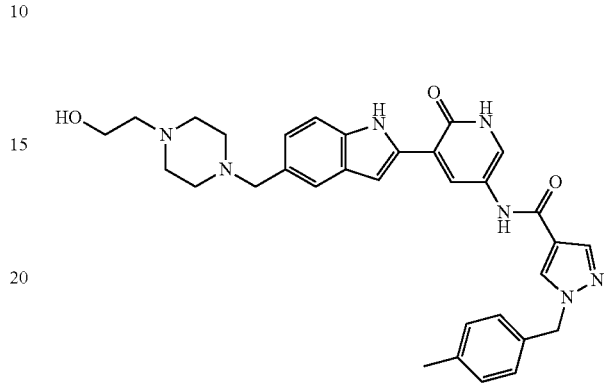

The title compound was prepared by the route outlined in Scheme 8, following the same experimental procedures as for Example 51.

The title compound was purified by trituration with acetonitrile, and isolated as a yellow solid, 26 mg, 23%.

LC/MS: RT=1.38 Min (270 nm), m/z=566 [M+H]. Total run time 3.75 min (short pos).

$^1$H NMR (d$_6$ DMSO): δ 2.29 (s, 3H), 2.32-2.45 (m, 10H), 3.44-3.48 (m, 4H), 4.32 (t, 1H), 5.34 (s, 2H), 7.00-7.03 (m, 2H), 7.19 (m, 4H), 7.41-7.44 (m, 2H), 7.82 (d, 1H), 8.01 (s, 1H), 8.16 (d, 1H), 8.36 (s, 1H), 9.76 (s, 1H), 11.50 (s, 1H), 11.96 (br s, 1H).

Example 63

1-(4-Chloro-benzyl)-1H-pyrazole-4-carboxylic acid {5-[5-(3-fluoro-piperidin-1-ylmethyl)-1H-indol-2-yl]-6-oxo-1,6-dihydro-pyridin-3-yl}-amide

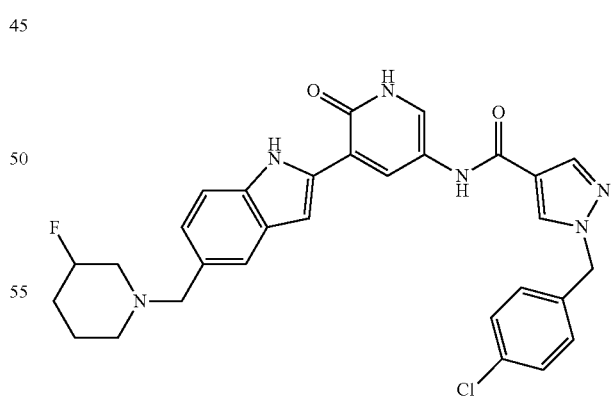

The title compound was prepared by the route outlined in Scheme 8, following the same experimental procedures as for Example 51.

The title compound was purified by preparative HPLC at pH 9 and isolated as a yellow solid, 4 mg, 6%.

LC/MS: RT=0.95 Min (270 nm), m/z=559 [M+H]. Total run time 1.9 min (super short pos).

¹H NMR (d₆ DMSO): δ 1.39-1.55 (m, 2H), 1.64-1.73 (m, 1H), 1.76-1.89 (m, 1H), 2.19-2.25 (m, 1H), 2.28-2.35 (m, 1H), 2.41-2.46 (m, 1H), 2.64-2.76 (m, 1H), 3.54-3.55 (d, 2H), 4.50-4.70 (m, 1H), 5.41 (s, 2H), 7.00-7.48 (m, 8H), 7.82-7.83 (d, 1H), 8.04 (s, 1H), 8.17-8.18 (d, 1H), 8.42 (s, 1H), 9.79 (s, 1H), 11.52 (s, 1H), 11.93-12.02 (br s, 1H).

Example 64

1-Benzyl-1H-pyrazole-4-carboxylic acid {5-[5-(4,4-difluoro-piperidin-1-ylmethyl)-1H-indol-2-yl]-6-oxo-1,6-dihydro-pyridin-3-yl}-amide

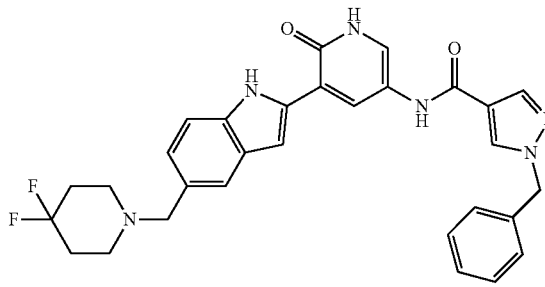

The title compound was prepared by the route outlined in Scheme 8, following the same experimental procedures as for Example 51.

The title compound was purified by trituration with acetonitrile, and isolated as a yellow solid, 17 mg, 48%.

LC/MS: RT=0.94 Min (270 nm), m/z=422 [other]. Total run time 1.9 min (super short pos).

¹H NMR (d₆ DMSO): δ 1.90-1.99 (m, 4H), 3.56 (s, 2H), 5.41 (s, 2H), 7.01-7.46 (m, 9H), 7.82-7.83 (d, 1H), 8.04 (s, 1H), 8.19-8.20 (d, 1H), 8.42 (s, 1H), 9.82 (s, 1H), 11.54 (s, 1H).

Example 65

1-Benzyl-1H-pyrazole-4-carboxylic acid (5-{5-[4-(2-hydroxy-ethyl)-piperazin-1-ylmethyl]-1H-indol-2-yl}-6-oxo-1,6-dihydro-pyridin-3-yl)-amide

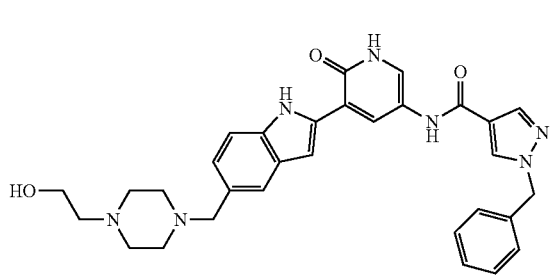 [SMILES: O=C(Nc1c[nH]c(=O)c(-c2cc3cc(CN4CCN(CCO)CC4)ccc3[nH]2)c1)c1cnn(Cc2ccccc2)c1]

The title compound was prepared by the route outlined in Scheme 8, following the same experimental procedures as for Example 51.

The title compound was purified by preparative HPLC at pH 4 and isolated as a yellow solid, 4 mg, 5%.

LC/MS: RT=0.85 Min (270 nm), m/z=552 [M+H]. Total run time 1.9 min (super short pos).

¹H NMR (d₄ MeOD): δ 2.74-3.13 (m, 10H), 3.70-3.73 (t, 2H), 3.97 (s, 2H), 5.40 (s, 2H), 7.05-7.58 (m, 9H), 7.90-7.91 (d, 1H), 8.05 (s, 1H), 8.24-8.25 (d, 1H), 8.50 (s, 1H).

Example 66

1-(4-Chloro-benzyl)-1H-pyrazole-4-carboxylic acid (5-{5-[4-(2-hydroxy-ethyl)-piperazin-1-ylmethyl]-1H-indol-2-yl}-6-oxo-1,6-dihydro-pyridin-3-yl)-amide

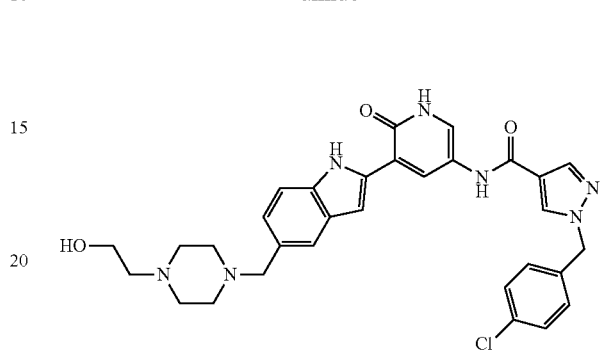

The title compound was prepared by the route outlined in Scheme 8, following the same experimental procedures as for Example 51.

The title compound was purified by preparative HPLC at pH 9 followed by trituration with acetonitrile and isolated as a yellow solid, 0.5 mg, 1%.

LC/MS: RT=0.89 Min (270 nm), m/z=586 [M+H]. Total run time 1.9 min (super short pos).

¹H NMR (d₄ MeOD): δ 2.48-2.71 (m, 8H), 3.62-3.68 (m, 4H), 5.40 (s, 2H), 7.02-7.51 (m, 8H), 7.93-7.94 (d, 1H), 8.06 (s, 1H), 8.21-8.22 (d, 1H), 8.28 (s, 1H), 8.54 (s, 1H).

Example 67

1-(4-Chloro-benzyl)-1H-pyrazole-4-carboxylic acid [5-(5-morpholin-4-ylmethyl-1H-indol-2-yl)-6-oxo-1,6-dihydro-pyridin-3-yl]-amide

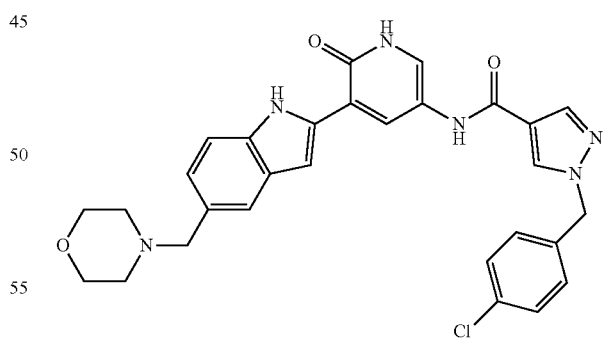

The title compound was prepared by the route outlined in Scheme 8, following the same experimental procedures as for Example 51.

The title compound was purified by preparative HPLC at pH 9 and isolated as a yellow solid, 6 mg, 10%.

LC/MS: RT=0.92 Min (270 nm), m/z=456 [Fragment]. Total run time 1.9 min (super short pos).

¹H NMR (d₆ DMSO): δ 2.32-2.38 (m, 4H), 3.49 (s, 2H), 3.55-3.57 (m, 4H), 5.41 (s, 2H), 7.01-7.05 (m, 2H), 7.28-

7.32 (m, 2H), 7.41-7.47 (m, 4H), 7.82-7.83 (d, 1H), 8.05 (s, 1H), 8.17-8.18 (d, 1H), 8.42 (s, 1H), 9.81 (s, 1H), 11.53 (s, 1H), 11.96-12.04 (br s, 1H).

Example 68

1-Benzyl-1H-pyrazole-4-carboxylic acid (5-{5-[(2-methanesulfonyl-ethylamino)-methyl]-1H-indol-2-yl}-6-oxo-1,6-dihydro-pyridin-3-yl)-amide

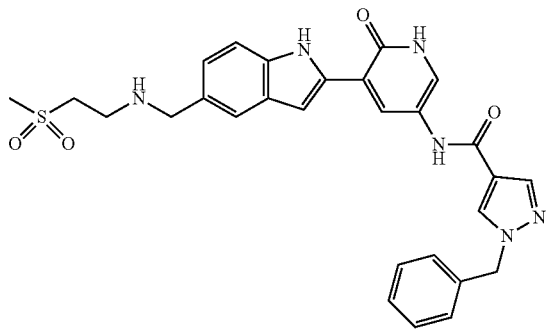 [SMILES: CS(=O)(=O)CCNCc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51.

The title compound was purified by preparative HPLC at pH 9 and isolated as a yellow solid, 3 mg, 4%.

LC/MS: RT=0.86 Min (270 nm), m/z=422 [Fragment]. Total run time 1.9 min (super short pos).

$^1$H NMR (d$_6$ DMSO): δ 3.13 (s, 3H), 3.52-3.62 (m, 4H), 4.22-4.28 (m, 2H), 5.41 (s, 2H), 7.12-7.40 (m, 7H), 7.58-7.60 (d, 1H), 7.69 (s, 1H), 7.80 (s, 1H), 8.05 (s, 1H), 8.26-8.27 (d, 1H), 8.43 (s, 1H), 9.85 (s, 1H), 11.75 (s, 1H), 12.04-12.11 (br s, 1H).

Example 69

1-Benzyl-1H-pyrazole-4-carboxylic acid {5-[5-(2,6-dimethyl-morpholin-4-ylmethyl)-1H-indol-2-yl]-6-oxo-1,6-dihydro-pyridin-3-yl}-amide

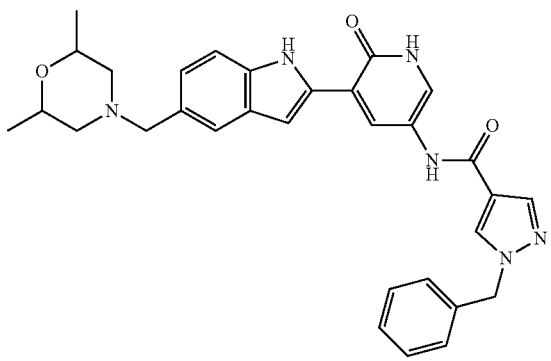 [SMILES: CC1CN(Cc2ccc3[nH]c(-c4cc(NC(=O)c5cnn(Cc6ccccc6)c5)c[nH]c4=O)cc3c2)CC(C)O1]

The title compound was prepared by the route outlined in Scheme 8, following the same experimental procedures as for Example 51.

The title compound was purified by trituration with acetonitrile, and isolated as a yellow solid, 2 mg, 10%.

LC/MS: RT=0.92 Min (254 nm), m/z=537 [M+H]. Total run time 1.9 min (super short pos).

$^1$H NMR (d$_4$ MeOD): δ 1.10 (d, 6H), 1.76, (t, 2H), 2.79 (d, 2H), 3.58 (s, 2H), 3.62-3.72 (m, 2H), 5.4 (s, 2H), 7.01 (s, 1H), 7.12 (dd, 1H), 7.28-7.42 (m, 6H), 7.49 (s, 1H), 7.94 (d, 1H), 8.06 (s, 1H), 8.22 (d, 1H), 8.25 (s, 1H)

Example 70

1-Benzyl-1H-pyrazole-4-carboxylic acid {5-[5-(3,4-dimethyl-piperazin-1-ylmethyl)-1H-indol-2-yl]-6-oxo-1,6-dihydro-pyridin-3-yl}-amide

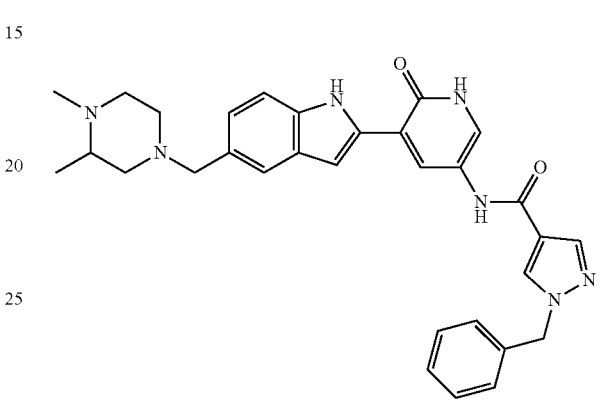

The title compound was prepared by the route outlined in Scheme 8, following the same experimental procedures as for Example 51.

The title compound was purified by trituration with acetonitrile, and isolated as a yellow solid, 17 mg, 23%.

LC/MS: RT=0.87 Min (254 nm), m/z=536 [M+H]. Total run time 1.9 min (super short pos).

$^1$H NMR (d$_4$ MeOD): δ 1.03 (d, 3H), 1.91 (t, 1H), 2.15-2.26 (br m, 2H), 2.27 (s, 3H), 2.34 (m, 1H), 2.75-2.88 (m, 3H), 3.55-3.63 (m, 2H), 5.4 (s, 2H), 7.12 (s, 1H), 8.04-8.1 (dd, 1H), 7.28-7.41 (m, 6H), 7.48 (s, 1H), 7.94 (d, 1H), 8.06 (s, 1H), 8.21 (d, 1H), 8.25 (s, 1H).

Example 71

1-Benzyl-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide

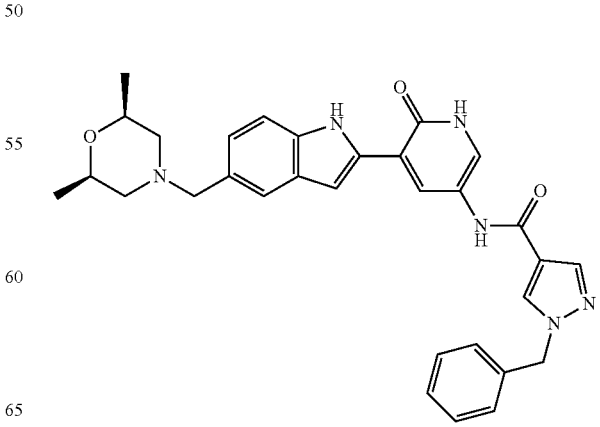

The title compound was prepared by the route outlined in Scheme 8, following the same experimental procedures as for Example 51.

The title compound was purified by trituration with acetonitrile, and isolated as a yellow solid, 84 mg, 62%.

LC/MS: RT=1.56 Min (270 nm), m/z=537 [M+H]. Total run time 3.75 min (short pos).

$^1$H NMR (d$_6$ DMSO): δ 1.00 (d, 6H), 1.62 (m, 2H), 2.68 (m, 2H), 3.47 (s, 2H), 3.55 (m, 2H), 5.41 (s, 2H), 7.01-7.04 (m, 2H), 7.28-7.46 (m, 7H), 7.82 (d, 1H), 8.03 (s, 1H), 8.16 (d, 1H), 8.41 (s, 1H), 9.79 (s, 1H), 11.53 (s, 1H), 11.99 (br s, 1H).

Example 72

1-(4-Isopropylbenzyl)-1H-pyrazole-4-carboxylic acid {5-[5-(2,6-dimethylmorpholin-4-ylmethyl)-1H-indol-2-yl)-6-oxo-1,6-dihydropyridin-3-yl}-amide

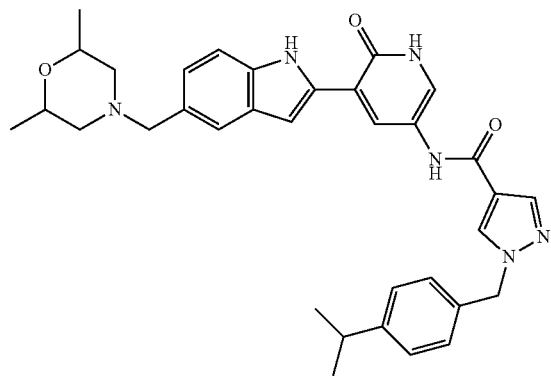 [SMILES: CC1CN(Cc2ccc3[nH]c(-c4cc(NC(=O)c5cnn(Cc6ccc(C(C)C)cc6)c5)c[nH]c4=O)cc3c2)CC(C)O1]

The title compound was prepared by the route outlined in Scheme 8, following the same experimental procedures as for Example 51.

The title compound was purified by flash chromatography on silica eluting with dichloromethane/methanol (19:1) to give a pale brown gum followed by trituration with diethyl ether, and isolated as a yellow powder, 30 mg, 23%.

LC/MS: RT=1.76 Min (270 nm), m/z=579 [M+H]. Total run time 3.75 min (short pos).

$^1$H NMR (d$_6$ DMSO): δ 1.10 (br s, 6H), 1.25 (d, 6H), 1.70 (br s, 2H), 2.80 (br m, 2H), 2.90 (m, 1H), 3.60 (br m, 3H), 5.40 (s, 2H), 7.10 (br s, 1H), 7.30 (m, 3H), 7.50 (br s, 2H), 7.90 (br s, 1H), 8.10 (s, 1H), 8.20 (br s, 1H), 8.50 (s, 1H), 9.85 (s, 1H), 11.52 (br s, 1H), 12.00 (br s, 1H).

Example 73

1-(4-Isopropylbenzyl)-1H-pyrazole-4-carboxylic acid {5-[5-(4-fluoropiperidin-1-ylmethyl)-1H-indol-2-yl)-6-oxo-1,6-dihydropyridin-3-yl}-amide

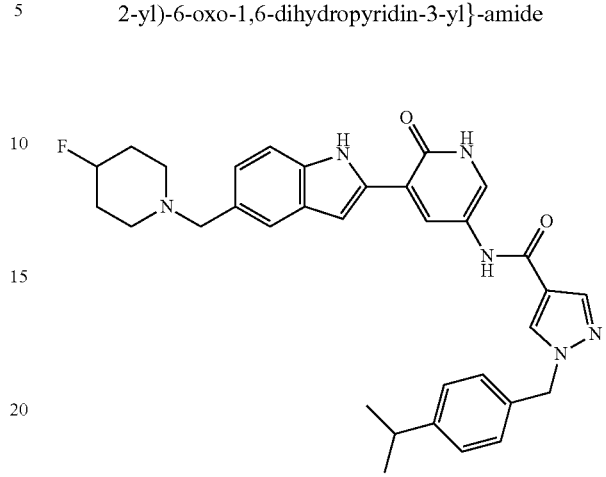

The title compound was prepared by the route outlined in Scheme 8, following the same experimental procedures as for Example 51.

The title compound was purified by flash chromatography on silica eluting with dichloromethane/methanol (19:1) to give a pale brown gum followed by trituration with diethyl ether, and isolated as a yellow powder, 35 mg, 23%.

LC/MS: RT=1.65 Min (270 nm), m/z=567 [M+H]. Total run time 3.75 min (short pos).

$^1$H NMR (d$_6$ DMSO): δ 1.25 (d, 6H), 1.75 (br m, 2H), 1.90 (br m, 2H), 2.35 (br m, 2H), 2.90 (m, 1H), 3.60 (s, 2H), 4.70 (br s, 1H), 4.80 (br s, 1H), 5.40 (s, 2H), 7.00 (m, 2H), 7.30 (m, 4H), 7.50 (m, 2H), 7.85 (d, 1H), 8.10 (s, 1H), 8.20 (d, 1H), 8.45 (s, 1H), 9.85 (s, 1H), 11.54 (br s, 1H), 12.00 (br s, 1H).

Example 74

1-(4-Methyl-benzyl)-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide

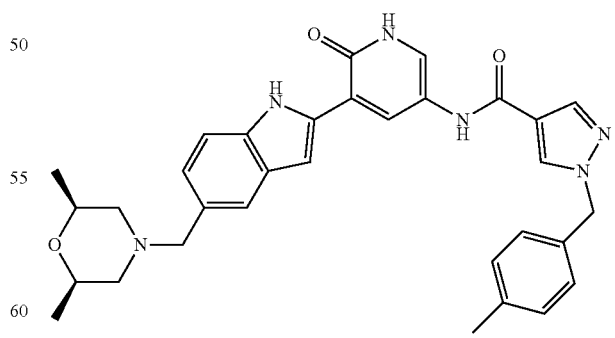

The title compound was prepared by the route outlined in Scheme 8, following the same experimental procedures as for Example 51.

The title compound was purified by trituration with acetonitrile, and isolated as a yellow solid, 34 mg, 42%.

LC/MS: RT=0.98 Min (270 nm), m/z=551 [M+H]. Total run time 1.9 min (super short pos).
¹H NMR (d₆ DMSO): δ 1.0 (d, 6H), 1.62 (dd, 2H), 2.3 (s, 3H), 2.68 (dd, 2H) 3.46 (s, 2H), 3.5-3.6 (m, 2H), 5.35 (s, 2H), 7.0-7.05 (m, 2H), 7.2 (s, 4H), 7.40-7.46 (m, 2H), 7.82 (d, 1H), 8.01 (s, 1H), 8.16 (s, 1H), 8.37 (s, 1H), 9.79 (br s, 1H), 11.55 (br s, 1H), 11.95 (br s, 1H)

Example 75

1-(4-Methyl-benzyl)-1H-pyrazole-4-carboxylic acid [5-(5-diethylaminomethyl-1H-indol-2-yl)-6-oxo-1,6-dihydro-pyridin-3-yl]-amide

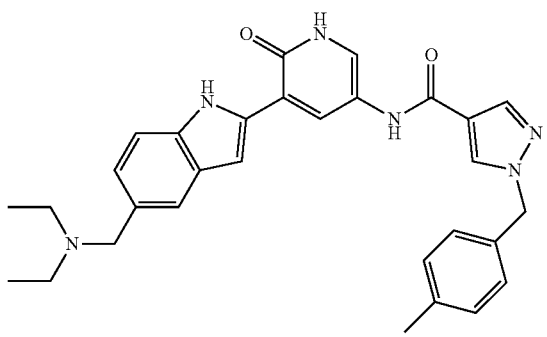 [SMILES: CCN(CC)Cc1ccc2[nH]c(-c3cc(NC(=O)c4cnn(Cc5ccc(C)cc5)c4)c[nH]c3=O)cc2c1]

The title compound was prepared by the route outlined in Scheme 8, following the same experimental procedures as for Example 51.
The title compound was purified by trituration with acetonitrile, and isolated as a yellow solid, 36 mg, 48%.
LC/MS: RT=0.95 Min (270 nm), m/z=509 [M+H]. Total run time 1.9 min (super short pos).
¹H NMR (d₆ DMSO): δ 0.98 (q, 6H), 2.28 (s, 3H), 2.46 (q, 4H), 3.55 (s, 2H), 5.34 (s, 2H), 7.0 (d, 1H), 7.05 (dd, 1H), 7.19 (s, 4H), 7.41-7.44 (m, 2H), 7.81 (d, 1H), 8.01 (s, 1H), 8.15 (s, 1H), 8.37 (s, 1H), 9.78 (br s, 1H), 11.5 (br s, 1H), 11.95 (br s, 1H)

Example 76

1-(4-Fluoro-benzyl)-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide

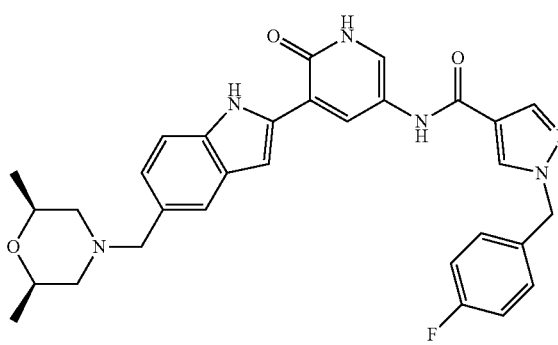

The title compound was prepared by the route outlined in Scheme 8, following the same experimental procedures as for Example 51.

The title compound was purified by trituration with acetonitrile, and isolated as a yellow solid, 2 mg, 6%.
LC/MS: RT=1.57 Min (270 nm), m/z=555 [M+H]. Total run time 3.75 min (short pos).
¹H NMR (d₆ DMSO): δ 1.00 (d, 6H), 1.60 (t, 2H), 2.7 (d, 2H), 3.45 (s, 2H), 3.55 (m, 2H), 5.40 (s, 2H), 6.89 (br, 1H), 7.00 (dd, 1H), 7.20 (t, 2H), 7.40 (m, 4H), 7.82 (d, 1H), 8.05 (s, 1H), 8.15 (br, 1H), 8.40 (s, 1H), 9.70 (s, 1H).

Example 77

1-Benzyl-1H-pyrazole-4-carboxylic acid (5-{5-[(cyclohexyl-methyl-amino)-methyl]-1H-indol-2-yl}-6-oxo-1,6-dihydro-pyridin-3-yl)-amide

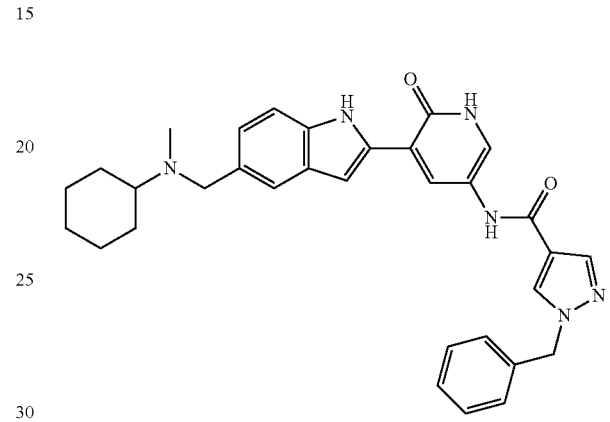

The title compound was prepared by the route outlined in Scheme 8, following the same experimental procedures as for Example 51.
The title compound was purified by trituration with acetonitrile, and isolated as a yellow solid, 26 mg, 44%.
LC/MS: RT=1.65 Min (270 nm), m/z=535 [M+H]. Total run time 3.75 min (short pos).
¹H NMR (d₆ DMSO): δ 1.05-1.33 (m, 5H), 1.57 (m, 1H), 1.73-1.81 (m, 4H), 2.09 (s, 3H), 2.41 (m, 1H), 3.57 (s, 2H), 5.41 (s, 2H), 6.98-7.04 (m, 2H), 7.28-7.43 (m, 7H), 7.82 (d, 1H), 8.03 (s, 1H), 8.15 (d, 1H), 8.41 (s, 1H), 9.79 (s, 1H), 11.50 (s, 1H), 11.98 (br s, 1H).

Example 78

1-Benzyl-1H-pyrazole-4-carboxylic acid {5-[5-(4-methyl-piperidin-1-ylmethyl)-1H-indol-2-yl]-6-oxo-1,6-dihydro-pyridin-3-yl}-amide

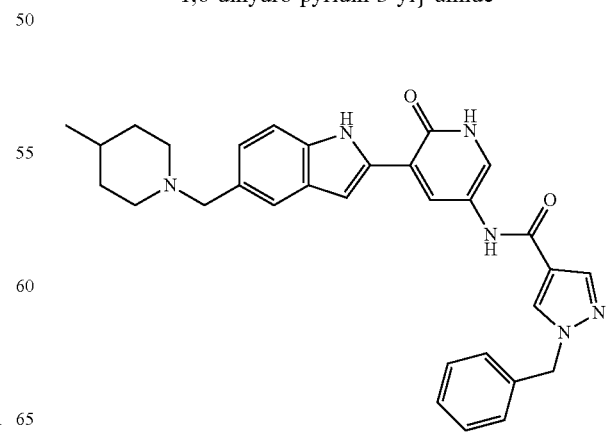

The title compound was prepared by the route outlined in Scheme 8, following the same experimental procedures as for Example 51.

The title compound was purified by trituration with acetonitrile, and isolated as a yellow solid, 34 mg, 62%.

LC/MS: RT=1.61 Min (270 nm), m/z=521 [M+H]. Total run time 3.75 min (short pos).

$^1$H NMR (d$_6$ DMSO): δ 0.87 (d, 3H), 1.12 (m, 2H), 1.29 (m, 1H), 1.53 (d, 2H), 1.87 (t, 2H), 2.78 (d, 2H), 3.46 (s, 2H), 5.41 (s, 2H), 7.00-7.02 (m, 2H), 7.28-7.44 (m, 7H), 7.82 (d, 1H), 8.03 (s, 1H), 8.16 (d, 1H), 8.41 (s, 1H), 9.79 (s, 1H), 11.50 (s, 1H), 11.99 (br s, 1H).

Example 79

1-Benzyl-1H-pyrazole-4-carboxylic acid [5-(5-{[(2-methoxy-ethyl)-methyl-amino]-methyl}-1H-indol-2-yl)-6-oxo-1,6-dihydro-pyridin-3-yl]-amide

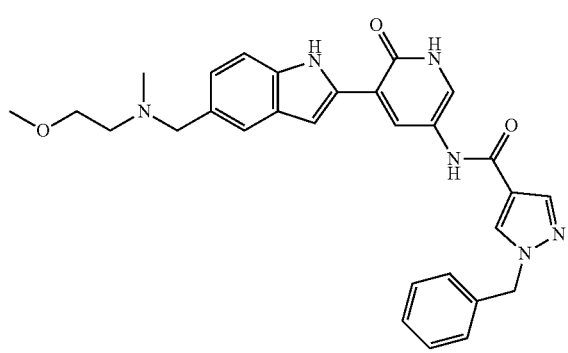 [SMILES: COCCN(C)Cc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51.

The title compound was purified by trituration with acetonitrile, and isolated as a yellow solid, 20 mg, 31%.

LC/MS: RT=1.52 Min (270 nm), m/z=511 [M+H]. Total run time 3.75 min (short pos).

$^1$H NMR (d$_6$ DMSO): δ 2.15 (s, 3H), 2.50 (t, 2H), 3.22 (s, 3H), 3.44 (t, 2H), 3.52 (s, 2H), 5.41 (s, 2H), 7.00-7.04 (m, 2H), 7.28-7.45 (m, 7H), 7.82 (d, 1H), 8.03 (s, 1H), 8.16 (d, 1H), 8.41 (s, 1H), 9.79 (s, 1H), 11.51 (s, 1H), 11.99 (br s, 1H).

Example 80

1-(4-Fluoro-benzyl)-1H-pyrazole-4-carboxylic acid [6-oxo-5-(5-piperidin-1-ylmethyl-1H-indol-2-yl)-1,6-dihydro-pyridin-3-yl]-amide

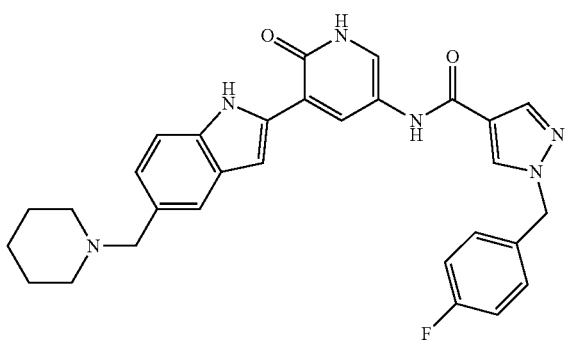 [SMILES: O=C(Nc1c[nH]c(=O)c(-c2cc3cc(CN4CCCCC4)ccc3[nH]2)c1)c1cnn(Cc2ccc(F)cc2)c1]

The title compound was prepared by the route outlined in Scheme 8, following the same experimental procedures as for Example 51.

The title compound was purified by trituration with acetonitrile followed by preparative HPLC at pH 4 and isolated as a yellow solid, 3 mg, 5%.

LC/MS: RT=0.93 Min (270 nm), m/z=525 [M+H]. Total run time 1.9 min (super short pos).

$^1$H NMR (d$_6$ DMSO): δ 1.4 (m, 2H), 1.50 (m, 5H), 2.40 (m, 3H), 3.45 (s, 2H), 5.40 (s, 2H), 7.02 (br, 2H), 7.05 (m, 1H), 7.22 (t, 1H), 7.35 (m, 2H), 7.45 (m, 2H), 7.80 (d, 1H), 8.05 (s, 1H), 8.16 (d, 1H), 8.40 (s, 1H), 9.80 (s, 1H), 11.52 (s, 1H)

Example 81

1-(4-Fluoro-benzyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

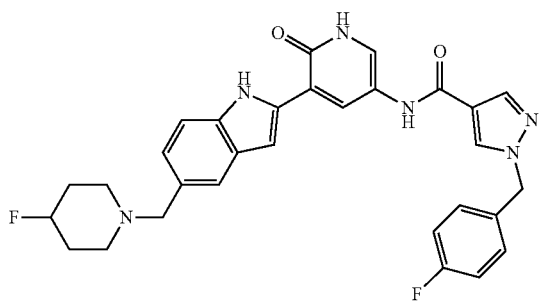 [SMILES: O=C(Nc1c[nH]c(=O)c(-c2cc3cc(CN4CCC(F)CC4)ccc3[nH]2)c1)c1cnn(Cc2ccc(F)cc2)c1]

The title compound was prepared by the route outlined in Scheme 8, following the same experimental procedures as for Example 51.

The title compound was purified by trituration with acetonitrile, and isolated as a yellow solid, 20 mg, 37%.

LC/MS: RT=1.58 Min (270 nm), m/z=543 [M+H]. Total run time 3.75 min (short pos).

$^1$H NMR (d$_6$ DMSO): δ 1.70 (m, 2H), 1.85 (m, 2H), 2.3 (m, 2H), 3.50 (s, 2H), 4.65 (br d, 1H), 5.40 (s, 2H), 6.95 (br s, 1H), 7.00 (dd, 1H), 7.25 (t, 2H), 7.40 (m, 4H), 7.85 (d, 1H), 8.05 (s, 1H), 8.15 (s, 1H), 8.40 (s, 1H), 9.75 (s, 1H),

Example 82

1-(4-Fluoro-benzyl)-1H-pyrazole-4-carboxylic acid {5-[5-(4-methyl-piperidin-1-ylmethyl)-1H-indol-2-yl]-6-oxo-1,6-dihydro-pyridin-3-yl}-amide

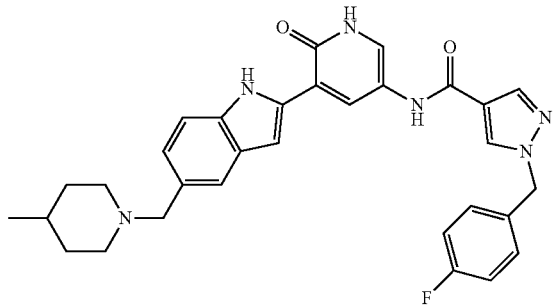 [SMILES: CC1CCN(Cc2ccc3[nH]c(-c4cc(NC(=O)c5cnn(Cc6ccc(F)cc6)c5)c[nH]c4=O)cc3c2)CC1]

The title compound was prepared by the route outlined in Scheme 8, following the same experimental procedures as for Example 51.

The title compound was purified by trituration with acetonitrile, and isolated as a yellow solid, 49 mg, 48%.

LC/MS: RT=1.63 Min (270 nm), m/z=539 [M+H]. Total run time 3.75 min (short pos).

$^1$H NMR (d$_6$ DMSO): δ 0.90 (d, 3H), 1.10 (m, 2H), 1.30 (m, 1H), 1.58 (d, 2H), 1.85 (t, 2H), 2.80 (d, 2H), 3.40 (s, 2H), 5.4 (s, 2H), 6.90 (br, 1H), 7.00 (dd, 1H), 7.22 (t, 2H), 7.38 (m, 4H), 7.84 (d, 1H), 8.05 (s, 1H), 8.10 (s, 1H), 8.40 (s, 1H), 9.75 (s, 1H),

Example 83

1-(4-Fluoro-benzyl)-1H-pyrazole-4-carboxylic acid [5-(5-ethylaminomethyl-1H-indol-2-yl)-6-oxo-1,6-dihydro-pyridin-3-yl]-amide

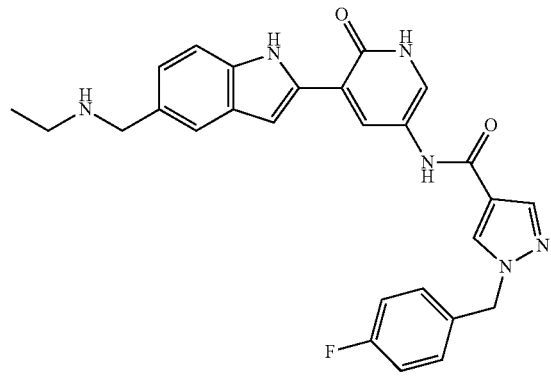 [SMILES: CCNCc1ccc2[nH]c(-c3cc(NC(=O)c4cnn(Cc5ccc(F)cc5)c4)c[nH]c3=O)cc2c1]

The title compound was prepared by the route outlined in Scheme 8, following the same experimental procedures as for Example 51.

The title compound was purified by trituration with acetonitrile followed by preparative HPLC at pH 4, to furnish the title compound as a yellow solid, 16 mg, 18%.

LC/MS: RT=0.92 Min (270 nm), m/z=440 [Fragment]. Total run time 1.9 min (super short pos).

$^1$H NMR (d$_6$ DMSO): δ 1.05 (t, 3H), 2.65 (q, 2H), 3.88 (s, 2H), 5.4 (s, 2H), 7.04 (d, 1H), 7.06 (dd, 1H), 7.22 (t, 2H), 7.38 (m, 2H), 7.55 (dd, 1H), 7.58 (s, 1H), 7.80 (s, 1H), 8.05 (s, 1H), 8.25 (d, 1H), 8.35 (s, 1H), 8.44 (s, 1H) 9.85 (s, 1H), 11.6 (s, 1H).

Example 84

1-(4-Fluoro-benzyl)-1H-pyrazole-4-carboxylic acid (5-{5-(cyclohexyl-methyl-amino)-methyl]-1H-indol-2-yl}-6-oxo-1,6-dihydropyridin-3-yl)-amide

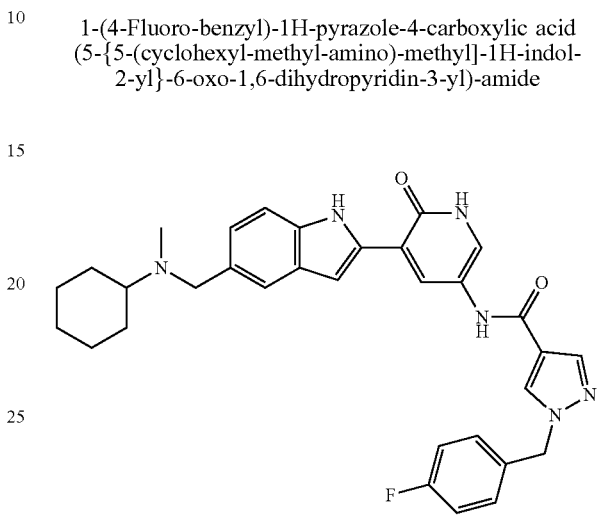

The title compound was prepared by the route outlined in Scheme 8, following the same experimental procedures as for Example 51.

The title compound was purified by trituration with acetonitrile followed by preparative HPLC at pH 9, to furnish the title compound as a yellow solid, 12 mg, 15%.

LC/MS: RT=1.68 Min (270 nm), m/z=553 [M+H]. Total run time 3.75 min (short pos).

$^1$H NMR (d$_6$ DMSO): δ 1.0-1.2 (m, 4H), 1.2-1.4 (m, 2H), 1.6 (d, 1H), 1.66-1.84 (m, 4H), 2.28 (s, 3H), 3.62, (s, 2H), 5.4 (s, 2H), 7.02 (d, 1H), 7.04-7.08 (dd, 1H), 7.24 (t, 2H), 7.34-7.40 (m, 2H), 7.42-7.46 (m, 2H), 7.8 (d, 1H), 8.02 (s, 1H), 8.18 (s, 1H), 8.20 (s, 1H), 9.56 (s, 1H), 11.5 (s, 1H).

Example 85

1-(1-Phenyl-ethyl)-1H-pyrazole-4-carboxylic acid [6-oxo-5-(5-piperidin-1-ylmethyl-1H-indol-2-yl)-1,6-dihydro-pyridin-3-yl]-amide

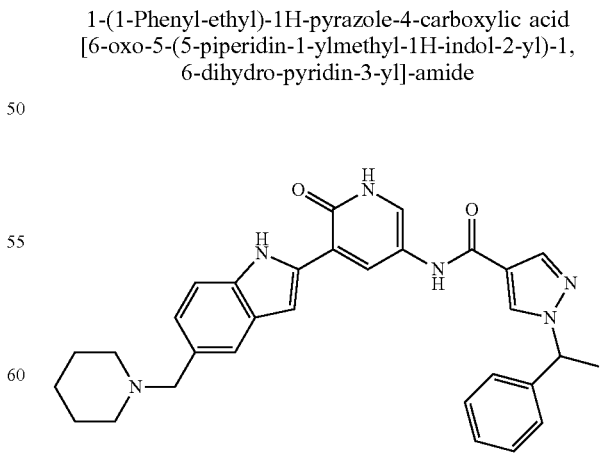

The title compound was prepared by the route outlined in Scheme 8, following the same experimental procedures as for Example 51.

The title compound was purified by trituration with acetonitrile, and isolated as a yellow solid, 37 mg, 54%.

LC/MS: RT=0.95 Min (270 nm), m/z=521 [M+H]. Total run time 1.9 min (super short pos).

$^1$H NMR (d$_6$ DMSO): δ 1.32-1.42 (m, 2H), 1.43-1.52 (m, 4H), 1.83-1.84 (d, 3H), 2.25-2.36 (m, 4H), 3.45 (s, 2H), 5.67-5.72 (q, 1H), 7.01-7.44 (m, 9H), 7.82-7.83 (d, 1H), 8.03 (s, 1H), 8.16-8.17 (d, 1H), 8.45 (s, 1H), 9.78 (s, 1H), 11.51 (s, 1H), 11.92-12.03 (br s, 1H).

Example 86

1-(1-Phenyl-ethyl)-1H-pyrazole-4-carboxylic acid [5-(5-morpholin-4-ylmethyl-1H-indol-2-yl)-6-oxo-1,6-dihydro-pyridin-3-yl]-amide

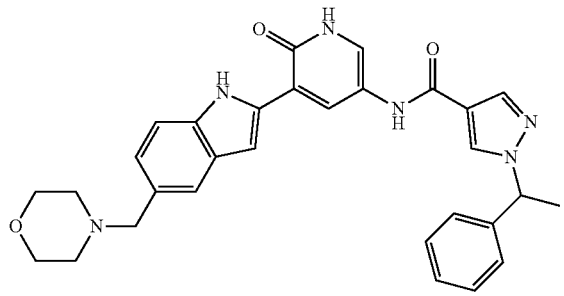 [SMILES: CC(c1ccccc1)n1cc(C(=O)Nc2c[nH]c(=O)c(-c3cc4cc(CN5CCOCC5)ccc4[nH]3)c2)cn1]

The title compound was prepared by the route outlined in Scheme 8, following the same experimental procedures as for Example 51.

The title compound was purified by trituration with acetonitrile, and isolated as a yellow solid, 15 mg, 23%.

LC/MS: RT=0.89 Min (270 nm), m/z=523 [M+H]. Total run time 1.9 min (super short pos).

$^1$H NMR (d$_6$ DMSO): δ 1.83-1.85 (d, 3H), 2.35 (m, 4H), 3.49 (s, 2H), 3.55-3.57 (m, 4H), 5.67-5.74 (q, 1H), 6.99-7.46 (m, 9H), 7.82-7.83 (d, 1H), 8.04 (s, 1H), 8.16-8.17 (d, 1H), 8.45 (s, 1H), 9.78 (s, 1H), 11.53 (s, 1H), 11.90-12.05 (br s, 1H).

Example 87

1-(1-Phenyl-ethyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

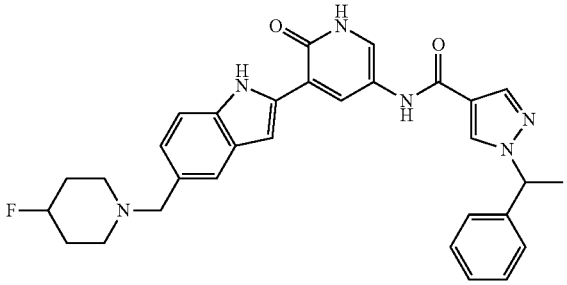 [SMILES: CC(c1ccccc1)n1cc(C(=O)Nc2c[nH]c(=O)c(-c3cc4cc(CN5CCC(F)CC5)ccc4[nH]3)c2)cn1]

The title compound was prepared by the route outlined in Scheme 8, following the same experimental procedures as for Example 51.

The title compound was purified by trituration with acetonitrile, and isolated as a yellow solid, 16 mg, 46%.

LC/MS: RT=0.93 Min (270 nm), m/z=539 [M+H]. Total run time 1.9 min (super short pos).

$^1$H NMR (d$_6$ DMSO): δ 1.66-1.76 (m, 2H), 1.83-1.85 (m, 5H), 2.23-2.32 (m, 2H), 3.50 (s, 2H), 4.60-4.70 (d, 1H), 5.67-5.72 (q, 1H), 7.0-7.05 (m, 2H), 7.26-7.45 (m, 7H), 7.82-7.83 (d, 1H), 8.04 (s, 1H), 8.16-8.17 (d, 1H), 8.45 (s, 1H), 9.78 (s, 1H), 11.53 (s, 1H), 11.95-12.00 (br s, 1H).

Example 88

1-[1-(4-Fluoro-phenyl)-ethyl]-1H-pyrazole-4-carboxylic acid [6-oxo-5-(5-piperidin-1-ylmethyl-1-H-indol-2-yl)-1,6-dihydro-pyridin-3-yl]-amide

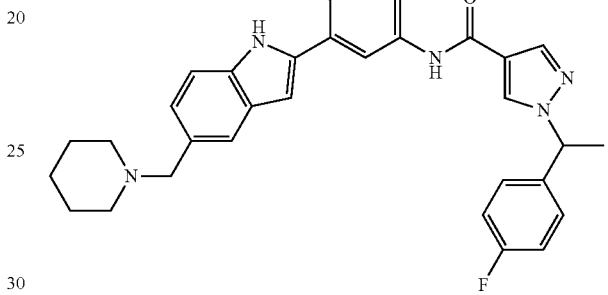

The title compound was prepared by the route outlined in Scheme 8, following the same experimental procedures as for Example 51.

The title compound was purified by trituration with acetonitrile, and isolated as a yellow solid, 3 mg, 9%.

LC/MS: RT=0.95 Min (254 nm), m/z=539 [M+H]. Total run time 1.9 min (super short pos).

$^1$H NMR (d$_6$ DMSO): δ 1.36-1.40 (br s, 2H), 1.43-1.50 (br m, 4H), 1.82 (d, 3H), 2.26-2.32 (br m, 4H), 3.44 (s, 2H), 5.70 (q, 1H), 7.00 (m, 2H), 7.20 (m, 2H), 7.32-7.44 (m, 4H), 7.82 (d, 1H), 8.02 (s, 1H), 8.18 (d, 1H), 8.44 (s, 1H), 9.80 (s, 1H), 11.52 (s, 1H), 12.00 (br s, 1H)

Example 89

1-[1-(4-Fluoro-phenyl)-ethyl]-1H-pyrazole-4-carboxylic acid {5-[5-(4-methylpiperazin-1-ylmethyl)-1H-indol-2-yl]-6-oxo-1,6-dihydro-pyridin-3-yl}-amide

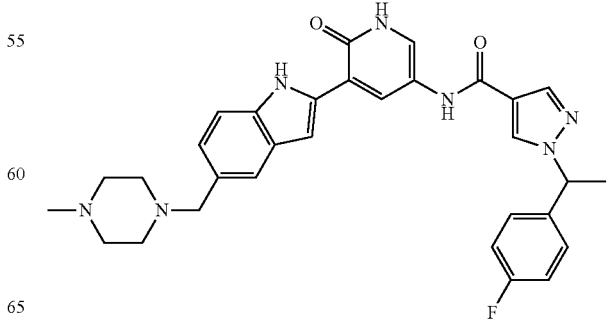

The title compound was prepared by the route outlined in Scheme 8, following the same experimental procedures as for Example 51.

The title compound was purified by trituration with acetonitrile, and isolated as a yellow solid, 9 mg, 30%.

LC/MS: RT=0.89 Min (254 nm), m/z=554 [M+H]. Total run time 1.9 min (super short pos).

¹H NMR (d₆ DMSO): δ 1.80 (d, 3H), 2.15 (s, 3H), 2.2-2.4 (br m, 8H), 3.42 (s, 2H), 5.70 (q, 1H), 7.00 (m, 2H), 7.18-7.22 (m, 2H), 7.36-7.40 (m, 2H), 7.4-7.48 (m, 2H), 7.82 (d, 1H), 8.04 (s, 1H), 8.16 (d, 1H), 8.44 (s, 1H), 9.78 (s, 1H), 11.52 (s, 1H), 12.00 (br s, 1H).

Example 90

1-[1-(Fluoro-phenyl)-ethyl]-1H-pryrazole-4-carboxylic acid {5-[5-(4-fluoro-piperidin-1ylmethyl)-1H-indol-2-yl]-6-oxo-1,6-dihydro-pyridin-3-yl}-amide

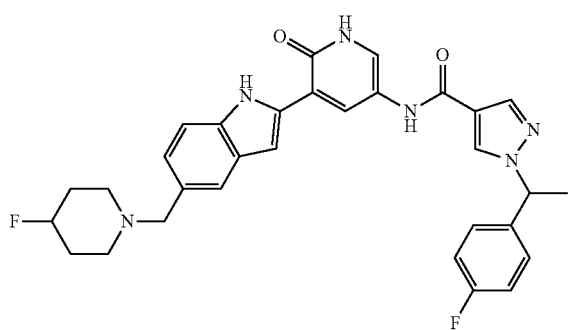 [SMILES: CC(c1ccc(F)cc1)n1cc(C(=O)Nc2c[nH]c(=O)c(-c3cc4cc(CN5CCC(F)CC5)ccc4[nH]3)c2)cn1]

The title compound was prepared by the route outlined in Scheme 8, following the same experimental procedures as for Example 51.

The title compound was purified by trituration with acetonitrile, and isolated as a yellow solid, 2 mg, 14%.

LC/MS: RT=0.95 Min (254 nm), m/z=557 [M+H]. Total run time 1.9 min (super short pos).

¹H NMR (d₆ DMSO): δ 1.60-1.73 (m, 2H), 1.73-1.90 (m, 2H), 1.81 (d, 3H), 2.20-2.30 (m, 2H), 2.43-2.55 (m, 2H obscured by DMSO peak), 3.50 (s, 2H), 4.56-4.76 (m, 1H), 5.70 (q, 1H), 7.00 (m, 2H), 7.20 (m, 2H), 7.32-7.38 (m, 2H), 7.4-7.46 (m, 2H), 7.82 (d, 1H), 8.04 (s, 1H), 8.16 (d, 1H), 8.44 (s, 1H), 9.78 (s, 1H), 11.52 (s, 1H), 11.98 (br s, 1H)

Example 91

1-(1-Phenyl-ethyl)-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide

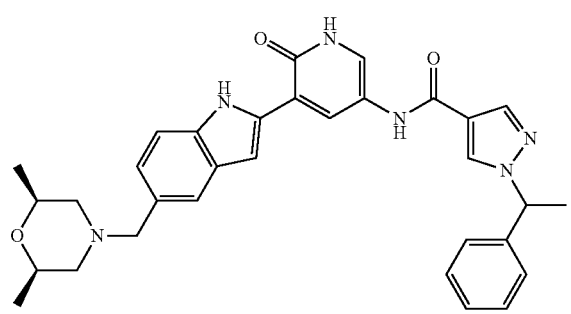 [SMILES: CC(c1ccccc1)n1cc(C(=O)Nc2c[nH]c(=O)c(-c3cc4cc(CN5C[C@@H](C)O[C@@H](C)C5)ccc4[nH]3)c2)cn1]

The title compound was prepared by the route outlined in Scheme 8, following the same experimental procedures as for Example 51.

The title compound was purified by trituration with acetonitrile, and isolated as a yellow solid, 34 mg, 31%.

LC/MS: RT=1.61 Min (270 nm), m/z=550 [M+H]. Total run time 3.75 min (short pos).

¹H NMR (d₆ DMSO): δ 1.0 (d, 6H), 1.62 (t, 2H), 1.82 (d, 3H), 2.68 (m, 2H), 3.48 (s, 2H), 3.55 (m, 2H), 5.7 (q, 1H), 7.0 (m, 2H), 7.20-7.42 (m, 7H), 7.80 (d, 1H), 8.05 (s, 1H), 8.10 (s, 1H), 8.42 (s, 1H), 9.78 (s, 1H),

Example 92

1-(1-Phenyl-ethyl)-1H-pyrazole-4-carboxylic acid {5-[5-(4-methyl-piperidin-1-ylmethyl)-1H-indol-2-yl]-6-oxo-1,6-dihydro-pyridin-3-yl}-amide

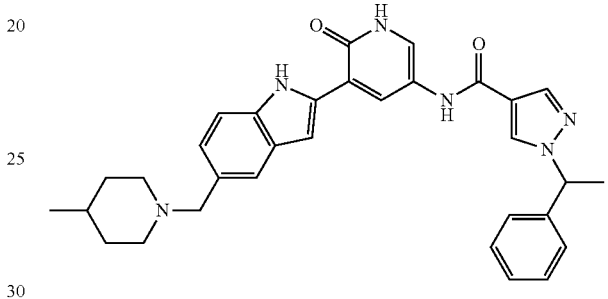

The title compound was prepared by the route outlined in Scheme 8, following the same experimental procedures as for Example 51. The title compound was purified by trituration with acetonitrile, and isolated as a yellow solid, 57 mg, 49%.

LC/MS: RT=1.66 Min (270 nm), m/z=535 [M+H]. Total run time 3.75 min (short pos).

¹H NMR (d₆ DMSO): δ 0.87 (d, 3H), 1.12 (m, 2H), 1.30 (m, 1H), 1.54 (m, 2H), 1.84 (d, 3H), 1.87 (m, 2H), 2.78 (m, 2H), 3.46 (s, 2H), 5.70 (q, 1H), 7.00-7.03 (m, 2H), 7.28-7.44 (m, 7H), 7.82 (d, 1H), 8.04 (s, 1H), 8.15 (d, 1H), 8.45 (s, 1H), 9.78 (s, 1H), 11.51 (s, 1H), 11.99 (br s, 1H).

Example 93

1-(1-Phenylethyl)-1H-pyrazole-4-carboxylic acid [5-(1H-indol-2-yl)-6-oxo-1,6-dihydropyridin-3-yl]-amide

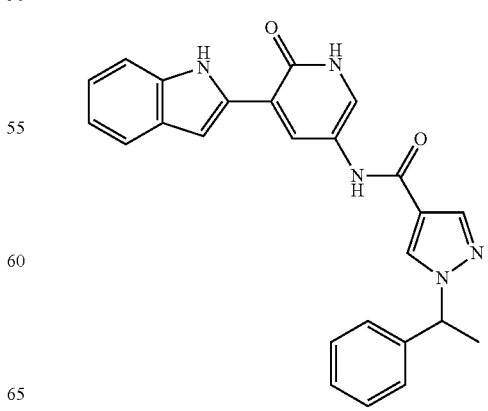

The title compound was prepared by the route outlined in Scheme 6, following the same experimental procedures as for Example 20, except that the relevant carboxylic acid, 1-(1-phenyl-ethyl)-1H-pyrazole-4-carboxylic acid, was converted to 1-(1-phenyl-ethyl)-1H-pyrazole-4-carbonyl chloride and then coupled to the amine using the same experimental described for Example 51.

The title compound was purified by flash chromatography on SiO$_2$ with ethyl acetate and isolated as a yellow solid, 57 mg, 49%.

LC/MS: RT=2.03 Min (270 nm), m/z=424 [M+H]. Total run time 3.75 min (short pos).

$^1$H NMR (d$_6$ DMSO): δ 1.85 (d, 3H), 5.70 (q, 1H), 6.95 (t, 1H), 7.10 (m, 2H), 7.30 (m, 3H), 7.35 (m, 2H), 7.55 (m, 2H), 7.80 (d, 1H), 8.05 (s, 1H), 8.20 (d, 1H), 8.45 (s, 1H), 9.75 (s, 1H), 11.54 (br s, 1H), 11.99 (br s, 1H).

Example 94

1-(3-Phenyl-propyl)-1H-pyrazole-4-carboxylic acid [5-(1H-indol-2-yl)-6-oxo-1,6-dihydro-pyridin-3-yl]-amide

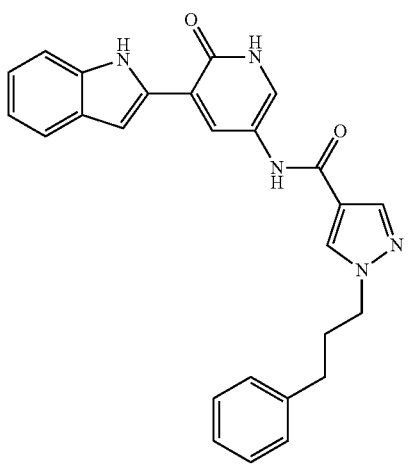 [SMILES: O=C(Nc1c[nH]c(=O)c(-c2cc3ccccc3[nH]2)c1)c1cnn(CCCc2ccccc2)c1]

The title compound was prepared by the route outlined in Scheme 6, following the same experimental procedures as for Example 20, except that the relevant carboxylic acid, 1-(3-Phenyl-propyl)-1H-pyrazole-4-carboxylic acid, was converted to 1-(3-Phenyl-propyl)-1H-pyrazole-4-carbonyl chloride, and then coupled to the amine using the same experimental described for Example 51.

The title compound was purified by trituration with acetonitrile, and isolated as a yellow solid, 30 mg, 48%.

LC/MS: RT=2.22 Min (270 nm), m/z=436 [M−H]. Total run time 3.75 min (short pos/neg).

$^1$H NMR (d$_6$ DMSO): δ 2.12 (t, 2H), 2.55 (m, 2H), 4.17 (t, 2H), 6.97 (m, 1H), 7.07 (m, 2H) 7.22 (m, 3H), 7.30 (m, 2H), 7.52 (t, 2H), 7.82 (s, 1H), 8.03 (s, 1H), 8.20 (s, 1H), 8.35 (s, 1H), 9.77 (br s, 1H), 11.57 (br s, 1H), 12.0 (br s, 1H)

Example 95

1-[2-(4-Fluoro-phenyl)-ethyl]-1H-pyrazole-4-carboxylic acid [6-oxo-5-(5-piperidin-1-ylmethyl-1H-indol-2-yl)-1,6-dihydro-pyridin-3-yl]-amide

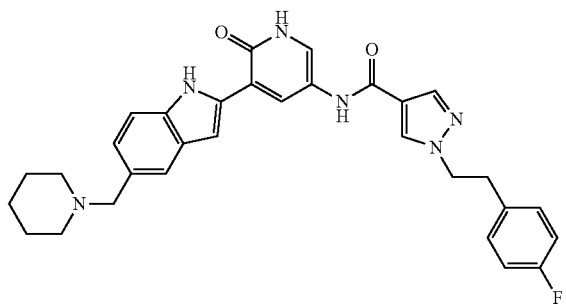 [SMILES: O=C(Nc1c[nH]c(=O)c(-c2cc3cc(CN4CCCCC4)ccc3[nH]2)c1)c1cnn(CCc2ccc(F)cc2)c1]

The title compound was prepared by the route outlined in Scheme 8, following the same experimental procedures as for Example 51.

The title compound was purified by trituration with diethyl ether, and isolated as a yellow solid, 30 mg, 42%.

LC/MS: RT=0.94 Min (270 nm), m/z=539 [M+H]. Total run time 1.9 min (super short pos).

$^1$H NMR (d$_6$ DMSO): δ 1.34-1.42 (m, 2H), 1.46-1.52 (m, 4H), 2.30-2.37 (m, 4H), 3.11-3.16 (m, 2H), 3.45 (s, 2H), 4.38-4.42 (t, 2H), 6.97-7.21 (m, 6H), 7.40-7.43 (m, 2H), 7.82-7.83 (d, 1H), 8.03 (s, 1H), 8.17-8.18 (d, 1H), 8.19 (s, 1H), 9.76 (s, 1H), 11.58 (s, 1H), 11.95-12.00 (br s, 1H).

Example 96

1-[2-(4-Fluoro-phenyl)-ethyl]-1H-pyrazole-4-carboxylic acid {5-[5-(4-fluoro-piperidin-1-ylmethyl)-1H-indol-2-yl]-6-oxo-1,6-dihydro-pyridin-3-yl}-amide

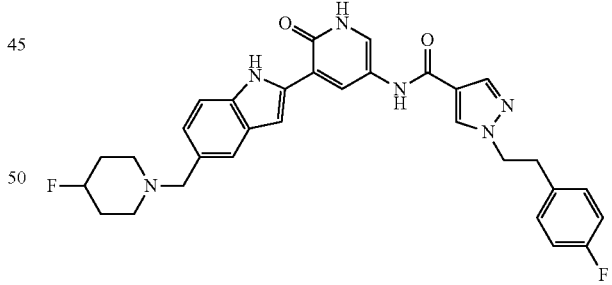

The title compound was prepared by the route outlined in Scheme 8, following the same experimental procedures as for Example 51. The title compound was purified by trituration with diethyl ether, and isolated as a yellow solid, 36 mg, 51%.

LC/MS: RT=0.94 Min (270 nm), m/z=557 [M+H]. Total run time 1.9 min (super short pos).

$^1$H NMR (d$_6$ DMSO): δ 1.69-1.92 (m, 4H), 2.24-2.33 (m, 2H), 3.11-3.18 (m, 4H), 3.50 (s, 2H), 4.38-4.42 (t, 2H), 4.59-4.75 (m, 1H), 7.00-7.21 (m, 6H), 7.41-7.44 (m, 2H), 7.83-7.84 (d, 1H), 8.03 (s, 1H), 8.19-8.20 (m, 2H), 9.78 (s, 1H), 11.62-11.69 (br s, 1H).

Example 97

5-[5-(4-Fluoro-piperidin-1-ylmethyl)-1H-indol-2-yl]-6-oxo-1,6-dihydro-pyridine-3-carboxylic acid [1-(3,4-difluoro-benzyl)-1H-pyrazol-4-yl]-amide

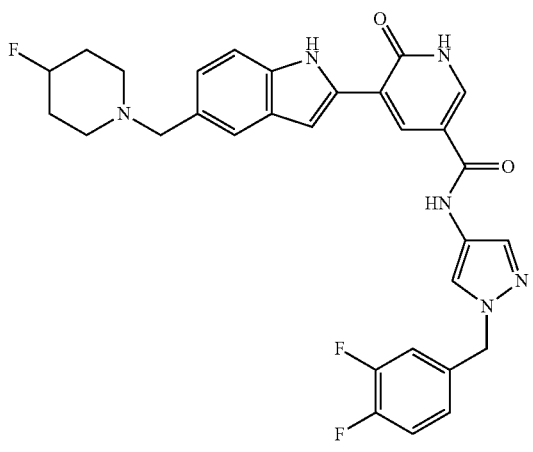 [SMILES: O=C(Nc1cnn(Cc2ccc(F)c(F)c2)c1)c1c[nH]c(=O)c(-c2cc3cc(CN4CCC(F)CC4)ccc3[nH]2)c1]

The title compound was prepared by the route outlined in Scheme 9, using intermediate (8b) and applying the same the experimental procedures as for Example 1. The title compound was purified by trituration with acetonitrile followed by preparative HPLC at pH 4 and isolated as a yellow solid, 24 mg, 14%.

LC/MS: RT=0.95 Min (270 nm), m/z=561 [M+H]. Total run time 1.9 min (super short pos).

$^1$H NMR (d$_6$ DMSO): δ 1.75 (br m, 2H), 1.85 (br m, 2H), 2.30 (br m, 2H), 2.55 (br m, 2H), 3.53 (s, 2H), 4.65 (m, 1H), 5.35 (s, 2H), 7.05 (dd, 1H), 7.15 (m, 1H), 7.25 (d, 1H), 7.30 (m, 1H), 7.45 (m, 3H), 7.55 (d, 1H), 8.10 (d, 1H), 8.15 (s, 1H), 8.25 (s, 1H), 8.55 (d, 1H), 10.40 (s, 1H), 11.48 (br s, 1H).

Example 98

6-Oxo-5-(5-pyrrolidin-1-ylmethyl-1H-indol-2-yl)-1,6-dihydro-pyridine-3-carboxylic acid [1-(3,4-difluoro-benzyl)-1H-pyrazol-4-yl]-amide

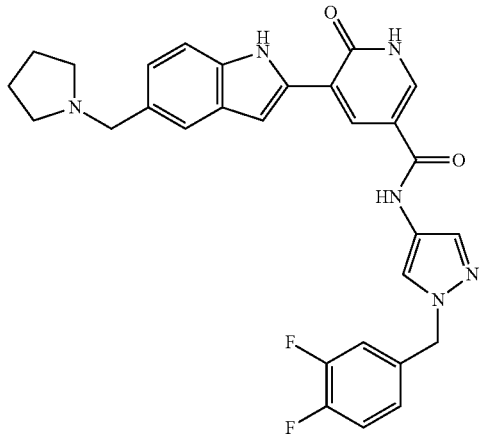 [SMILES: O=C(Nc1cnn(Cc2ccc(F)c(F)c2)c1)c1c[nH]c(=O)c(-c2cc3cc(CN4CCCC4)ccc3[nH]2)c1]

The title compound was prepared by the route outlined in Scheme 9, using intermediate (8b) and applying the same the experimental procedures as for Example 1. The title compound was purified by trituration with acetonitrile followed by preparative HPLC at pH 4 and isolated as a yellow solid, 12 mg, 8%.

LC/MS: RT=0.95 Min (270 nm), m/z=529 [M+H]. Total run time 1.9 min (super short pos).

$^1$H NMR (d$_6$ DMSO): δ 1.75 (br s, 4H), 2.60 (s, 4H), 3.75 (s, 2H), 5.30 (s, 2H), 7.10 (m, 2H), 7.20 (d, 1H), 7.45 (m, 3H), 7.65 (d, 1H), 8.10 (d, 1H), 8.15 (s, 1H), 8.25 (br s, 1H), 8.55 (d, 1H), 10.40 (s, 1H), 11.51 (br s, 1H).

Example 99

5-(5-Morpholin-4-ylmethyl-1H-indol-2-yl)-6-oxo-1,6-dihydro-pyridine-3-carboxylic acid [1-(3,4-difluoro-benzyl)-1H-pyrazol-4-yl]-amide

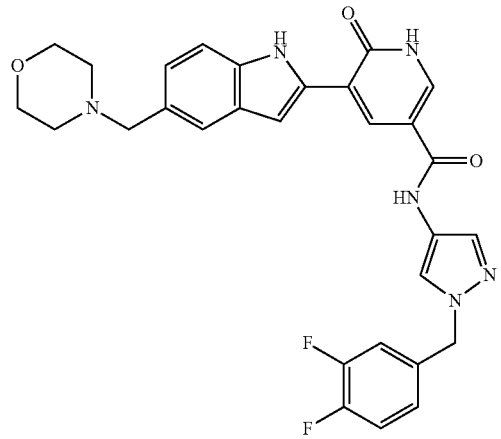 [SMILES: O=C(Nc1cnn(Cc2ccc(F)c(F)c2)c1)c1c[nH]c(=O)c(-c2cc3cc(CN4CCOCC4)ccc3[nH]2)c1]

The title compound was prepared by the route outlined in Scheme 9, using intermediate (8b) and applying the same the experimental procedures as for Example 1. The title compound was purified by trituration with acetonitrile, and isolated as a yellow solid, 65 mg, 27%.

LC/MS: RT=1.70 Min (270 nm), m/z=545 [M+H]. Total run time 3.75 min (short pos).

$^1$H NMR (d$_6$ DMSO): δ 2.40 (br s, 4H), 3.50 (s, 2H), 3.60 (t, 4H), 5.30 (s, 2H), 7.10 (m, 2H), 7.20 (d, 1H), 7.35 (m, 1H), 7.45 (m, 3H), 7.65 (d, 1H), 8.15 (d, 1H), 8.20 (d, 1H), 8.65 (d, 1H), 10.35 (s, 1H), 11.46 (br s, 1H), 12.44 (br s, 1H).

Example 100

5-[5-(4-Hydroxypiperidin-1-ylmethyl)-1H-indol-2yl]-6-oxo-1,6-dihydropyridine-3-carboxylic acid[1-(3,4-difluorobenzyl)-1H-pyrazol-4-yl]-amide

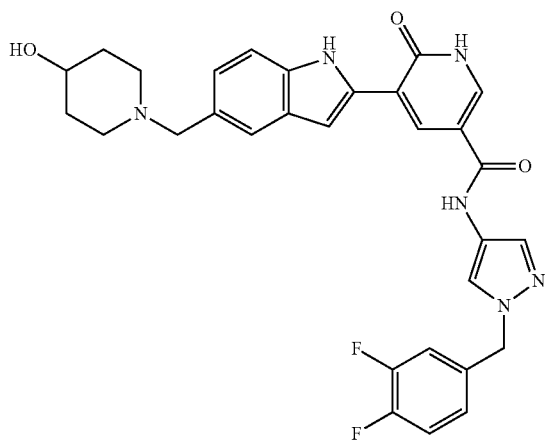 [SMILES: O=C(Nc1cnn(Cc2ccc(F)c(F)c2)c1)c1c[nH]c(=O)c(-c2cc3cc(CN4CCC(O)CC4)ccc3[nH]2)c1]

The title compound was prepared by the route outlined in Scheme 9, using intermediate (8b) and applying the same the experimental procedures as for Example 1. The crude product was purified by preparative HPLC at pH 4 and isolated as a yellow solid, 15 mg (7%)

LC/MS: RT=0.91 Min (270 nm); m/z=559 [M+H]. Total run time 1.9 min (super short pos).

$^1$H NMR (d$_6$ DMSO): δ 1.45 (m, 2H), 1.85 (m, 2H), 2.25 (m, 2H), 2.85 (m, 2H), 3.55 (m, 1H), 3.75 (s, 2H), 5.40 (s, 2H), 7.10 (m, 2H), 7.25 (d, 1H), 7.35 (m, 1H), 7.45 (m, 3H), 7.65 (d, 1H), 8.15 (d, 1H), 8.20 (d, 1H), 8.35 (br s, 1H), 8.65 (d, 1H), 10.45 (s, 1H), 11.52 (br s, 1H).

Example 101

5-(5-{[(2-Hydroxyethyl)-methylamino]-methyl}-1H-indol-2yl)-6-oxo-1,6-dihydropyridine-3-carboxylic acid[1-(3,4-difluorobenzyl)-1H-pyrazol-4-yl]-amide

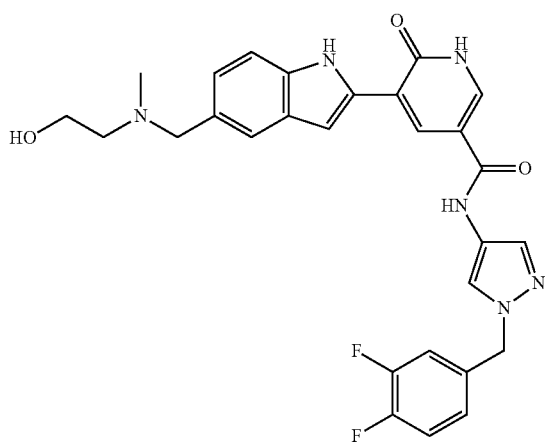 [SMILES: CN(CCO)Cc1ccc2[nH]c(-c3cc(C(=O)Nc4cnn(Cc5ccc(F)c(F)c5)c4)c[nH]c3=O)cc2c1]

The title compound was prepared by the route outlined in Scheme 9, using intermediate (8b) and applying the same the experimental procedures as for Example 1. The crude product was purified by preparative HPLC at pH 4 to give the product as a yellow solid, 21 mg, 11%.

LC/MS: RT=0.91 Min (270 nm), m/z=533 [M+H]. Total run time 1.9 min (super short pos).

$^1$H NMR (d$_6$ DMSO): δ 2.25 (s, 3H), 2.45 (t, 2H), 3.55 (t, 2H), 3.65 (s, 2H), 5.35 (s, 2H), 7.10 (m, 2H), 7.25 (d, 1H), 7.35 (m, 1H), 7.45 (m, 3H), 7.65 (d, 1H), 8.10 (d, 1H), 8.15 (d, 1H), 8.25 (br s, 1H), 8.60 (d, 1H), 10.35 (s, 1H), 11.50 (br s, 1H).

Example 102

5-(5-{[Ethyl-(2-hydroxyethyl)amino]-methyl}-1H-indol-2yl)-6-oxo-1,6-dihydropyridine-3-carboxylic acid[1-(3,4-difluorobenzyl)-1H-pyrazol-4-yl]-amide

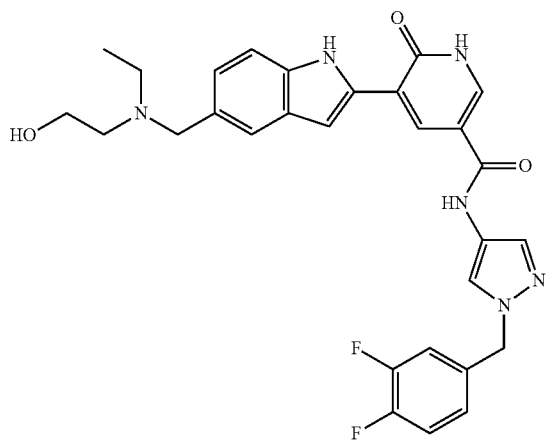 [SMILES: CCN(CCO)Cc1ccc2[nH]c(-c3cc(C(=O)Nc4cnn(Cc5ccc(F)c(F)c5)c4)c[nH]c3=O)cc2c1]

The title compound was prepared by the route outlined in Scheme 9, using intermediate (8b) and applying the same the experimental procedures as for Example 1. The crude product was purified by preparative HPLC at pH 4 to give the product as a yellow solid, 18 mg, 9%.

LC/MS: RT=0.93 Min (270 nm), m/z=547.2 [M+H]. Total run time 1.9 min (super short pos).

$^1$H NMR (d$_6$ DMSO): δ 1.05 (t, 3H), 2.55 (t, 2H), 2.60 (t, 2H), 3.50 (t, 2H), 3.69 (s, 2H), 5.35 (s, 2H), 7.10 (dd, 2H), 7.25 (d, 1H), 7.35 (m, 1H), 7.45 (m, 3H), 7.65 (d, 1H), 8.10 (d, 1H), 8.15 (d, 1H), 8.25 (br s, 1H), 8.60 (d, 1H), 10.35 (s, 1H), 11.50 (br s, 1H).

Example 103

5-{5-[(2-Hydroxyethylamino)-methyl]-1H-indol-2yl}-6-oxo-1,6-dihydropyridine-3-carboxylic acid[1-(3,4-difluorobenzyl)-1H-pyrazol-4-yl]-amide

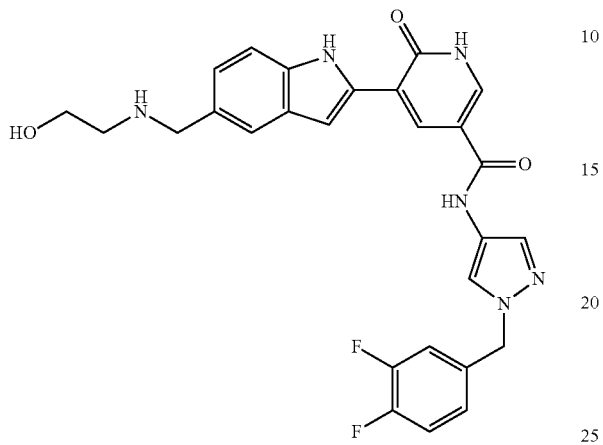

The title compound was prepared by the route outlined in Scheme 9, using intermediate (8b) and applying the same the experimental procedures as for Example 1. The crude product was purified by preparative HPLC at pH 4 to give the product as a yellow solid, 12 mg, 6%.

LC/MS: RT=0.91 Min (270 nm), m/z=458 [Fragment]. Total run time 1.9 min (super short pos).

$^1$H NMR (d$_6$ DMSO): δ 2.75 (t, 2H), 3.55 (t, 2H), 3.93 (s, 2H), 5.35 (s, 2H), 7.10 (m, 1H), 7.15 (d, 1H), 7.25 (m, 1H), 7.35 (m, 1H), 7.45 (m, 2H), 7.55 (s, 1H), 7.65 (d, 1H), 8.10 (d, 1H), 8.15 (d, 1H), 8.20 (s, 1H), 8.30 (br s, 1H), 8.60 (d, 1H), 10.40 (s, 1H), 11.58 (br s, 1H).

Example 104

5-[5-(4-Methyl-piperazin-1-ylmethyl)-1H-indol-2-yl]-6-oxo-1,6-dihydro-pyridine-3-carboxylic acid [1-(3,4-difluoro-benzyl)-1H-pyrazol-4-yl]-amide

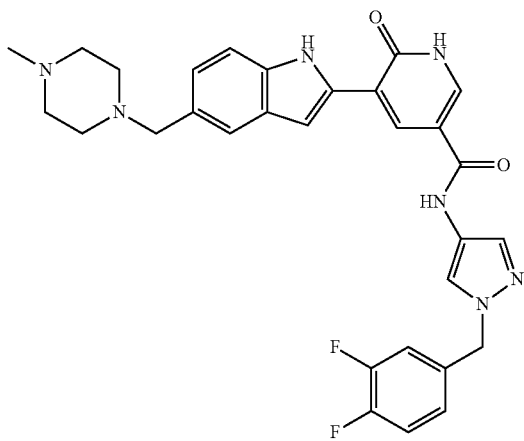 [SMILES: CN1CCN(Cc2ccc3[nH]c(-c4cc(C(=O)Nc5cnn(Cc6ccc(F)c(F)c6)c5)c[nH]c4=O)cc3c2)CC1]

The title compound was prepared by the route outlined in Scheme 9, using intermediate (8b) and applying the same the experimental procedures as for Example 1. The crude product was purified by preparative HPLC at pH 4 to give the product as a yellow solid, 10 mg, 5%.

LC/MS: RT=0.92 Min (270 nm), m/z=558 [M+H]. Total run time 1.9 min (super short pos).

$^1$H NMR (d$_6$ DMSO): δ 2.35 (s, 3H), 2.55 (br s, 6H), 3.95 (br s, 4H), 5.50 (s, 2H), 7.20 (dd, 1H), 7.25 (m, 1H), 7.40 (d, 1H), 7.50 (m, 1H), 7.60 (m, 3H), 7.80 (s, 1H), 8.25 (d, 1H), 8.30 (d, 1H), 8.75 (d, 1H), 10.50 (s, 1H), 11.50 (br s, 1H).

Example 105

5-{5-[4-(2-Hydroxyethyl)-piperazin-1-ylmethyl]-1H-indol-2yl}-6-oxo-1,6-dihydropyridine-3-carboxylic acid[1-(3,4-difluorobenzyl)-1H-pyrazol-4-yl]-amide

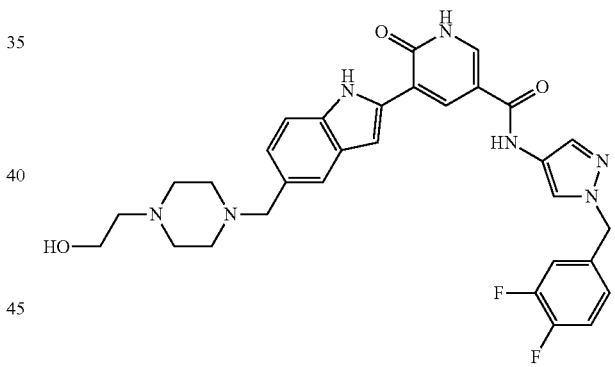

The title compound was prepared by the route outlined in Scheme 9, using intermediate (8b) and applying the same the experimental procedures as for Example 1. The crude product was purified by preparative HPLC at pH 4 to give the product as a yellow solid, 8 mg, 3%.

LC/MS: RT=0.91 Min (270 nm), m/z=588 [M+H]. Total run time 1.9 min (super short pos).

$^1$H NMR (d$_6$ DMSO): δ 2.40 (m, 10H), 3.45 (m, 4H), 5.35 (s, 2H), 7.04 (dd, 1H), 7.10 (m, 1H), 7.21 (d, 1H), 7.33 (m, 1H), 7.42 (m, 3H), 7.63 (s, 1H), 8.15 (d, 1H), 8.20 (s, 1H), 8.25 (br s, 1H), 8.60 (d, 1H), 10.40 (s, 1H), 11.50 (br s, 1H).

Example 106

1-Benzyl-1H-pyrazole-4-carboxylic acid [5-(4-dimethylaminomethyl-1H-indol-2-yl)-6-oxo-1,6-dihydro-pyridin-3-yl]-amide

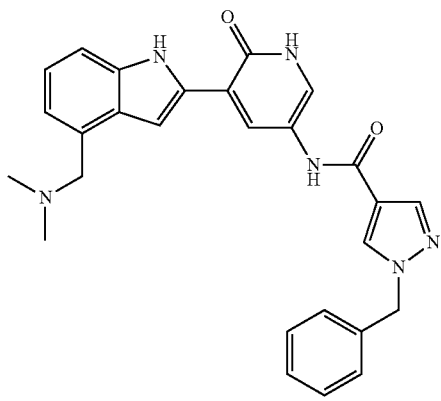 [SMILES: CN(C)Cc1cccc2[nH]c(-c3cc(NC(=O)c4cnn(Cc5ccccc5)c4)c[nH]c3=O)cc12]

The title compound was prepared by the route outlined in Scheme 8, following the same experimental procedures as for Example 51, except (1H-Indol-4-yl)-methanol was used.

The title compound was purified by trituration with acetonitrile, and isolated as a yellow solid, 13 mg, 33%.

LC/MS RT=0.88 Min (270 nm), m/z=467 [M+H]. Total run time 1.9 min (super short pos/neg).

$^1$H NMR (d$_6$ DMSO): δ 2.19 (s, 3H), 2.49 (s, 3H), 3.64 (s, 2H), 5.40 (s, 2H), 6.89 (d, 1h), 7.01 (t, 1H), 7.14 (br d, 1h), 7.38 (m, 6H), 7.88 (br s, 1H), 8.03 (s, 1H), 8.20 (d, 1H), 8.41 (s, 1H), 9.89 (s, 1H), 11.60 (s, 1H)

Example 107

1-Benzyl-1H-pyrazole-4-carboxylic acid {5-[4-(4-methyl-piperazin-1-ylmethyl)-1H-indol-2-yl]-6-oxo-1,6-dihydro-pyridin-3-yl}-amide

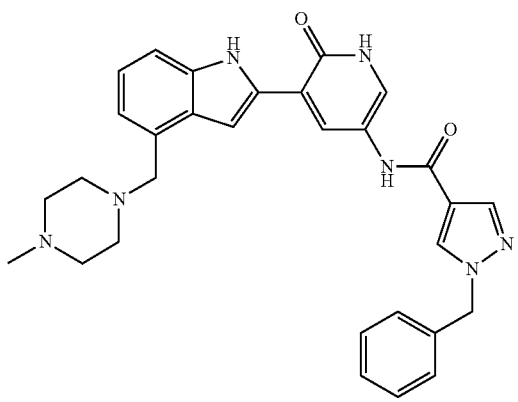 [SMILES: CN1CCN(Cc2cccc3[nH]c(-c4cc(NC(=O)c5cnn(Cc6ccccc6)c5)c[nH]c4=O)cc23)CC1]

The title compound was prepared by the route outlined in Scheme 8, following the same experimental procedures as for Example 51, except (1H-Indol-4-yl)-methanol was used.

The title compound was purified by trituration with acetonitrile, and isolated as a yellow solid, 17 mg, 26%.

LC/MS RT=0.89 Min (270 nm), m/z=522 [M+H]. Total run time 1.9 min (super short pos/neg).

$^1$H NMR (d$_6$ DMSO): δ ☐2.13 (s, 3H), 2.33 (br s, 4H), 2.41 (br s, 4H), 3.33 (s, 2H), 4.29 (s, 2H), 6.91 (d, 1H), 7.02 (d, 1H), 7.14 (br s, 1H), 7.34 (m, 6H), 7.85 (br s, 1H), 8.03 (s, 1H), 8.19 (d, 1H), 8.41 (s, 1H), 9.78 (s, 1H), 11.56 (s, 1H), 12.00 (br s, 1H)

Example 108

1-Benzyl-1H-pyrazole-4-carboxylic acid [6-oxo-5-(4-piperidin-1-ylmethyl-1H-indol-2-yl)-1,6-dihydro-pyridin-3-yl]-amide

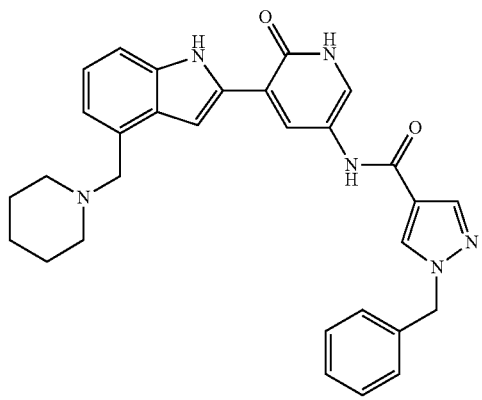 [SMILES: O=C(Nc1c[nH]c(=O)c(-c2cc3c(CN4CCCCC4)cccc3[nH]2)c1)c1cnn(Cc2ccccc2)c1]

The title compound was prepared by the route outlined in Scheme 8, following the same experimental procedures as for Example 51, except (1H-Indol-4-yl)-methanol was used. The final step, deprotection, was achieved using the following alternative to the usual procedure. 2-[5-[(1-Benzyl-1H-pyrazole-4-carbonyl)-amino]-2-oxo-1-(2-trimethylsilanyl-ethoxymethyl)-1,2-dihydro-pyridin-3-yl]-4-piperidin-1-ylmethyl-indole-1-carboxylic acid tert-butyl ester (110 mg, 0.149 mmol) was stirred in dichloromethane (5 mL) at −78° C. and then boron tribromide 1.0M solution in dichloromethane (2 mL, 2 mmol) was added drop wise. After addition the cooling was removed and the reaction was stirred at RT for 1 hour. The reaction mixture was cooled to −78° C. and methanol (2 mL) was added. Again the cooling was removed and the reaction stirred at RT, followed by concentration in vacuo. The residue was partitioned between ethyl acetate and water. The organics were separated, washed with sodium hydrogen bicarbonate, dried (Na$_2$SO$_4$) and concentrated in vacuo to furnish a dark yellow solid. This was purified by trituration with ethyl acetate to give the title compound as a yellow solid, 31 mg, 41%.

LC/MS RT=1.55 Min (270 nm), m/z=507 [M+H]. Total run time 3.75 min (short pos).

$^1$H NMR (d$_4$-MeOD): δ 1.57 (m, 2H), 1.73 (m, 4H) 2.92 (m, 4H), 4.17 (m, 2H), 5.43 (s, 2H), 7.13 (d, 1H), 7.20 (m, 1H), 7.28 (s, 1H), 7.36 (m, 5H), 7.48 (m, 1H), 7.88 (s, 1H), 8.08 (s, 1H), 8.29 (s, 1H), 8.34 (s, 1H).

Example 109

1-Benzyl-1H-pyrazole-4-carboxylic acid {5-[4-(cis-2,6-dimethyl-morpholin-4-ylmethyl)-1H-indol-2-yl]-6-oxo-1,6-dihydro-pyridin-3-yl}-amide

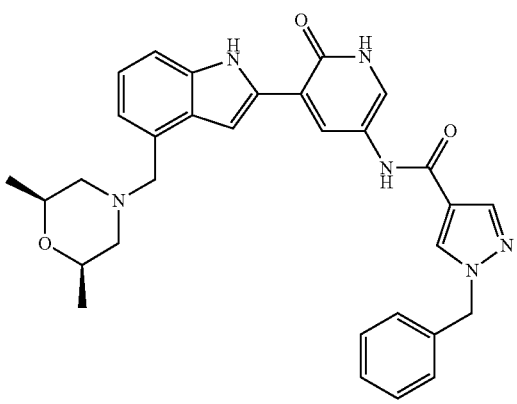 [SMILES: C[C@@H]1CN(Cc2cccc3[nH]c(-c4cc(NC(=O)c5cnn(Cc6ccccc6)c5)c[nH]c4=O)cc23)C[C@H](C)O1]

The title compound was prepared by the route outlined in Scheme 8, following the same experimental procedures as for Example 51, except (1H-Indol-4-yl)-methanol was used and the alternative deprotection method described for Example 108 was adopted.

The title compound was purified by trituration with ethyl acetate, and isolated as a yellow solid, 45 mg, 56%.

LC/MS RT=1.56 Min (270 nm), m/z=537 [M+H]. Total run time 3.75 min (short pos).

$^1$H NMR (d$_4$-MeOD): δ 1.11 (d, 6H), 1.88 (t, 2H) 2.86 (d, 2H), 3.70 (m, 2H), 3.83 (s, 2H), 5.42 (s, 2H), 7.03 (m, 1H), 7.13 (m, 1H), 7.25 (s, 1H), 7.37 (m, 6H), 7.95 (d, 1H), 8.09 (s, 1H), 8.28 (m, 2H).

Example 110

5-(1H-Indol-2-yl)-6-oxo-1,6-dihydro-pyridine-3-carboxylic acid [1-(6-fluoro-pyridin-3-ylmethyl)-1H-pyrazol-4-yl]-amide

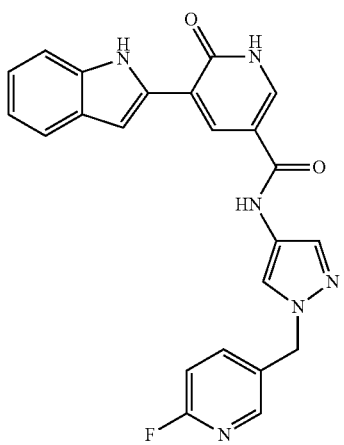 [SMILES: O=C(Nc1cnn(Cc2ccc(F)nc2)c1)c1c[nH]c(=O)c(-c2cc3ccccc3[nH]2)c1]

The title compound was prepared by the route outlined in Scheme 1, following the same experimental procedures as for Examples 1 and 2.

The title compound was purified by trituration with acetonitrile, and isolated as a yellow solid, 4 mg, 8%.

LC/MS RT=1.12 Min (270 nm), m/z=429 [M+H]. Total run time 1.9 min (super short pos/neg).

$^1$H NMR (d$_6$ DMSO): δ 5.38 (s, 2H), 7.00 (td, 1H), 7.09 (td, 1H), 7.19 (dd, 1H), 7.24 (br d, 1H), 7.49 (br d, 1H), 7.55 (br d, 1H), 7.62 (s, 1H), 7.87 (td, 1H), 8.11 (d, 1H), 8.19 (s, 1H), 8.21 (br s, 1H), 8.55 (d, 1H), 10.31 (br s, 1H), 11.50 (br s, 1H).

Example 111

1-(6-Fluoro-pyridin-3-ylmethyl)-1H-pyrazole-4-carboxylic acid [5-(1H-indol-2-yl)-6-oxo-1,6-dihydro-pyridin-3-yl]-amide

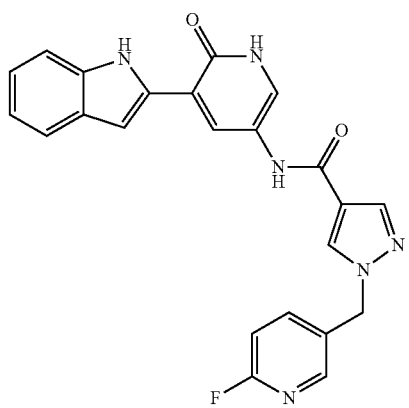 [SMILES: O=C(Nc1c[nH]c(=O)c(-c2cc3ccccc3[nH]2)c1)c1cnn(Cc2ccc(F)nc2)c1]

The title compound was prepared by the route outlined in Scheme 6, following the same experimental procedures as for Examples 20 and 21.

The crude product was purified by preparative HPLC at pH 4 to give the product as a yellow solid, 3 mg, 11%.

LC/MS RT=1.08 Min (270 nm), m/z=429 [M+H]. Total run time 1.9 min (super short pos/neg).

$^1$H NMR (d$_4$-MeOD): δ 5.45 (s, 2H), 7.00 (t, 1H), 7.02 (s, 1H), 7.09 (m, 2H), 7.41 (d, 1H), 7.53 (d, 1H), 7.92 (m, 2H), 8.07 (s, 1H), 8.21 (m, 2H), 8.33 (s, 1H).

Example 112

1-(4-Methyl-benzyl)-1H-pyrazole-4-carboxylic acid {5-[5-(4-methyl-piperazin-1-yl)-1H-indol-2-yl]-6-oxo-1,6-dihydro-pyridin-3-yl}-amide

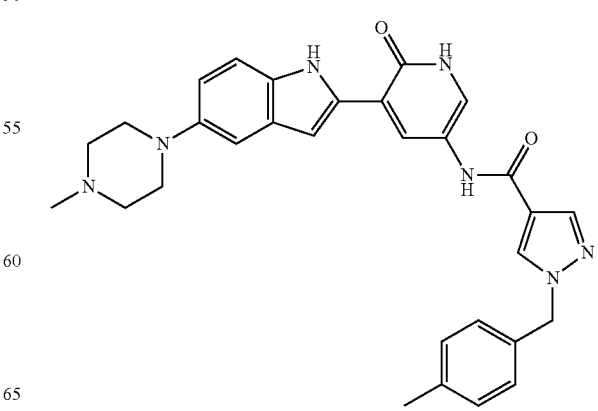

The title compound was prepared according to the route outlined in Scheme 10.

Step 1: Preparation of 1-Methyl-4-(3-methyl-4-nitro-phenyl)-piperazine (10a)

A mixture of 5-fluoro-2-nitrotoluene (2.5 g, 16 mmol), N-methylpiperazine (2 mL, 18 mmol) and potassium carbonate (2.7 g, 19 mmol) in DMSO (7 mL) was stirred and heated at 100° C. for 2 hours. The reaction mixture was cooled to ambient temperature and then diluted with ethyl acetate (100 mL), washed with water (3×30 mL), brine, dried (MgSO$_4$) and concentrated in vacuo. The resultant crude product was purified by flash chromatography on SiO$_2$ eluting with dichloromethane—40% methanol/dichloromethane (gradient) to afford the desired title compound as a yellow solid, 3.67 g, 97%.

Step 2: Preparation of 5-(4-Methyl-piperazin-1-yl)-1H-indole (10b)

A solution of 1-methyl-4-(3-methyl-4-nitro-phenyl)-piperazine (10a), (2.63 g, 11.2 mmol), N,N-dimethylformamide dimethyl acetal (4.7 mL, 35.84 mmol) and pyrrolidine (1.5 mL, 17.9 mmol) in anhydrous N,N-dimethylformamide (20 mL) was heated at 120° C. for 18 hours. The reaction mixture was concentrated in vacuo, taken up in ethanol (50 mL) containing 2 mL of water and to this was added ammonium formate (3.67 g, 58.2 mmol). Palladium, 10 wt. % on activated carbon (0.84 g) was added and the suspension was stirred and heated at 50° C. for 30 minutes. The reaction mixture was then filtered through a celite pad and the pad rinsed with hot methanol (20 mL). The combined filtrate and washings were concentrated in vacuo and the residue was taken up in ethyl acetate (100 mL), washed with aqueous saturated sodium bicarbonate solution (2×100 mL), brine, dried (MgSO$_4$) and concentrated in vacuo. The resultant crude product was purified by flash chromatography on SiO$_2$ eluting first with hexane and then 15% ethyl acetate/hexane to afford the desired title compound as an off-white solid, 1.44 g, 60%.

Step 3: Preparation of 5-(4-Methyl-piperazin-1-yl)-indole-1-carboxylic acid tert-butyl ester (10c)

A solution of 5-(4-methyl-piperazin-1-yl)-1H-indole (10b), (1.67 g, 7.7 mmol) in dichloromethane (40 mL) was added di-tert-butyl dicarbonate (1.87 g, 8.6 mmol) drop wise at ambient temperature as a solution in dichloromethane (5 mL). 4-Dimethylaminopyridine (0.095 g, 0.8 mmol) was added and the reaction stirred at ambient temperature for 18 hours. The reaction mixture was washed with aqueous saturated sodium bicarbonate solution (100 mL), brine, dried (MgSO$_4$) and concentrated in vacuo. The resultant crude product was purified by flash chromatography on SiO$_2$ eluting with dichloromethane..15% methanol/dichloromethane (gradient) to afford the desired title compound as a yellow solid, 2.33 g, 95%.

Step 4: Preparation of 5-(4-Methyl-piperazin-1-yl)-2-[5-nitro-2-oxo-1-(2-trimethylsilanyl-ethoxymethyl)-1,2-dihydro-pyridin-3-yl]-indole-1-carboxylic acid tert-butyl ester (10d)

The title compound was prepared by the route outlined in Scheme 10 and using the experimental from Example 37, Step 3, with intermediate (10c), 5-(4-methyl-piperazin-1-yl)-indole-1-carboxylic acid tert-butyl ester (2.33 g, 7.4 mmol) and 3-iodo-5-nitro-1-(2-trimethylsilanyl-ethoxymethyl)-1H-pyridin-2-one (2.66 g, 6.7 mmol) which had been synthesized according to the protocol described for intermediate (6a) in example 20. The resultant solid was purified via trituration using diethyl ether, to afford the title compound as a pale brown solid, 1.73 g, 40%.

Step 5: Preparation of 2-[5-Amino-2-oxo-1-(2-trimethylsilanyl-ethoxymethyl)-1,2-dihydro-pyridin-3-yl]-5-(4-methyl-piperazin-1-yl)-indole-1-carboxylic acid tert-butyl ester (10e)

The title compound was prepared by the route outlined in Scheme 10 and using the experimental from Example 20, Step 3, with intermediate (10d), 5-(4-methyl-piperazin-1-yl)-2-[5-nitro-2-oxo-1-(2-trimethylsilanyl-ethoxymethyl)-1,2-dihydro-pyridin-3-yl]-indole-1-carboxylic acid tert-butyl ester (0.73 g, 1.2 mmol). The resultant crude product was purified by flash chromatography on SiO$_2$ eluting with dichloromethane—20% methanol/dichloromethane (gradient) to afford the desired title compound as a dark yellow foam, 0.435 g, 63%.

Step 6: preparation of 2-[5-{[1-(4-Methyl-benzyl)-1H-pyrazole-4-carbonyl]-amino}-2-oxo-1-(2-trimethylsilanyl-ethoxymethyl)-1,2-dihydro-pyridin-3-yl]-5-(4-methyl-piperazin-1-yl)-indole-1-carboxylic acid tert-butyl ester (10f)

The title compound was prepared by the route outlined in Scheme 10 and using the experimental from Example 115, Step 4, with intermediate (10e), 2-[5-amino-2-oxo-1-(2-trimethylsilanyl-ethoxymethyl)-1,2-dihydro-pyridin-3-yl]-5-(4-methyl-piperazin-1-yl)-indole-1-carboxylic acid tert-butyl ester (0.1 g, 0.18 mmol) and 1-(4-methyl-benzyl)-1H-pyrazole-4-carbonyl chloride (0.047 g, 0.2 mmol). The resultant crude product was purified by flash chromatography on SiO$_2$ eluting with dichloromethane—8% methanol/dichloromethane (gradient) to afford the desired title compound as a pale brown solid, 0.107 g, 79%.

Step 7: Preparation of the Title Compound: 1-(4-Methyl-benzyl)-1H-pyrazole-4-carboxylic acid {5-[5-(4-methyl-piperazin-1-yl)-1H-indol-2-yl]-6-oxo-1,6-dihydro-pyridin-3-yl}-amide The title compound was prepared by the route outlined in Scheme 10, following the same experimental procedures as for Example 37. It was purified by trituration with acetonitrile, and isolated as a yellow solid, 43 mg, 59%.

LC/MS: RT=1.45 Min (270 nm), m/z=522 [M+H]. Total run time 3.75 min (short pos).

$^1$H NMR (d$_6$ DMSO): δ 2.23 (s, 3H), 2.29 (s, 3H), 2.48 (m, 4H), 3.04 (m, 4H), 5.34 (s, 2H), 6.86-6.89 (m, 2H), 6.97 (m, 1H), 7.19 (m, 4H), 7.37 (d, 1H), 7.82 (d, 1H), 8.01 (s, 1H), 8.11 (d, 1H), 8.37 (s, 1H), 9.76 (s, 1H), 11.37 (s, 1H), 11.96 (br s, 1H).

Example 113

1-Benzyl-1H-pyrazole-4-carboxylic acid {5-[5-(4-methyl-piperazin-1-yl)-1H-indol-2-yl]-6-oxo-1,6-dihydro-pyridin-3-yl}-amide

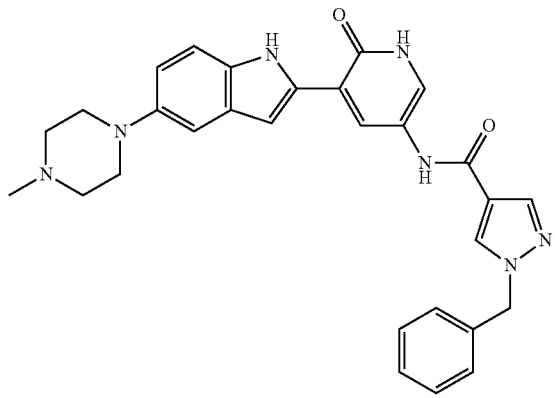 [SMILES: CN1CCN(c2ccc3[nH]c(-c4cc(NC(=O)c5cnn(Cc6ccccc6)c5)c[nH]c4=O)cc3c2)CC1]

The title compound was prepared by the route outlined in Scheme 10, following the same experimental procedures as for Example 112. The title compound was purified by trituration with acetonitrile, and isolated as a yellow solid, 40 mg, 61%.

LC/MS: RT=1.49 Min (270 nm), m/z=508 [M+H]. Total run time 3.75 min (short pos).

$^1$H NMR (d$_6$ DMSO): δ 2.23 (s, 3H), 2.48 (m, 4H), 3.05 (m, 4H), 5.40 (s, 2H), 6.86-6.89 (m, 2H), 6.97 (m, 1H), 7.28-7.40 (m, 6H), 7.82 (d, 1H), 8.03 (s, 1H), 8.12 (d, 1H), 8.41 (s, 1H), 9.78 (s, 1H), 11.36 (s, 1H), 11.97 (br s, 1H).

Example 114

1-(4-Fluoro-benzyl)-1H-pyrazole-4-carboxylic acid {5-[5-(4-methyl-piperazin-1-yl)-1H-indol-2-yl]-6-oxo-1,6-dihydro-pyridin-3-yl}-amide

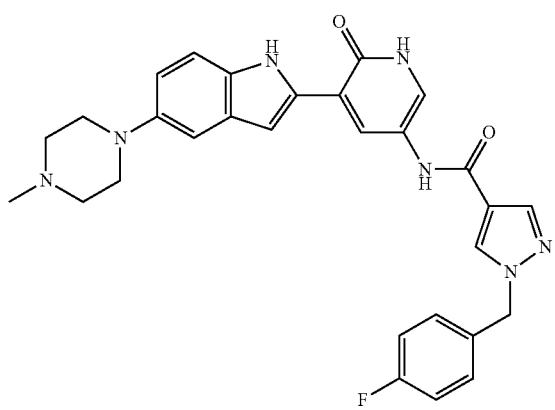 [SMILES: CN1CCN(c2ccc3[nH]c(-c4cc(NC(=O)c5cnn(Cc6ccc(F)cc6)c5)c[nH]c4=O)cc3c2)CC1]

The title compound was prepared by the route outlined in Scheme 10, following the same experimental procedures as for Example 112. The title compound was purified by trituration with acetonitrile, and isolated as a yellow solid, 38 mg, 57%.

LC/MS: RT=1.52 Min (270 nm), m/z=526 [M+H]. Total run time 3.75 min (short pos).

$^1$H NMR (d$_6$ DMSO): δ 2.22 (s, 3H), 2.48 (m, 4H), 3.05 (m, 4H), 5.39 (s, 2H), 6.86-6.89 (m, 2H), 6.97 (m, 1H), 7.19-7.24 (m, 2H), 7.34-7.39 (m, 3H), 7.82 (d, 1H), 8.03 (s, 1H), 8.12 (d, 1H), 8.41 (s, 1H), 9.78 (s, 1H), 11.36 (s, 1H), 11.97 (br s, 1H).

Example 115

1-(4-Methyl-benzyl)-1H-pyrazole-4-carboxylic acid {6-oxo-5-[5-(2-piperidin-1-yl-ethoxy)-1H-indol-2-yl]-1,6-dihydro-pyridin-3-yl}-amide

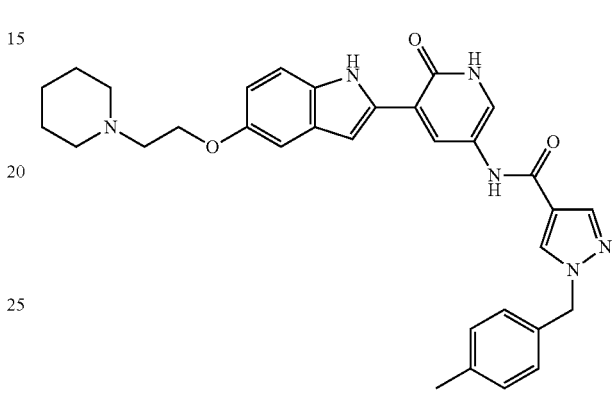

The title compound was prepared according to the route outlined in Scheme 11.

Step 1: Preparation of 5-(tert-Butyl-dimethyl-silanyloxy)-indole-1-carboxylic acid tert-butyl ester (11a)

The title compound was prepared by the route outlined in Scheme 11 and using the experimental from Example 37, Step 2, with intermediate 1H-Indol-5-ol (5.54 g, 7.4 mmol). The resultant crude product was purified by flash chromatography on SiO$_2$ with hexane—10% ethyl acetate/hexane (gradient) to afford the title compound as a white solid, 13.41 g, 93%.

Step 2: Preparation of 5-(tert-Butyl-dimethyl-silanyloxy)-2-[5-nitro-2-oxo-1-(2-trimethylsilanyl-ethoxymethyl)-1,2-dihydro-pyridin-3-yl]-indole-1-carboxylic acid tert-butyl ester (11b)

The title compound was prepared by the route outlined in Scheme 11 and using the experimental from Example 37, Step 3, with intermediate 5-(tert-butyl-dimethyl-silanyloxy)-indole-1-carboxylic acid tert-butyl ester (11a) (2.90 g, 8.3 mmol) and (6a), 3-iodo-5-nitro-1-(2-trimethylsilanyl-ethoxymethyl)-1H-pyridin-2-one (3 g, 7.6 mmol). The resultant crude product was purified by flash chromatography on SiO$_2$ with hexane—20% ethyl acetate/hexane (gradient) to afford after trituration using hexane, the title compound as a pale yellow solid, 3.67 g, 79%.

Step 3: Preparation of 2-[5-Amino-2-oxo-1-(2-trimethylsilanyl-ethoxymethyl)-1,2-dihydro-pyridin-3-yl]-5-(tert-butyl-dimethyl-silanyloxy)-indole-1-carboxylic acid tert-butyl ester (11c)

The title compound was prepared by the route outlined in Scheme 11 and using the experimental from Example 20, Step 3, with intermediate (11b) 5-(tert-butyl-dimethyl-silanyloxy)-2-[5-nitro-2-oxo-1-(2-trimethylsilanyl-ethoxymethyl)-1,2-dihydro-pyridin-3-yl]-indole-1-carboxylic acid tert-butyl ester (3.65 g, 5.93 mmol). The resultant crude product was purified by flash chromatography on SiO$_2$ with hexane—40% ethyl acetate/hexane (gradient) to afford the title compound as a dark yellow foam, 2.615 g, 75%.

Step 4: Preparation of 5-(tert-Butyl-dimethyl-silanyloxy)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (11d)

Intermediate (11c), 2-[5-amino-2-oxo-1-(2-trimethylsilanyl-ethoxymethyl)-1,2-dihydro-pyridin-3-yl]-5-(tert-butyl-dimethyl-silanyloxy)-indole-1-carboxylic acid tert-butyl ester (1.3 g, 2.2 mmol) was stirred in dichloromethane (50 mL) at RT with triethylamine (444 mg, 0.612 mL, 4.4 mmol). The reaction mixture was cooled to 5° C. and then a solution of 1-(4-methyl-benzyl)-1H-pyrazole-4-carbonyl chloride (2.86 mmol, 0.67 g), which had been prepared according to the protocol below, in dichloromethane (10 ml), was added drop wise. After addition the reaction was stirred at RT for 3 hrs and then the reaction mixture was washed with saturated sodium hydrogen carbonate solution (2×50 mL), brine (50 ml), dried (Na$_2$SO$_4$) and concentrated in vacuo. The resultant crude product was purified by flash chromatography on SiO$_2$ eluting with hexane—50% ethyl acetate/hexane (gradient) and further purified via trituration with isohexane (20 mL) and diethyl ether (20 mL). The solids were separated by filtration and dried in vacuo to afford the desired intermediate as a white solid, 1.56 g, 90%.

Preparation of 1-(4-Methyl-benzyl)-1H-pyrazole-4-carbonyl chloride used in Step 4, above.

1-(4-Methyl-benzyl)-1H-pyrazole-4-carboxylic acid (0.618 g, 2.86 mmol), which had been prepared according to the protocol described for intermediate (6e), in Example 21, was stirred in toluene (20 mL) at RT and thionyl chloride (681 mg, 0.42 mL, 5.72 mmol) was added. The reaction mixture was slowly heated to 90° C. and heating continued for 3 hrs. After cooling the reaction was concentrated in vacuo. Toluene was added to the residue and concentrated in vacuo. This was repeated a further three times and the crude solid obtained was triturated using isohexane. The solids were separated by filtration washed with isohexane and dried in vacuo to afford 1-(4-methyl-benzyl)-1H-pyrazole-4-carbonyl chloride as a white solid, 0.67 g, quant.

Step 5: Preparation of 5-Hydroxy-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (11e)

Intermediate (11d), 5-(tert-butyl-dimethyl-silanyloxy)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (1.55 g, 1.97 mmol) was stirred in tetrahydrofuran (40 mL) and cooled to 0° C. Tetrabutylammonium fluoride solution 1.0M in tetrahydrofuran (2.08 mL, 2.08 mmol) was added drop wise at 0° C., and then the reaction was allowed to attain ambient temperature, where it was stirred for a further 2 hours. The reaction mixture was diluted with ethyl acetate (30 mL), washed with water (30 mL), aqueous 0.5N hydrochloric acid solution (30 mL), brine, dried (Na$_2$SO$_4$) and concentrated in vacuo. The resultant green foam was purified via trituration using diethyl ether, to afford the title compound as a pale yellow solid, 0.946 g, 71%.

Step 6: Preparation of 2-[5-{[1-(4-Methyl-benzyl)-1H-pyrazole-4-carbonyl]-amino}-2-oxo-1-(2-trimethylsilanyl-ethoxymethyl)-1,2-dihydro-pyridin-3-yl]-5-(2-piperidin-1-yl-ethoxy)-indole-1-carboxylic acid tert-butyl ester (11f)

To a solution of intermediate (11e), 5-hydroxy-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester (150 mg, 0.22 mmol) in N,N-dimethylformamide (3 mL) was added 1-(2-chloroethyl)-piperidine hydrochloride (62 mg, 0.33 mmol) and cesium carbonate (219 mg, 0.67 mmol). The reaction mixture was heated at 50° C. for 5 hours, and cooled to ambient temperature. The reaction mixture was cooled and partitioned between ethyl acetate and water. The ethyl acetate layer was separated and washed with brine, dried (Na$_2$SO$_4$) and concentrated in vacuo. The title compound was purified by flash chromatography on SiO$_2$ eluting with dichloromethane—5% methanol/dichloromethane (gradient) to afford the desired title compound as a pale yellow solid, 94 mg, 54%.

Step 7: Preparation of the Title Compound: 1-(4-Methyl-benzyl)-1H-pyrazole-4-carboxylic acid {6-oxo-5-[5-(2-piperidin-1-yl-ethoxy)-1H-indol-2-yl]-1,6-dihydro-pyridin-3-yl}-amide The title compound was prepared according to the experimental used in Example 37, Step 8 with intermediate (11f), 2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-5-(2-piperidin-1-yl-ethoxy)-indole-1-carboxylic acid tert-butyl ester. Purification of the crude product was accomplished using trituration with acetonitrile. The title compound was isolated as a yellow solid, 41 mg, 62%.

LC/MS: RT=1.76 Min (270 nm), m/z=551 [M+H]. Total run time 3.75 min (short pos).

$^1$H NMR (d$_6$ DMSO): δ 1.38 (m, 2H), 1.50 (m, 4H), 2.29 (s, 3H), 2.44 (m, 4H), 2.65 (t, 2H), 4.04 (t, 2H), 5.34 (s, 2H), 6.71 (dd, 1H), 6.92 (m, 1H), 7.03 (d, 1H), 7.19 (m, 4H), 7.39 (d, 1H), 7.82 (d, 1H), 8.01 (s, 1H), 8.14 (d, 1H), 8.37 (s, 1H), 9.76 (s, 1H), 11.46 (s, 1H), 11.97 (br s, 1H).

Example 116

1-(4-Methyl-benzyl)-1H-pyrazole-4-carboxylic acid (5-{5-[2-(3-fluoro-piperidin-1-yl)-ethoxy]-1H-indol-2-yl}-6-oxo-1,6-dihydro-pyridin-3-yl)-amide

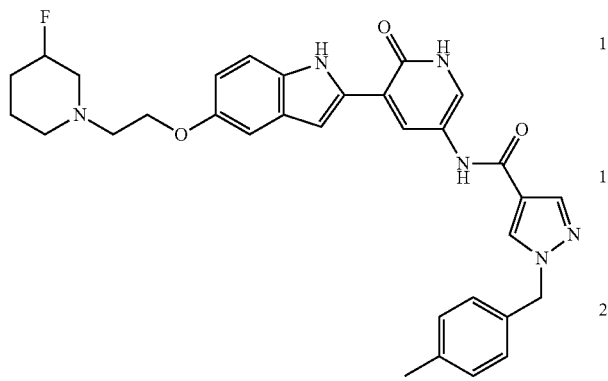

The title compound was prepared by the route outlined in Scheme 11, following the same experimental procedures as for Example 115.

The title compound was purified by trituration with acetonitrile, and isolated as a yellow solid, 21 mg, 75%.

LC/MS: RT=1.74 Min (270 nm), m/z=569 [M+H]. Total run time 3.75 min (short pos).

$^1$H NMR (d$_6$ DMSO): δ 1.42-1.56 (m, 2H), 1.67-1.88 (m, 2H), 2.29 (s, 3H), 2.33-2.57 (m, 3H), 2.75 (d, 2H), 2.86 (m, 1H), 4.06 (t, 2H), 4.63 (m, 1H), 5.34 (s, 2H), 6.71 (dd, 1H), 6.93 (m, 1H), 7.04 (d, 1H), 7.19 (m, 4H), 7.40 (d, 1H), 7.82 (d, 1H), 8.01 (s, 1H), 8.14 (d, 1H), 8.37 (s, 1H), 9.76 (s, 1H), 11.45 (s, 1H), 11.98 (br s, 1H).

Example 117

1-(4-Methyl-benzyl)-1H-pyrazole-4-carboxylic acid {5-[5-(3-morpholin-4-yl-propoxy)-1H-indol-2-yl]-6-oxo-1,6-dihydro-pyridin-3-yl}-amide

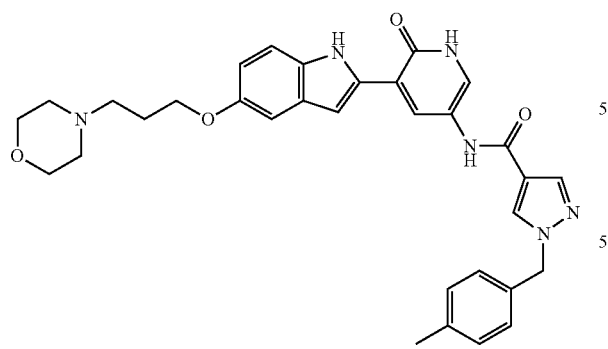

The title compound was prepared by the route outlined in Scheme 11, following the same experimental procedures as for Example 115.

The title compound was purified by trituration with acetonitrile, and isolated as a yellow solid, 51 mg, 71%.

LC/MS: RT=1.72 Min (270 nm), m/z=567 [M+H]. Total run time 3.75 min (short pos).

$^1$H NMR (d$_6$ DMSO): δ 1.88 (m, 2H), 2.29 (s, 3H), 2.37 (m, 4H), 2.44 (d, 2H), 3.58 (m, 4H), 3.99 (t, 2H), 5.34 (s, 2H), 6.71 (dd, 1H), 6.93 (m, 1H), 7.01 (d, 1H), 7.19 (m, 4H), 7.40 (d, 1H), 7.82 (d, 1H), 8.01 (s, 1H), 8.14 (d, 1H), 8.37 (s, 1H), 9.77 (s, 1H), 11.44 (s, 1H), 11.98 (br s, 1H).

Example 118

1-(4-Methyl-benzyl)-1H-pyrazole-4-carboxylic acid {5-[5-(2-morpholin-4-yl-ethoxy)-1H-indol-2-yl]-6-oxo-1,6-dihydro-pyridin-3-yl}-amide

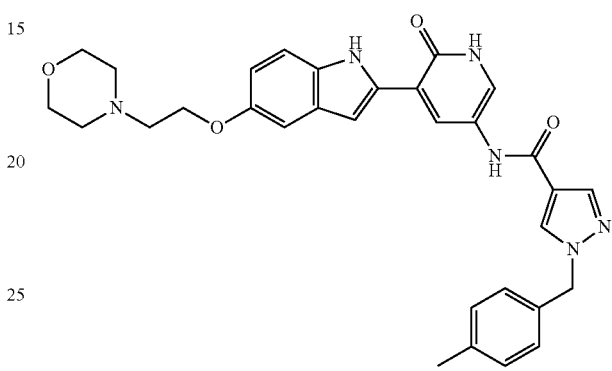 [SMILES: Cc1ccc(Cn2cc(C(=O)Nc3c[nH]c(=O)c(-c4cc5cc(OCCCN6CCOCC6)ccc5[nH]4)c3)cn2)cc1]

The title compound was prepared by the route outlined in Scheme 11, following the same experimental procedures as for Example 115.

The title compound was purified by trituration with acetonitrile, and isolated as a yellow solid, 20 mg, 63%.

LC/MS: RT=1.71 Min (270 nm), m/z=553 [M+H]. Total run time 3.75 min (short pos).

$^1$H NMR (d$_6$ DMSO): δ 2.29 (s, 3H), 2.50 (m, 4H), 2.70 (d, 2H), 3.59 (m, 4H), 4.07 (t, 2H), 5.34 (s, 2H), 6.72 (dd, 1H), 6.93 (m, 1H), 7.04 (d, 1H), 7.19 (m, 4H), 7.40 (d, 1H), 7.82 (d, 1H), 8.01 (s, 1H), 8.14 (d, 1H), 8.37 (s, 1H), 9.76 (s, 1H), 11.45 (s, 1H), 11.96 (br s, 1H).

Example 119

1-(4-Methyl-benzyl)-1H-pyrazole-4-carboxylic acid {6-oxo-5-[5-(3-piperidin-1-yl-propoxy)-1H-indol-2-yl]-1,6-dihydro-pyridin-3-yl}-amide

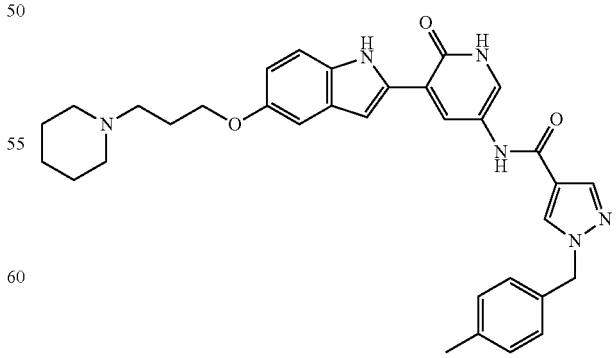

The title compound was prepared by the route outlined in Scheme 11, following the same experimental procedures as for Example 115.

The title compound was purified by trituration with acetonitrile, and isolated as a yellow solid, 47 mg, 87%.

LC/MS: RT=1.78 Min (270 nm), m/z=565 [M+H]. Total run time 3.75 min (short pos).

¹H NMR (d₆ DMSO): δ 1.38 (m, 2H), 1.49 (m, 4H), 1.86 (m, 2H), 2.29 (s, 3H), 2.33 (m, 4H), 2.39 (t, 2H), 3.97 (t, 2H), 5.34 (s, 2H), 6.70 (dd, 1H), 6.92 (m, 1H), 7.01 (d, 1H), 7.19 (m, 4H), 7.39 (d, 1H), 7.82 (d, 1H), 8.01 (s, 1H), 8.13 (d, 1H), 8.37 (s, 1H), 9.77 (s, 1H), 11.45 (s, 1H), 11.98 (br s, 1H).

Example 120

1-Benzyl-1H-pyrazole-4-carboxylic acid {5-[5-(3-dimethylamino-2,2-dimethyl-propoxy)-1H-indol-2-yl]-6-oxo-1,6-dihydro-pyridin-3-yl}-amide

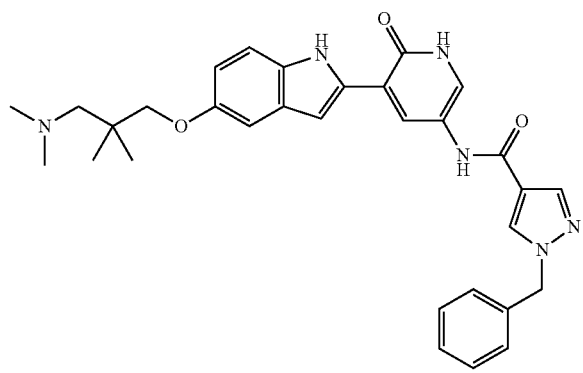 [SMILES: CN(C)CC(C)(C)COc1ccc2[nH]c(-c3cc(NC(=O)c4cnn(Cc5ccccc5)c4)c[nH]c3=O)cc2c1]

The title compound was prepared by the route outlined in Scheme 11, following the same experimental procedures as for Example 115.

The title compound was purified by trituration with acetonitrile, and isolated as a yellow solid, 65 mg, 39%.

LC/MS: RT=1.58 Min (270 nm), m/z=539 [M+H]. Total run time 3.75 min (short pos).

¹H NMR (d₆ DMSO): δ 0.96 (s, 6H), 2.21 (s, 6H), 2.24 (s, 2H), 3.67 (s, 2H), 5.41 (s, 2H), 6.72 (dd, 1H), 6.92 (d, 1H), 7.01 (d, 1H), 7.28-7.40 (m, 6H), 7.84 (d, 1H), 8.03 (s, 1H), 8.14 (d, 1H), 8.41 (s, 1H), 9.79 (s, 1H), 11.43 (s, 1H), 11.99 (br s, 1H).

Example 121

1-(4-Trifluoromethyl-benzyl)-1H-pyrazole-4-carboxylic acid {6-oxo-5-[5-(2-piperidin-1-yl-ethoxy)-1H-indol-2-yl]-1,6-dihydro-pyridin-3-yl}-amide

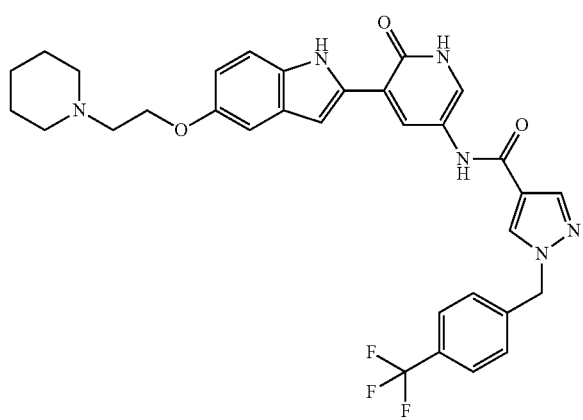 [SMILES: O=C(Nc1c[nH]c(=O)c(-c2cc3cc(OCCN4CCCCC4)ccc3[nH]2)c1)c1cnn(Cc2ccc(C(F)(F)F)cc2)c1]

The title compound was prepared by the route outlined in Scheme 11, following the same experimental procedures as for Example 115, but with the following modification to Step 6. A 3-5 mL microwave vial was charged with 5-hydroxy-2-[2-oxo-5-{[1-(4-trifluoromethyl-benzyl)-1H-pyrazole-4-carbonyl]-amino}-1-(2-trimethylsilanyl-ethoxymethyl)-1,2-dihydro-pyridin-3-yl]-indole-1-carboxylic acid tert-butyl ester (150 mg, 0.207 mmol), triphenyl phosphine (87 mg, 0.33 mmol), tetrahydrofuran (3 mL), 1-(2-hydroxyethyl)piperidine (40 mg, 41 µL 0.31 mmol) and diisopropyl azidocarboxylate (67 mg, 65 µL, 0.33 mmol). The reaction mixture was then heated to 140° C. in the microwave for 30 mins. The crude reaction mixture was purified by flash chromatography on SiO₂, eluting dichloromethane—15% methanol/dichloromethane (gradient) to afford the title compound as a yellow solid, 87 mg, 50%.

The title compound was purified by trituration with acetonitrile, and isolated as a yellow solid, 33 mg, 52%.

LC/MS: RT=1.69 Min (270 nm), m/z=605 [M+H]. Total run time 3.75 min (short pos).

¹H NMR (d₆ DMSO): δ 1.38 (m, 2H), 1.50 (m, 4H), 2.44 (m, 4H), 2.66 (t, 2H), 4.04 (t, 2H), 5.54 (s, 2H), 6.71 (dd, 1H), 6.92 (m, 1H), 7.03 (d, 1H), 7.40 (d, 1H), 7.46 (m, 2H), 7.76 (m, 2H), 7.83 (d, 1H), 8.07 (s, 1H), 8.15 (d, 1H), 8.47 (s, 1H), 9.81 (s, 1H), 11.44 (s, 1H), 11.99 (br s, 1H).

Example 122

1-(4-Methyl-benzyl)-1H-pyrazole-4-carboxylic acid {5-[5-(3-dimethylamino-propoxy)-1H-indol-2-yl]-6-oxo-1,6-dihydro-pyridin-3-yl}-amide

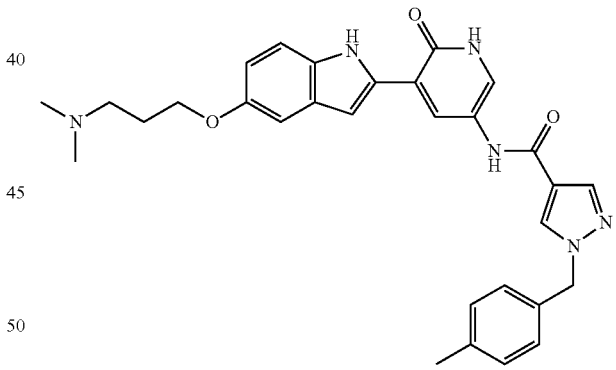 [SMILES: CCN(CC)CCCOc1ccc2[nH]c(-c3cc(NC(=O)c4cnn(Cc5ccc(C)cc5)c4)c[nH]c3=O)cc2c1]

The title compound was prepared by the route outlined in Scheme 11, following the same experimental procedures as for Example 115.

The title compound was purified by trituration with acetonitrile, and isolated as a yellow solid, 6 mg, 23%.

LC/MS: RT=0.92 Min (270 nm), m/z=525 [M+H]. Total run time 1.9 min (super short pos).

¹H NMR (d₆ DMSO): δ 1.81-1.88 (m, 2H), 2.15 (s, 6H), 2.29 (s, 3H), 2.34-2.38 (m, 2H), 3.96-3.99 (t, 2H), 5.34 (s, 2H), 6.69-6.72 (dd, 1H), 6.92 (s, 1H), 7.00-7.01 (d, 1H), 7.19 (m, 4H), 7.38-7.41 (d, 1H), 7.82-7.83 (d, 1H), 8.01 (s, 1H), 8.14-8.15 (d, 1H), 8.37 (s, 1H), 9.77 (s, 1H), 11.47 (s, 1H), 11.92-12.00 (br s, 1H).

Example 123

1-(4-Methyl-benzyl)-1H-pyrazole-4-carboxylic acid {5-[5-(3-diethylamino-propoxy)-1H-indol-2-yl]-6-oxo-1,6-dihydro-pyridin-3-yl}-amide

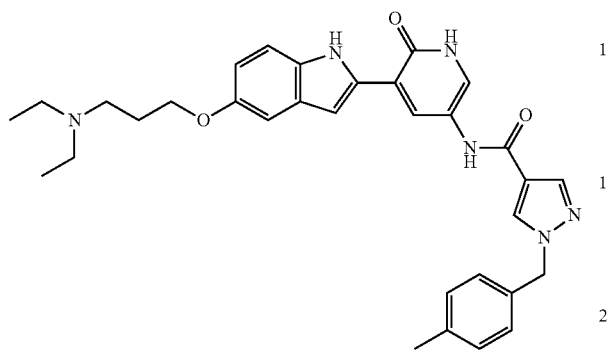

The title compound was prepared by the route outlined in Scheme 11, following the same experimental procedures as for Example 121.

The title compound was purified by trituration with acetonitrile, and isolated as a brown solid, 8 mg, 35%.

LC/MS: RT=1.63 Min (270 nm), m/z=553 [M+H]. Total run time 3.75 min (short pos).

$^1$H NMR (d$_6$ DMSO): δ 0.93-0.97 (t, 6H), 1.79-1.83 (m, 2H), 2.29 (s, 3H), 3.96-3.99 (t, 2H), 5.34 (s, 2H), 6.68-6.70 (d, 1H), 6.89 (s, 1H), 7.00 (s, 1H), 7.19 (s, 4H), 7.37-7.39 (d, 1H), 7.84 (s, 1H), 8.02 (s, 1H), 8.14 (s, 1H), 8.37 (s, 1H), 9.78 (s, 1H), 11.62-11.70 (br s, 1H).

Example 124

1-(4-Methyl-benzyl)-1H-pyrazole-4-carboxylic acid (5-{5-[3-(4-methyl-piperazin-1-yl)-propoxy]-1H-indol-2-yl}-6-oxo-1,6-dihydro-pyridin-3-yl)-amide

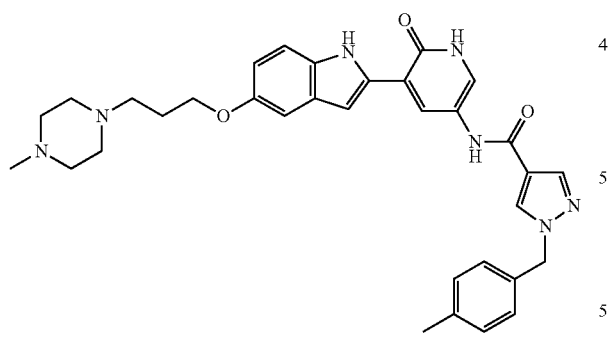

The title compound was prepared by the route outlined in Scheme 11, following the same experimental procedures as for Example 121.

The title compound was purified by trituration with acetonitrile, and isolated as a yellow solid, 13 mg, 29%.

LC/MS: RT=0.91 Min (270 nm), m/z=580 [M+H]. Total run time 1.9 min (super short pos).

$^1$H NMR (d$_6$ DMSO): δ 1.83-1.89 (m, 2H), 2.14 (s, 3H), 2.29 (s, 3H), 2.41-2.44 (t, 2H), 2.31-2.44 (br m, 8H), 3.96-3.99 (t, 2H), 5.34 (s, 2H), 6.69-6.72 (dd, 1H), 6.92 (s, 1H), 7.00-7.01 (d, 1H), 7.19 (s, 4H), 7.38-7.40 (d, 1H), 7.82-7.83 (d, 1H), 8.01 (s, 1H), 8.13-8.14 (d, 1H), 8.37 (s, 1H), 9.78 (s, 1H), 11.46 (s, 1H), 11.90-12.00 (br s, 1H).

Example 125

1-(4-Methyl-benzyl)-1H-pyrazole-4-carboxylic acid {5-[5-(2-diethylamino-ethoxy)-1H-indol-2-yl]-6-oxo-1,6-dihydro-pyridin-3-yl}-amide

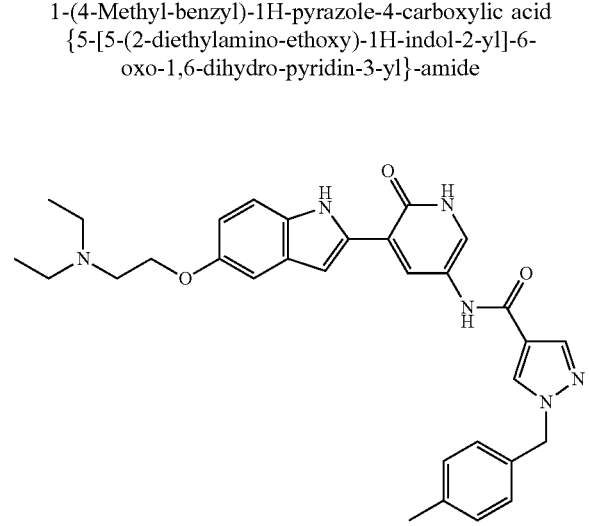

The title compound was prepared by the route outlined in Scheme 11, following the same experimental procedures as for Example 115.

The title compound was purified by trituration with acetonitrile, and isolated as a brown solid, 28 mg, 44%.

LC/MS: RT=0.93 Min (270 nm), m/z=539 [M+H]. Total run time 1.9 min (super short pos).

$^1$H NMR (d$_6$ DMSO): δ 0.97-1.00 (t, 6H), 2.29 (s, 3H), 2.53-2.59 (q, 4H), 2.76-2.79 (t, 2H), 3.98-4.01 (t, 2H), 5.34 (s, 2H), 6.69-6.72 (dd, 1H), 6.93 (s, 1H), 7.02-7.03 (d, 1H), 7.19 (s, 4H), 7.39-7.41 (d, 1H), 7.82-7.83 (d, 1H), 8.01 (s, 1H), 8.14-8.15 (d, 1H), 8.37 (s, 1H), 9.78 (s, 1H), 11.45 (s, 1H).

Example 126

1-(4-Methyl-benzyl)-1H-pyrazole-4-carboxylic acid (5-{5-[2-(4-methyl-piperazin-1-yl)-ethoxy]-1H-indol-2-yl}-6-oxo-1,6-dihydro-pyridin-3-yl)-amide

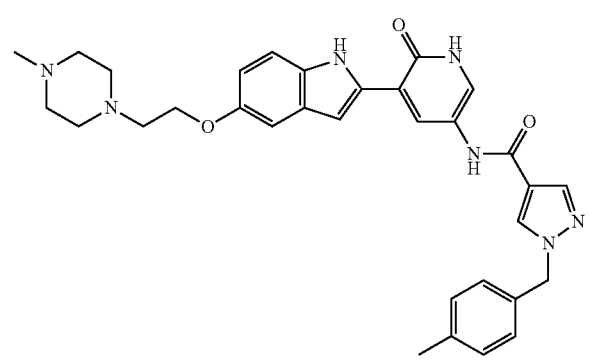 [SMILES: Cc1ccc(Cn2cc(C(=O)Nc3c[nH]c(=O)c(-c4cc5cc(OCCN6CCN(C)CC6)ccc5[nH]4)c3)cn2)cc1]

The title compound was prepared by the route outlined in Scheme 11, following the same experimental procedures as for Example 115.

The title compound was purified by trituration with acetonitrile, and isolated as a yellow solid, 2 mg, 23%.

LC/MS: RT=0.92 Min (270 nm), m/z=566 [M+H]. Total run time 1.9 min (super short pos).

$^1$H NMR (d$_6$ DMSO): δ 2.14 (s, 3H), 2.29 (s, 3H), 2.24-2.40 (br m, 8H), 2.64-2.70 (m, 2H), 4.03-4.06 (t, 2H), 5.34 (s, 2H), 6.69-6.72 (dd, 1H), 6.91 (s, 1H), 7.02-7.03 (d, 1H), 7.19 (s, 4H), 7.38-7.40 (d, 1H), 7.82-7.83 (d, 1H), 8.02 (s, 1H), 8.13-8.14 (d, 1H), 8.37 (s, 1H), 9.77 (s, 1H), 11.48-11.61 (br s, 1H).

Example 127

1-(3-Ethyl-benzyl)-1H-pyrazole-4-carboxylic acid (5-{5-[3-(4-methyl-piperazin-1-yl)-propoxy]-1H-indol-2-yl}-6-oxo-1,6-dihydro-pyridin-3-yl)-amide

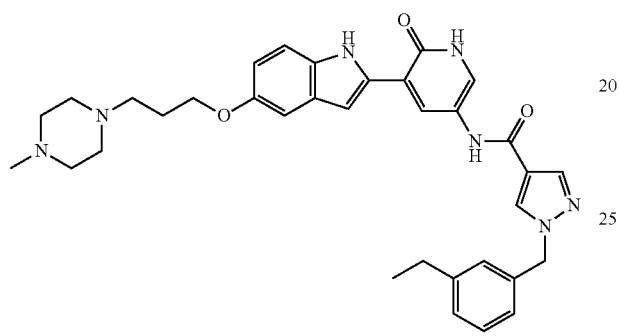

The title compound was prepared by the route outlined in Scheme 11, following the same experimental procedures as for Example 121.

The title compound was purified by trituration with acetonitrile, and isolated as a yellow solid, 7 mg, 24%.

LC/MS: RT=0.96 Min (270 nm), m/z=594 [M+H]. Total run time 1.9 min (super short pos).

$^1$H NMR (d$_6$ DMSO): δ 1.15-1.19 (t, 3H), 1.84-1.88 (m, 2H), 2.14 (s, 3H), 2.30-2.46 (br m, 8H), 2.41-2.44 (t, 2H), 2.57-2.62 (q, 2H), 3.96-3.99 (t, 2H), 5.37 (s, 2H), 6.69-6.72 (dd, 1H), 6.92 (s, 1H), 7.00-7.01 (d, 1H), 7.07-7.09 (d, 1H), 7.15 (s, 1H), 7.18 (s, 1H), 7.27-7.31 (m, 1H), 7.38-7.41 (d, 1H), 7.82-7.83 (d, 1H), 8.03 (s, 1H), 8.14-8.15 (d, 1H), 8.40 (s, 1H), 9.79 (s, 1H), 11.48 (s, 1H), 11.90-12.00 (br m, 1H).

Example 128

1-(3-Ethyl-benzyl)-1H-pyrazole-4-carboxylic acid {5-[5-(2-dimethylamino-ethoxy)-1H-indol-2-yl]-6-oxo-1,6-dihydro-pyridin-3-yl}-amide

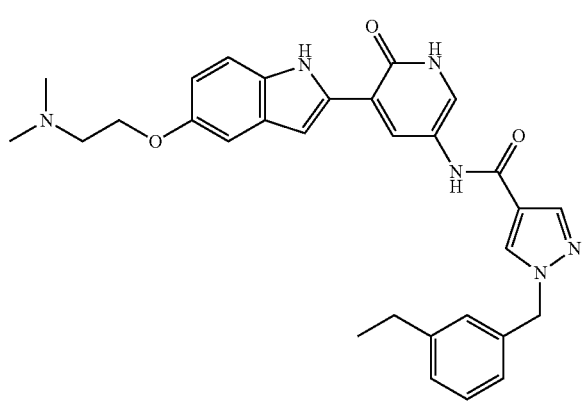 [SMILES: CCc1cccc(Cn2cc(C(=O)Nc3c[nH]c(=O)c(-c4cc5cc(OCCN(C)C)ccc5[nH]4)c3)cn2)c1]

The title compound was prepared by the route outlined in Scheme 11, following the same experimental procedures as for Example 121.

The title compound was purified by trituration with acetonitrile, and isolated as a yellow solid, 16 mg, 39%.

LC/MS: RT=0.95 Min (270 nm), m/z=525 [M+H]. Total run time 1.9 min (super short pos).

$^1$H NMR (d$_6$ DMSO): δ 1.15-1.19 (t, 3H), 2.22 (s, 6H), 2.58-2.64 (m, 4H), 4.01-4.04 (t, 2H), 5.37 (s, 2H), 6.69-6.72 (dd, 1H), 6.91 (s, 1H), 7.02-7.03 (d, 1H), 7.07-7.09 (d, 1H), 7.15 (s, 1H), 7.18 (s, 1H), 7.27-7.31 (t, 1H), 7.38-7.41 (d, 1H), 7.82-7.83 (d, 1H), 8.03 (s, 1H), 8.14-8.15 (d, 1H), 8.40 (s, 1H), 9.78 (s, 1H), 11.50-11.61 (s, 1H), 11.86-12.00 (br s, 1H).

Example 129

1-(3-Ethyl-benzyl)-1H-pyrazole-4-carboxylic acid {5-[5-(3-dimethylamino-propoxy)-1H-indol-2-yl]-6-oxo-1,6-dihydro-pyridin-3-yl}-amide

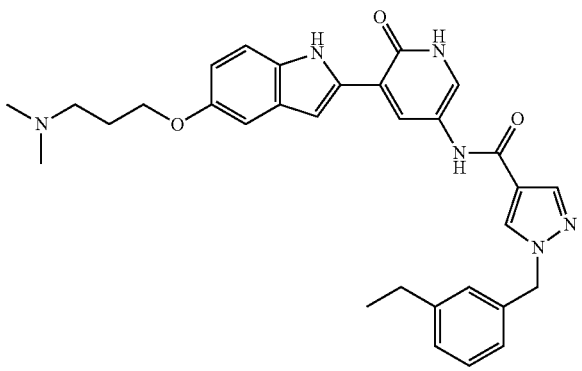 [SMILES: CCc1cccc(Cn2cc(C(=O)Nc3c[nH]c(=O)c(-c4cc5cc(OCCCN(C)C)ccc5[nH]4)c3)cn2)c1]

The title compound was prepared by the route outlined in Scheme 11, following the same experimental procedures as for Example 121.

The title compound was purified by trituration with acetonitrile, and isolated as a yellow solid, 6 mg, 20%.

LC/MS: RT=0.97 Min (270 nm), m/z=539 [M+H]. Total run time 1.9 min (super short pos).

$^1$H NMR (d$_6$ DMSO): δ 1.15-1.19 (t, 3H), 1.85 (m, 2H), 2.15 (s, 6H), 2.33-2.40 (m, 4H), 3.96-3.98 (t, 2H), 5.37 (s, 2H), 6.69-6.72 (d, 1H), 6.91 (s, 1H), 7.01 (s, 1H), 7.07-7.09 (d, 1H), 7.15 (s, 1H), 7.18 (s, 1H), 7.27-7.31 (t, 1H), 7.38-7.40 (d, 1H), 7.84 (s, 1H), 8.03 (s, 1H), 8.15 (s, 1H), 8.41 (s, 1H), 9.78 (s, 1H), 11.50 (s, 1H).

Example 130

1-(3-Ethyl-benzyl)-1H-pyrazole-4-carboxylic acid {5-[5-(2-diethylamino-ethoxy)-1H-indol-2-yl]-6-oxo-1,6-dihydro-pyridin-3-yl}-amide

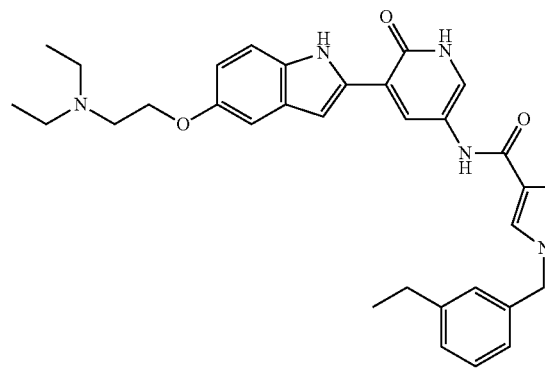

The title compound was prepared by the route outlined in Scheme 11, following the same experimental procedures as for Example 121.

The title compound was purified by trituration with acetonitrile, and isolated as a brown solid, 2 mg, 3%.

LC/MS: RT=0.98 Min (270 nm), m/z=553 [M+H]. Total run time 1.9 min (super short pos).

$^1$H NMR (d$_6$ DMSO): δ 0.97-1.00 (t, 6H), 1.15-1.19 (t, 3H), 2.53-2.60 (m, 6H), 2.76-2.79 (t, 2H), 3.98-4.01 (t, 2H), 5.37 (s, 2H), 6.69-6.72 (dd, 1H), 6.92-6.41 (m, 7H), 7.83 (m, 1H), 8.03 (s, 1H), 8.14-8.15 (s, 1H), 8.40 (s, 1H), 9.79 (s, 1H), 11.44 (s, 1H), 11.90-12.00 (br m, 1H).

Example 131

1-(4-Methyl-benzyl)-1H-pyrazole-4-carboxylic acid (5-{5-[2-(2,6-dimethyl-morpholin-4-yl)-ethoxy]-1H-indol-2-yl}-6-oxo-1,6-dihydro-pyridin-3-yl)-amide

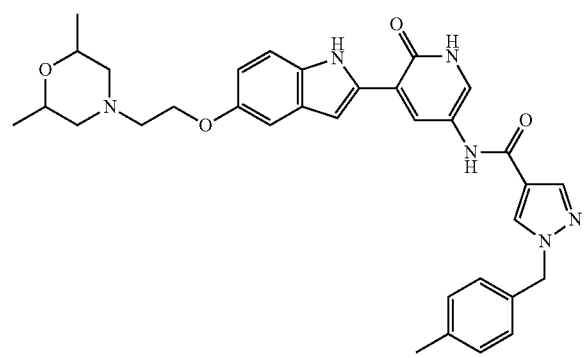 [SMILES: Cc1ccc(Cn2cc(C(=O)Nc3c[nH]c(=O)c(-c4cc5cc(OCCN6CC(C)OC(C)C6)ccc5[nH]4)c3)cn2)cc1]

The title compound was prepared by the route outlined in Scheme 11, following the same experimental procedures as for Example 121.

The title compound was purified by trituration with acetonitrile, and isolated as a yellow solid, 2 mg, 5%.

LC/MS: RT=0.98 Min (270 nm), m/z=581 [M+H]. Total run time 1.9 min (super short pos).

$^1$H NMR (d$_6$ DMSO): δ 1.04 (d, 6H), 1.73 (t, 2H), 2.29 (s, 3H), 2.68 (m, 2H), 2.84 (d, 2H), 3.52-3.61 (m, 2H), 4.06 (t, 2H), 5.34 (s, 2H), 6.71 (dd, 1H), 6.92 (d, 1H), 7.03 (d, 1H), 7.19 (s, 4H), 7.40 (d, 1H), 7.82 (d, 1H), 8.01 (s, 1H), 8.15 (d, 1H), 8.37 (s, 1H), 9.77 (s, 1H), 11.47 (br s, 1H), 11.92 (br s, 1H)

Example 132

1-(4-Methyl-benzyl)-1H-pyrazole-4-carboxylic acid {5-[5-(2-dimethylamino-ethoxy)-1H-indol-2-yl]-6-oxo-1,6-dihydro-pyridin-3-yl}-amide

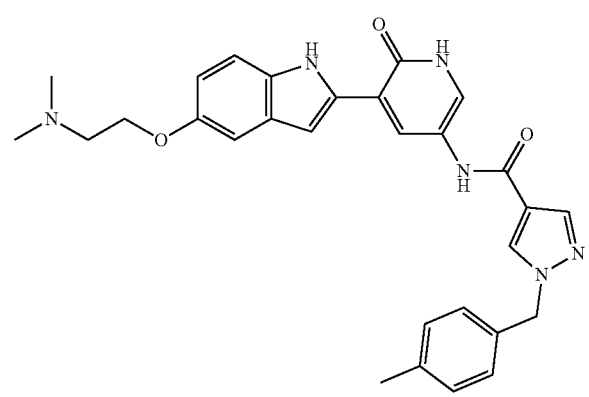 [SMILES: Cc1ccc(Cn2cc(C(=O)Nc3c[nH]c(=O)c(-c4cc5cc(OCCN(C)C)ccc5[nH]4)c3)cn2)cc1]

The title compound was prepared by the route outlined in Scheme 11, following the same experimental procedures as for Example 115.

The title compound was purified by preparative HPLC at pH 9 and isolated as a yellow solid, 2 mg, 3%.

LC/MS: RT=0.91 Min (270 nm), m/z=511 [M+H]. Total run time 1.9 min (super short pos).

$^1$H NMR (d$_6$ DMSO): δ 2.23 (s, 6H), 2.29 (s, 3H), 2.63 (t, 2H), 4.03 (t, 2H), 5.34 (s, 2H), 6.72 (dd, 1H), 6.93 (d, 1H), 7.03 (d, 1H), 7.19 (s, 4H), 7.40 (d, 1H), 7.83 (d, 1H), 8.02 (s, 1H), 8.15 (d, 1H), 8.37 (s, 1H), 9.78 (s, 1H), 11.45 (br s, 1H), 11.98 (br s, 1H)

Example 133

1-(3-Ethyl-benzyl)-1H-pyrazole-4-carboxylic acid (5-{5-[2-(4-methyl-piperazin-1-yl)-ethoxy]-1H-indol-2-yl}-6-oxo-1,6-dihydro-pyridin-3-yl)-amide

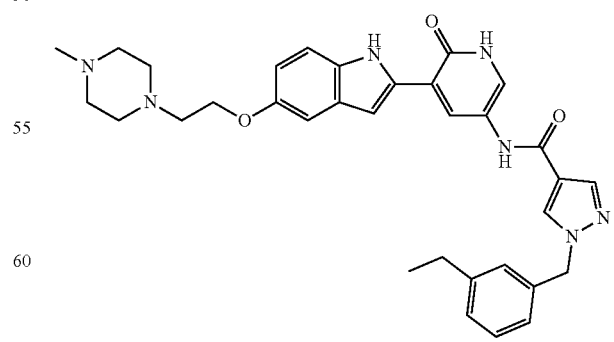

The title compound was prepared by the route outlined in Scheme 11, following the same experimental procedures as for Example 121.

The title compound was purified by trituration with acetonitrile, and isolated as a yellow solid, 12 mg, 20%.

LC/MS: RT=0.97 Min (270 nm), m/z=580 [M+H]. Total run time 1.9 min (super short pos).

$^1$H NMR (d$_6$ DMSO): δ 1.17 (t, 3H), 1.23 (m, 2H), 2.14 (s, 3H), 2.24-2.38 (m, 4H), 2.59 (q, 2H), 2.68 (t, 2H), 4.05 (t, 2H), 5.37 (s, 2H), 6.71 (dd, 1H), 6.92 (d, 1H), 7.03 (d, 1H), 7.08 (d, 1H), 7.14-7.19 (m, 2H), 7.26-7.31 (m, 1H), 7.39 (d, 1H), 7.83 (d, 1H), 8.03 (s, 1H), 8.15 (d, 1H), 8.4 (s, 1H), 9.78 (s, 1H), 11.47 (br s, 1H), 11.95 (br s, 1H)

Example 134

1-(3-Ethyl-benzyl)-1H-pyrazole-4-carboxylic acid {6-oxo-5-[5-(3-piperidin-1-yl-propoxy)-1H-indol-2-yl]-1,6-dihydro-pyridin-3-yl}-amide

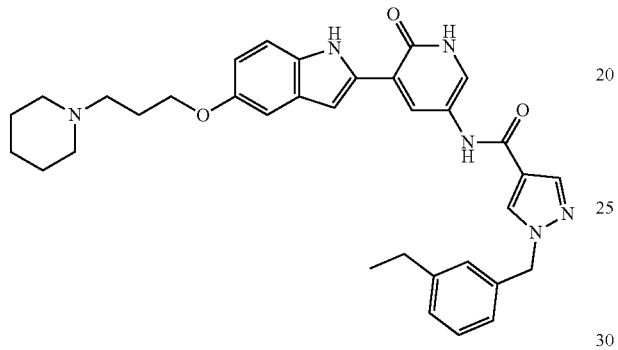

The title compound was prepared by the route outlined in Scheme 11, following the same experimental procedures as for Example 121.

The title compound was purified by trituration with acetonitrile, and isolated as a yellow solid, 13 mg, 25%.

LC/MS: RT=1.02 Min (270 nm), m/z=579 [M+H]. Total run time 1.9 min (super short pos).

$^1$H NMR (d$_6$ DMSO): δ 1.17 (t, 3H), 1.33-1.41 (m, 2H), 1.46-1.52 (m, 4H), 1.85 (quintet, 2H), 2.30-2.35 (m, 4H), 2.39 (t, 2H), 2.59 (q, 2H), 3.97 (t, 2H), 5.37 (s, 2H), 6.71 (dd, 1H), 6.92 (d, 1H), 7.01 (d, 1H), 7.08 (d, 1H), 7.14-7.20 (m, 2H), 7.26-7.31 (m, 1H), 7.4 (d, 1H), 7.82 (d, 1H), 8.03 (s, 1H), 8.15 (d, 1H), 8.4 (s, 1H), 9.79 (s, 1H), 11.46 (br s, 1H), 11.95 (br s, 1H)

Example 135

1-(3-Ethyl-benzyl)-1H-pyrazole-4-carboxylic acid {6-oxo-5-[5-(2-piperidin-1-yl-ethoxy)-1H-indol-2-yl]-1,6-dihydro-pyridin-3-yl}-amide

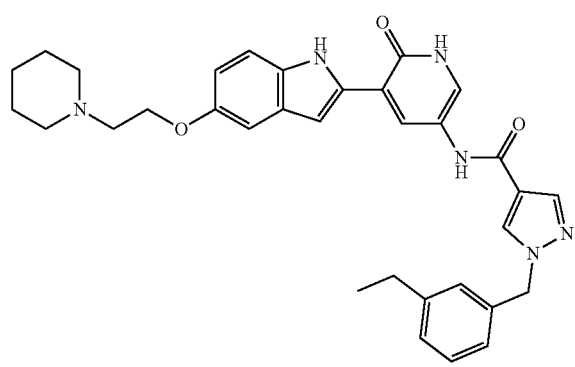 [SMILES: CCc1cccc(Cn2cc(C(=O)Nc3c[nH]c(=O)c(-c4cc5cc(OCCN6CCCCC6)ccc5[nH]4)c3)cn2)c1]

The title compound was prepared by the route outlined in Scheme 11, following the same experimental procedures as for Example 121.

The title compound was purified by trituration with acetonitrile, and isolated as a yellow solid, 13 mg, 23%.

LC/MS: RT=1.74 Min (270 nm), m/z=565 [M+H]. Total run time 3.75 min (short pos).

$^1$H NMR (d$_6$ DMSO): δ 1.17 (t, 3H), 1.4 (m, 2H), 1.5 (m, 4H), 2.45 (m, 4H), 2.6 (q, 2H), 2.65 (t, 2H), 4.04 (t, 2H), 5.37 (s, 2H), 6.71 (dd, 1H), 6.92 (s, 1H), 7.03 (d, 1H), 7.07 (d, 1H), 7.15-7.2 (m, 2H), 7.26-7.31 (m, 1H), 7.4 (d, 1H), 7.82 (d, 1H), 8.03 (s, 1H), 8.15 (d, 1H), 8.4 (s, 1H), 9.78 (br s, 1H), 11.45 (br s, 1H), 11.98 (br s, 1H)

Example 136

1-(3-Ethyl-benzyl)-1H-pyrazole-4-carboxylic acid {5-[5-(3-diethylamino-propoxy)-1H-indol-2-yl]-6-oxo-1,6-dihydro-pyridin-3-yl}-amide

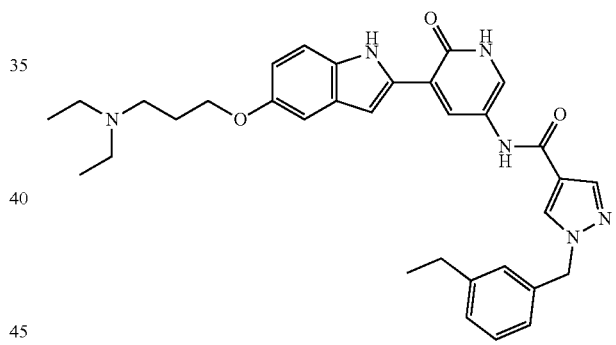

The title compound was prepared by the route outlined in Scheme 11, following the same experimental procedures as for Example 121.

The title compound was purified by preparative HPLC at pH 9 and isolated as a yellow solid, 6 mg, 12%.

LC/MS: RT=1.01 Min (270 nm), m/z=567 [M+H]. Total run time 1.9 min (super short pos).

$^1$H NMR (d$_6$ DMSO): δ 0.96 (t, 6H), 1.17 (t, 3H), 1.83 (quintet, 2H), 2.44-2.52 (multiplicity partially obscured by residual DMSO peak, 4H), 2.54-2.62 (m, 4H), 3.98 (t, 2H), 5.37 (s, 2H), 6.71 (dd, 1H), 6.93 (d, 1H), 7.01 (d, 1H), 7.08 (d, 1H), 7.14-7.19 (m, 2H), 7.29 (m, 1H), 7.40 (d, 1H), 7.83 (d, 1H), 8.03 (s, 1H), 8.16 (d, 1H), 8.40 (s, 1H), 9.81 (s, 1H), 11.45 (br s, 1H), 11.96 (br s, 1H)

Example 137

1-(4-Methyl-benzyl)-1H-pyrazole-4-carboxylic acid {5-[5-(3-dimethylamino-2,2-dimethyl-propoxy)-1H-indol-2-yl]-6-oxo-1,6-dihydro-pyridin-3-yl}-amide

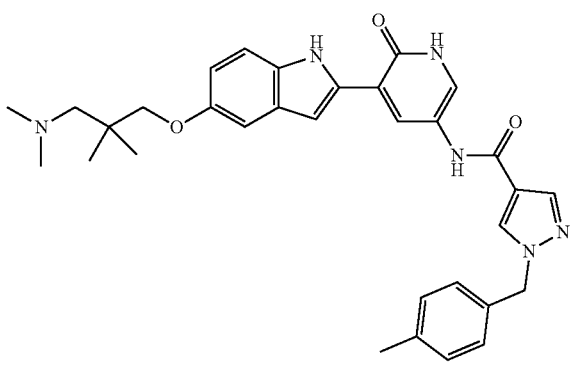 [SMILES: Cc1ccc(Cn2cc(C(=O)Nc3c[nH]c(=O)c(-c4cc5cc(OCC(C)(C)CN(C)C)ccc5[nH]4)c3)cn2)cc1]

The title compound was prepared by the route outlined in Scheme 11, following the same experimental procedures as for Example 121.

The title compound was purified by trituration with diethyl ether, and isolated as a yellow solid, 4 mg, 7%.

LC/MS: RT=1.67 Min (270 nm), m/z=553 [M+H]. Total run time 3.75 min (short pos).

$^1$H NMR (d$_6$ DMSO): δ 0.96 (s, 6H), 2.2 (s, 6H), 2.24 (s, 2H), 2.29 (s, 3H), 3.67 (s, 2H), 5.34 (s, 2H), 6.72 (dd, 1H), 6.92 (d, 1H) 7.01 (d, 1H), 7.19 (s, 4H), 7.39 (d, 1H), 7.84 (s, 1H), 8.01 (s, 1H), 8.13 (s, 1H), 8.37 (s, 1H), 9.77 (br s, 1H), 11.43 (br s, 1H), 11.98 (br s, 1H)

Example 138

1-(3-Ethyl-benzyl)-1H-pyrazole-4-carboxylic acid (5-{5-[2-(2,6-dimethyl-morpholin-4-yl)-ethoxy]1H-indol-2-yl}-6-oxo-1,6-dihydro-pyridin-3-yl)-amide

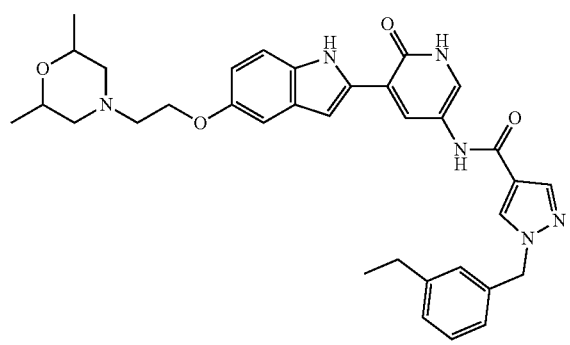 [SMILES: CCc1cccc(Cn2cc(C(=O)Nc3c[nH]c(=O)c(-c4cc5cc(OCCN6CC(C)OC(C)C6)ccc5[nH]4)c3)cn2)c1]

The title compound was prepared by the route outlined in Scheme 11, following the same experimental procedures as for Example 121.

The title compound was purified by preparative HPLC at pH 4 and isolated as a brown solid, 5 mg, 19%.

LC/MS: RT=1.01 Min (270 nm), m/z=595 [M+H]. Total run time 1.9 min (super short pos).

$^1$H NMR (d$_6$ DMSO): δ 1.04 (d, 6H), 1.17 (t, 3H), 1.73 (t, 2H), 2.59 (q, 2H), 2.68 (m, 2H), 2.84 (d, 2H), 3.52-3.60 (m, 2H), 4.06 (m, 2H), 5.37 (s, 2H), 6.72 (dd, 1H), 6.92 (d, 1H), 7.03 (d, 1H), 7.08 (d, 1H), 7.14-7.19 (m, 2H), 7.29 (m, 1H), 7.40 (d, 1H), 7.83 (d, 1H), 8.03 (s, 1H), 8.17 (d, 1H), 8.40 (s, 1H), 9.80 (s, 1H), 11.45 (br s, 1H), 11.95 (br s, 1H)

Example 139

1-Benzyl-1H-pyrazole-4-carboxylic acid {5-[5-(3-diethylamino-propoxy)-1H-indol-2-yl]-6-oxo-1,6-dihydro-pyridin-3-yl}-amide

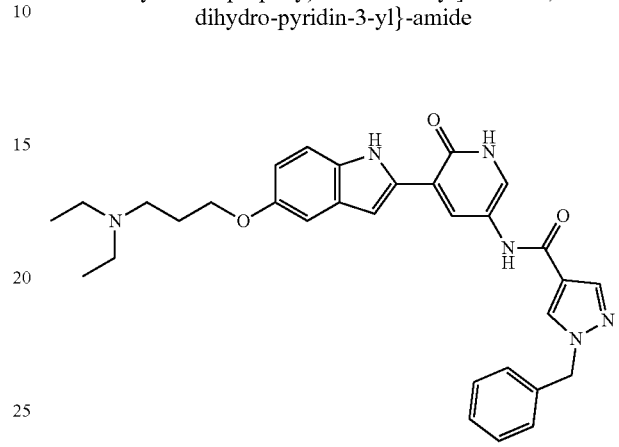

The title compound was prepared by the route outlined in Scheme 11, following the same experimental procedures as for Example 121.

The title compound was purified by trituration with acetonitrile, and isolated as a yellow solid, 7 mg, 16%.

LC/MS: RT=0.92 Min (254 nm), m/z=539 [M+H]. Total run time 1.9 min (super short pos).

$^1$H NMR (d$_6$ DMSO): δ 0.95 (t, 6H), 1.80 (quintet, 2H), 2.45 (q, 4H), 2.53 (t, 2H), 3.98 (t, 2H), 5.40 (s, 2H), 6.68-6.72 (dd, 1H), 6.92 (d, 1H), 7.02 (d, 1H), 7.26-7.41 (m, 6H), 7.83 (d, 1H), 8.04 (s, 1H), 8.14 (d, 1H), 8.40 (s, 1H), 9.77 (s, 1H), 11.44 (s, 1H), 11.98 (br s, 1H)

Example 140

1-Benzyl-1H-pyrazole-4-carboxylic acid (5-{5-[3-(4-methyl-piperazin-1-yl)-propoxy]-1H-indol-2-yl}-6-oxo-1,6-dihydro-pyridin-3-yl)-amide

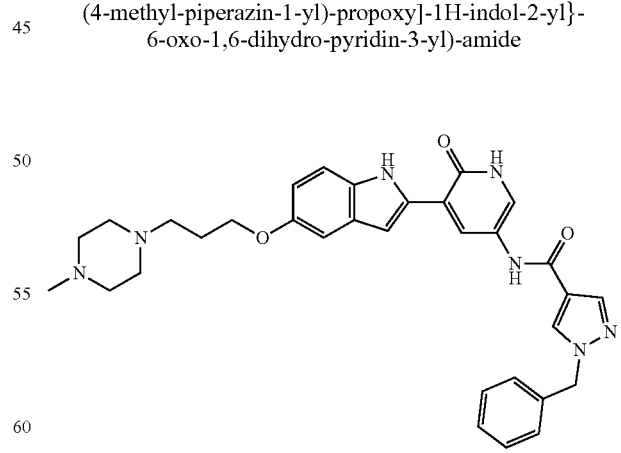

The title compound was prepared by the route outlined in Scheme 11, following the same experimental procedures as for Example 121.

The title compound was purified by trituration with acetonitrile, and isolated as a yellow solid, 17 mg, 36%.

LC/MS: RT=0.88 Min (254 nm), m/z=566 [M+H]. Total run time 1.9 min (super short pos).

¹H NMR (d₆ DMSO): δ 1.85 (quintet, 2H), 2.14 (s, 3H), 2.20-2.50 (br m, 8H), 2.42 (t, 2H), 3.98 (t, 2H), 5.4 (s, 2H), 6.68-6.72 (dd, 1H), 6.91 (d, 1H), 7 (d, 1H), 7.27-7.42 (m, 6H), 7.82 (d, 1H), 8.03 (s, 1H), 8.14 (d, 1H), 8.40 (s, 1H), 9.78 (s, 1H), 11.45 (s, 1H), 11.98 (br s, 1H).

Example 141

1-Benzyl-1H-pyrazole-4-carboxylic acid {5-[5-(2-diethylamino-ethoxy)-1H-indol-2-yl]-6-oxo-1,6-dihydro-pyridin-3-yl}-amide

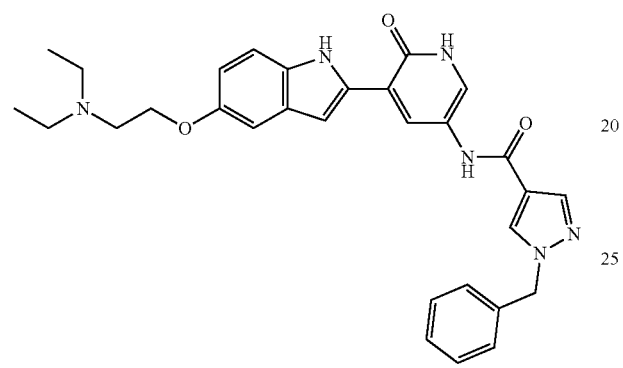

The title compound was prepared by the route outlined in Scheme 11, following the same experimental procedures as for Example 121.

The title compound was purified by trituration with acetonitrile, and isolated as a yellow solid, 14 mg, 32%.

LC/MS: RT=1.59 Min (254 nm), m/z=525 [M+H]. Total run time 3.75 min (short pos).

¹H NMR (d₆ DMSO): δ 0.98 (t, 6H), 2.56 (q, 4H), 2.77 (t, 2H), 4, (t, 2H), 5.40 (s, 2H), 6.68-6.72 (dd, 1H), 6.92 (d, 1H), 7.03 (d, 1H), 7.27-7.42 (m, 6H), 7.83 (d, 1H), 8.03 (s, 1H), 8.15 (d, 1H), 8.41 (s, 1H), 9.78 (s, 1H), 11.45 (s, 1H), 11.98 (br s, 1H)

Example 142

1-Benzyl-1H-pyrazole-4-carboxylic acid {5-[5-(2-dimethylamino-ethoxy)-1H-indol-2-yl]-6-oxo-1,6-dihydro-pyridin-3-yl}-amide

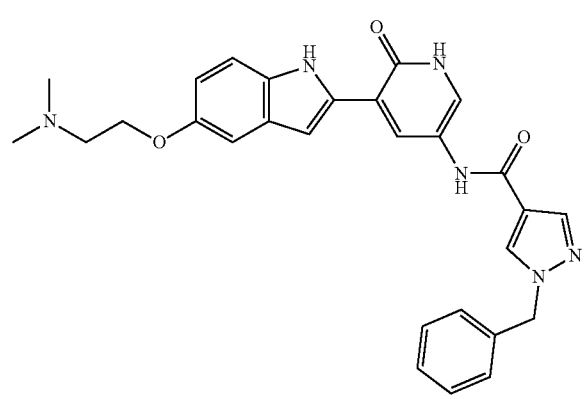

The title compound was prepared by the route outlined in Scheme 11, following the same experimental procedures as for Example 121.

The title compound was purified by trituration with acetonitrile, and isolated as a yellow solid, 5 mg, 22%.

LC/MS: RT=1.53 Min (254 nm), m/z=497 [M+H]. Total run time 3.75 min (short pos).

¹H NMR (d₆ DMSO): δ 2.22 (s, 6H), 2.63 (t, 2H), 4.02 (t, 2H), 5.4 (s, 2H), 6.7-6.74 (dd, 1H), 6.93 (d, 1H), 7.03 (d, 1H), 7.26-7.42 (m, 6H), 7.82 (d, 1H), 8.04 (s, 1H), 8.14 (d, 1H), 8.41 (s, 1H), 9.78 (s, 1H), 11.45 (s, 1H), 11.98 (br s, 1H)

Example 143

1-Benzyl-1H-pyrazole-4-carboxylic acid {6-oxo-5-[5-(3-piperdin-1-yl-propoxy)-1H-indol-2-yl]-1,6-dihydro-pyridin-3-yl}-amide

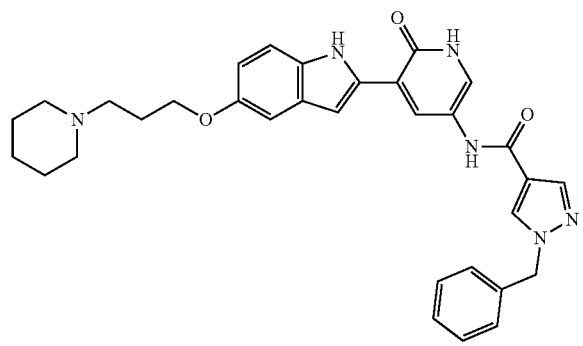 [SMILES: O=C(Nc1c[nH]c(=O)c(-c2cc3cc(OCCCN4CCCCC4)ccc3[nH]2)c1)c1cnn(Cc2ccccc2)c1]

The title compound was prepared by the route outlined in Scheme 11, following the same experimental procedures as for Example 121.

The title compound was purified by trituration with acetonitrile, and isolated as a yellow solid, 13 mg, 30%.

LC/MS: RT=1.62 Min (254 nm), m/z=551 [M+H]. Total run time 3.75 min (short pos).

¹H NMR (d₆ DMSO): δ 1.37-1.41 (br m, 2H), 1.46-1.54 (m, 4H), 1.85 (quintet, 2H), 2.30-2.36 (br m, 4H), 2.39 (t, 2H), 3.98 (t, 2H), 5.40 (s, 2H), 6.68-6.72 (dd, 1H), 6.92 (d, 1H), 7.01 (d, 1H), 7.26-7.42 (m, 6H), 7.82 (d, 1H), 8.03 (s, 1H), 8.15 (d, 1H), 8.40 (s, 1H), 9.78 (s, 1H), 11.45 (s, 1H), 11.98 (br s, 1H)

Example 144

1-Benzyl-1H-pyrazole-4carboxylic acid {6-oxo-5-[5-(2-pyrrolidin-1-yl-ethoxy)-1H-indol-2-yl]-1,6-dihydro-pyridin-3-yl}-amide

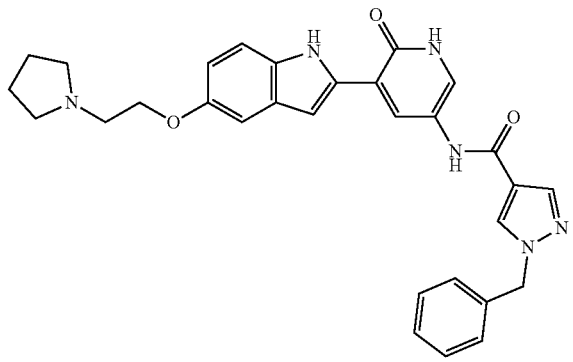 [SMILES: O=C(Nc1c[nH]c(=O)c(-c2cc3cc(OCCN4CCCC4)ccc3[nH]2)c1)c1cnn(Cc2ccccc2)c1]

The title compound was prepared by the route outlined in Scheme 11, following the same experimental procedures as for Example 121.

The title compound was purified by trituration with acetonitrile, and isolated as a yellow solid, 14 mg, 42%.

LC/MS: RT=1.53 Min (254 nm), m/z=523 [M+H]. Total run time 3.75 min (short pos).

$^1$H NMR (d$_6$ DMSO): δ 1.68 (m, 4H), 2.52 (m, obscured by DMSO peak, 4H), 2.78 (t, 2H), 4.04 (t, 2H), 5.40 (s, 2H), 6.68-6.72 (dd, 1H), 6.92 (d, 1H), 7.02 (d, 1H), 7.26-7.42 (m, 6H), 7.82 (d, 1H), 8.04 (s, 1H), 8.15 (d, 1H), 8.41 (s, 1H), 9.78 (s, 1H), 11.46 (s, 1H), 11.98 (br s, 1H)

Example 145

1-Benzyl-1H-pyrazole-4-carboxylic acid {5-[5-(3-dimethylamino-propoxy)-1H-indol-2-yl]-6oxo-1,6-dihydro-pyridin-3-yl}-amide

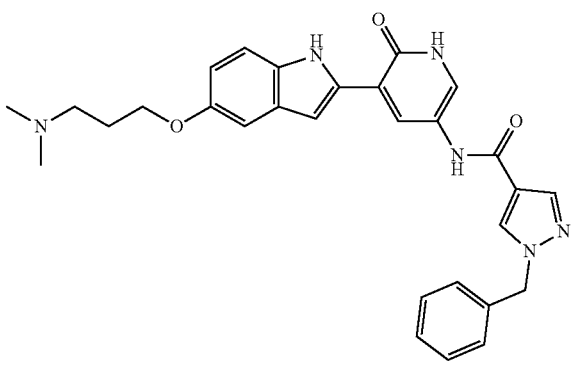 [SMILES: CN(C)CCCOc1ccc2[nH]c(-c3cc(NC(=O)c4cnn(Cc5ccccc5)c4)c[nH]c3=O)cc2c1]

The title compound was prepared by the route outlined in Scheme 11, following the same experimental procedures as for Example 121.

The title compound was purified by trituration with acetonitrile, and isolated as a yellow solid, 14 mg, 28%.

LC/MS: RT=1.55 Min (254 nm), m/z=511 [M+H]. Total run time 3.75 min (short pos).

$^1$H NMR (d$_6$ DMSO): δ 1.85 (quintet, 2H), 2.15 (s, 6H), 2.38 (t, 2H), 3.98 (t, 2H), 5.40 (s, 2H), 6.68-6.72 (dd, 1H), 6.92 (d, 1H), 7.02 (d, 1H), 7.26-7.42 (m, 6H), 7.82 (d, 1H), 8.04 (s, 1H), 8.15 (d, 1H), 8.40 (s, 1H), 9.78 (s, 1H), 11.45 (s, 1H), 11.98 (br s, 1H)

Example 146

1-Benzyl-1H-pyrazole-4-carboxylic acid (5-{5-[2-(4-methyl-piperazin-1-yl-ethoxy]-1H-indol-2-yl}-6-oxo-1,6-dihydro-pyridin-3-yl)-amide

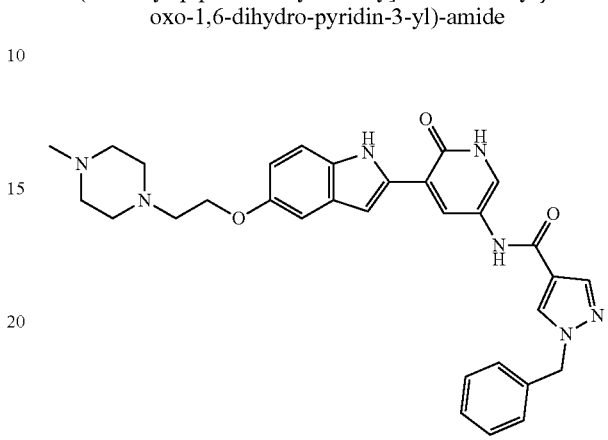

The title compound was prepared by the route outlined in Scheme 11, following the same experimental procedures as for Example 121.

The title compound was purified by trituration with acetonitrile, and isolated as a yellow solid, 11 mg, 27%.

LC/MS: RT=1.52 Min (254 nm), m/z=552 [M+H]. Total run time 3.75 min (short pos).

$^1$H NMR (d$_6$ DMSO): δ 2.14 (s, 3H), 2.20-2.40 (br m, 4H), 2.68 (t, 2H), 4.05 (t, 2H), 5.40 (s, 2H), 6.69-6.74 (dd, 1H), 6.97 (d, 1H), 7.04 (d, 1H), 7.27-7.42 (m, 6H), 7.83 (d, 1H), 8.04 (s, 1H), 8.15 (d, 1H), 8.40 (s, 1H), 9.78 (s 1H), 11.45 (s, 1H), 11.98 (br s, 1H)

Example 147

1-Benzyl-1H-pyrazole-4-caroxylic acid (5-{5-[2-(2,6-dimethyl-morpholin-4-yl)-ethoxy]-1H-indol-2-yl}-6oxo-1,6-dihydro-pyridin-3-yl)-amide

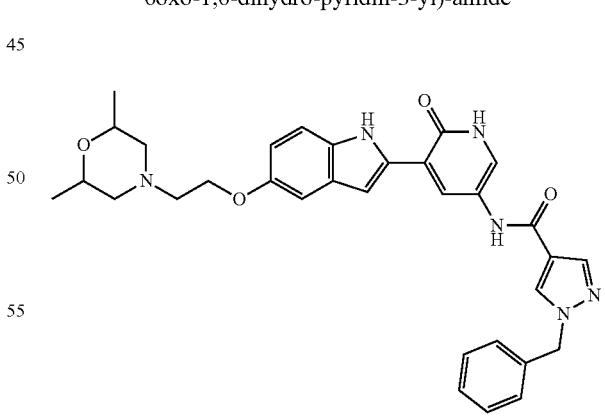

The title compound was prepared by the route outlined in Scheme 11, following the same experimental procedures as for Example 121.

The title compound was purified by trituration with acetonitrile, and isolated as a yellow solid, 5 mg, 11%.

LC/MS: RT=0.93 Min (254 nm), m/z=567 [M+H]. Total run time 1.9 min (super short pos).

¹H NMR (d₆ DMSO): δ 1.04 (d, 6H), 1.72 (t, 2H), 2.67 (m, 2H), 2.84 (d, 2H), 3.57 (m, 2H), 4.06 (t, 2H), 5.40 (s, 2H), 6.7-6.73 (dd, 1H), 6.93 (d, 1H), 7.04 (d, 1H), 7.28-7.42 (m, 6H), 7.82 (d, 1H), 8.03 (s 1H), 8.15 (d, 1H), 8.41 (s, 1H), 9.78 (s, 1H), 11.44 (s, 1H), 11.98 (br s, 1H)

Example 148

1-Benzyl-1H-pyrazole-4-carboxylic acid (6-oxo-5-{5-[3-(2-oxo-pyrrolidin-1-yl)-propoxy]-1H-indole-2-yl}-1,6-dihydro-pridin-3-yl)-amide

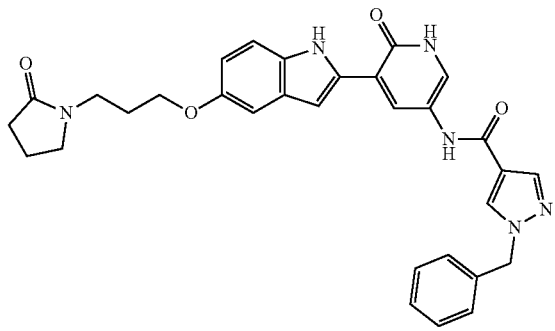 [SMILES: O=C(Nc1c[nH]c(=O)c(-c2cc3cc(OCCCN4CCCC4=O)ccc3[nH]2)c1)c1cnn(Cc2ccccc2)c1]

The title compound was prepared by the route outlined in Scheme 11, following the same experimental procedures as for Example 121.

The title compound was purified by preparative HPLC at pH 4 and isolated as a yellow solid, 8 mg, 12%.

LC/MS: RT=1.08 Min (254 nm), m/z=551 [M+H]. Total run time 1.9 min (super short pos).

¹H NMR (d₆ DMSO): δ 1.85-1.95 (m, 4H), 2.20 (t, 2H), 3.35 (m, partially obscured by water peak, 4H), 3.90 (t, 2H), 5.40 (s, 2H), 6.7-6.73 (dd, 1H), 6.94 (d, 1H), 7.00 (d, 1H), 7.28-7.42 (m, 6H), 7.82 (d, 1H), 8.00 (s, 1H), 8.14 (d, 1H), 8.41 (s, 1H), 9.79, (s, 1H), 11.45 (s, 1H), 11.98 (br s, 1H).

Example 149

1-Benzyl-1H-pyrazole-4-carboxylic acid {6-oxo-5-[5-(2-piperidin-1-yl-ethoxy)-1H-indol-2-yl]-1,6-dihydro-pyridin-3-yl}-amide

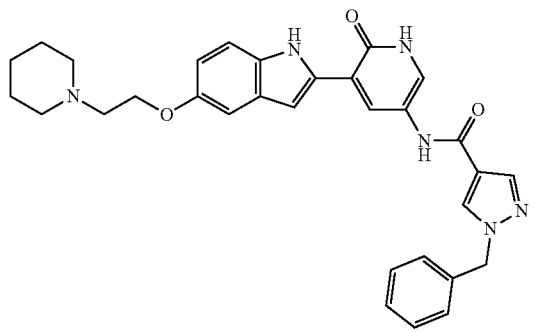 [SMILES: O=C(Nc1c[nH]c(=O)c(-c2cc3cc(OCCN4CCCCC4)ccc3[nH]2)c1)c1cnn(Cc2ccccc2)c1]

The title compound was prepared by the route outlined in Scheme 11, following the same experimental procedures as for Example 115.

The title compound was purified by trituration with acetonitrile, and isolated as a yellow solid, 16 mg, 33%.

LC/MS: RT=1.73 Min (270 nm), m/z=537 [M+H]. Total run time 3.75 min (short pos).

¹H NMR (d₆ DMSO): δ 1.4 (m, 3H), 1.50 (m, 4H), 2.40 (m, 2H), 2.70 (m, 3H), 4.0 (t, 2H), 5.40 (s, 2H), 6.70 (dd, 2H), 6.8 (s, 1H), 7.00 (s, 1H), 7.3 (m, 5H), 7.80 (s, 1H), 8.0 (s, 1H), 8.10 (s, 1H), 8.40 (s, 1H), 9.70 (s, 1H), 12.00 (br, 1H)

Example 150

1-(4-Isopropylbenzyl)-1H-pyrazole-4-carboxylic acid-{6-oxo-5-[5-(3-piperidin-1-ylpropoxy)-1H-indol-2-yl]-1,6-dihydropyridin-3-yl}-amide

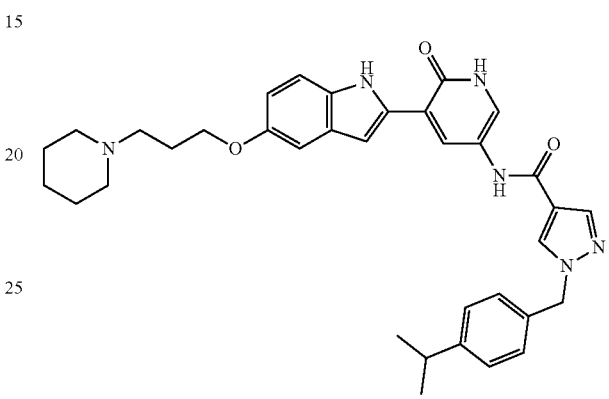

The title compound was prepared by the route outlined in Scheme 11, following the same experimental procedures as for Example 121.

The title compound was purified by trituration with diethyl ether, and isolated as a yellow solid, 70 mg, 35%.

LC/MS: RT=1.82 Min (270 nm), m/z=593 [M+H]. Total run time 3.75 min (short pos).

¹H NMR (d₆ DMSO): δ 1.20 (d, 6H), 1.40 (br s, 2H), 1.55 (br s, 4H), 1.90 (br m, 2H), 2.40 (br s, 4H), 2.90 (m, 1H), 4.00 (t, 2H), 5.35 (s, 2H), 6.70 (dd, 1H), 6.95 (d, 1H), 7.05 (d, 1H), 7.25 (m, 4H), 7.40 (d, 1H), 7.85 (d, 1H), 8.00 (s, 1H), 8.20 (d, 1H), 8.45 (s, 1H), 9.85 (s, 1H), 11.44 (br s, 1H), 11.98 (br s, 1H).

Example 151

1-(4-tert-Butylbenzyl)-1H-pyrazole-4-carboxylic acid {5-[5-(2-piperidin-1-ylethoxy)-1H-indol-2-yl)-6-oxo-1,6-dihydropyridin-3-yl}-amide

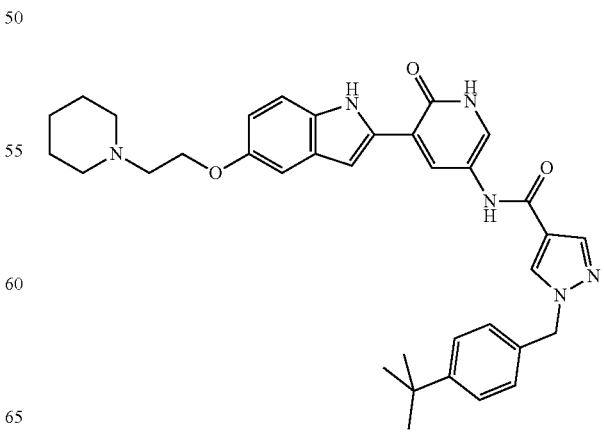

The title compound was prepared by the route outlined in Scheme 11, following the same experimental procedures as for Example 121.

The title compound was purified by trituration with diethyl ether, and isolated as a yellow solid, 60 mg, 40%.

LC/MS: RT=1.84 Min (270 nm), m/z=593 [M+H]. Total run time 3.75 min (short pos).

$^1$H NMR (d$_6$ DMSO): δ 1.30 (s, 9H), 1.45 (br m, 2H), 1.55 (m, 4H), 2.45 (br s, 4H), 2.70 (t, 2H), 4.05 (t, 2H), 5.35 (s, 2H), 6.70 (dd, 1H), 6.95 (d, 1H), 7.05 (d, 1H), 7.25 (d, 2H), 7.45 (m, 3H), 7.85 (d, 1H), 8.00 (s, 1H), 8.20 (d, 1H), 8.45 (s, 1H), 9.85 (s, 1H), 11.44 (br s, 1H).

Example 152

1-(4-Isopropylbenzyl)-1H-pyrazole-4-carboxylic acid {5-[5-(2-piperidin-1-ylethoxy)-1H-indol-2-yl)-6-oxo-1,6-dihydropyridin-3-yl}-amide

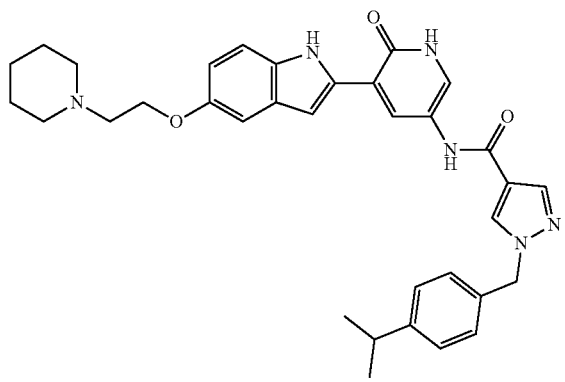 [SMILES: CC(C)c1ccc(Cn2cc(C(=O)Nc3c[nH]c(=O)c(-c4cc5cc(OCCN6CCCCC6)ccc5[nH]4)c3)cn2)cc1]

The title compound was prepared by the route outlined in Scheme 11, following the same experimental procedures as for Example 121.

The title compound was purified by trituration with diethyl ether, and isolated as a yellow solid, 60 mg, 47%.

LC/MS: RT=1.80 Min (270 nm), m/z=579 [M+H]. Total run time 3.75 min (short pos).

$^1$H NMR (d$_6$ DMSO): δ 1.20 (d, 6H), 1.40 (br m, 2H), 1.55 (m, 4H), 2.45 (br s, 4H), 2.70 (t, 2H), 2.90 (m, 1H), 4.10 (t, 2H), 5.35 (s, 2H), 6.70 (dd, 1H), 6.95 (d, 1H), 7.05 (d, 1H), 7.25 (m, 4H), 7.40 (d, 1H), 7.85 (d, 1H), 8.00 (s, 1H), 8.20 (d, 1H), 8.45 (s, 1H), 9.85 (s, 1H), 11.44 (br s, 1H), 11.90 (br s, 1H).

Example 153

1-(4-tert-Butylbenzyl)-1H-pyrazole-4-carboxylic acid-{6-oxo-5-[5-(3-piperidin-1-ylpropoxy)-1H-indol-2-yl]-1,6-dihydropyridin-3-yl}-amide

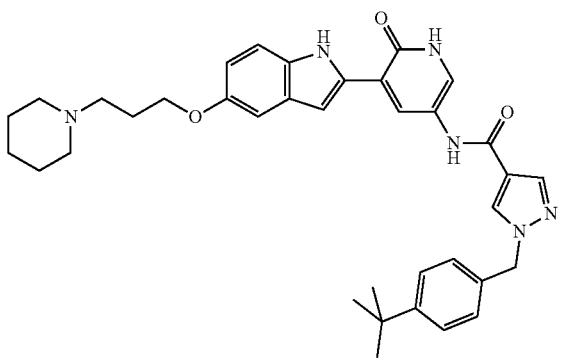 [SMILES: CC(C)(C)c1ccc(Cn2cc(C(=O)Nc3c[nH]c(=O)c(-c4cc5cc(OCCCN6CCCCC6)ccc5[nH]4)c3)cn2)cc1]

The title compound was prepared by the route outlined in Scheme 11, following the same experimental procedures as for Example 121.

The title compound was purified by preparative HPLC at pH 4 to give the product as a yellow solid, 50 mg, 28%.

LC/MS: RT=1.08 Min (270 nm), m/z=607 [M+H]. Total run time 1.9 min (super short pos).

$^1$H NMR (d$_6$ DMSO): δ 1.30 (s, 9H), 1.40 (br m, 2H), 1.55 (m, 4H), 1.90 (m, 2H), 2.45 (br s, 4H), 4.00 (t, 2H), 5.35 (s, 2H), 6.70 (dd, 1H), 6.95 (d, 1H), 7.00 (dd, 1H), 7.20 (d, 2H), 7.40 (m, 3H), 7.85 (d, 1H), 8.00 (s, 1H), 8.20 (d, 1H), 8.45 (s, 1H), 9.85 (s, 1H), 11.46 (br s, 1H).

Example 154

1-(4-tert-Butylbenzyl)-1H-pyrazole-4-carboxylic acid {5-[5-(2-dimethylaminoethoxy)-1H-indol-2-yl)-6-oxo-1,6-dihydropyridin-3-yl}-amide

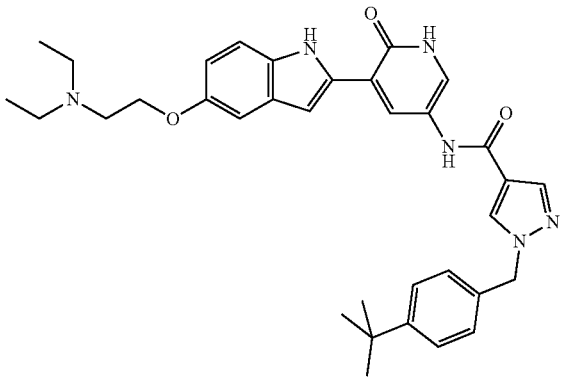 [SMILES: CCN(CC)CCOc1ccc2[nH]c(-c3cc(NC(=O)c4cnn(Cc5ccc(C(C)(C)C)cc5)c4)c[nH]c3=O)cc2c1]

The title compound was prepared by the route outlined in Scheme 11, following the same experimental procedures as for Example 121.

The title compound was purified by trituration with diethyl ether, and isolated as a yellow solid, 65 mg, 40%.

LC/MS: RT=1.82 Min (270 nm), m/z=581 [M+H]. Total run time 3.75 min (short pos).

¹H NMR (d₆ DMSO): δ 1.00 (br t, 6H), 1.30 (s, 9H), 2.60 (br s, 4H), 2.85 (br s, 2H), 4.00 (br s, 2H), 5.35 (s, 2H), 6.75 (dd, 1H), 6.95 (d, 1H), 7.05 (d, 1H), 7.25 (d, 2H), 7.40 (m, 3H), 7.85 (d, 1H), 8.00 (s, 1H), 8.20 (d, 1H), 8.45 (s, 1H), 9.85 (s, 1H), 11.44 (br s, 1H), 11.98 (br s, 1H).

Example 155

1-(4-Isopropylbenzyl)-1H-pyrazole-4-carboxylic acid {5-[5-(2-diethylaminoethoxy)-1H-indol-2-yl)-6-oxo-1,6-dihydropyridin-3-yl}-amide

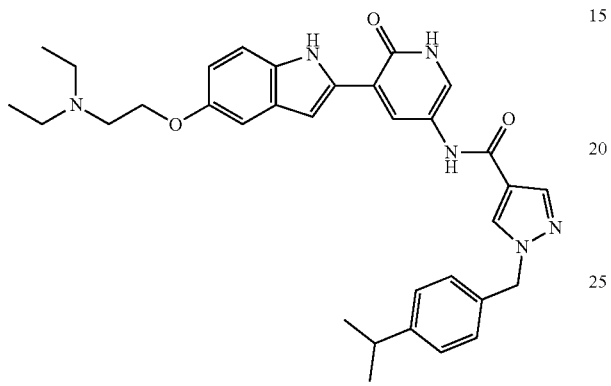

The title compound was prepared by the route outlined in Scheme 11, following the same experimental procedures as for Example 121.

The title compound was purified by trituration with diethyl ether, and isolated as a yellow solid, 110 mg, 55%.

LC/MS: RT=1.78 Min (270 nm), m/z=567 [M+H]. Total run time 3.75 min (short pos).

¹H NMR (d₆ DMSO): δ 1.00 (t, 6H), 1.20 (d, 6H), 2.60 (br q, 4H), 2.85 (br s, 2H), 2.90 (m, 1H), 4.00 (t, 2H), 5.35 (s, 2H), 6.70 (dd, 1H), 6.95 (d, 1H), 7.05 (d, 1H), 7.25 (m, 4H), 7.40 (d, 1H), 7.85 (d, 1H), 8.00 (s, 1H), 8.20 (d, 1H), 8.45 (s, 1H), 9.85 (s, 1H), 11.44 (br s, 1H), 11.98 (br s, 1H).

Example 156

1-(4-tert-butylbenzyl)-1H-pyrazole-4-carboxylic acid {5-[5-(3-dimethylaminopropoxy)-1H-indol-2-yl)-6-oxo-1,6-dihydropyridin-3-yl}-amide

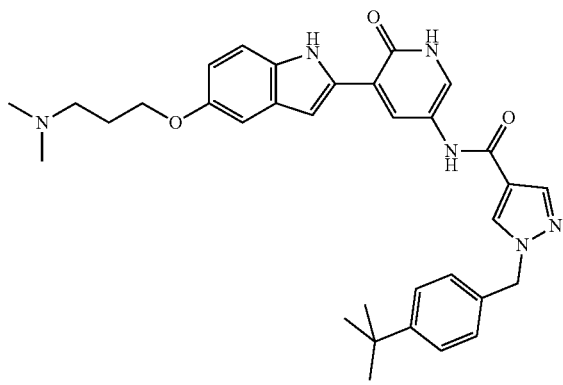 [SMILES: CN(C)CCCOc1ccc2[nH]c(-c3cc(NC(=O)c4cnn(Cc5ccc(C(C)(C)C)cc5)c4)c[nH]c3=O)cc2c1]

The title compound was prepared by the route outlined in Scheme 11, following the same experimental procedures as for Example 121.

The title compound was purified by trituration with diethyl ether, and isolated as a yellow solid, 80 mg, 56%.

LC/MS: RT=1.80 Min (270 nm), m/z=567 [M+H]. Total run time 3.75 min (short pos).

¹H NMR (d₆ DMSO): δ 1.30 (s, 9H), 1.90 (m, 2H), 2.20 (s, 6H), 2.40 (t, 2H), 4.00 (t, 2H), 5.35 (s, 2H), 6.75 (dd, 1H), 6.95 (d, 1H), 7.05 (d, 1H), 7.25 (d, 2H), 7.40 (m, 3H), 7.85 (d, 1H), 8.00 (s, 1H), 8.20 (d, 1H), 8.45 (s, 1H), 9.85 (s, 1H), 11.44 (br s, 1H), 11.94 (br s, 1H).

Example 157

1-(4-Isopropylbenzyl)-1H-pyrazole-4-carboxylic acid {5-[5-(3-dimethylaminopropoxy)-1H-indol-2-yl)-6-oxo-1,6-dihydropyridin-3-yl}-amide

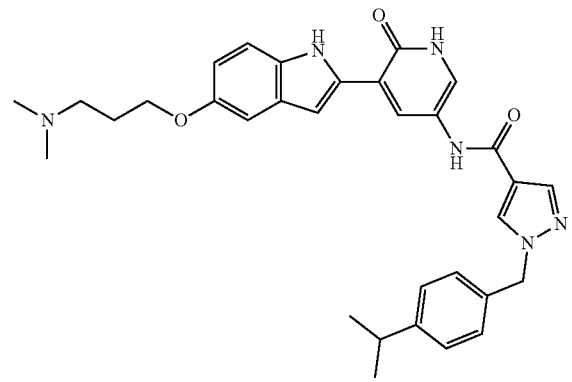 [SMILES: CC(C)c1ccc(Cn2cc(C(=O)Nc3c[nH]c(=O)c(-c4cc5cc(OCCCN(C)C)ccc5[nH]4)c3)cn2)cc1]

The title compound was prepared by the route outlined in Scheme 11, following the same experimental procedures as for Example 121.

The title compound was purified by trituration with diethyl ether, and isolated as a yellow solid, 115 mg, 68%.

LC/MS: RT=1.75 Min (270 nm), m/z=553 [M+H]. Total run time 3.75 min (short pos).

¹H NMR (d₆ DMSO): δ 1.25 (d, 6H), 1.75 (m, 2H), 2.15 (s, 6H), 2.40 (t, 2H), 2.90 (m, 1H), 4.00 (t, 2H), 5.35 (s, 2H), 6.70 (dd, 1H), 6.95 (d, 1H), 7.05 (d, 1H), 7.25 (m, 4H), 7.40 (d, 1H), 7.85 (d, 1H), 8.00 (s, 1H), 8.20 (d, 1H) 8.45 (s, 1H), 9.85 (s, 1H), 11.44 (br s, 1H), 11.96 (br s, 1H).

Example 158

1-Benzyl-1H-pyrazole-4-carboxylic acid {5-[4-(2-amino-ethoxy)-1H-indol-2-yl]-6-oxo-1,6-dihydro-pyridin-3-yl}-amide

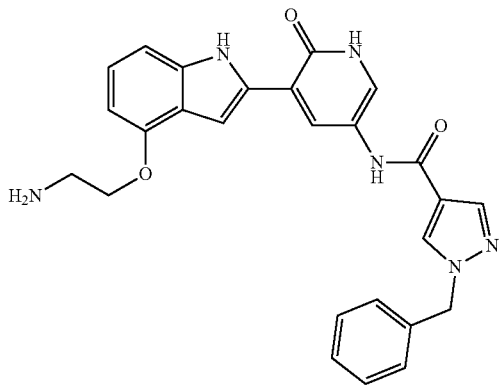 [SMILES: NCCOc1cccc2[nH]c(-c3cc(NC(=O)c4cnn(Cc5ccccc5)c4)c[nH]c3=O)cc12]

The title compound was prepared by the route outlined in Scheme 11, following the same experimental procedures as for Example 115, except 1H-Indol-4-ol was used and the alternative deprotection method described for Example 108 was adopted.

The title compound was purified by trituration with ethyl acetate, and isolated as a yellow solid, 7 mg, 10%.

LC/MS: RT=1.48 Min (270 nm), m/z=469 [M+H]. Total run time 3.75 min (short pos).

$^1$H NMR ($d_4$ MeOD): δ 3.17 (t, 2H), 4.20 (t, 2H), 5.40 (s, 2H), 6.52 (dd, 1H), 7.06 (m, 2H), 7.20 (s, 1H), 7.33 (m, 5H), 7.86 (d, 1H), 8.05 (s, 1H), 8.23 (d, 1H), 8.26 (s, 1H).

Example 159

1-Benzyl-1H-pyrazole-4-carboxylic acid {5-[4-(2-dimethylamino-ethoxy)-1H-indol-2-yl]-6-oxo-1,6-dihydro-pyridin-3-yl}-amide

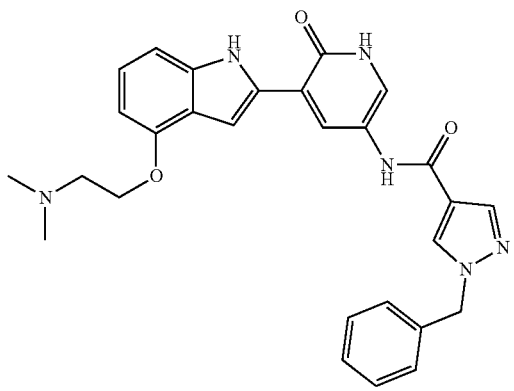 [SMILES: CN(C)CCOc1cccc2[nH]c(-c3cc(NC(=O)c4cnn(Cc5ccccc5)c4)c[nH]c3=O)cc12]

The title compound was prepared by the route outlined in Scheme 11, following the same experimental procedures as for Example 115, except 1H-Indol-4-ol was used and the alternative deprotection method described for Example 108 was adopted.

The title compound was purified by trituration with ethyl acetate, and isolated as a yellow solid, 22 mg, 29%.

LC/MS: RT=1.51 Min (270 nm), m/z=497 [M+H]. Total run time 3.75 min (short pos).

$^1$H NMR ($d_4$ MeOD): δ 2.47 (s, 6H), 2.94 (t, 2H), 4.29 (t, 2H), 5.43 (s, 2H), 6.53 (d, 1H), 7.06 (m, 2H), 7.17 (s, 1H), 7.40 (m, 5H), 7.95 (d, 1H), 8.09 (s, 1H), 8.23 (d, 1H), 8.29 (s, 1H).

Example 160

1-((S)-1-Phenyl-ethyl)-1H-pyrazole-4-carboxylic acid [5-(1H-indol-2-yl)-6-oxo-1,6-dihydro-pyridin-3-yl]-amide

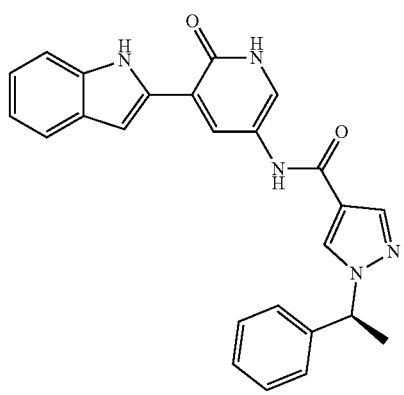 [SMILES: C[C@@H](c1ccccc1)n1cc(C(=O)Nc2c[nH]c(=O)c(-c3cc4ccccc4[nH]3)c2)cn1]

The title compound was prepared by the route outlined in Scheme 6, following the same procedures as for Example 20, apart from a modified coupling procedure in Step 4 which utilized intermediate (6h).

Preparation of 1-((S)-1-Phenyl-ethyl)-1H-pyrazole-4-carbonyl chloride (6h)

A 20 mL microwave vial was charged with 1H-pyrazole-4-carboxylic acid ethyl ester (1 g, 7.1 mmol), (R)-1-phenylethanol (1.31 mL, 10.7 mmol), triphenylphosphine (3 g, 11.4 mmol) and tetrahydrofuran (15 mL). The reaction was stirred at ambient temperature for 10 minutes before adding diisopropyl azodicarboxylate (2.25 mL, 11.14 mmol) with cooling. The vial was heated under microwave irradiation at 140° C. for 15 mins. After cooling, the solvent was removed in vacuo and the residue purified by flash chromatography on SiO$_2$ with hexane—30% ethyl acetate/hexane (gradient) to afford intermediate (6f), 1-((S)-1-Phenyl-ethyl)-1H-pyrazole-4-carboxylic acid ethyl ester as an oil, 1.646 g, 94%.

Intermediate (6f), 1-((S)-1-Phenyl-ethyl)-1H-pyrazole-4-carboxylic acid ethyl ester (1.525 g, 6.2 mmol) was stirred in a mixture of tetrahydrofuran (20 mL) and water (20 mL). Lithium hydroxide (0.524 g, 12.5 mmol) was added and the reaction stirred at ambient temperature for 24 hours. The reaction mixture was reduced in volume and extracted with diethyl ether (3×20 mL). The aqueous layer was carefully acidified using an aqueous 6N hydrochloric acid solution. The resulting precipitate was filtered, washed with copious amounts of water and dried in vacuo to afford intermediate (6g), 1-((S)-1-Phenyl-ethyl)-1H-pyrazole-4-carboxylic acid as a white solid, 0.664 g, 49%.

Intermediate (6g), 1-((S)-1-Phenyl-ethyl)-1H-pyrazole-4-carboxylic acid (0.5 g, 2.31 mmol) was stirred in toluene (20 mL) at RT and thionyl chloride (0.34 mL, 4.62 mmol) was added. The reaction mixture was slowly heated to 90° C. and heating continued for 3 hrs. After cooling the reaction was concentrated in vacuo. Toluene was added to the residue and concentrated in vacuo. This was repeated a further three times and the title compound, intermediate (6h), 1-((S)-1-Phenyl-ethyl)-1H-pyrazole-4-carbonyl chloride, was isolated as an oil, 0.544 g, quantitative.

Modified procedure for Step 4.

Intermediate (6c), 2-[5-Amino-2-oxo-1-(2-trimethylsilanyl-ethoxymethyl)-1,2-dihydro-pyridin-3-yl]-indole-1-carboxylic acid tert-butyl ester (100 mg, 0.22 mmol) was stirred in dichloromethane (5 mL) at RT with triethylamine (0.092 mL, 0.66 mmol). The reaction mixture was cooled to 5° C. and then a solution of intermediate (6h), 1-((S)-1-Phenyl-ethyl)-1H-pyrazole-4-carbonyl chloride, (54 mg, 0.231 mmol) in dichloromethane (1 mL) was added drop wise. After addition the reaction was stirred at RT for 1 hour and then the reaction mixture was concentrated in vacuo and the residue partitioned between ethyl acetate (10 mL) and aqueous saturated sodium hydrogen carbonate solution (10 mL). The organic layer was separated and the aqueous was extracted with a further portion of ethyl acetate (10 mL). The combined ethyl acetate layers were washed with brine, dried ($Na_2SO_4$) and concentrated in vacuo. The resultant crude product was purified by flash chromatography on $SiO_2$ eluting with hexane—50% ethyl acetate/hexane (gradient) to afford the desired intermediate, 2-(1-Methyl-2-oxo-5-{[1-((S)-1-phenyl-ethyl)-1H-pyrazole-4-carbonyl]-amino}-1,2-dihydro-pyridin-3-yl)-indole-1-carboxylic acid tert-butyl ester, 0.108 g, 76%.

The title compound was purified by flash chromatography on $SiO_2$ eluting with dichloromethane—10% methanol/dichloromethane (gradient) to afford the desired title compound as a yellow solid, 22 mg, 31%.

LC/MS: RT=2.07 Min (270 nm), m/z=424 [M+H]. Total run time 3.75 min (short pos).

$^1$H NMR ($d_6$ DMSO): δ 1.84 (d, 3H), 5.69 (q, 1H), 6.98 (m, 1H), 7.05-7.09 (m, 2H), 7.28-7.39 (m, 5H), 7.49-7.54 (m, 2H), 7.81 (d, 1H), 8.04 (s, 1H), 8.18 (d, 1H), 8.45 (s, 1H), 9.77 (s, 1H), 11.56 (s, 1H), 12.00 (br s, 1H).

Example 161

1-((R)-1-Phenyl-ethyl)-1H-pyrazole-4-carboxylic acid [5-(1H-indol-2-yl)-6-oxo-1,6-dihydro-pyridin-3-yl]-amide

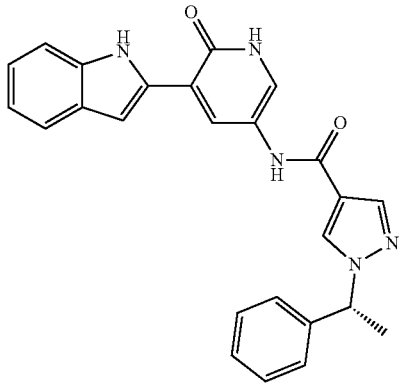 [SMILES: C[C@H](c1ccccc1)n1cc(C(=O)Nc2c[nH]c(=O)c(-c3cc4ccccc4[nH]3)c2)cn1]

The title compound was prepared by the route outlined in Scheme 6, following the same procedures as for Example 160, except intermediate (6k), 1-((R)-1-Phenyl-ethyl)-1H-pyrazole-4-carbonyl chloride, was used in the coupling procedure in Step 4.

Intermediate (6k), 1-((R)-1-Phenyl-ethyl)-1H-pyrazole-4-carbonyl chloride, was synthesized using the same procedures as for intermediate (6h), but starting from (S)-1-phenylethanol. The title compound was purified by trituration with acetonitrile, and isolated as a yellow solid, 34 mg, 45%.

LC/MS: RT=2.07 Min (270 nm), m/z=424 [M+H]. Total run time 3.75 min (short pos).

$^1$H NMR ($d_6$ DMSO): δ 1.84 (d, 3H), 5.69 (q, 1H), 6.98 (m, 1H), 7.05-7.09 (m, 2H), 7.28-7.39 (m, 5H), 7.49-7.54 (m, 2H), 7.81 (d, 1H), 8.04 (s, 1H), 8.18 (d, 1H), 8.45 (s, 1H), 9.77 (s, 1H), 11.56 (s, 1H), 12.00 (br s, 1H).

Example 162

1-((S)-1-Phenyl-ethyl)-1H-pyrazole-4carboxylic acid [6-oxo-5-(5-piperidin-1-ylmethyl-1H-indol-2-yl)-1,6-dihydro-pyridin-3-yl]-amide

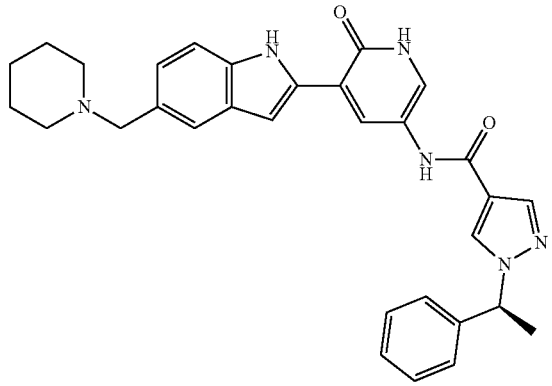 [SMILES: C[C@@H](c1ccccc1)n1cc(C(=O)Nc2c[nH]c(=O)c(-c3cc4cc(CN5CCCCC5)ccc4[nH]3)c2)cn1]

The title compound was prepared by the route outlined in Scheme 8, following the same experimental procedures as for Example 37, reacting intermediate (8d), 2-[5-Amino-2-oxo-1-(2-trimethylsilanyl-ethoxymethyl)-1,2-dihydro-pyridin-3-yl]-5-(tert-butyl-dimethyl-silanyloxymethyl)-indole-1-carboxylic acid tert-butyl with intermediate (6h), 1-((S)-1-Phenyl-ethyl)-1H-pyrazole-4-carbonyl chloride in the coupling step as described for Example 160.

The title compound was purified by trituration with acetonitrile, and isolated as a yellow solid, 131 mg, 71%.

LC/MS: RT=1.58 Min (270 nm), m/z=521 [M+H]. Total run time 3.75 min (short pos).

$^1$H NMR ($d_6$ DMSO): δ 1.37-1.50 (m, 6H), 1.84 (d, 3H), 2.31 (m, 4H), 3.44 (s, 2H), 5.69 (q, 1H), 7.00-7.03 (m, 2H), 7.28-7.44 (m, 7H), 7.82 (d, 1H), 8.03 (s, 1H), 8.15 (d, 1H), 8.45 (s, 1H), 9.78 (s, 1H), 11.50 (s, 1H), 11.97 (br s, 1H).

Example 163

1-((S)-1-Phenyl-ethyl)-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide

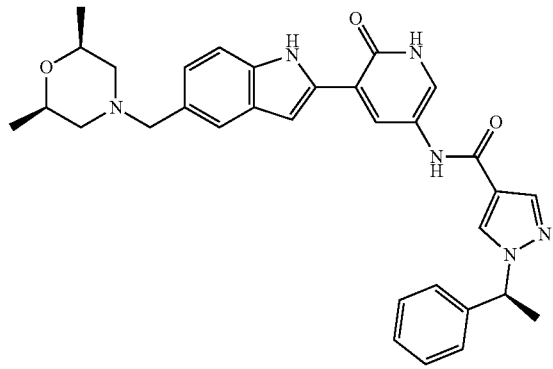 [SMILES: C[C@@H]1CN(Cc2ccc3[nH]c(-c4cc(NC(=O)c5cnn([C@@H](C)c6ccccc6)c5)c[nH]c4=O)cc3c2)C[C@H](C)O1]

The title compound was prepared by the route outlined in Scheme 8, following the same experimental procedures as for Example 162. The title compound was purified by trituration with acetonitrile, and isolated as a yellow solid, 25 mg, 38%.

LC/MS: RT=1.59 Min (270 nm), m/z=551 [M+H]. Total run time 3.75 min (short pos).

$^1$H NMR (d$_6$ DMSO): δ 1.00 (d, 6H), 1.62 (t, 2H), 1.84 (d, 3H), 2.68 (d, 2H), 3.47 (s, 2H), 3.54 (m, 2H), 5.70 (q, 1H), 7.01-7.04 (m, 2H), 7.28-7.46 (m, 7H), 7.82 (d, 1H), 8.04 (s, 1H), 8.16 (d, 1H), 8.45 (s, 1H), 9.78 (s, 1H), 11.53 (s, 1H), 11.99 (br s, 1H).

Example 164

1-((S)-1-Phenyl-ethyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

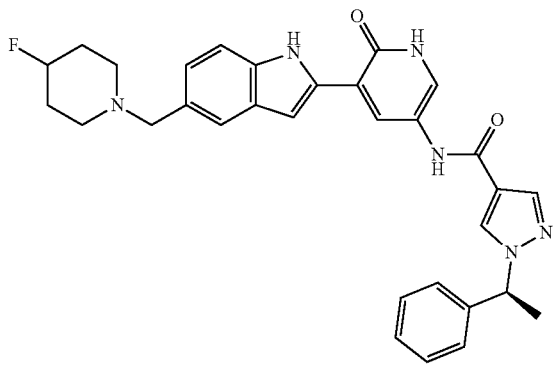 [SMILES: C[C@@H](c1ccccc1)n1cc(C(=O)Nc2c[nH]c(=O)c(-c3cc4cc(CN5CCC(F)CC5)ccc4[nH]3)c2)cn1]

The title compound was prepared by the route outlined in Scheme 8, following the same experimental procedures as for Example 162. The title compound was purified by trituration with acetonitrile, and isolated as a yellow solid, 37 mg, 57%.

LC/MS: RT=1.59 Min (270 nm), m/z=539 [M+H]. Total run time 3.75 min (short pos).

$^1$H NMR (d$_6$ DMSO): δ 1.68 (m, 2H), 1.79 (m, 2H), 1.84 (d, 3H), 2.28 (m, 2H), 2.50 (m, 2H), 3.50 (s, 2H), 4.60-4.72 (m, 1H), 5.70 (q, 1H), 7.01-7.04 (m, 2H), 7.28-7.45 (m, 7H), 7.82 (d, 1H), 8.03 (s, 1H), 8.15 (d, 1H), 8.45 (s, 1H), 9.78 (s, 1H), 11.53 (s, 1H), 11.99 (br s, 1H).

Example 165

1-((S)-1-Phenyl-ethyl)-1H-pyrazole-4-carboxylic acid {5-[5-(4-methyl-piperidin-1-ylmethyl)-1H-indol-2-yl]-6-oxo-1,6-dihydro-pyridin-3-yl}-amide

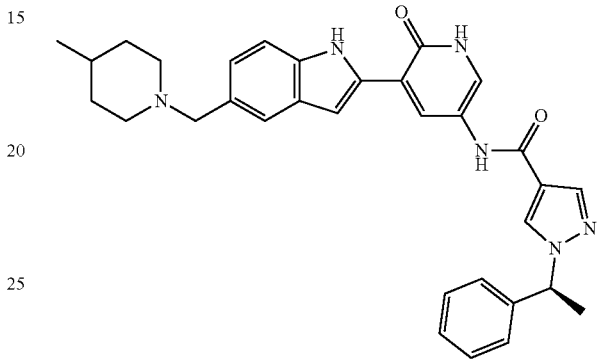

The title compound was prepared by the route outlined in Scheme 8, following the same experimental procedures as for Example 162. The title compound was purified by trituration with acetonitrile, and isolated as a yellow solid, 40 mg, 54%.

LC/MS: RT=1.65 Min (270 nm), m/z=535 [M+H]. Total run time 3.75 min (short pos).

$^1$H NMR (d$_6$ DMSO): δ 0.87 (d, 3H), 1.12 (m, 2H), 1.30 (m, 1H), 1.54 (m, 2H), 1.84 (d, 3H), 1.87 (m, 2H), 2.78 (m, 2H), 3.45 (s, 2H), 5.70 (q, 1H), 7.00-7.03 (m, 2H), 7.28-7.44 (m, 7H), 7.82 (d, 1H), 8.03 (s, 1H), 8.15 (d, 1H), 8.45 (s, 1H), 9.78 (s, 1H), 11.51 (s, 1H), 11.99 (br s, 1H).

Example 166

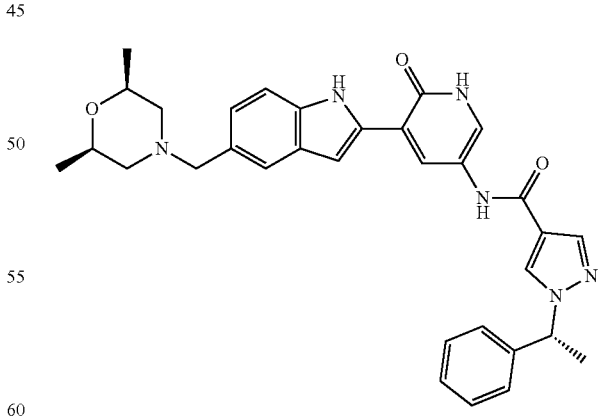

The title compound was prepared by the route outlined in Scheme 8, following the same experimental procedures as for Example 37, reacting intermediate (8d), 2-[5-Amino-2-oxo-1-(2-trimethylsilanyl-ethoxymethyl)-1,2-dihydro-pyridin-3-yl]-5-(tert-butyl-dimethyl-silanyloxymethyl)-indole-1-carboxylic acid tert-butyl with intermediate (6k), 1-((R)-

1-Phenyl-ethyl)-1H-pyrazole-4-carbonyl chloride in the coupling step as described for Example 161. The title compound was purified by trituration with acetonitrile, and isolated as a yellow solid, 47 mg, 55%.

LC/MS: RT=1.61 Min (270 nm), m/z=551 [M+H]. Total run time 3.75 min (short pos).

¹H NMR (d₆ DMSO): δ 1.01 (d, 6H), 1.62 (t, 2H), 1.84 (d, 3H), 2.68 (m, 2H), 3.47 (s, 2H), 3.54 (m, 2H), 5.70 (q, 1H), 7.01-7.04 (m, 2H), 7.28-7.46 (m, 7H), 7.82 (d, 1H), 8.03 (s, 1H), 8.15 (d, 1H), 8.45 (s, 1H), 9.78 (s, 1H), 11.53 (s, 1H), 11.99 (br s, 1H).

Example 167

1-((R)-1-Phenyl-ethyl)-1H-pyrazole-4-carboxylic acid {5-[5-(4-methyl-piperidin-1-ylmethyl)-1H-indol-2-yl]-6-oxo-1,6-dihydro-pyridin-3-yl}-amide

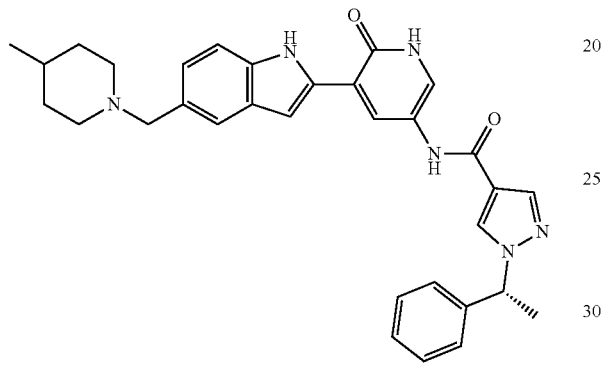

The title compound was prepared by the route outlined in Scheme 8, following the same experimental procedures as for Example 166. The title compound was purified by trituration with acetonitrile, and isolated as a yellow solid, 54 mg, 56%.

LC/MS: RT=1.66 Min (270 nm), m/z=535 [M+H]. Total run time 3.75 min (short pos).

¹H NMR (d₆ DMSO): δ 0.87 (d, 3H), 1.12 (m, 2H), 1.30 (m, 1H), 1.54 (m, 2H), 1.84 (d, 3H), 1.87 (m, 2H), 2.78 (m, 2H), 3.46 (s, 2H), 5.70 (q, 1H), 7.00-7.03 (m, 2H), 7.28-7.44 (m, 7H), 7.82 (d, 1H), 8.03 (s, 1H), 8.15 (d, 1H), 8.45 (s, 1H), 9.78 (s, 1H), 11.51 (s, 1H), 11.99 (br s, 1H).

Example 168

1-((R)-1-Phenyl-ethyl)-1H-pyrazole-4carboxylic acid [6-oxo-5-(5-piperidin-1-ylmethyl-1H-indol-2-yl)-1,6-dihydro-pyridin-3-yl]-amide

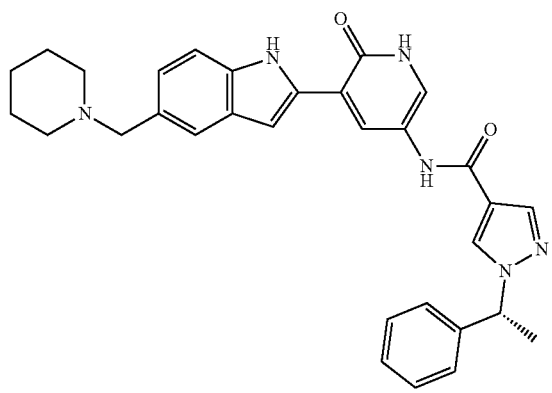 [SMILES: C[C@H](c1ccccc1)n1cc(C(=O)Nc2c[nH]c(=O)c(-c3cc4cc(CN5CCCCC5)ccc4[nH]3)c2)cn1]

The title compound was prepared by the route outlined in Scheme 8, following the same experimental procedures as for Example 166. The title compound was purified by trituration with acetonitrile, and isolated as a yellow solid, 48 mg, 58%.

LC/MS: RT=1.60 Min (270 nm), m/z=521 [M+H]. Total run time 3.75 min (short pos).

¹H NMR (d₆ DMSO): δ 1.37-1.50 (m, 6H), 1.84 (d, 3H), 2.31 (m, 4H), 3.44 (s, 2H), 5.70 (q, 1H), 7.00-7.03 (m, 2H), 7.28-7.44 (m, 7H), 7.82 (d, 1H), 8.03 (s, 1H), 8.15 (d, 1H), 8.45 (s, 1H), 9.78 (s, 1H), 11.51 (s, 1H), 11.99 (br s, 1H).

Example 169

1-((R)-1-Phenyl-ethyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide

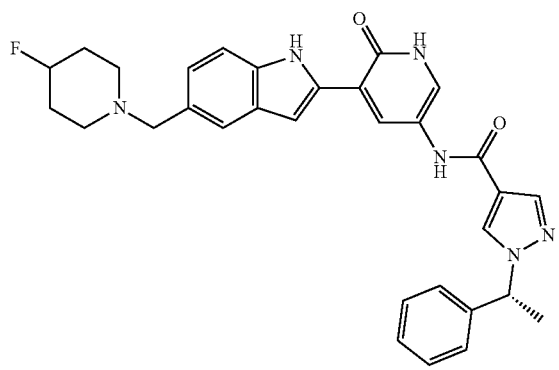 [SMILES: C[C@H](c1ccccc1)n1cc(C(=O)Nc2c[nH]c(=O)c(-c3cc4cc(CN5CCC(F)CC5)ccc4[nH]3)c2)cn1]

The title compound was prepared by the route outlined in Scheme 8, following the same experimental procedures as for Example 166. The title compound was purified by trituration with acetonitrile, and isolated as a yellow solid, 49 mg, 53%.

LC/MS: RT=1.56 Min (270 nm), m/z=539 [M+H]. Total run time 3.75 min (short pos).

¹H NMR (d₆ DMSO): δ 1.68 (m, 2H), 1.79 (m, 2H), 1.84 (d, 3H), 2.28 (m, 2H), 2.52 (m, 2H), 3.50 (s, 2H), 4.60-4.72 (m, 1H), 5.70 (q, 1H), 7.01-7.04 (m, 2H), 7.28-7.45 (m, 7H), 7.83 (d, 1H), 8.03 (s, 1H), 8.16 (d, 1H), 8.45 (s, 1H), 9.78 (s, 1H), 11.52 (s, 1H), 11.99 (br s, 1H).

Example 170

1-Benzyl-1H-pyrazole-4-carboxylic acid [5-(5-{[(2-dimethylamino-ethyl)-methyl-amino]-methyl}-1H-indol-2-yl)-6-oxo-1,6-dihydro-pyridin-3-yl]-amide

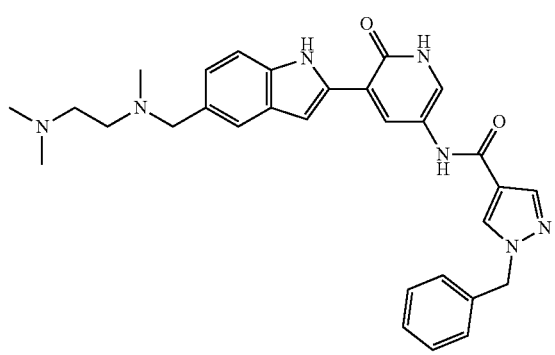 [SMILES: CN(C)CCN(C)Cc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51.

The title compound was purified by trituration with acetonitrile, and isolated as a yellow solid, 28 mg, 24%.

LC/MS: RT=1.45 Min (270 nm), m/z=522 [M−H]. Total run time 3.75 min (short neg).

$^1$H NMR (d$_6$ DMSO): δ 2.15 (s, 9H), 2.42 (s, 4H), 3.52 (s, 2H), 5.41 (s, 2H), 6.98-7.06 (m, 2H), 7.25-7.45 (m, 7H), 7.82 (s, 1H), 8.04 (s, 1H), 8.17 (d, 1H), 8.42 (s, 1H), 9.81 (br s, 1H), 11.52 (br s, 1H), 12.0 (br s, 1H).

Example 171

1-Benzyl-1H-pyrazole-4-carboxylic acid {5-[5-((S)-2-methyl-piperidin-1-ylmethyl)-1H-indol-2-yl]-6-oxo-1,6-dihydro-pyridin-3-yl}-amide

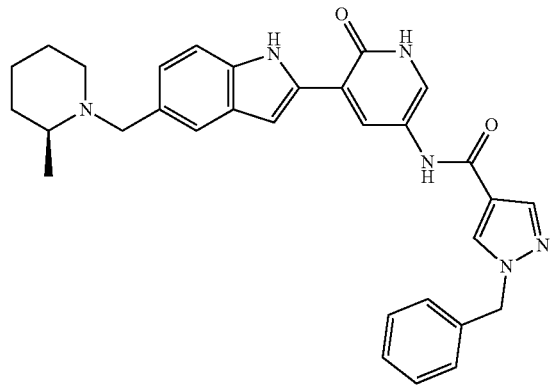 [SMILES: C[C@H]1CCCCN1Cc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51.

The title compound was purified by trituration with acetonitrile, and isolated as a yellow solid, 58 mg, 56%.

LC/MS: RT=1.68 Min (270 nm), m/z=519 [M−H]. Total run time 3.75 min (short neg).

$^1$H NMR (d$_6$ DMSO): δ 1.15 (d, 3H), 1.22-1.36 (m, 4H), 1.88 (m, 1H), 2.3 (m, 1H), 2.65 (m, 1H), 3.12 (d, 1H), 4.0 (d, 1H), 5.4 (s, 2H), 6.99-7.04 (m, 2H), 7.27-7.44 (m, 7H), 7.82 (m, 1H), 8.03 (s, 1H), 8.15 (d, 1H), 8.41 (s, 1H), 9.8 (br s, 1H), 11.5 (br s, 1H), 11.99 (br s, 1H).

Example 172

1-Benzyl-1H-pyrazole-4-carboxylic acid {5-[5-((R)-3-dimethylamino-pyrrolidin-1-ylmethyl)-1H-indol-2-yl]-6-oxo-1,6-dihydro-pyridin-3-yl}-amide

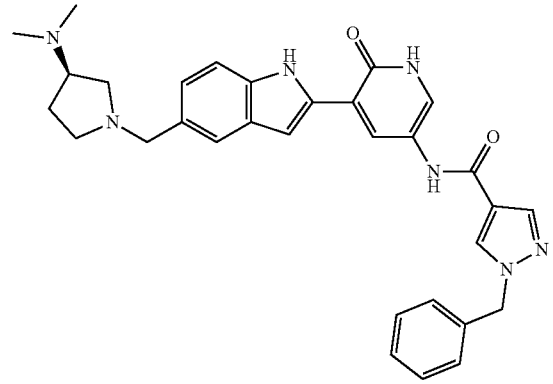 [SMILES: CN(C)[C@@H]1CCN(Cc2ccc3[nH]c(-c4cc(NC(=O)c5cnn(Cc6ccccc6)c5)c[nH]c4=O)cc3c2)C1]

The title compound was prepared by the route outlined in Scheme 8, following the same experimental procedures as for Example 51.

The title compound was purified by trituration with acetonitrile, and isolated as a yellow solid, 42 mg, 31%.

LC/MS: RT=1.45 Min (270 nm), m/z=534 [M−H]. Total run time 3.75 min (short neg).

$^1$H NMR (d$_6$ DMSO): δ 1.58 (m 1H), 1.82 (m, 1H), 2.05 (s, 6H), 2.22 (m, 1H), 2.42 (m, 1H), 2.56 (m, 1H), 2.66 (m, 2H), 3.58 (dd, 2H), 5.41 (s, 2H), 7.01 (m, 2H), 7.25-7.45 (m, 7H), 7.82 (s, 1H), 8.03 (s, 1H), 8.17 (s, 1H), 8.41 (s, 1H), 9.8 (br s, 1H), 11.5 (br s, 1H), 11.99 (br s, 1H).

Example 173

1-Benzyl-1H-pyrazole-4-carboxylic acid {5-[5-((R)-2-methyl-piperidin-1-ylmethyl)-1H-indol-2-yl]-6-oxo-1,6-dihydro-pyridin-3-yl}-amide

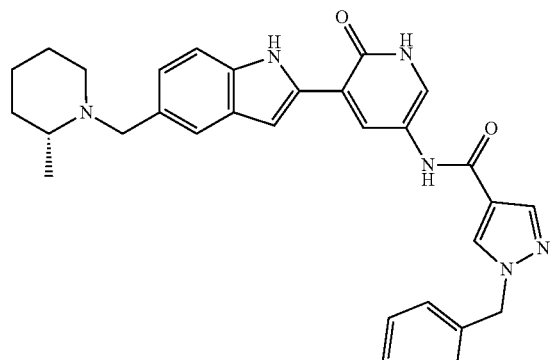

The title compound was prepared by the route outlined in Scheme 8, following the same experimental procedures as for Example 51.

The title compound was purified by trituration with acetonitrile, and isolated as a yellow solid, 20 mg, 20%.

LC/MS: RT=1.69 Min (270 nm), m/z=519 [M−H]. Total run time 3.75 min (short neg).

$^1$H NMR (d$_6$ DMSO): δ 1.15 (d, 3H), 1.22-1.36 (m, 4H), 1.88 (m, 1H), 2.3 (m, 1H), 2.65 (m, 1H), 3.12 (d, 1H), 4.0 (d, 1H), 5.4 (s, 2H), 6.99-7.04 (m, 2H), 7.27-7.44 (m, 7H), 7.82 (m, 1H), 8.03 (s, 1H), 8.15 (d, 1H), 8.41 (s, 1H), 9.82 (br s, 1H), 11.51 (br s, 1H), 11.99 (br s, 1H).

Example 174

1-Benzyl-1H-pyrazole-4-carboxylic acid {5-[5-((R)-3-fluoro-pyrrolidin-1-ylmethyl)-1H-indol-2-yl]-6-oxo-1,6-dihydro-pyridin-3-yl}-amide

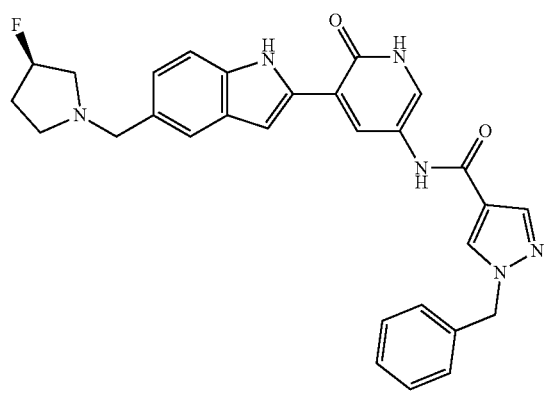 [SMILES: O=C(Nc1c[nH]c(=O)c(-c2cc3cc(CN4CC[C@@H](F)C4)ccc3[nH]2)c1)c1cnn(Cc2ccccc2)c1]

The title compound was prepared by the route outlined in Scheme 8, following the same experimental procedures as for Example 51.

The title compound was purified by trituration with acetonitrile, and isolated as a yellow solid, 20 mg, 20%.

LC/MS: RT=1.63 Min (270 nm), m/z=509 [M−H]. Total run time 3.75 min (short neg).

$^1$H NMR (d$_6$ DMSO): δ 1.77-1.93 (m, 1H), 2.05-2.2 (m, 1H), 2.3 (q, 1H), 2.53-2.64 (m, 1H), 2.7-2.82 (m, 2H), 3.63 (s, 2H), 5.18 (dt, 1H), 5.4 (s, 2H), 7.0-7.07 (m, 2H), 7.27-7.46 (m, 7H), 7.82 (d, 1H), 8.03 (s, 1H), 8.17 (d, 1H), 8.41 (s, 1H), 9.79 (s, 1H), 11.52 (br s, 1H), 12.01 (br s, 1H).

Example 175

1-Benzyl-1H-pyrazole-4-carboxylic acid {5-[5-((S)-3-fluoro-pyrrolidin-1-ylmethyl)-1H-indol-2-yl]-6-oxo-1,6-dihydro-pyridin-3-yl}-amide

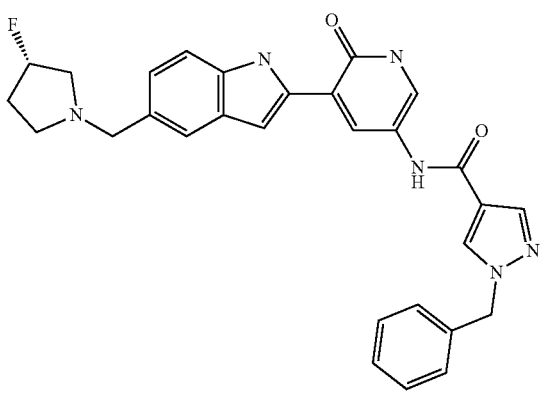 [SMILES: O=C(Nc1c[nH]c(=O)c(-c2cc3cc(CN4CC[C@H](F)C4)ccc3[nH]2)c1)c1cnn(Cc2ccccc2)c1]

The title compound was prepared by the route outlined in Scheme 8, following the same experimental procedures as for Example 51.

The title compound was purified by trituration with acetonitrile, and isolated as a yellow solid, 76 mg, 81%.

LC/MS: RT=1.62 Min (270 nm), m/z=509 [M−H]. Total run time 3.75 min (short neg).

$^1$H NMR (d$_6$ DMSO): δ 1.77-1.93 (m, 1H), 2.05-2.2 (m, 1H), 2.3 (q, 1H), 2.53-2.64 (m, 1H), 2.7-2.82 (m, 2H), 3.63 (s, 2H), 5.18 (dt, 1H), 5.4 (s, 2H), 7.0-7.07 (m, 2H), 7.27-7.46 (m, 7H), 7.82 (d, 1H), 8.03 (s, 1H), 8.17 (d, 1H), 8.41 (s, 1H), 9.8 (s, 1H), 11.52 (br s, 1H), 12.01 (br s, 1H).

Example 176

1-Benzyl-1H-pyrazole-4-carboxylic acid [5-(5-{[(3-dimethylamino-2,2-dimethyl-propyl)-ethyl-amino]-methyl}-1H-indol-2-yl)-6-oxo-1,6-dihydro-pyridin-3-yl]-amide

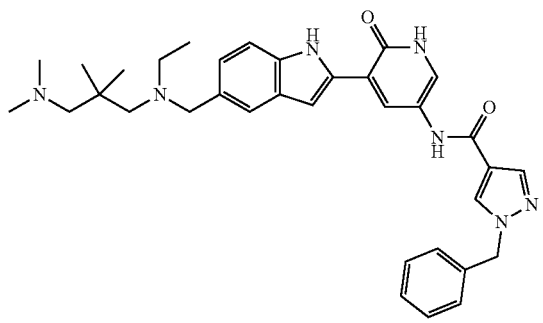 [SMILES: CCN(Cc1ccc2[nH]c(-c3cc(NC(=O)c4cnn(Cc5ccccc5)c4)c[nH]c3=O)cc2c1)CC(C)(C)CN(C)C]

The title compound was prepared by the route outlined in Scheme 8, following the same experimental procedures as for Example 51.

Purification by trituration with acetonitrile afforded the title compound as a yellow solid, 30 mg, 43%

LC/MS: RT=1.49 Min (270 nm), m/z=580 [M+H]. Total run time 3.75 min (short pos).

¹H NMR (d₆ DMSO): δ 0.86 (s, 6H), 0.92 (t, 3H), 2.09 (s, 2H), 2.19 (s, 6H), 2.31 (s, 2H), 2.42 (q, 2H), 3.64 (s, 2H), 5.41 (s, 2H), 7.01 (s, 1H), 7.11 (dd, 1H), 7.28-7.45 (m, 7H), 7.80 (d, 1H), 8.03 (s, 1H), 8.16 (d, 1H), 8.41 (s, 1H), 9.79 (s, 1H), 11.49 (s, 1H), 11.99 (br s, 1H)

Example 177

1-Benzyl-1H-pyrazole-4-carboxylic acid {5-[5-(cis-2,6-dimethyl-piperidin-1-ylmethyl)-1H-indol-2-yl]-6-oxo-1,6-dihydro-pyridin-3-yl}-amide

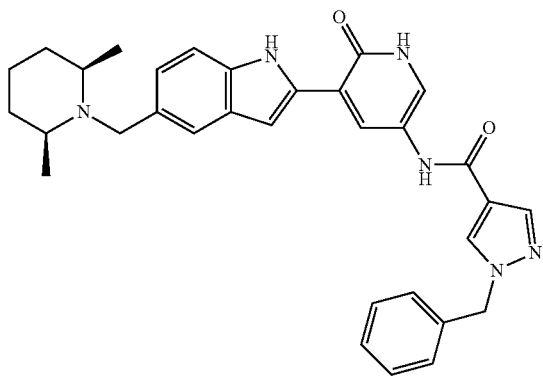 [SMILES: C[C@@H]1CCC[C@H](C)N1Cc1ccc2[nH]c(-c3cc(NC(=O)c4cnn(Cc5ccccc5)c4)c[nH]c3=O)cc2c1]

The title compound was prepared by the route outlined in Scheme 8, following the same experimental procedures as for Example 51, with the following modification.

Deprotection of intermediate (8e), 5-(tert-Butyl-dimethyl-silanyloxymethyl)-2-[5-{[1-(4-methyl-benzyl)-1H-pyrazole-4-carbonyl]-amino}-2-oxo-1-(2-trimethylsilanyl-ethoxymethyl)-1,2-dihydro-pyridin-3-yl]-indole-1-carboxylic acid tert-butyl ester, in the usual manner, yielded 2-[5-[(1-benzyl-1H-pyrazole-4-carbonyl)-amino]-2-oxo-1-(2-trimethylsilanyl-ethoxymethyl)-1,2-dihydro-pyridin-3-yl]-5-hydroxymethyl-indole-1-carboxylic acid tert-butyl ester. DIPEA (153 μL, 0.9 mmol) and 2-[5-[(1-benzyl-1H-pyrazole-4-carbonyl)-amino]-2-oxo-1-(2-trimethylsilanyl-ethoxymethyl)-1,2-dihydro-pyridin-3-yl]-5-hydroxymethyl-indole-1-carboxylic acid tert-butyl ester (0.2 g, 0.3 mmol) were stirred in 1,2-dichloroethane (5 mL) and cooled to 0° C. Methanesulfonyl chloride (27 μL, 0.36 mmol) was added drop wise at 0° C. and stirred for a further 2 hours at 0° C. cis-2,6-Dimethylpiperidine (118 μL 0.9 mmol) was added drop wise at 0° C. and then the reaction was allowed to attain ambient temperature. The reaction mixture was heated at reflux overnight followed by cooling to ambient temperature. The reaction mixture was diluted with ethyl acetate (30 mL), washed with water (30 mL), saturated sodium hydrogen carbonate solution (30 mL), brine, dried (Na₂SO₄) and concentrated in vacuo. The resultant crude product was taken up in methanol (1 mL) and loaded onto a 5 g SCX column. The column was flushed with methanol and then eluted with ammonia solution 7N in methanol. The eluent was concentrated in vacuo to afford the title compound as a light brown solid, 120 mg, 53%.

Global deprotection in the usual manner afforded the title compound which was purified by trituration with diethyl ether, and isolated as a yellow solid, 20 mg, 24%.

LC/MS: RT=1.72 Min (270 nm), m/z=535 [M+H]. Total run time 3.75 min (short pos).

¹H NMR (d₆ DMSO): δ 1.02 (d, 6H), 1.26 (m, 3H), 1.53-1.60 (m, 3H), 2.45 (m, 2H), 3.78 (s, 2H), 5.41 (s, 2H), 7.00 (s, 1H), 7.08 (d, 1H), 7.28-7.40 (m, 6H), 7.49 (s, 1H), 7.80 (s, 1H), 8.03 (s, 1H), 8.14 (d, 1H), 8.41 (s, 1H), 9.79 (s, 1H), 11.45 (s, 1H), 11.98 (br s, 1H).

Example 178

1-Benzyl-1H-pyrazole-4-carboxylic acid {5-[5-(3-diethylamino-2,2-dimethyl-propoxy)-1H-indol-2-yl]-6-oxo-1,6-dihydro-pyridin-3-yl}-amide

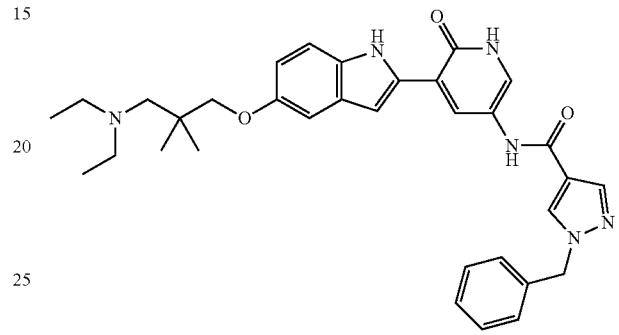

The title compound was prepared by the route outlined in Scheme 11, following the same experimental procedures as for Example 115.

The title compound was purified by trituration with acetonitrile, and isolated as a yellow solid, 50 mg, 47%.

LC/MS: RT=1.78 Min (270 nm), m/z=567.3 [M+H]. Total run time 3.75 min (short pos).

¹H NMR (d₆ DMSO): δ 0.90 (t, 6H), 0.95 (s, 6H), 2.35 (s, 2H), 2.50 (q, 4H), 3.65 (s, 2H), 5.40 (s, 2H), 6.70 (dd, 1H), 6.90 (d, 1H), 7.00 (d, 1H), 7.25-7.45 (m, 6H), 7.85 (d, 1H), 8.05 (s, 1H), 8.15 (d, 1H), 8.40 (s, 1H), 9.80 (s, 1H), 11.40 (s, 1H), 12.00 (br s, 1H).

Example 179

1-Benzyl-1H-pyrazole-4-carboxylic acid {5-[5-(2-dimethylamino-1,1-dimethyl-ethoxy)-1H-indol-2-yl]-6-oxo-1,6-dihydro-pyridin-3-yl}-amide

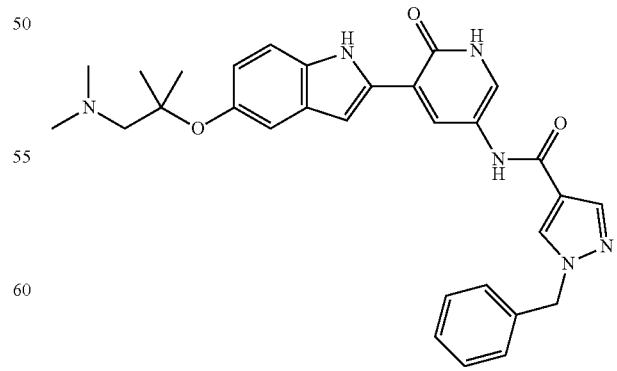

The title compound was prepared by the route outlined in Scheme 11, following the same experimental procedures as for Example 115. In this instance the chloroalkyl intermediate, (2-chloro-2-methyl-propyl)-dimethyl-amine hydrochloride, required for Step 6 was not commercially available and was synthesized according to the following methodology.

Preparation of (2-chloro-2-methyl-propyl)-dimethyl-amine hydrochloride

2-Dimethylamino-2-methyl-propan-1-ol as an 80% solution in water (10 mL, 9.1 g, 78 mmol) was dissolved in toluene (100 mL) and then after stirring for 30 mins, the organic layer separated, dried over $Mg_2SO_4$ and then concentrated to a volume of approximately 50 mL. Thionyl chloride (95 mmol, 6.9 mL, 11.3 g) was added to this solution and the mixture heated at 80° C. for 3 hrs. After cooling, the mixture was concentrated in vacuo. Anhydrous toluene was added and the mixture was concentrated in vacuo. This process was repeated a further three times with toluene and once with isohexane. The residue obtained was slurried in diethyl ether, separated via filtration and washed with copious amounts of diethylether before being dried in vacuo at RT. The compound obtained was a mixture of the desired title compound (2-chloro-2-methyl-propyl)-dimethyl-amine hydrochloride (70%) and the isomer (2-chloro-1,1-dimethyl-ethyl)-dimethyl-amine (30%) by NMR. The total yield was 5.23 g (49%).

This mixture containing 70% desired intermediate and 30% undesired isomer was used in the subsequent alkylation step without further purification and so a mixture of two possible products was obtained. These two products were duly separated, prior to global deprotection, by flash chromatography on $SiO_2$ and the desired product was eluted using dichloromethane—10% methanol/dichloromethane (gradient). The undesired product of this reaction remained on the column.

The title compound was purified by trituration with diethyl ether, and isolated as a yellow solid, 58 mg, 64%.

LC/MS: RT=1.65 Min (270 nm), m/z=523 [M−H]. Total run time 3.75 min (short neg).

$^1$H NMR (d$_6$ DMSO): δ 1.21 (s, 6H), 2.34 (s, 6H) 5.41 (s, 2H), 6.74 (dd, 1H), 6.97 (s, 1H), 7.1 (s, 1H), 7.27-7.41 (m, 6H), 7.82 (d, 1H), 8.03 (s, 1H), 8.15 (d, 1H), 8.42 (s, 1H), 9.8 (br s, 1H), 11.48 (s, 1H), 12.0 (br s, 1H).

Example 180

1-Benzyl-1H-pyrazole-4-carboxylic acid {5-[5-(2,2-dimethyl-3-pyrrolidin-1-yl-propoxy)-1H-indol-2-yl]-6-oxo-1,6-dihydro-pyridin-3-yl}-amide

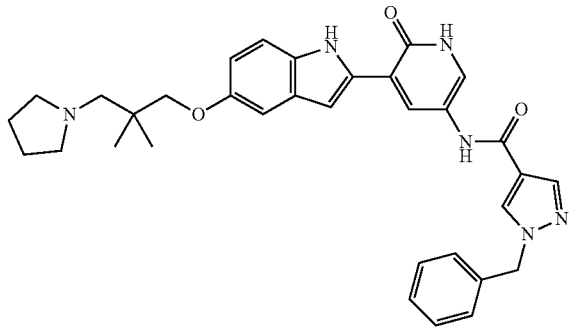 [SMILES: CC(C)(COc1ccc2[nH]c(-c3cc(NC(=O)c4cnn(Cc5ccccc5)c4)c[nH]c3=O)cc2c1)CN1CCCC1]

The title compound was prepared by the route outlined in Scheme 11, following the same experimental procedures as for Example 115. In this instance the chloroalkyl intermediate, 1-(3-chloro-2,2-dimethyl-propyl)-pyrrolidine, required for Step 6, was not commercially available and was synthesized according to the following methodology.

Preparation of 1-(3-Chloro-2,2-dimethyl-propyl)-pyrrolidine

3-Chloro-2,2-dimethyl-propionyl chloride (0.5 g, 3.2 mmol) was stirred in dichloromethane (20 mL) at RT with triethylamine (0.9 mL, 6.4 mmol). The reaction mixture was cooled to 5° C. and then pyrrolidine (0.32 mL, 3.9 mmol), was added drop wise. After addition the reaction was stirred at RT for 1 hr, and then the reaction mixture was washed with saturated sodium hydrogen carbonate solution (2×50 mL), brine (50 ml), dried (Na$_2$SO$_4$) and concentrated in vacuo to afford 3-chloro-2,2-dimethyl-1-pyrrolidin-1-yl-propan-1-one as a yellow solid, 0.576 g, 94%.

To this intermediate, 3-chloro-2,2-dimethyl-1-pyrrolidin-1-yl-propan-1-one (0.57 g, 3 mmol) in anhydrous THF (20 mL) was slowly added a 1M anhydrous THF solution of lithium aluminium hydride (7.5 mL, 7.5 mmol) at room temperature. The resulting clear solution was stirred overnight at room temperature under nitrogen to give a cloudy suspension. Water (0.3 mL) was carefully added to the reaction mixture followed by 15% w/v aqueous sodium hydroxyde solution (0.3 mL) and water (0.9 mL). The reaction was filtered and the filtrate evaporated to dryness to give the title compound which was used without further purification.

The title compound was purified by trituration with acetonitrile, and isolated as a yellow solid, 104 mg, 54%.

LC/MS: RT=1.77 Min (270 nm), m/z=565 [M+H]. Total run time 3.75 min (short pos).

$^1$H NMR (d$_6$ DMSO): δ 0.98 (s, 6H), 1.63 (m, 4H), 2.45 (s, 2H), 2.53 (m, 4H), 3.68 (s, 2H), 5.40 (s, 2H), 6.72 (dd, 1H), 6.92 (s, 1H), 7.01 (d, 1H), 7.28-7.40 (m, 6H), 7.84 (d, 1H), 8.03 (s, 1H), 8.14 (d, 1H), 8.41 (s, 1H), 9.79 (s, 1H), 11.44 (s, 1H), 11.98 (br s, 1H).

Example 181

1-Benzyl-1H-pyrazole-4-carboxylic acid (5-{5-[3-(3,3-difluoro-pyrrolidin-1-yl)-2,2-dimethyl-propoxy]-1H-indol-2-yl}-6-oxo-1,6-dihydro-pyridin-3-yl)-amide

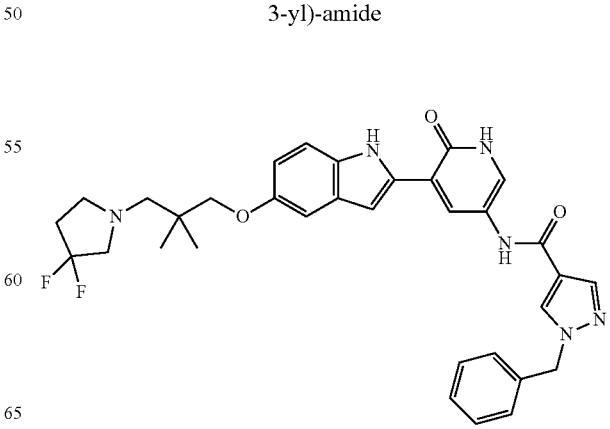

The title compound was prepared by the route outlined in Scheme 11, following the same experimental procedures as for Example 115. In this instance the relevant chloroalkyl intermediate, required for Step 6, was not commercially available and was synthesized according to the protocol given for Example 180.

The title compound was purified by trituration with acetonitrile, and isolated as a yellow solid, 20 mg, 10%.

LC/MS: RT=2.11 Min (270 nm), m/z=601 [M+H]. Total run time 3.75 min (short pos).

$^1$H NMR (d$_6$ DMSO): δ 0.98 (s, 6H), 2.18 (m, 2H), 2.47 (s, 2H), 2.78 (t, 2H), 2.94 (t, 2H), 3.67 (s, 2H), 5.41 (s, 2H), 6.72 (dd, 1H), 6.92 (s. 1H), 7.02 (d, 1H), 7.28-7.41 (m, 6H), 7.84 (d, 1H), 8.03 (s, 1H), 8.14 (d, 1H), 8.41 (s, 1H), 9.79 (s, 1H), 11.44 (s, 1H), 12.0 (br s, 1H).

Example 182

1-Benzyl-1H-pyrazole-4-carboxylic acid (5-{5-[3-((R)-3-fluoro-pyrrolidin-1-yl)-2,2-dimethyl-propoxy]-1H-indol-2-yl}-6-oxo-1,6-dihydro-pyridin-3-yl)-amide

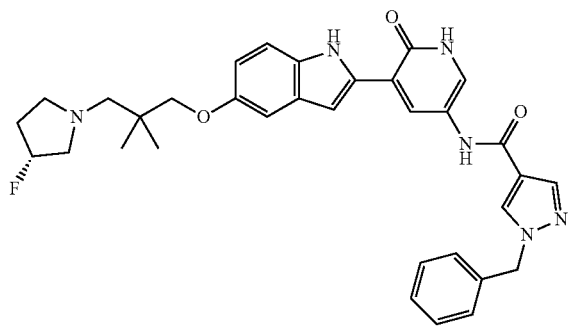 [SMILES: CC(C)(COc1ccc2[nH]c(-c3cc(NC(=O)c4cnn(Cc5ccccc5)c4)c[nH]c3=O)cc2c1)CN1CC[C@@H](F)C1]

The title compound was prepared by the route outlined in Scheme 11, following the same experimental procedures as for Example 115. In this instance the relevant chloroalkyl intermediate, required for Step 6, was not commercially available and was synthesized according to the protocol given for Example 180.

The title compound was purified by trituration with acetonitrile, and isolated as a yellow solid, 30 mg, 17%.

LC/MS: RT=1.56 Min (270 nm), m/z=583 [M+H]. Total run time 3.75 min (short pos).

$^1$H NMR (d$_6$ DMSO): δ 0.98 (s, 6H), 1.75-2.11 (m, 2H), 2.45 (m, 3H), 2.73-2.86 (m, 3H), 3.68 (s, 2H), 5.05-5.17 (m, 1H), 5.41 (s, 2H), 6.72 (dd, 1H), 6.92 (s, 1H), 7.02 (d, 1H), 7.28-7.41 (m, 6H), 7.84 (d, 1H), 8.03 (s, 1H), 8.14 (d, 1H), 8.41 (s, 1H), 9.79 (s, 1H), 11.44 (s, 1H), 11.99 (br s, 1H)

Example 183

1-Benzyl-1H-pyrazole-4-carboxylic acid (5-{5-[3-((S)-3-fluoro-pyrrolidin-1-yl)-2,2-dimethyl-propoxy]-1H-indol-2-yl}-6-oxo-1,6-dihydro-pyridin-3-yl)-amide

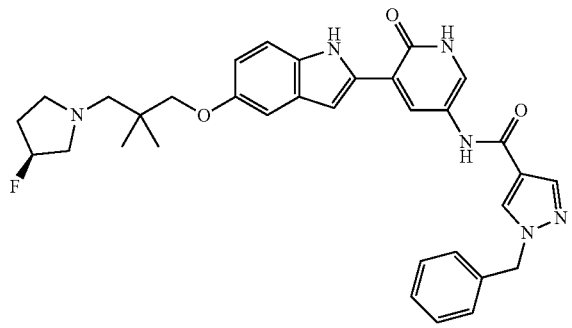 [SMILES: CC(C)(COc1ccc2[nH]c(-c3cc(NC(=O)c4cnn(Cc5ccccc5)c4)c[nH]c3=O)cc2c1)CN1CC[C@H](F)C1]

The title compound was prepared by the route outlined in Scheme 11, following the same experimental procedures as for Example 115. In this instance the relevant chloroalkyl intermediate, required for Step 6, was not commercially available and was synthesized according to the protocol given for Example 180.

The title compound was purified by trituration with acetonitrile, and isolated as a yellow solid, 31 mg, 18%.

LC/MS: RT=1.57 Min (270 nm), m/z=583 [M+H]. Total run time 3.75 min (short pos).

$^1$H NMR (d$_6$ DMSO): δ 0.98 (s, 6H), 1.77-2.11 (m, 2H), 2.45 (m, 3H), 2.71-2.86 (m, 3H), 3.68 (s, 2H), 5.06-5.17 (m, 1H), 5.41 (s, 2H), 6.72 (dd, 1H), 6.92 (s, 1H), 7.02 (d, 1H), 7.28-7.41 (m, 6H), 7.84 (d, 1H), 8.03 (s, 1H), 8.14 (d, 1H), 8.41 (s, 1H), 9.79 (s, 1H), 11.44 (s, 1H), 11.99 (br s, 1H)

Example 184

1-Benzyl-1H-pyrazole-4-carboxylic acid {5-[5-(2,2-dimethyl-3-morpholin-4-yl-propoxy)-1H-indol-2-yl]-6-oxo-1,6-dihydro-pyridin-3-yl}-amide

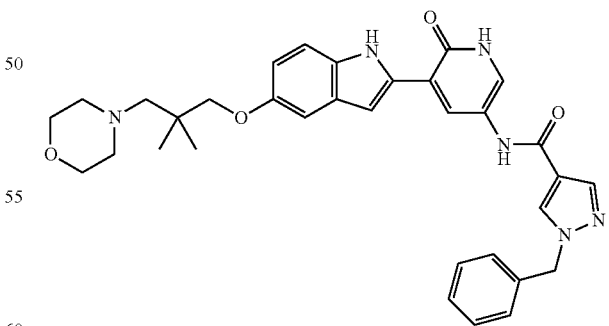

The title compound was prepared by the route outlined in Scheme 11, following the same experimental procedures as for Example 115. In this instance the relevant chloroalkyl intermediate, required for Step 6, was not commercially available and was synthesized according to the protocol given for Example 180.

The title compound was purified by trituration with acetonitrile, and isolated as a yellow solid, 16 mg, 18%.

LC/MS: RT=1.74 Min (270 nm), m/z=581 [M+H]. Total run time 3.75 min (short pos).

$^1$H NMR (d$_6$ DMSO): δ 0.98 (s, 6H), 2.27 (s, 2H), 2.43 (m, 4H), 3.50 (m, 4H), 3.67 (s, 2H), 5.41 (s, 2H), 6.72 (dd, 1H), 6.91 (s, 1H), 7.01 (d, 1H), 7.28-7.40 (m, 6H), 7.84 (d, 1H), 8.03 (s, 1H), 8.14 (d, 1H), 8.41 (s, 1H), 9.79 (s, 1H), 11.43 (s, 1H), 11.99 (br s, 1H).

Example 185

1-Benzyl-1H-pyrazole-4-carboxylic acid {5-[5-(2,2-dimethyl-3-piperidin-1-yl-propoxy)-1H-indol-2-yl]-6-oxo-1,6-dihydro-pyridin-3-yl}-amide

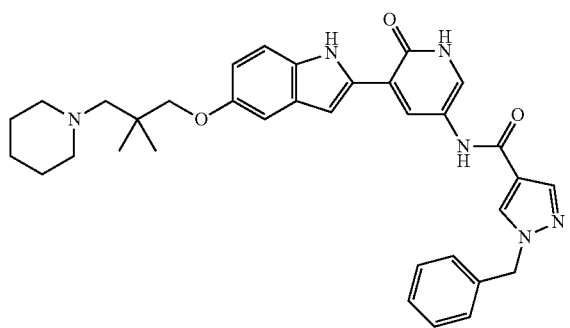 [SMILES: CC(C)(COc1ccc2[nH]c(-c3cc(NC(=O)c4cnn(Cc5ccccc5)c4)c[nH]c3=O)cc2c1)CN1CCCCC1]

The title compound was prepared by the route outlined in Scheme 11, following the same experimental procedures as for Example 115. In this instance the relevant chloroalkyl intermediate required for Step 6 was not commercially available and was synthesized according to the protocol given for Example 180.

The title compound was purified by trituration with acetonitrile, and isolated as a yellow solid, 123 mg, 64%.

LC/MS: RT=1.79 Min (270 nm), m/z=579 [M+H]. Total run time 3.75 min (short pos).

$^1$H NMR (d$_6$ DMSO): δ 0.94 (s, 6H), 1.30 (m, 2H), 1.42 (m, 4H), 2.22 (s, 2H), 2.40 (m, 4H), 3.65 (s, 2H), 5.41 (s, 2H), 6.71 (dd, 1H), 6.92 (s, 1H), 7.00 (d, 1H), 7.28-7.40 (m, 6H), 7.83 (d, 1H), 8.03 (s, 1H), 8.14 (d, 1H), 8.41 (s, 1H), 9.79 (s, 1H), 11.43 (s, 1H), 11.97 (br s, 1H).

Example 186

1-Benzyl-1H-pyrazole-4-carboxylic acid {5-[5-(1-diethylaminomethyl-cyclopropylmethoxy)-1H-indol-2-yl]-6-oxo-1,6-dihydro-pyridin-3-yl}-amide

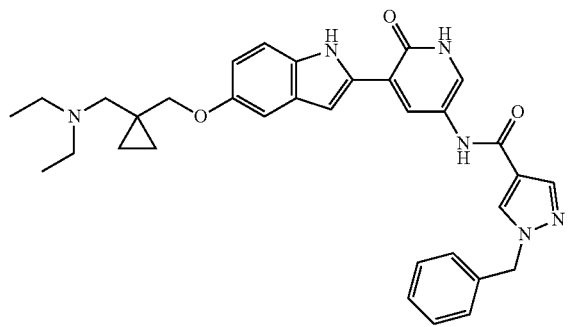 [SMILES: CCN(CC)CC1(COc2ccc3[nH]c(-c4cc(NC(=O)c5cnn(Cc6ccccc6)c5)c[nH]c4=O)cc3c2)CC1]

The title compound was prepared by the route outlined in Scheme 11, following the same experimental procedures as for Example 115. In this instance the chloroalkyl intermediate, 1-(1-chloromethyl-cyclopropylmethyl)-pyrrolidine hydrochloride, required for Step 6, was not commercially available and was synthesized according to the following methodology.

Preparation of
1-(1-chloromethyl-cyclopropylmethyl)-pyrrolidine hydrochloride

Oxalyl chloride (12.5 mL, 2M) in dichloromethane was added to a solution of cyclopropane-1,1-dicarboxylic acid methyl ester (2.90 g, 20 mmol) in dichloromethane (50 mL) at 0° C. (ice/water) and the solution stirred. DMF (100 μL) was added and the solution stirred for ~2 hrs. at room temperature, to give a pale yellow solution. The solution was concentrated to a yellow semi-solid.

The semi-solid was taken up in THF (20 ml) and the solution cooled, 0° C. (ice/water), and pyrrolidine (6 mL, 71 mmol) was added slowly and the resulting suspension stirred for ~60 mins. Ethyl acetate (150 mL) was added and the mixture washed with water (2×75 mL) and saturated aqueous sodium chloride solution (75 mL). The solution was dried over anhydrous magnesium sulphate and concentrated to yield 1-(pyrrolidine-1-carbonyl)-cyclopropanecarboxylic acid methyl ester as a yellow/brown oil 2.20 g, 55%.

Lithium aluminium hydride solution (20 mL, 1M) in THF was added slowly to a solution of 1-(pyrrolidine-1-carbonyl)-cyclopropanecarboxylic acid methyl ester (2.2 g, 11 mmol) in THF at 0° C. (ice/water), under a nitrogen atmosphere, and the resulting solution stirred for ~3 hrs at room temperature. The solution was cooled, 0° C. (ice/water), and sodium sulphate decahydrate (4.9 g, 15 mmol) was added portion-wise to give a white suspension. Diethyl ether (25 mL) was added and the suspension stirred for ~18 hrs. at room temperature. The resulting suspension was filtered, through celite, and the solids washed with diethyl ether (2×50 mL). The combined filtrates were concentrated to give (1-pyrrolidin-1-ylmethyl-cyclopropyl)-methanol as a pale yellow oil 1.45 g, 84%.

Thionyl chloride (1 mL, 13.7 mmol) was added to a solution of (1-pyrrolidin-1-ylmethyl-cyclopropyl)-methanol (1.45 g, 9.3 mmol) in toluene (20 mL) to give a pale brown suspension. The suspension was heated, 110° C., for ~3 hrs. to give a dark brown suspension. The resulting suspension was allowed to cool and concentrated to a brown solid. Trituration with diethyl ether (40 mL) gave the desired intermediate, 1-(1-chloromethyl-cyclopropylmethyl)-pyrrolidine hydrochloride as a brown powder 1.6 g, 82%.

The title compound was purified by trituration with acetonitrile, and isolated as a yellow solid, 145 mg, 58%.

LC/MS: RT=1.76 Min (270 nm), m/z=565.3 [M+H]. Total run time 3.75 min (short pos).

$^1$H NMR (d$_6$ DMSO): δ 0.40 (t, 2H), 0.60 (t, 2H), 0.95 (t, 6H), 2.45 (s, 2H), 2.50 (q, 4H), 3.85 (s, 2H), 5.40 (s, 2H), 6.70 (dd, 1H), 6.90 (d, 1H), 7.00 (d, 1H), 7.25-7.45 (m, 6H), 7.85 (d, 1H), 8.00 (s, 1H), 8.15 (d, 1H), 8.40 (s, 1H), 9.80 (s, 1H), 11.40 (s, 1H), 11.95 (br s, 1H).

Example 187

1-Benzyl-1H-pyrazole-4-carboxylic acid {6-oxo 5-[5-(1-pyrrolidin-1-ylmethyl-cyclopropylmethoxy)-1H-indol-2-yl]-1,6-dihydro-pyridin-3-yl}-amide

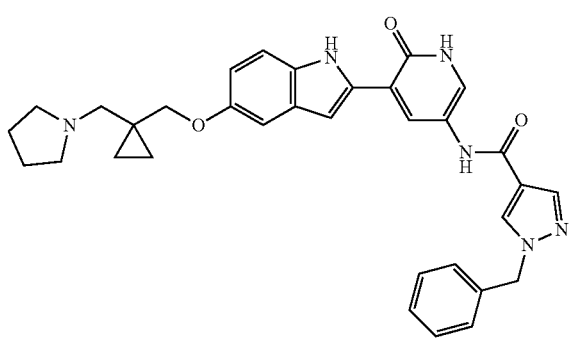

The title compound was prepared by the route outlined in Scheme 11, following the same experimental procedures as for Example 115. In this instance the relevant chloroalkyl intermediate, required for Step 6, was not commercially available and was synthesized according to the protocol given for Example 186.

The title compound was purified by trituration with acetonitrile, and isolated as a yellow solid, 175 mg, 62%.

LC/MS: RT=1.73 Min (270 nm), m/z=563.3 [M+H]. Total run time 3.75 min (short pos).

$^1$H NMR (d$_6$ DMSO): δ 0.40 (t, 2H), 0.50 (t, 2H), 1.65 (br s, 4H), 2.45 (s, 2H), 2.50 (br s, 4H), 3.85 (s, 2H), 5.40 (s, 2H), 6.75 (dd, 1H), 6.90 (d, 1H), 7.00 (d, 1H), 7.25-7.40 (m, 6H), 7.85 (d, 1H), 8.05 (s, 1H), 8.15 (d, 1H), 8.40 (s, 1H), 9.80 (s, 1H), 11.40 (s, 1H), 11.95 (br s, 1H).

Example 188

1-Benzyl-1H-pyrazole-4-carboxylic acid {5-[5-(1-dimethylaminomethyl-cyclopropylmethoxy)-1H-indol-2-yl]-6-oxo-1,6-dihydro-pyridin-3-yl}-amide

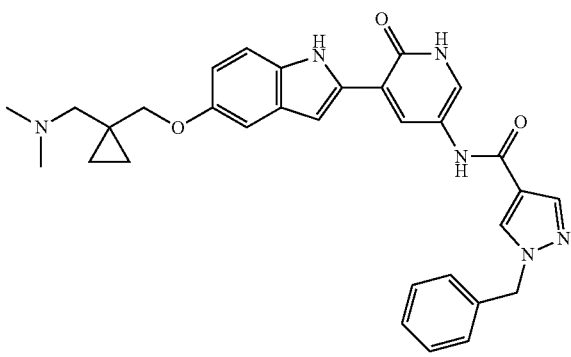 [SMILES: CN(C)CC1(COc2ccc3[nH]c(-c4cc(NC(=O)c5cnn(Cc6ccccc6)c5)c[nH]c4=O)cc3c2)CC1]

The title compound was prepared by the route outlined in Scheme 11, following the same experimental procedures as for Example 115. In this instance the relevant chloroalkyl intermediate, required for Step 6, was not commercially available and was synthesized according to the protocol given for Example 186.

The title compound was purified by trituration with acetonitrile, and isolated as a yellow solid, 190 mg, 66%.

LC/MS: RT=1.71 Min (270 nm), m/z=537.3 [M+H]. Total run time 3.75 min (short pos).

$^1$H NMR (d$_6$ DMSO): δ 0.40 (q, 2H), 0.60 (q, 2H), 2.21 (s, 6H), 2.25 (s, 2H), 3.85 (s, 2H), 5.40 (s, 2H), 6.70 (dd, 1H), 6.90 (d, 1H), 7.00 (d, 1H), 7.25-7.45 (m, 6H), 7.85 (d, 1H), 8.05 (s, 1H), 8.15 (d, 1H), 8.45 (s, 1H), 9.80 (s, 1H), 11.40 (s, 1H), 11.95 (br s, 1H).

General Procedures

All reagents obtained from commercial sources were used without further purification. Anhydrous solvents were obtained from commercial sources and used without further drying. Flash chromatography was performed with pre-packed silica-gel cartridges (Strata Si-1, 61 Å, Phenomenex, Cheshire, UK or IST Flash II, 54 Å, Argonaut, Hengoed, UK). Thin layer chromatography was conducted with 5×10 cm plates coated with Merck Type 60 F$_{254}$ silica-gel. Microwave heating was performed with a Biotage Initiator™ 2.0 instrument.

The compounds of the present invention were characterized by high performance liquid chromatography-mass spectroscopy (HPLC-MS) on either an Agilent HP1200 Rapid Resolution Mass detector 6140 multi mode source M/z range 150 to 1000 amu or an Agilent HP1100 Mass detector 1946D ESI source M/z range 150 to 1000 amu. The conditions and methods listed below are identical for both machines.

Column for 3.75 min run: Gemini 5 μm, C18, 30 mm×4.6 mm (Phenomenex).
Temperature: 35 C.
Column for 1.9 min run: LunaHST 2.5 μm, C18, 50×2 mm (Phenomenex).
Temperature: 55 C.
Mobile Phase: A—Water+10 mMol/ammonium formate+ 0.08% (v/v) formic acid at pH ca 3.5.
B—95% Acetonitrile+5% A+0.08% (v/v) formic acid
Injection Volume: 2 μL
"Short" method gradient table, either positive (pos) or positive and negative (pos/neg) ionization

| Time (min) | Solvent A (%) | Solvent B (%) | Flow (mL/min) |
|---|---|---|---|
| 0 | 95 | 5 | 2 |
| 0.25 | 95 | 5 | 2 |
| 2.50 | 95 | 5 | 2 |
| 2.55 | 5 | 95 | 3 |
| 3.60 | 5 | 95 | 3 |
| 3.65 | 5 | 95 | 2 |
| 3.70 | 95 | 5 | 2 |
| 3.75 | 95 | 5 | 2 |

"Super Short" method gradient table, either positive (pos) or positive and negative (pos/neg) ionization

| Time (min) | Solvent A (%) | Solvent B (%) | Flow (mL/min) |
|---|---|---|---|
| 0 | 95 | 5 | 1.1 |
| 0.12 | 95 | 5 | 1.1 |
| 1.30 | 5 | 95 | 1.1 |
| 1.35 | 5 | 95 | 1.7 |
| 1.85 | 5 | 95 | 1.7 |
| 1.90 | 5 | 95 | 1.1 |
| 1.95 | 95 | 5 | 1.1 |

Detection: UV detection at 230, 254 and 270 nm.
The compounds of the present invention were also characterized by Nuclear Magnetic Resonance (NMR). Analysis was performed with a Bruker DPX400 spectrometer and proton NMR spectra were measured at 400 MHz. The spectral reference was the known chemical shift of the solvent. Proton NMR data is reported as follows: chemical shift (δ) in ppm, followed by the multiplicity, where s=singlet, d=doublet, t=triplet, q=quartet, m=multiplet, dd=doublet of doublets, dt=doublet of triplets, dm=doublet of multiplets, ddd=doublet of double doublets, td=triplet of doublets, qd=quartet of doublets and br=broad, and finally the integration.

Some compounds of the invention were purified by preparative HPLC. These were performed on a Waters FractionLynx MS autopurification system, with a Gemini® 5 µm C18(2), 100 mm×20 mm i.d. column from Phenomenex, running at a flow rate of 20 cm$^3$ min$^{-1}$ with UV diode array detection (210-400 nm) and mass-directed collection. Gradients used for each compound are shown in Table 1.

At pH 4: solvent A=10 mM ammonium acetate in HPLC grade water+0.08% v/v formic acid. Solvent B=95% v/v HPLC grade acetonitrile+5% v/v solvent A+0.08% v/v formic acid.

At pH 9: solvent A=10 mM ammonium acetate in HPLC grade water+0.08% v/v ammonia solution. Solvent B=95% v/v HPLC grade acetonitrile+5% v/v solvent A+0.08% v/v ammonia solution.

The mass spectrometer was a Waters Micromass ZQ2000 spectrometer, operating in positive or negative ion electrospray ionisation modes, with a molecular weight scan range of 150 to 1000.

IUPAC chemical names were generated using AutoNom Standard.

Assay Protocols
(i) CHK1 Enzyme Assay

Assays for the CHK1 kinase activity were carried out by monitoring the phosphorylation of a synthetic peptide Chktide with the amino acid sequence, KKKVSRSGLYR-SPSMPENLNRPR. The assay mixture containing the inhibitor and CHK1 enzyme was mixed together in a microtiter plate in a final volume of 50 µl and incubated for 40 minutes at 30° C.

The assay mixture contained 0.01 mM unlabeled ATP, 0.5 µCi $^{33}$P-γ-ATP, 14.8 µM Chktide, 0.1 mg/mL BSA, 50 mM Hepes-NaOH pH 7.5 and 12.5 nM His-CHK1 (Invitrogen) enzyme. The reaction was stopped by adding 504 of 50 mM phosphoric acid. 90 µL of the mixture was transferred to a pre-wetted 96-well multi-screen MAPHNOB filtration plate (Millipore) and filtered on a vacuum manifold. The filter plate was washed with 3 successive additions of 200 µl 50 mM phosphoric acid and then with 100 µL methanol. The filtration plate was dried for 10 min at 65° C., scintillant added and phosphorylated peptide quantified in a scintillation counter (Trilux, PerkinElmer).

The compounds tested in the above assay were assigned to one of three activity ranges, namely A=IC$_{50}$<100 nM, B=IC$_{50}$>100 nM and <500 nM or C=IC$_{50}$>500 nM and <1500 nM as indicated in the table below.

Table of CHK1 Enzyme Activities

| Example | Activity |
|---|---|
| 1 | A |
| 2 | B |
| 3 | C |
| 4 | A |
| 5 | B |
| 6 | B |
| 7 | C |
| 8 | B |
| 9 | A |
| 10 | A |
| 11 | A |
| 12 | B |
| 13 | A |
| 14 | B |
| 15 | A |
| 16 | A |
| 17 | C |
| 18 | C |
| 19 | B |
| 20 | A |
| 21 | A |
| 22 | A |
| 23 | A |
| 24 | A |
| 25 | B |
| 26 | A |
| 27 | A |
| 28 | A |
| 29 | A |
| 30 | B |
| 31 | A |
| 32 | B |
| 33 | B |
| 34 | C |
| 35 | A |
| 36 | B |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |

Table of CHK1 Enzyme Activities

| Example | Activity |
|---|---|
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | B |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | C |
| 155 | A |
| 156 | A |
| 157 | A |
| 158 | A |
| 159 | A |
| 160 | B |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |

(ii) CHK1 Cellular Assay Gemcitabine $EC_{50}$ Assay

The gemcitabine $EC_{50}$ assay was developed as a rapid method for screening CHK1 inhibitors to determine their relative cell activity. This assay utilizes a feature of the effect of CHK1 inhibitors on gemcitabine toxicity. In the absence of a CHK1 inhibitor, gemcitabine acts predominantly as an anti-metbolite and therefore induces very little cell death, even at high concentrations. This can be as high as 70-80% survival at concentrations in excess of 1 µM. However, in the presence of a CHK1 inhibitor, the mechanism of action of gemcitabine switches to a more classical cytotoxic mode of action. For example, the fraction of cells surviving can be reduced to around 30% and below.

Concentrations of gemcitabine can be selected that in the absence of a CHK1 inhibitor, have no effect on cell survival but in the presence of a CHK1 inhibitor are highly cytotoxic. 10000 HT29 cells were plated per well of a 96 well plate and allowed to attach at 37° C. in a 5% CO2 humidified incubator for 18 hours. CHK1 inhibitors were then titrated in the presence of 10, 15 and 20 nM gemcitabine for 72 hours and the $EC_{50}$ determined by staining with sulforhodamine B (SRB) and determining the absorbance at 540 nm.

The compounds were tested in the above assay in the presence of gemcitabine at 10 nM, and assigned to one of two activity ranges, namely A=$EC_{50}$<100 nM or B=$EC_{50}$>100 nM and <500 nM as indicated in the table below.

Table of CHK1 Cellular Activities

| Example | Activity |
|---|---|
| 20 | B |
| 38 | B |

-continued

Table of CHK1 Cellular Activities

| Example | Activity |
|---------|----------|
| 49 | A |
| 52 | A |
| 71 | A |
| 78 | A |
| 87 | A |
| 120 | A |
| 166 | A |
| 171 | A |
| 173 | A |
| 176 | B |
| 177 | A |
| 178 | A |
| 179 | A |
| 180 | A |
| 185 | A |
| 186 | A |

(iii) HT 29 Xenograft in Nude Mouse $5 \times 10^6$ HT29 cells were subcutaneously implanted into the flanks of Balb-c nude mice. Upon reaching approximately 100 mm$^3$, animals were randomized into control and treatment groups. Animals were dosed twice per week with low dose gemcitabine (10 mg/kg) ie on days 1, 4, 8, and 11, and where indicated with compound at its maximum tolerated dose (MTD) 24 and 30 hours post the gemcitabine dose. Tumour volume was determined three times per week by caliper measurement. Vehicle was dosed instead of active ingredient in control animals.

FIG. 1 shows the In vivo potentiation results of the compound of Example 20 in combination with gemcitabine. Dosing Schedule: Gemcitabine 10 mg/kg i.p. days 1, 4, 8 and 11 (squares) or gemcitabine 10 mg/kg i.p. plus Example 20 at 30 mg/kg i.v. 24 and 30 hours post gemcitabine (triangles). Vehicle (circles) was dosed instead of active ingredient in control animals. Tumour volumes were determined by calliper measurement 3 times per week.

The invention claimed is:

1. A method of treating a mammal suffering from a cancer responsive to inhibition of CHK1 activity, comprising administering to the mammal an amount of a compound of formula (I), or a pharmaceutically acceptable salt thereof, effective to inhibit CHK1 activity, wherein the compound of formula (I) is:

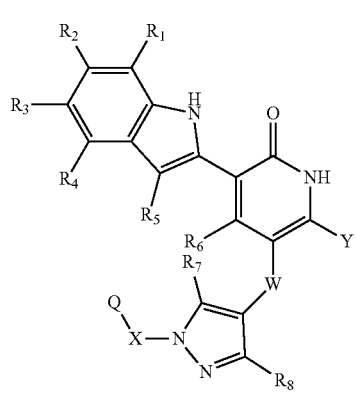

(I)

wherein
$R_1$, $R_2$, $R_5$ and $R_6$ are independently selected from hydrogen, hydroxy, methyl, trifluoromethyl, hydroxymethyl, methoxy, trifluoromethoxy, methylamino and dimethylamino;
$R_3$, and $R_4$ are independently selected from —N($R_{11}$)—$R_{12}$, -Alk-N($R_{11}$)—$R_{12}$ and —O-Alk-N($R_{11}$)—$R_{12}$;
Alk is a straight or branched chain divalent $C_1$-$C_6$ alkylene radical;
$R_7$ and $R_8$ are independently selected from hydrogen, hydroxy, or $C_1$-$C_3$ alkoxy;
X is a straight chain divalent $C_1$-$C_3$ alkylene radical, optionally substituted on one or more carbons by $R_9$ and/or $R_{10}$;
$R_9$ and $R_{10}$ are independently selected from methyl, hydroxy, or fluoro;
$R_{11}$ and $R_{12}$ are independently selected from methyl and ethyl, or
$R_{11}$ is methyl or ethyl and $R_{12}$ is —N($R_{18}$)—$R_{19}$;
$R_{13}$ is hydrogen, $C_1$-$C_3$ alkyl, fluoro-($C_1$-$C_3$)-alkyl, or a radical of formula -Alk-N($R_{14}$)—$R_{15}$;
$R_{14}$ and $R_{15}$ are independently selected from hydrogen, $C_1$-$C_3$ alkyl, or fluoro-($C_1$-$C_3$)-alkyl;
W is selected from —C(=O)—N(—$R_{16}$)— or —N(—$R_{17}$)—C(=O)—;
$R_{16}$ or $R_{17}$ is selected from hydrogen, $C_1$-$C_3$ alkyl, or fluoro-($C_1$-$C_3$)-alkyl;
$R_{18}$ and $R_{19}$ are independently selected from methyl and ethyl;
Y is hydrogen, $C_1$-$C_3$ alkyl, $C_1$-$C_3$ alkoxy, or halo; and
Q is selected from optionally substituted phenyl, optionally substituted cyclohexyl, or an optionally substituted 6-membered monocyclic heteroaryl ring
wherein optionally substituted means optionally substituted by at least one substituent selected from the group consisting of ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo, trifluoromethyl, trifluoromethoxy, nitro, nitrile, (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, and —NR$^A$CONR$^A$R$^B$ wherein R$^A$ and R$^B$ are independently a ($C_1$-$C_6$)alkyl group.

2. The method as claimed in claim 1 wherein Alk is —CH$_2$—, —CH$_2$CH$_2$—, —CH$_2$CH$_2$CH$_2$—, —CH$_2$C(CH$_3$)$_2$CH$_2$— or is a divalent radical of formula (II):

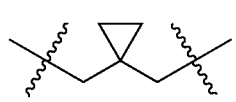

(II)

3. The method as claimed in claim 1 wherein $R_1$, $R_2$, $R_5$ and $R_6$ are each hydrogen.

4. The method as claimed in claim 1 wherein $R_1$, $R_2$, $R_4$, $R_5$ and $R_6$ are each hydrogen.

5. The method as claimed in claim 1 wherein Y is hydrogen or methyl.

6. The method as claimed in claim 1 wherein W is —NH—C(=O)— wherein the carbonyl group is linked to the pyrazole ring.

7. The method as claimed in claim 1 wherein $R_7$ and $R_8$ are both hydrogen.

8. The method as claimed in claim 1 wherein X is —$CH_2$—, —$CH(CH_3)$— or —$C(CH_3)_2$—.

9. The method as claimed in claim 1 wherein Q is optionally substituted phenyl.

10. The method as claimed in claim 9 wherein the substituent or substituents on the phenyl ring is/are selected from methyl, trifluoromethyl, methoxy, fluoro, chloro, or cyano.

11. The method as claimed in claim 9 wherein Q is 2-methyl-phenyl, 3-methyl-phenyl, 4-methyl-phenyl, 3-trifluoromethyl-phenyl, 4-trifluoromethyl-phenyl, 4-methoxyphenyl, 2-fluoro-phenyl, 3-fluoro-phenyl, 4-fluoro-phenyl, 3-chloro-phenyl, 4-chloro-phenyl, 3-cyano-phenyl, 4-cyano-phenyl, 3,4-difluoro-phenyl, 3,5-difluoro-phenyl, or 3-fluoro-4-methyl-phenyl.

12. The method as claimed in claim 1 wherein Q is cyclohexyl or pyrid-3-yl.

13. The method as claimed in claim 1 wherein:
$R_1$, $R_2$, $R_4$, $R_5$, $R_6$, $R_7$ and $R_8$ are each hydrogen;
Y is hydrogen or methyl;
W is —NH—C(=O)— wherein the carbonyl group is linked to the pyrazole ring;
$R_3$ is —N($R_{11}$)—$R_{12}$, -Alk-N($R_{11}$)—$R_{12}$, or —O-Alk-N($R_{11}$)—$R_{12}$;
$R_{11}$ and $R_{12}$ are independently selected from methyl and ethyl; or $R_{11}$ is methyl or ethyl and $R_{12}$ is —N($R_{18}$)—$R_{19}$ wherein $R_{18}$ and $R_{19}$ are independently selected from methyl and ethyl;
Alk is —$CH_2$—, —$CH_2CH_2$—, —$CH_2CH_2CH_2$—, —$CH_2C(CH_3)_2CH_2$— or is a divalent radical of formula (II):

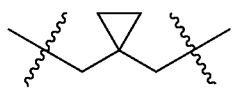

(II)

X is —$CH_2$—, —$CH(CH_3)$— or —$C(CH_3)_2$—; and
Q is phenyl, optionally substituted by one or two substituents selected from $C_1$-$C_3$ alkyl, fluoro-($C_1$-$C_3$) alkyl, $C_1$-$C_3$ alkoxy, fluoro-($C_1$-$C_3$) alkoxy, halo, and cyano.

14. The method as claimed in claim 1, wherein the compound of Formula (I) is selected from the group consisting of:
1-Benzyl-1H-pyrazole-4-carboxylic acid [5-(1H-indol-2-yl)-6-oxo-1,6-dihydro-pyridin-3-yl]-amide,
1-(4-Methyl-benzyl)-1H-pyrazole-4-carboxylic acid [6-oxo-5-(5-piperidin-1-ylmethyl-1H-indol-2-yl)-1,6-dihydro-pyridin-3-yl]-amide,
1-Benzyl-1H-pyrazole-4-carboxylic acid {5-[5-(4-fluoro-piperidin-1-ylmethyl)-1H-indol-2-yl]-6-oxo-1,6-dihydro-pyridin-3-yl}-amide,
1-Benzyl-1H-pyrazole-4-carboxylic acid [6-oxo-5-(5-piperidin-1-ylmethyl-1H-indol-2-yl)-1,6-dihydro-pyridin-3-yl]-amide,
1-Benzyl-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide,
1-Benzyl-1H-pyrazole-4-carboxylic acid {5-[5-(4-methyl-piperidin-1-ylmethyl)-1H-indol-2-yl]-6-oxo-1,6-dihydro-pyridin-3-yl}-amide,
1-(1-Phenyl-ethyl)-1H-pyrazole-4-carboxylic acid {5-[5-(4-fluoro-piperidin-1-ylmethyl)-1H-indol-2-yl]-6-oxo-1,6-dihydro-pyridin-3-yl}-amide,
1-Benzyl-1H-pyrazole-4-carboxylic acid {5-[5-(3-dimethylamino-2,2-dimethyl-propoxy)-1H-indol-2-yl]-6-oxo-1,6-dihydro-pyridin-3-yl}-amide,
1-((R)-1-Phenyl-ethyl)-1H-pyrazole-4-carboxylic acid {5-[5-(cis-2,6-dimethyl-morpholin-4-ylmethyl)-1H-indol-2-yl]-6-oxo-1,6-dihydro-pyridin-3-yl}-amide,
1-Benzyl-1H-pyrazole-4-carboxylic acid {5-[5-((S)-2-methyl-piperidin-1-ylmethyl)-1H-indol-2-yl]-6-oxo-1,6-dihydro-pyridin-3-yl}-amide,
1-Benzyl-1H-pyrazole-4-carboxylic acid {5-[5-((R)-2-methyl-piperidin-1-ylmethyl)-1H-indol-2-yl]-6-oxo-1,6-dihydro-pyridin-3-yl}-amide,
1-Benzyl-1H-pyrazole-4-carboxylic acid [5-({[5-(3-dimethylamino-2,2-dimethyl-propyl)-ethyl-amino]-methyl}-1H-indol-2-yl)-6-oxo-1,6-dihydro-pyridin-3-yl]-amide,
1-Benzyl-1H-pyrazole-4-carboxylic acid {5-[5-(cis-2,6-dimethyl-piperidin-1-ylmethyl)-1H-indol-2-yl]-6-oxo-1,6-dihydro-pyridin-3-yl}-amide,
1-Benzyl-1H-pyrazole-4-carboxylic acid {5-[5-(3-diethylamino-2,2-dimethyl-propoxy)-1H-indol-2-yl]-6-oxo-1,6-dihydro-pyridin-3-yl}-amide,
1-Benzyl-1H-pyrazole-4-carboxylic acid {5-[5-(2-dimethylamino-1,1-dimethyl-ethoxy)-1H-indol-2-yl]-6-oxo-1,6-dihydro-pyridin-3-yl}-amide,
1-Benzyl-1H-pyrazole-4-carboxylic acid {5-[5-(2,2-dimethyl-3-pyrrolidin-1-yl-propoxy)-1H-indol-2-yl]-6-oxo-1,6-dihydro-pyridin-3-yl}-amide,
1-Benzyl-1H-pyrazole-4-carboxylic acid {5-[5-(2,2-dimethyl-3-piperidin-1-yl-propoxy)-1H-indol-2-yl]-6-oxo-1,6-dihydro-pyridin-3-yl}-amide,
1-Benzyl-1H-pyrazole-4-carboxylic acid {5-[5-(1-diethylaminomethyl-cyclopropylmethoxy)-1H-indol-2-yl]-6-oxo-1,6-dihydro-pyridin-3-yl}-amide,
and pharmaceutically acceptable salt thereof.

15. The method of claim 1, wherein the administration is parenteral administration.

16. The method of claim 1 further comprising administering the compound in combination with radiotherapy or chemotherapy.

* * * * *